US010112954B2

(12) United States Patent
Jung et al.

(10) Patent No.: US 10,112,954 B2
(45) Date of Patent: Oct. 30, 2018

(54) BICYCLIC HETEROARYL DERIVATIVES HAVING INHIBITORY ACTIVITY FOR PROTEIN KINASE

(75) Inventors: Seung Hyun Jung, Goyang-si (KR); Young Hee Jung, Seoul (KR); Wha Il Choi, Seoul (KR); Jung Beom Son, Hwaseong-si (KR); Eun Ju Jeon, Hwaseong-si (KR); In Ho Yang, Yongin-si (KR); Tae Hun Song, Hwaseong-si (KR); Mi Kyoung Lee, Seoul (KR); Myoung Sil Ko, Yongin-si (KR); Young Gil Ahn, Seongnam-si (KR); Maeng Sup Kim, Seoul (KR); Young Jin Ham, Seoul (KR); Tae Bo Sim, Seoul (KR); Hwan Geun Choi, Seoul (KR); Jung Mi Hah, Seoul (KR); Dong-sik Park, Busan (KR); Hwan Kim, Goyang-si (KR)

(73) Assignees: HANMI PHARM. CO., LTD., Hwaseong-si (KR); HANMI SCIENCE CO., LTD., Hwaseong-si (KR)

( * ) Notice: Subject to any disclaimer, the term of this patent is extended or adjusted under 35 U.S.C. 154(b) by 177 days.

(21) Appl. No.: 13/575,799

(22) PCT Filed: Jan. 28, 2011

(86) PCT No.: PCT/KR2011/000615
§ 371 (c)(1),
(2), (4) Date: Jul. 27, 2012

(87) PCT Pub. No.: WO2011/093672
PCT Pub. Date: Aug. 4, 2011

(65) Prior Publication Data
US 2012/0302567 A1   Nov. 29, 2012

(30) Foreign Application Priority Data

Jan. 29, 2010  (KR) ........................ 10-2010-0008720

(51) Int. Cl.
| C07D 495/04 | (2006.01) |
| A61K 31/519 | (2006.01) |
| A61P 35/00 | (2006.01) |
| A61P 25/28 | (2006.01) |
| A61P 29/00 | (2006.01) |
| A61P 19/02 | (2006.01) |

(52) U.S. Cl.
CPC ................................ C07D 495/04 (2013.01)

(58) Field of Classification Search
CPC ........................... C07D 495/04; A61K 31/519
USPC ...................................... 544/278; 514/260.1
See application file for complete search history.

(56) References Cited

U.S. PATENT DOCUMENTS

| 6,169,091 B1 * | 1/2001 | Cockerill et al. .......... 514/228.2 |
| 6,281,227 B1 * | 8/2001 | Choi-Sledeski ....... A61K 31/00 514/210.02 |
| 2004/0038992 A1 | 2/2004 | Bemis et al. |
| 2006/0004002 A1 | 1/2006 | Thrash et al. |
| 2006/0035912 A1 | 2/2006 | Marx et al. |
| 2008/0161559 A1 | 7/2008 | Penning et al. |

FOREIGN PATENT DOCUMENTS

| EP | 1 475 094 A1 | 11/2004 |
| EP | 2 004 656 A1 | 12/2008 |
| JP | 2013-503188 A | 1/2013 |
| WO | 97/13771 A1 | 4/1997 |
| WO | 97/49706 A1 | 12/1997 |
| WO | 00/56738 A1 | 9/2000 |
| WO | 2005/116009 A1 | 12/2005 |
| WO | 2006/014404 A1 | 2/2006 |
| WO | 2006/023704 A2 | 3/2006 |
| WO | 2006/072831 A1 | 7/2006 |
| WO | WO 2006124874 | * 11/2006 |
| WO | 2007/115822 A1 | 10/2007 |
| WO | 2007/117995 A2 | 10/2007 |
| WO | 2009/013545 A2 | 1/2009 |
| WO | 2011/025940 A1 | 3/2011 |
| WO | WO 2012007375 | * 1/2012 |

OTHER PUBLICATIONS

STN search report, (Alchem Pharmtech, Inc., Registry # 1211596-20-1, dated Mar. 19, 2010, p. 10).*
Japanese Patent Office, Office Action dated Feb. 25, 2014 issued in JP Application No. 2012-551091.
European Patent Office, European Search Report issued in corresponding EP Application No. 11 737 311.8, dated Jul. 8, 2013.
State Intellectual Property Office of P.R. China, Office Action dated Dec. 20, 2013, issued in Chinese Patent Application No. 201180007509.3.
Buchanan, et al., "C-Nucleoside Studies. Part 21. Synthesis of Some Hydroxyalkylated Pyrroloand Thieno-[3.2-d]pyrimidines Related to Known Antiviral Acyclonucleosides," J. Chem. Soc. Perkin Trans. 1, 1991, vol. 1, pp. 195-202.
Popil'nichenko, et al., "Syntheses of Functionalized Thieno[3,4-d]imidazoles and Thieno[3,2-d]pyrimidines from Chlorine-Containing Enamidonitriles," Russian Journal of General Chemistry, 2006, vol. 76, No. 12, pp. 1943-1947.
Folkes et al., "The Identification of 2-(1H-Indazol-4-yl)-6-(4-methanesulfonyl-piperazin-1-ylmethyl)-4-morpholin-4-yl-thieno[3,2-d]pyrimidine (GDC-0941) as a Potent, Selective, Orally Bioavailable Inhibitor of Class I PI3 Kinase for the Treatment of Cancer," J. Med. Chem., 2008, vol. 51, pp. 5522-5532.

(Continued)

Primary Examiner — Susanna Moore
(74) Attorney, Agent, or Firm — Sughrue Mion, PLLC

(57) ABSTRACT

The present invention relates to a novel bicyclic heteroaryl derivative, a pharmaceutically acceptable salt thereof, a hydrate thereof, and a solvate thereof having an improved inhibitory activity for protein kinases, and a pharmaceutical composition for preventing or treating an abnormal cell growth disorder comprising same as an active ingredient.

7 Claims, No Drawings

(56) References Cited

OTHER PUBLICATIONS

Kemnitzer et al., "Discovery of 4-anilino-N-methylthieno[3,2-d]pyrimidines and 4-anilino-N-methylthieno[2,3-d]pyrimidines as Potent Apoptosis Inducers," Bioorganic & Medicinal Chemistry Letters, 2009, vol. 19, pp. 3536-3640.
Database Registry [online], XP002764856, Apr. 27, 2008, (total 1 page).
Database Registry [online], XP002764857, Jun. 10, 2008, (total 1 page).
Gahman et al., "Nitrogen-containing heterocyclic compounds as inhibitors of B-Rafkinase", Database Registry [online], XP002764858, 2006, (total 11 pages).
Communication dated Jan. 10, 2017 from the European Patent Office in counterpart European Application No. 16190699.5.

\* cited by examiner
BICYCLIC HETEROARYL DERIVATIVES HAVING INHIBITORY ACTIVITY FOR PROTEIN KINASE

CROSS REFERENCE TO RELATED APPLICATIONS

This application is a National Stage of International Application No. PCT/KR2011/000615 filed Jan. 28, 2011, claiming priority based on Korean Patent Application No. 10-2010-0008720 filed Jan. 29, 2010, the contents of all of which are incorporated herein by reference in their entirety.

FIELD OF THE INVENTION

The present invention relates to a novel bicyclic heteroaryl derivative having an inhibitory activity for protein kinases, and a pharmaceutical composition for preventing or treating an abnormal cell growth disorder comprising same.

BACKGROUND OF THE INVENTION

There are many signal transduction systems in cells which are functionally linked to each other to control the proliferation, growth, metastasis and apoptosis of cells (Kaelin, *Nature Reviews Cancer*, 2005, 5:689). The breakdown of the intracellular controlling system by genetic and environmental factors causes abnormal amplification or destruction of the signal transduction system leading to tumor cell generation (Hanahan and Weinberg, *Cell*, 2000, 100:57).

Protein tyrosine kinases play important roles in such cellular regulation (Melnikova and Golden, *Nature Reviews Drug Discovery*, 2004, 3:993), and their abnormal expression or mutation has been observed in cancer cells.

The protein tyrosine kinase is an enzyme which catalyzes the transportation of phosphate groups from ATP to tyrosines located on protein substrates. Many growth factor receptor proteins function as tyrosine kinases to transport cellular signals. The interaction between growth factors and their receptors normally controls the cellular growth, but abnormal signal transduction caused by the mutation or overexpression of any of the receptors often induces tumor cells and cancers.

Protein tyrosine kinases have been classified into many families in accordance with their growth factor types, and epithelial cell growth factor (EGF)-related EGF receptor (EGFR) tyrosine kinases, in particular, have been intensely studied (Hynes and Lane, *Nature Reviews Cancer*, 2005, 5:341). An EGFR tyrosine kinase is composed of a receptor and a tyrosine kinase, and delivers extracellular signals to cell nucleus through the cellular membrane. Various EGFR tyrosine kinases are classified based on their structural differences into EGFR (Erb-B1), Erb-B2, Erb-B3 and Erb-B4, and each of the above members can form a homodimer- or heterodimer-signal delivery complex. Also, the overexpression of more than one of such heterodimers is often observed in malignant cells. In addition, it is known that both EGFR and Erb-B2 significantly contribute to the formation of heterodimer-signal delivery complexes.

Several drugs as small molecules for the inhibition of EGFR tyrosine kinases have been developed, e.g., Gefitinib, Erlotinib, Lapatinib, and others. Gefitinib or Erlotinib selectively and reversibly inhibits EGFR, and Lapatinib simultaneously inhibits EGFR and Erb-B2, thereby arresting the growth of tumors to significantly extend the life time of the patient and provide therapeutic advantages.

Fibroblast growth factor receptor (FGFR) tyrosine kinases consisting of about 800 amino acids are one of Class V receptor tyrosine kinases having three immunoglobulin (Ig)-like domains, i.e., D1, D2 and D3. FGFR tyrosine kinases are classified into FGFR1, FGFR2, FGFR3 and FGFR4, and specifically classified into 48 families. A soluble FGFR tyrosine kinase (FGFR5) has 4 families. A fibroblast growth factor (FGF), a FGFR ligand, is a heparin-binding growth factor, and 23 types thereof have been reported. Generally, one of FGF tends to activate several FGFR tyrosine kinases, however, FGF-7 induces to activate only FGFR2B.

A non-covalent homodimer or heterodimer complex of FGFR formed by binding FGF with immunoglobulin-like domains II and III induces autophosphorylation in an activation loop of an FGFR kinase domain. The autophosphorylation site of FGFR1 binds to an Src homology 2 (SH2) domain of phopholipase C (PLC), and the interaction thereof induces phosphorylation and activation of PLC (Hubbard, *Progress in Biophysics & Molecular Biology*, 1999, 71:343), which successively initiates a signal transduction through MAPK or PI3K/AKT cellular pathway.

The signal transduction induced by FGF/FGFR is associated with the cell differentiation, proliferation, apoptosis and vascularization, especially it has been known to play an important role in fetal generation and wound treatment. However, abnormal signal transduction caused by the FGF/FGFR overexpression and activated mutation often leads to tumor cell generation, e.g., bladder cancer, breast cancer, prostatic carcinoma, gastric cancer, lung cancer, blood cancer, and the like.

For example, an activated FGFR3 mutation and loss of heterozygosity (LOH) of chromosome 9 are most related to generation of superficial urothelial cell carcinoma (UCC). Also, it has been well known that the activated FGFR3 mutation such as S249C point mutation is strongly related to generation of non-infilltrative bladder cancer (Sibley et al., *Oncogene*, 2001, 20:4416).

The bladder cancer induced by an FGFR3-S249C mutant can be treated by inhibiting cell proliferation using FGFR3 shRNA or RNAi. The FGFR3-S249C mutant forms a disulfide bond with a molecule, thereby initiating a heterodimer formation of an FGFR extracellular domain, which makes FGFR to maintain its activated state (Tomlinson et al., *Oncogene*, 2007, 26:5889). Also, it has been recently reported that H-Ras mutation is found in about 30% of the patients suffering from the urothelial cell carcinoma (Dinney et al., *Cancer Cell*, 2004, 6:111).

FGFR3 has been known to generate hematological malignancies such as multiple myeloma (MM), and the multiple myeloma is caused by dysfunction of t (4; 14)(p16.3; q32.3) chromosome containing FGFR3 in about 15% of MM patients (Chesi et al., *Nat. Genet.*, 1997, 16:260). Moreover, K650E point mutation induced by a modified FGFR3 gene has been reported to generate thanatophoric dysplasia type II (Tavormina et al., *Hum. Mol. Genet.*, 1995, 4:2175). CHIR-258 (TKI258), a benzimidazoloquinolinone derivative, inhibits various tyrosine kinases, especially strongly inhibits FGFR3, and is currently in the clinical stage.

G374R mutation in the activation loop of an FGFR3 kinase domain is found in about 98% of patients suffering from achondroplasia (Richette et al., *Joint Bone Spine*, 2008, 75:125). The activated FGFR3 induced by G374R mutation in chondrocytes leads to a premature synchondrosis closure and facilitates osteoblast differenciation. Also, the signal transduction of the activated FGFR3 induces to increase bone morphorgenetic protein 7 (BMP7), or to inhibit an expression of Noggin (BMP antagonist) mRNA with a MAPK-dependent manner (Matsushita et al., *Human Molecular Genetics,* 2009, 18:227).

FGFR3b and FGFR3c mutants were found in 93% of patients suffering from cervix carcinomas, and the activated FGFR3 mutants (e.g., S249C, G372C and K652E) were found in 25% of the cervix carcinomas (Cappellen et al., *Nat. Genet.,* 199, 23:18).

Meanwhile, FGFR3 mutants were found in about 40% of patients suffering from seborrheic keratose. Among of which, most point mutations were R248C, and A393E mutation was also observed in a relatively low frequency (Hafner et al., *J. Invest. Dermatol.,* 2006, 126:2404).

Vascular endothelial growth factor receptor-2 (VEGFR-2) has been known as a kinase insert domain-containing receptor/fetal liver kinase (KDR/Flk-1), belongs to Class III in a subclass of the receptor tyrosine kinases, and closely associates with angiogenesis. Angiogenesis may generate cancer, rheumatic diseases, diabetic retinopathy and neovascular glaucoma. VEGFR-2 is considered as an important molecular target for anticancer treatments based on the fact that inhibition on VEGFR-2 can result in inhibition of angiogenesis. In this connection, various VEGFR-2 low-molecular inhibitors have been discovered and most of them are currently in the clinical stage (Schenone et al., *Curr. Med. Chem.,* 2007, 14:2495). For examples, Sorafenib and Sunitinib are commercially marketable against various tyrosine kinases including VEGFR-2.

Tie-2, which is another receptor tyrosine kinase associated with angiogenesis, is extensively expressed in vascular endothelial cells, and also found in haematopoietic cells. Angiopoietin known as a ligand of Tie-2 is divided into Ang 1 and Ang 2, Ang 1 causing autophosphorylation of Tie-2 by binding to the extracellular domain thereof, and Ang 2 playing an important role in a lymphatic vascular system (Davis et al., *Cell,* 1996, 87:1161). In an experiment using a mouse, it has been confirmed that angiogenesis and growth of tumor cell became blocked by inhibiting Tie-2 (Lin et al., *Proc. Natl. Acad. Sci., USA* 1998, 95:8829).

Rearranged during transfection (RET) is one of receptor tyrosine kinases expressed in protooncogens of nerve and excretion systems. An N-terminal extracellular domain of RET is composed of cadherin-like repeats (CLR), a calcium-binding site, nine N-glycosylation sites, and a cysteine-rich region (Airaksinen et al., *Nat. Rev. Neurosci.,* 2002, 3:383). The N-terminal extracellular domain of RET comprises at least 12 tyrosines having an autophosphorylation capability. For example, there are 16 tyrosines in the extracellular domain of RET9. A GFL/GFR complex causes the autophosphorylation and activation of the kinase domain by binding to the extracellular domain of RET (Aiaksinen et al., *Nat. Rev. Neurosci.,* 2002, 3:383). RET has been reported to play an important role in development and increasing of parasympathetic and enteric nervous systems (Pachnis et al., *Development,* 1993, 119:1005).

Hirschsprung's disease, which is an apriority congenital megacolon, occurs by an RET dysfunction induced by germline mutation (Manie et al., *Trends Genet.* 2001, 17:580). Cancer such as multiple endocrine neoplasia (MEN) types 2A and 2B, and familial medullary thyroid carcinoma (FMTC) occurs by a hyper-function by RET mutation. Also, RET is considered as a molecular target to thyoid cancer (Cote and Gagel, *N. Engl. J. Med.,* 2003, 349:1566).

SUMMARY OF THE INVENTION

Accordingly, it is an object of the present invention to provide a novel bicyclic heteroaryl derivative having an improved inhibitory activity for protein kinases.

It is another object of the present invention to provide a pharmaceutical composition for preventing or treating an abnormal cell growth disorder comprising said bicyclic heteroaryl derivative as an active ingredient.

In accordance with one aspect of the present invention, there is provided a compound which is selected from the group consisting of a bicyclic heteroaryl derivative of formula (I), a pharmaceutically acceptable salt thereof, a hydrate thereof, and a solvate thereof:

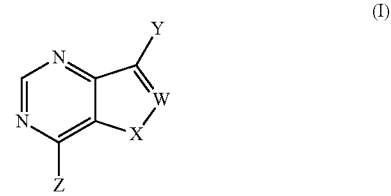

(I)

wherein,

W is CH or N;

X is $CH_2$, S, or $NR^1$;

$R^1$ is H, $C_{1-4}$ alkyl, or $C_{1-4}$ alkyl substituted with $C_{3-14}$ aryl;

Y is $-(CH_2)_2R^3$, $-CHCR^2R^3$, $-CCR^3$, $-(CH_2)_nNR^2R^3$, $-(CH_2)_nOR^3$, $-C(O)R^3$, $-C(O)OR^3$, $-C(O)NR^2R^3$, $-NR^2C(O)R^3$, or $-S(O)_2NR^2R^3$;

n is an integer of 0 to 3;

$R^2$ is H or $C_{1-6}$ alkyl;

$R^3$ is H, $C_{1-6}$ alkyl, $C_{3-7}$ cycloalkyl, $C_{3-14}$ aryl, $C_{2-13}$ heteroaryl, or $C_{2-7}$ heterocycloalkyl, wherein $R^3$ is optionally substituted with one or more substituents selected from the group consisting of halogen, $-CF_3$, $-NO_2$, $-CN$, $C_{1-6}$ alkyl, $C_{3-7}$ cycloalkyl, $C_{2-6}$ alkenyl, $C_{2-6}$ alkynyl, $-NR^6R^7$, $-OR^6$, $-C(O)NR^6R^7$, and $-NR^6C(O)R^7$;

$R^6$ and $R^7$ are each independently H, $C_{1-6}$ alkyl, or $C_{3-7}$ cycloalkyl;

Z is H, halogen, $C_{1-6}$ alkyl, $-OR^5$, $-SR^5$, $-S(O)R^5$, $-S(O)_2R^5$, $-NR^4R^5$, $-NR^4C(O)R^5$, $-NR^4C(O)NR^4R^5$, $-NR^4C(S)NR^4R^5$, or $-NR^4S(O)_2R^5$;

$R^4$ is H or $C_{1-6}$ alkyl;

$R^5$ is H, $C_{1-6}$ alkyl, $C_{3-7}$ cycloalkyl, $C_{3-14}$ aryl, $C_{2-13}$ heteroaryl, or $C_{2-7}$ heterocycloalkyl, wherein $R^5$ is optionally substituted with one or more substituents selected from the group consisting of halogen, $-CF_3$, $-NO_2$, $-CN$, $C_{1-6}$ alkyl, $C_{3-7}$ cycloalkyl, $C_{2-6}$ alkenyl, $C_{2-6}$ alkynyl, $C_{3-14}$ aryl, $C_{2-13}$ heteroaryl, $C_{2-7}$ heterocycloalkyl, $-(CH_2)_mNR^8R^9$, $-(CH_2)_mOR^9$, $-(CH_2)_mC(O)OR^9$, $-(CH_2)_mC(O)NR^8R^9$, $-(CH_2)_mNR^8C(O)R^9$, $-(CH_2)_mSR^9$, $-(CH_2)_mS(O)R^9$, and $-(CH_2)_mS(O)_2R^9$;

m is an integer of 0 to 3;

$R^8$ and $R^9$ are each independently H, $-CF_3$, $-NO_2$, $-CN$, $C_{1-6}$ alkyl, $C_{3-7}$ cycloalkyl, $C_{2-6}$ alkenyl, $C_{2-6}$ alkynyl, $C_{3-14}$ aryl, $C_{2-13}$ heteroaryl, or $C_{2-7}$ heterocycloalkyl, wherein $R^8$ and $R^9$ are each independently optionally substituted with one or more substituents selected from the group consisting of halogen, $-CF_3$, $-NO_2$, $-CN$, $C_{1-6}$ alkyl, $C_{3-7}$ cycloalkyl, $C_{2-6}$ alkenyl, $C_{2-6}$ alkynyl, $-NR^{10}R^{10}$, $C_{3-14}$ aryl, $C_{2-13}$ heteroaryl, and $C_{2-7}$ heterocycloalkyl; and $R^{10}$ is H or $C_{1-6}$ alkyl.

In accordance with another aspect of the present invention, there is provided a pharmaceutical composition for preventing or treating an abnormal cell growth disorder induced by an excessive expression of a protein kinase which comprises said compound as an active ingredient.

DETAILED DESCRIPTION OF THE INVENTION

In a preferred embodiment of the present invention, W is CH; and X is S. Also, preferably Y is —(CH$_2$)$_2$R$^3$, —CHCR$^2$R$^3$, —CCR$^3$, —C(O)OR$^3$, or —C(O)NR$^2$R$^3$; and Z is —NR$^4$R$^5$, —NR$^4$C(O)R$^5$, —NR$^4$C(O)NR$^4$R$^5$, or —NR$^4$C(O)NR$^4$R$^5$, wherein R$^2$ to R$^5$ have the same meanings as defined in formula (I).

More preferably, Y is —(CH$_2$)$_2$R$^3$, —CHCR$^2$R$^3$, —CCR$^3$, —C(O)OR$^3$, or —C(O)NR$^2$R$^3$; R$^2$ is H; and R$^3$ is selected from the group consisting of phenyl, 2-fluorophenyl, 2-hydroxyphenyl, 4-aminophenyl, 4-methoxyphenyl, 4-nitrophenyl, 2-(cyclopropylcarbamoyl)phenyl, 3-(cyclopropylcarbamoyl)phenyl, 4-(cyclopropylcarbamoyl)phenyl, 2,6-dimethylphenyl, 2-chloro-6-methylphenyl, 3,5-dimethoxyphenyl, 3-cyano-5-methoxyphenyl, 3-carbamoyl-5-methoxyphenyl, 4-chloro-3-fluorophenyl, 2,3-dichlorophenyl, 4-chloro-3-(trifluoromethyl)phenyl, 2-chloro-4-methylphenyl, 5-fluoro-2-methylphenyl, 5-fluoro-2-hydroxyphenyl, 2-methyl-5-nitrophenyl, 2-methyl-5-carboethoxyphenyl, 2-methyl-5-(cyclopropylcarbamoyl)phenyl, 2-methyl-5-(cyclopropylcarbonylamino)phenyl, 4-amino-3-fluorophenyl, 4-amino-2-methylphenyl, 5-amino-2-methylphenyl, 4-amino-2-fluorophenyl, 2-chloro-3,5-dimethoxyphenyl, 3,4,5-trimethoxyphenyl, 4-bromo-3,5-dimethoxyphenyl, 5-chloro-2,4-dimethoxyphenyl, 2,6-dichloro-3,5-dimethoxyphenyl, 2,6-dichloro-3,5-dimethylphenyl, 2,6-difluoro-3,5-dimethoxyphenyl, 2,6-dichloro-3-hydroxy-5-methoxyphenyl, 2,6-dichloro-3,5-dihydroxyphenyl, 2,6-dichloro-3-(2-(dimethylamino)ethoxy)-5-methoxyphenyl, 4-bromo-3,5-dimethoxyphenyl, 2,4,6-trichloro-3,5-dimethoxyphenyl, 4-bromo-2,6-dichloro-3,5-dimethoxyphenyl, 4-aminonaphthalen-1-yl, 2-chloropyridin-4-yl, 2,3-diaminopyridin-4-yl, 6-acetylthiophen-2-yl, 3-(cyclopropylcarbamoyl)cumarin-6-yl, 1H-pyrazol-4-yl, 6-methoxybenzofuran-4-yl, 6-methoxyquinolin-8-yl, 6-methylpyridin-3-yl, 3-phenoxyphenyl, and benzo[d][1,3]dioxol-5-yl.

Also, more preferably, Z is selected from the group consisting of amino, diethylamino, 2-hydroxyethylamino, cyclopropylamino, 2-(dimethylamino)ethylamino, 2-morpholinoethylamino, phenethylamino, 2-hydroxyethylamino, (hydroxycarbonyl)methylamino, (ethoxycarbonyl)methylamino, 2-(phenylamino)ethylamino, 3-(diethylamino)propylamino, 3-(4-ethylpiperazin-1-yl)propylamino, 3-(1H-imidazol-1-yl)propylamino, 4-(diethylamino)butylamino, 4-(4-ethylpiperazin-1-yl)butylamino, 4-(1H-imidazol-1-yl)butylamino, 5-(diethylamino)pentylamino, 5-(4-ethylpiperazin-1-yl)pentylamino, 5-(1H-imidazol-1-yl)pentylamino, piperidin-4-ylamino, 2,4-dimethoxybenzylamino, phenyl, 2,3,4-trifluorophenylamino, 3-chloro-4-fluorophenylamino, 3,4,5-trimethoxyphenylamino, 4-(dimethylamino)phenylamino, 4-morpholinophenylamino, 4-(4-hydroxypiperidin-1-yl)phenylamino, 4-(4-(pyrrolidin-1-yl)piperidin-1-yl)phenylamino, 3-(4-ethylpiperazin-1-yl)phenylamino, 4-(piperazin-1-yl)phenylamino, 4-(4-ethylpiperazin-1-yl)phenylamino, 4-(4-(2-hydroxyethyl)piperazin-1-yl)phenylamino, 4-(4-propionylpiperazin-1-yl)phenylamino, 4-(4-(isopropylcarbamoyl)piperazin-1-yl)phenylamino, 4-(4-(ethoxycarbonyl)piperazin-1-yl)phenylamino, 4-(4-ethylpiperazin-1-yl)-2-methoxyphenylamino, 4-(2-hydroxyethyl)piperazin-1-yl)-2-methoxyphenylamino, 4-(4-ethylpiperazin-1-yl)-2-isopropoxyphenylamino, 4-(2-hydroxyethyl)piperazin-1-yl)-2-isopropoxyphenylamino, 4-(4-methylpiperazin-1-ylamino)phenylamino, 4-(1H-imidazol-1-yl)phenylamino, 4-(piperidin-4-ylamino)phenylamino, 4-(4-(1-methylpiperidin-4-yl)piperazin-1-yl)phenylamino, 4-(4-(pyridin-2-yl)piperazin-1-yl)phenylamino, 4-methoxyphenylamino, 4-(hydroxycarbonyl)phenylamino, 4-(2-hydroxyethyl)phenylamino, 4-((4-ethylpiperazin-1-yl)methyl)phenylamino, 4-(2-(4-ethylpiperazin-1-yl)-2-oxoethyl)phenylamino, 4-(2-(4-ethylpiperazin-1-yl)ethyl)phenylamino, 4-((4-ethylpiperazin-1-yl)methyl)-3-(trifluoromethyl)phenylamino, 4-(1-benzylpiperidin-4-ylcarbamoyl)phenylamino, 4-(4-ethylpiperazine-1-carbonyl)phenylamino, 4-(2-(diethylamino)ethoxy)phenylamino, pyridin-2-ylamino, pyridin-4-ylamino, 4-methylpyridin-2-ylamino, 5-methylpyridin-2-ylamino, 6-methylpyridin-3-ylamino, 5-chloropyridin-2-ylamino, 5-(4-ethylpiperazin-1-yl)pyridin-2-ylamino, 5-(2-(dimethylamino)acetamido)pyridin-2-ylamino, 5-(3-(diethylamino)propoxy)pyridin-2-ylamino, 4-(((2-hydroxyethyl)(methyl)amino)methyl)pyridin-2-ylamino, 4-((diethylamino)methyl)pyridin-2-ylamino, 4-((2-(diethylamino)ethylamino)methyl)pyridin-2-ylamino, 4-((4-ethylpiperazin-1-yl)methyl)pyridin-2-ylamino, 4-(morpholinomethyl)pyridin-2-ylamino, 5-((diethylamino)methyl)pyridin-2-ylamino, 6-((diethylamino)methyl)pyridin-2-ylamino, 4-(piperidin-1-ylmethyl)pyridin-2-ylamino, 5-((3-(diethylamino)propylamino)methyl)pyridin-2-ylamino, 5-((3-(4-ethylpiperazin-1-yl)propylamino)methyl)pyridin-2-ylamino, 5-((3-hydroxypyrrolidin-1-yl)methyl)pyridin-2-ylamino, 5-((4-methylpiperidin-1-yl)methyl)pyridin-2-ylamino, 5-((3-(trifluoromethyl)piperidin-1-yl)methyl)pyridin-2-ylamino, 5-((4-morpholinopiperidin-1-yl)methyl)pyridin-2-ylamino, 5-((4-ethylpiperazin-1-yl)methyl)pyridin-2-ylamino, 5-((4-(2-hydroxyethyl)piperazin-1-yl)methyl)pyridin-2-ylamino, 5-((4-acetylpiperazin-1-yl)methyl)pyridin-2-ylamino, 5-(morpholinomethyl)pyridin-2-ylamino, 5-((3,5-dimethylmorpholino)methyl)pyridin-2-ylamino, 5-((1H-imidazol-1-yl)methyl)pyridin-2-ylamino, 5-(2-morpholino-2-oxoethyl)pyridin-2-ylamino, 5-((3-oxopiperazin-1-yl)methyl)pyridin-2-ylamino, 5-((2-(diethylamino)ethoxy)methyl)pyridin-2-ylamino, 5-((2-(piperidin-1-yl)ethoxy)methyl)pyridin-2-ylamino, 5-((3-(diethylamino)propoxy)methyl)pyridin-2-ylamino, 5-((2-methoxyethoxy)methyl)pyridin-2-ylamino, 4-(diethylamino)pyridin-2-ylamino, 4-((2-(diethylamino)ethoxy)methyl)pyridin-2-ylamino, 4-(3-(diethylamino)propoxy)pyridin-2-ylamino, 4-(thiazolidin-3-ylmethyl)pyridin-2-ylamino, 4-(2-(diethylamino)-2-oxoethyl)pyridin-2-ylamino, 5-carbamoylpyridin-2-ylamino, 5-(3-(diethylamino)propylcarbamoyl)pyridin-2-ylamino, 5-(3-(4-ethylpiperazin-1-yl)propylcarbamoyl)pyridin-2-ylamino, 5-(morpholine-4-carbonyl)pyridin-2-ylamino, 5-(4-methylpiperazin-1-ylcarbamoyl)pyridin-2-ylamino, 6-(4-ethylpiperazin-1-yl)pyrimidin-4-ylamino, 6-(2-morpholinoethylamino)pyrimidin-4-ylamino, 6-(3-(diethylamino)propylamino)pyrimidin-4-ylamino, 6-(3-(4-ethylpiperazin-1-yl)propylamino)pyrimidin-4-ylamino, 6-(2-(dimethylamino)ethoxy)pyrimidin-4-ylamino, 4-methyl-6-(2-morpholinoethylamino)pyrimidine-2-ylamino, 6-(4-(2-hydroxyethyl)piperazin-1-yl)-2-methylpyrimidin-4-ylamino, 5-nitrothiazol-2-ylamino, 2-amino-1H-benzo[d]imidazol-1-yl, 2-amino-5-(4-ethylpiperazin-1-yl)-6-fluoro-1H-benzo[d]imidazol-1-yl, 1-(4-methoxybenzyl)-1H-benzo[d]imidazol-2-ylamino, 6-methylbenzo[d]thiazol-2-ylamino, 1H-indazol-6-ylamino, 5-methyl-1H-pyrazol-3-ylamino, 3-ethoxycarbonyl-1H-indazolyl-6-amino, acetamido, cyclopropanecarboxamido, benzamido, 4-(4-ethylpiperazin-1-yl)benzamido, 1-(4-methoxybenzyl)-1H-benzo[d]imidazol-2-ylamino, methylsulfonamido, 3-(3-(trifluoromethyl)phenyl)ureido, and 3-(ethoxycarbonyl)thioureido.

Most preferred examples of the inventive bicyclic heteroaryl derivative are as follows. A pharmaceutically acceptable salt, a hydrate and a solvate thereof are also included in the scope of the present invention:

1) ethyl 3-((4-(2-hydroxyethylamino)thieno[3,2-d]pyrimidin-7-yl)ethynyl)-4-methyl benzoate;
1a) 4-(methylthio)-7-((trimethylsilyl)ethynyl)thieno[3,2-d]pyrimidine;
1b) 7-ethynyl-4-(methylthio)thieno[3,2-d]pyrimidine;
1c) ethyl 4-methyl-3-((4-(methylthio)thieno[3,2-d]pyrimidin-7-yl)ethynyl)benzoate;
1d) ethyl 4-methyl-3-((4-(methylsulfinyl)thieno[3,2-d]pyrimidin-7-yl)ethynyl)benzoate;
2) ethyl 3-((4-(cyclopropylamino)thieno[3,2-d]pyrimidin-7-yl)ethynyl)-4-methyl benzoate;
3) ethyl 4-methyl-3-((4-(3,4,5-trimethoxyphenylamino)thieno[3,2-d]pyrimidin-7-yl)ethynyl)benzoate;
4) ethyl 3-((4-(4-(4-ethylpiperazin-1-yl)phenylamino)thieno[3,2-d]pyrimidin-7-yl)ethynyl)-4-methyl benzoate;
5) ethyl 4-methyl-3-((4-(4-morpholinophenylamino)thieno[3,2-d]pyrimidin-7-yl)ethynyl)benzoate;
6) N-cyclopropyl-7-((3,5-dimethoxyphenyl)ethynyl)thieno[3,2-d]pyrimidine-4-amine;
7) 7-(4-bromo-3,5-dimethoxyphenyl)ethynyl)-N-cyclopropylthieno[3,2-d]pyrimidine-4-amine;
8) 7-((4-bromo-2-chloro-3,5-dimethoxyphenyl)ethynyl)-N-cyclopropylthieno[3,2-d]pyrimidine-4-amine;
9) 7-((4-bromo-2,6-dichloro-3,5-dimethoxyphenyl)ethynyl)-N-cyclopropylthieno[3,2-d]pyrimidine-4-amine;
10) 7-((2-chloro-3,5-dimethoxyphenyl)ethynyl)-N-cyclopropylthieno[3,2-d]pyrimidine-4-amine;
11) 7-(4-bromo-3,5-dimethoxystyryl)thieno[3,2-d]pyrimidine-4-amine;
11a) 7-vinylthieno[3,2-d]pyrimidine-4-amine;
12) (E)-7-styrylthieno[3,2-d]pyrimidine-4-amine;
13) (E)-7-(4-methoxystyryl)thieno[3,2-d]pyrimidine-4-amine;
14) (E)-2-(2-(4-aminothieno[3,2-d]pyrimidin-7-yl)vinyl)phenol;
15) (E)-7-(4-aminostyryl)thieno[3,2-d]pyrimidine-4-amine;
16) (E)-ethyl 3-(2-(4-aminothieno[3,2-d]pyrimidin-7-yl)vinyl)-4-methyl benzoate;
17) (E)-2-(2-(4-aminothieno[3,2-d]pyrimidin-7-yl)vinyl)-N-cyclopropylbenzamide;
18) (E)-3-(2-(4-aminothieno[3,2-d]pyrimidin-7-yl)vinyl)-N-cyclopropylbenzamide;
19) (E)-4-(2-(4-aminothieno[3,2-d]pyrimidin-7-yl)vinyl)-N-cyclopropylbenzamide;
20) (E)-3-(2-(4-aminothieno[3,2-d]pyrimidin-7-yl)vinyl)-N-cyclopropyl-4-methylbenzamide;
21) (E)-7-(4-nitrostyryl)thieno[3,2-d]pyrimidine-4-amine;
22) (E)-2-(2-(4-aminothieno[3,2-d]pyrimidin-7-yl)vinyl)-4-fluorophenol;
23) (E)-7-(4-amino-2-fluorostyryl)thieno[3,2-d]pyrimidine-4-amine;
24) (E)-7-(2-(4-aminonaphthalen-1-yl)vinyl)thieno[3,2-d]pyrimidine-4-amine;
25) (E)-7-(2-(2-chloropyridin-4-yl)vinyl)thieno[3,2-d]pyrimidine-4-amine;
26) (E)-5-(2-(4-aminothieno[3,2-d]pyrimidin-7-yl)vinyl)pyridine-2,3-diamine;
27) (E)-1-(5-(2-(4-aminothieno[3,2-d]pyrimidin-7-yl)vinyl)thiophen-2-yl)ethanone;
28) (E)-6-(2-(4-aminothieno[3,2-d]pyrimidin-7-yl)vinyl)-N-cyclopropyl-2-oxo-2H-chromene-3-carboxamide;
29) (E)-7-(4-amino-3-fluorostyryl)thieno[3,2-d]pyrimidine-4-amine;
30) (E)-7-(2-methyl-5-nitrostyryl)thieno[3,2-d]pyrimidine-4-amine;
31) (E)-N-cyclopropyl-7-styrylthieno[3,2-d]pyrimidine-4-amine;
32) (E)-N-cyclopropyl-7-(4-methoxystyryl)thieno[3,2-d]pyrimidine-4-amine;
33) (E)-2-(2-(4-(cyclopropylamino)thieno[3,2-d]pyrimidin-7-yl)vinyl)phenol;
34) (E)-7-(4-aminostyryl)-N-cyclopropylthieno[3,2-d]pyrimidine-4-amine;
35) (E)-ethyl 3-(2-(4-(cyclopropylamino)thieno[3,2-d]pyrimidin-7-yl)vinyl)-4-methyl benzoate;
36) (E)-N-cyclopropyl-2-(2-(4-(cyclopropylamino)thieno[3,2-d]pyrimidin-7-yl)vinyl)benzamide;
37) (E)-N-cyclopropyl-3-(2-(4-(cyclopropylamino)thieno[3,2-d]pyrimidin-7-yl)vinyl)benzamide;
38) (E)-N-cyclopropyl-4-(2-(4-(cyclopropylamino)thieno[3,2-d]pyrimidin-7-yl)vinyl)benzamide;
39) (E)-N-cyclopropyl-3-(2-(4-(cyclopropylamino)thieno[3,2-d]pyrimidin-7-yl)vinyl)-4-methylbenzamide;
40) (E)-N-cyclopropyl-7-(4-nitrostyryl)thieno[3,2-d]pyrimidine-4-amine;
41) (E)-2-(2-(4-(cyclopropylamino)thieno[3,2-d]pyrimidin-7-yl)vinyl)-4-fluorophenol;
42) (E)-7-(4-amino-2-fluorostyryl)-N-cyclopropylthieno[3,2-d]pyrimidine-4-amine;
43) (E)-7-(2-(4-aminonaphthalen-1-yl)vinyl)-N-cyclopropylthieno[3,2-d]pyrimidine-4-amine;
44) (E)-7-(2-(2-chloropyridin-4-yl)vinyl)-N-cyclopropylthieno[3,2-d]pyrimidine-4-amine;
45) (E)-7-(2-(1H-pyrazol-4-yl)vinyl)-N-cyclopropylthieno[3,2-d]pyrimidine-4-amine;
46) (E)-5-(2-(4-(cyclopropylamino)thieno[3,2-d]pyrimidin-7-yl)vinyl)pyridine-2,3-diamine;
47) (E)-1-(5-(2-(4-(cyclopropylamino)thieno[3,2-d]pyrimidin-7-yl)vinyl)thiophen-2-yl)ethanone;
48) (E)-N-cyclopropyl-6-(2-(4-(cyclopropylamino)thieno[3,2-d]pyrimidin-7-yl)vinyl)-2-oxo-2H-chromene-3-carboxamide;
49) (E)-7-(4-amino-3-fluorostyryl)-N-cyclopropylthieno[3,2-d]pyrimidine-4-amine;
50) (E)-N-cyclopropyl-7-(2-methyl-5-nitrostyryl)thieno[3,2-d]pyrimidine-4-amine;
51) (E)-N-(3-(2-(4-(cyclopropylamino)thieno[3,2-d]pyrimidin-7-yl)vinyl)-4-methylphenyl)cyclopropanecarboxamide;
52) (E)-N-cyclopropyl-3-(2-(4-(3,4,5-trimethoxyphenylamino)thieno[3,2-d]pyrimidin-7-yl)vinyl)benzamide;
53) (E)-N-cyclopropyl-4-methyl-3-(2-(4-(3,4,5-trimethoxyphenylamino)thieno[3,2-d]pyrimidin-7-yl)vinyl)benzamide;
54) (E)-7-(2-(4-aminonaphthalen-1-yl)vinyl)-N-(3,4,5-trimethoxyphenyl)thieno[3,2-d]pyrimidine-4-amine;
55) (E)-N-(4-methyl-3-(2-(4-(3,4,5-trimethoxyphenylamino)thieno[3,2-d]pyrimidin-7-yl)vinyl)phenyl)cyclopropanecarboxamide;
56) (E)-N-cyclopropyl-4-methyl-3-(2-(4-(4-morpholinophenylamino)thieno[3,2-d]pyrimidin-7-yl)vinyl)benzamide;
57) (E)-N-(4-methyl-3-(2-(4-(4-morpholinophenylamino)thieno[3,2-d]pyrimidin-7-yl)vinyl)phenyl)cyclopropanecarboxamide;
58) (E)-N-(4-(4-ethylpiperazin-1-yl)phenyl)-7-styrylthieno[3,2-d]pyrimidine-4-amine;
59) (E)-N-(4-(4-ethylpiperazin-1-yl)phenyl)-7-(4-methoxystyryl)thieno[3,2-d]pyrimidine-4-amine;

60) (E)-2-(2-(4-(4-(4-ethylpiperazin-1-yl)phenylamino)thieno[3,2-d]pyrimidin-7-yl)vinyl)phenol;
61) (E)-7-(4-aminostyryl)-N-(4-(4-ethylpiperazin-1-yl)phenyl)thieno[3,2-d]pyrimidine-4-amine;
62) (E)-ethyl 3-(2-(4-(4-(4-ethylpiperazin-1-yl)phenylamino)thieno[3,2-d]pyrimidin-7-yl)vinyl)-4-methyl benzoate;
63) (E)-N-cyclopropyl-2-(2-(4-(4-(4-ethylpiperazin-1-yl)phenylamino)thieno[3,2-d]pyrimidin-7-yl)vinyl)benzamide;
64) (E)-N-cyclopropyl-3-(2-(4-(4-(4-ethylpiperazin-1-yl)phenylamino)thieno[3,2-d]pyrimidin-7-yl)vinyl)benzamide;
65) (E)-N-cyclopropyl-4-(2-(4-(4-(4-ethylpiperazin-1-yl)phenylamino)thieno[3,2-d]pyrimidin-7-yl)vinyl)benzamide;
66) (E)-N-cyclopropyl-3-(2-(4-(4-(4-ethylpiperazin-1-yl)phenylamino)thieno[3,2-d]pyrimidin-7-yl)vinyl)-4-methylbenzamide;
67) (E)-N-(4-(4-ethylpiperazin-1-yl)phenyl)-7-(4-nitrostyryl)thieno[3,2-d]pyrimidine-4-amine;
68) (E)-2-(2-(4-(4-(4-ethylpiperazin-1-yl)phenylamino)thieno[3,2-d]pyrimidin-7-yl)vinyl)-4-fluorophenol;
69) (E)-7-(4-amino-2-fluorostyryl)-N-(4-(4-ethylpiperazin-1-yl)phenyl)thieno[3,2-d]pyrimidine-4-amine;
70) (E)-7-(2-(4-aminonaphthalen-1-yl)vinyl)-N-(4-(4-ethylpiperazin-1-yl)phenyl)thieno[3,2-d]pyrimidine-4-amine;
71) (E)-7-(2-(2-chloropyridin-4-yl)vinyl)-N-(4-(4-ethylpiperazin-1-yl)phenyl)thieno[3,2-d]pyrimidine-4-amine;
72) (E)-N-(3-(2-(4-(4-(4-ethylpiperazin-1-yl)phenylamino)thieno[3,2-d]pyrimidin-7-yl)vinyl)-4-methylphenyl)cyclopropanecarboxamide;
73) (E)-N-(4-(4-ethylpiperazin-1-yl)phenyl)-7-(2-methyl-5-nitrostyryl)thieno[3,2-d]pyrimidine-4-amine;
74) 7-(3,5-dimethoxystyryl)thieno[3,2-d]pyrimidine-4-amine;
75) 7-(4-bromo-2,6-dichloro-3,5-dimethoxystyryl)thieno[3,2-d]pyrimidine-4-amine;
76) 7-(2,6-dichloro-3,5-dimethoxystyryl)thieno[3,2-d]pyrimidine-4-amine;
77) 7-phenethylthieno[3,2-d]pyrimidine-4-amine;
78) 6-(2-(4-aminothieno[3,2-d]pyrimidin-7-yl)ethyl)-N-cyclopropyl-2-oxo-2H-chromene-3-carboxamide;
79) 7-(4-amino-2-methylphenethyl)thieno[3,2-d]pyrimidine-4-amine;
80) N-cyclopropyl-7-(4-methoxyphenethyl)thieno[3,2-d]pyrimidine-4-amine;
81) 2-(2-(4-(cyclopropylamino)thieno[3,2-d]pyrimidin-7-yl)ethyl)phenol;
82) ethyl 3-(2-(4-(cyclopropylamino)thieno[3,2-d]pyrimidin-7-yl)ethyl)-4-methyl benzoate;
83) N-cyclopropyl-2-(2-(4-(cyclopropylamino)thieno[3,2-d]pyrimidin-7-yl)ethyl)benzamide;
84) N-cyclopropyl-3-(2-(4-(cyclopropylamino)thieno[3,2-d]pyrimidin-7-yl)ethyl)benzamide;
85) N-cyclopropyl-3-(2-(4-(cyclopropylamino)thieno[3,2-d]pyrimidin-7-yl)ethyl)-4-methylbenzamide;
86) 7-(4-aminophenethyl)-N-cyclopropylthieno[3,2-d]pyrimidine-4-amine;
87) 7-(2-(2-chloropyridin-4-yl)ethyl)-N-cyclopropylthieno[3,2-d]pyrimidine-4-amine;
88) 7-(2-(1H-pyrazol-4-yl)ethyl)-N-cyclopropylthieno[3,2-d]pyrimidine-4-amine;
89) 7-(5-amino-2-methylphenethyl)-N-cyclopropylthieno[3,2-d]pyrimidine-4-amine;
90) N-cyclopropyl-3-(2-(4-(3,4,5-trimethoxyphenylamino)thieno[3,2-d]pyrimidin-7-yl)ethyl)benzamide;
91) N-cyclopropyl-4-methyl-3-(2-(4-(3,4,5-trimethoxyphenylamino)thieno[3,2-d]pyrimidin-7-yl)ethyl)benzamide;
92) N-(4-(4-ethylpiperazin-1-yl)phenyl)-7-phenethylthieno[3,2-d]pyrimidine-4-amine;
93) N-(4-(4-ethylpiperazin-1-yl)phenyl)-7-(4-methoxyphenethyl)thieno[3,2-d]pyrimidine-4-amine;
94) 2-(2-(4-(4-(4-ethylpiperazin-1-yl)phenylamino)thieno[3,2-d]pyrimidin-7-yl)ethyl)phenol;
95) ethyl 3-(2-(4-(4-(4-ethylpiperazin-1-yl)phenylamino)thieno[3,2-d]pyrimidin-7-yl)ethyl)-4-methyl benzoate;
96) N-cyclopropyl-2-(2-(4-(4-(4-ethylpiperazin-1-yl)phenylamino)thieno[3,2-d]pyrimidin-7-yl)ethyl)benzamide;
97) N-cyclopropyl-3-(2-(4-(4-(4-ethylpiperazin-1-yl)phenylamino)thieno[3,2-d]pyrimidin-7-yl)ethyl)benzamide;
98) N-cyclopropyl-4-(2-(4-(4-(4-ethylpiperazin-1-yl)phenylamino)thieno[3,2-d]pyrimidin-7-yl)ethyl)benzamide;
99) N-cyclopropyl-3-(2-(4-(4-(4-ethylpiperazin-1-yl)phenylamino)thieno[3,2-d]pyrimidin-7-yl)ethyl)-4-methylbenzamide;
100) 7-(4-aminophenethyl)-N-(4-(4-ethylpiperazin-1-yl)phenyl)thieno[3,2-d]pyrimidine-4-amine;
101) 2-(2-(4-(4-(4-ethylpiperazin-1-yl)phenylamino)thieno[3,2-d]pyrimidin-7-yl)ethyl)-4-fluorophenol;
102) 7-(2-(4-aminonaphthalen-1-yl)ethyl)-N-(4-(4-ethylpiperazin-1-yl)phenyl)thieno[3,2-d]pyrimidine-4-amine;
103) N-(3-(2-(4-(4-(4-ethylpiperazin-1-yl)phenylamino)thieno[3,2-d]pyrimidin-7-yl)ethyl)-4-methylphenyl)cyclopropanecarboxamide;
104) 7-(5-amino-2-methylphenethyl)-N-(4-(4-ethylpiperazin-1-yl)phenyl)thieno[3,2-d]pyrimidine-4-amine;
105) 4-(methylthio)thieno[3,2-d]pyrimidine-7-carboxylic acid;
105a) 4-(methylthio)-7-vinylthieno[3,2-d]pyrimidine;
105b) 4-(methylthio)thieno[3,2-d]pyrimidine-7-carbaldehyde;
106) 4-amino-N-(3,5-dimethoxyphenyl)thieno[3,2-d]pyrimidine-7-carboxamide;
106a) N-(3,5-dimethoxyphenyl)-4-(methylthio)thieno[3,2-d]pyrimidine-7-carboxamide;
106b) N-(3,5-dimethoxyphenyl)-4-(methylsulfinyl)thieno[3,2-d]pyrimidine-7-carboxamide;
107) 4-chlorothieno[3,2-d]pyrimidine-7-carboxylic acid;
107c) 7-(bromomethyl)-4-chlorothieno[3,2-d]pyrimidine;
107d) (4-chlorothieno[3,2-d]pyrimidin-7-yl)methyl acetate;
107e) (4-chlorothieno[3,2-d]pyrimidin-7-yl)methanol;
107f) 4-chlorothieno[3,2-d]pyrimidine-7-carbaldehyde;
108) 4-(cyclopropylamino)-N-(2,6-difluoro-3,5-dimethoxyphenyl)thieno[3,2-d]pyrimidine-7-carboxamide;
108a) 4-chloro-N-(2,6-difluoro-3,5-dimethoxyphenyl)thieno[3,2-d]pyrimidine-7-carboxamide;
108b) 4-amino-N-(2,6-difluoro-3,5-dimethoxyphenyl)thieno[3,2-d]pyrimidine-7-carboxamide;
109) 4-chloro-N-(2-chloro-3,5-dimethoxyphenyl)thieno[3,2-d]pyrimidine-7-carboxamide;
110) N-(2-chloro-3,5-dimethoxyphenyl)-4-methoxythieno[3,2-d]pyrimidine-7-carboxamide;
111) 4-amino-N-(2-chloro-3,5-dimethoxyphenyl)thieno[3,2-d]pyrimidine-7-carboxamide;
112) 4-chloro-N-(6-methoxybenzofuran-4-yl)-3-methyl-3,4-dihydrothieno[3,2-d]pyrimidine-7-carboxamide;
113) 4-amino-N-(6-methoxybenzofuran-4-yl)-3-methyl-3,4-dihydrothieno[3,2-d]pyrimidine-7-carboxamide;
114) N-(6-methoxybenzofuran-4-yl)-3-methyl-4-(phenylamino)-3,4-dihydrothieno[3,2-d]pyrimidine-7-carboxamide;
115) 4-chloro-N-(3-cyano-5-methoxyphenyl)thieno[3,2-d]pyrimidine-7-carboxamide;

116) 4-amino-N-(3-carbamoyl-5-methoxyphenyl)thieno[3,2-d]pyrimidine-7-carboxamide;
117) 4-chloro-N-(6-methoxyquinolin-8-yl)thieno[3,2-d]pyrimidine-7-carboxamide;
118) 4-amino-N-(6-methoxyquinolin-8-yl)thieno[3,2-d]pyrimidine-7-carboxamide;
119) 4-chloro-N-(3,5-dimethoxyphenyl)thieno[3,2-d]pyrimidine-7-carboxamide;
120) N-(3,5-dimethoxyphenyl)-4-methoxythieno[3,2-d]pyrimidine-7-carboxamide;
121) 4-(2,4-dimethoxybenzylamino)-N-(3,5-dimethoxyphenyl)thieno[3,2-d]pyrimidine-7-carboxamide;
122) 4-amino-N-(3,4,5-trimethoxyphenyl)thieno[3,2-d]pyrimidine-7-carboxamide;
123) 4-amino-N-(4-chloro-3-fluorophenyl)thieno[3,2-d]pyrimidine-7-carboxamide;
124) 4-amino-N-(6-methylpyridin-3-yl)thieno[3,2-d]pyrimidine-7-carboxamide;
125) 4-amino-N-(3-phenoxyphenyl)thieno[3,2-d]pyrimidine-7-carboxamide;
126) 4-amino-N-(2,6-dimethylphenyl)thieno[3,2-d]pyrimidine-7-carboxamide;
127) 4-amino-N-(2-chloro-6-methylphenyl)thieno[3,2-d]pyrimidine-7-carboxamide;
128) 4-amino-N-(benzo[d][1,3]dioxol-5-yl)thieno[3,2-d]pyrimidine-7-carboxamide;
129) 4-amino-N-(5-chloro-2,4-dimethoxyphenyl)thieno[3,2-d]pyrimidine-7-carboxamide;
130) 4-amino-N-(2-fluorophenyl)thieno[3,2-d]pyrimidine-7-carboxamide;
131) 4-amino-N-(2,3-dichlorophenyl)thieno[3,2-d]pyrimidine-7-carboxamide;
132) 4-amino-N-(4-chloro-3-(trifluoromethyl)phenyl)thieno[3,2-d]pyrimidine-7-carboxamide;
133) 4-amino-N-(2-chloro-4-methylphenyl)thieno[3,2-d]pyrimidine-7-carboxamide;
134) 4-amino-N-(5-fluoro-2-methylphenyl)thieno[3,2-d]pyrimidine-7-carboxamide;
135) 4-amino-N-(2-methyl-5-nitrophenyl)thieno[3,2-d]pyrimidine-7-carboxamide;
136) 4-amino-N-(5-amino-2-methylphenyl)thieno[3,2-d]pyrimidine-7-carboxamide;
137) 4-chloro-N-(2,4,6-trichloro-3,5-dimethoxyphenyl)thieno[3,2-d]pyrimidine-7-carboxamide;
138) 4-methoxy-N-(2,4,6-trichloro-3,5-dimethoxyphenyl)thieno[3,2-d]pyrimidine-7-carboxamide;
139) 4-amino-N-(2,4,6-trichloro-3,5-dimethoxyphenyl)thieno[3,2-d]pyrimidine-7-carboxamide;
140) 4-(2-morpholinoethylamino)-N-(2,4,6-trichloro-3,5-dimethoxyphenyl)thieno[3,2-d]pyrimidine-7-carboxamide;
141) 4-(phenylamino)-N-(2,4,6-trichloro-3,5-dimethoxyphenyl)thieno[3,2-d]pyrimidine-7-carboxamide;
142) 4-(4-(4-ethylpiperazin-1-yl)phenylamino)-N-(2,4,6-trichloro-3,5-dimethoxyphenyl)thieno[3,2-d]pyrimidine-7-carboxamide;
143) 4-(4-(4-ethylpiperazin-1-yl)-2-methoxyphenylamino)-N-(2,4,6-trichloro-3,5-dimethoxyphenyl)thieno[3,2-d]pyrimidine-7-carboxamide;
144) 4-(4-(4-(2-hydroxyethyl)piperazin-1-yl)-2-methoxyphenylamino)-N-(2,4,6-trichloro-3,5-dimethoxyphenyl)thieno[3,2-d]pyrimidine-7-carboxamide;
145) 4-(4-(4-ethylpiperazin-1-yl)-2-isopropoxyphenylamino)-N-(2,4,6-trichloro-3,5-dimethoxyphenyl)thieno[3,2-d]pyrimidine-7-carboxamide;
146) 4-(4-(4-(2-hydroxyethyl)piperazin-1-yl)-2-isopropoxyphenylamino)-N-(2,4,6-trichloro-3,5-dimethoxyphenyl)thieno[3,2-d]pyrimidine-7-carboxamide;
147) 4-(pyridin-2-ylamino)-N-(2,4,6-trichloro-3,5-dimethoxyphenyl)thieno[3,2-d]pyrimidine-7-carboxamide;
148) N-(4-bromo-2,6-dichloro-3,5-dimethoxyphenyl)-4-chlorothieno[3,2-d]pyrimidine-7-carboxamide;
148b) N-(4-bromo-3,5-dimethoxyphenyl)-4-chlorothieno[3,2-d]pyrimidine-7-carboxamide;
148c) N-(4-bromo-3,5-dimethoxyphenyl)-4-(methylthio)thieno[3,2-d]pyrimidine-7-carboxamide;
149) 4-amino-N-(4-bromo-2,6-dichloro-3,5-dimethoxyphenyl)thieno[3,2-d]pyrimidine-7-carboxamide;
150) N-(4-bromo-2,6-dichloro-3,5-dimethoxyphenyl)-4-(2-(dimethylamino)ethylamino)thieno[3,2-d]pyrimidine-7-carboxamide;
151) N-(4-bromo-2,6-dichloro-3,5-dimethoxyphenyl)-4-(3-(diethylamino)propylamino)thieno[3,2-d]pyrimidine-7-carboxamide;
152) N-(4-bromo-2,6-dichloro-3,5-dimethoxyphenyl)-4-(4-(4-ethylpiperazin-1-yl)-2-methoxyphenylamino)thieno[3,2-d]pyrimidine-7-carboxamide;
153) N-(4-bromo-2,6-dichloro-3,5-dimethoxyphenyl)-4-(4-(4-(2-hydroxyethyl)piperazin-1-yl)-2-methoxyphenylamino)thieno[3,2-d]pyrimidine-7-carboxamide;
154) N-(4-bromo-2,6-dichloro-3,5-dimethoxyphenyl)-4-(4-(4-ethylpiperazin-1-yl)-2-isopropoxyphenylamino)thieno[3,2-d]pyrimidine-7-carboxamide;
155) N-(4-bromo-2,6-dichloro-3,5-dimethoxyphenyl)-4-(4-(4-(2-hydroxyethyl)piperazin-1-yl)-2-isopropoxyphenylamino)thieno[3,2-d]pyrimidine-7-carboxamide;
156) N-(4-bromo-2,6-dichloro-3,5-dimethoxyphenyl)-4-(4-(4-ethylpiperazin-1-yl)phenylamino)thieno[3,2-d]pyrimidine-7-carboxamide;
157) N-(4-bromo-2,6-dichloro-3,5-dimethoxyphenyl)-4-(4-(diethylamino)butylamino)thieno[3,2-d]pyrimidine-7-carboxamide;
158) N-(4-bromo-2,6-dichloro-3,5-dimethoxyphenyl)-4-(5-(diethylamino)pentylamino)thieno[3,2-d]pyrimidine-7-carboxamide;
159) N-(4-bromo-2,6-dichloro-3,5-dimethoxyphenyl)-4-(3-(4-ethylpiperazin-1-yl)propylamino)thieno[3,2-d]pyrimidine-7-carboxamide;
160) N-(4-bromo-2,6-dichloro-3,5-dimethoxyphenyl)-4-(4-(4-ethylpiperazin-1-yl)butylamino)thieno[3,2-d]pyrimidine-7-carboxamide;
161) N-(4-bromo-2,6-dichloro-3,5-dimethoxyphenyl)-4-(5-(4-ethylpiperazin-1-yl)pentylamino)thieno[3,2-d]pyrimidine-7-carboxamide;
162) 4-(3-(1H-imidazol-1-yl)propylamino)-N-(4-bromo-2,6-dichloro-3,5-dimethoxyphenyl)thieno[3,2-d]pyrimidine-7-carboxamide;
163) 4-(4-(1H-imidazol-1-yl)butylamino)-N-(4-bromo-2,6-dichloro-3,5-dimethoxyphenyl)thieno[3,2-d]pyrimidine-7-carboxamide;
164) 4-(5-(1H-imidazol-1-yl)pentylamino)-N-(4-bromo-2,6-dichloro-3,5-dimethoxyphenyl)thieno[3,2-d]pyrimidine-7-carboxamide;
165) N-(4-bromo-2,6-dichloro-3,5-dimethoxyphenyl)-4-(phenylamino)thieno[3,2-d]pyrimidine-7-carboxamide;
166) 4-chloro-N-(2,6-dichloro-3,5-dimethoxyphenyl)thieno[3,2-d]pyrimidine-7-carboxamide;
167) 4-amino-N-(2,6-dichloro-3,5-dimethoxyphenyl)thieno[3,2-d]pyrimidine-7-carboxamide;
168) 4-(cyclopropylamino)-N-(2,6-dichloro-3,5-dimethoxyphenyl)thieno[3,2-d]pyrimidine-7-carboxamide;

169) N-(2,6-dichloro-3,5-dimethoxyphenyl)-4-(2-(dimethylamino)ethylamino)thieno[3,2-d]pyrimidine-7-carboxamide;
170) N-(2,6-dichloro-3,5-dimethoxyphenyl)-4-(3-(diethylamino)propylamino)thieno[3,2-d]pyrimidine-7-carboxamide;
171) N-(2,6-dichloro-3,5-dimethoxyphenyl)-4-(3-(4-ethylpiperazin-1-yl)propylamino)thieno[3,2-d]pyrimidine-7-carboxamide;
172) 4-(4-(1H-imidazol-1-yl)butylamino)-N-(2,6-dichloro-3,5-dimethoxyphenyl)thieno[3,2-d]pyrimidine-7-carboxamide;
173) N-(2,6-dichloro-3,5-dimethoxyphenyl)-4-(4-(4-ethylpiperazin-1-yl)phenylamino)thieno[3,2-d]pyrimidine-7-carboxamide;
174) N-(3,5-dimethoxyphenyl)-N-(4-methoxybenzyl)-4-(methylthio)thieno[3,2-d]pyrimidine-7-carboxamide;
175) 4-acetamido-N-(2,6-dichloro-3,5-dimethoxyphenyl)thieno[3,2-d]pyrimidine-7-carboxamide;
176) 4-benzamido-N-(2,6-dichloro-3,5-dimethoxyphenyl)thieno[3,2-d]pyrimidine-7-carboxamide;
177) 4-(cyclopropanecarboxamido)-N-(2,6-dichloro-3,5-dimethoxyphenyl)thieno[3,2-d]pyrimidine-7-carboxamide;
178) N-(2,6-dichloro-3,5-dimethoxyphenyl)-4-(5-methylpyridine-2-ylamino)thieno[3,2-d]pyrimidine-7-carboxamide;
179) N-(2,6-dichloro-3,5-dimethoxyphenyl)-4-(5-((4-ethylpiperazin-1-yl)methyl)pyridin-2-ylamino)thieno[3,2-d]pyrimidine-7-carboxamide;
180) N-(2,6-dichloro-3,5-dimethoxyphenyl)-4-(5-((4-(2-hydroxyethyl)piperazin-1-yl)methyl)pyridin-2-ylamino)thieno[3,2-d]pyrimidine-7-carboxamide;
181) N-(2,6-dichloro-3,5-dimethoxyphenyl)-4-(5-(4-ethylpiperazin-1-yl)pyridin-2-ylamino)thieno[3,2-d]pyrimidine-7-carboxamide;
182) N-(2,6-dichloro-3,5-dimethoxyphenyl)-4-(6-(4-ethylpiperazin-1-yl)pyrimidin-4-ylamino)thieno[3,2-d]pyrimidine-7-carboxamide;
183) N-(2,6-dichloro-3,5-dimethoxyphenyl)-4-(6-(4-(2-hydroxyethyl)piperazin-1-yl)-2-methylpyrimidin-4-ylamino)thieno[3,2-d]pyrimidine-7-carboxamide;
184) N-(4-bromo-2,6-dichloro-3,5-dimethoxyphenyl)-4-(6-methylpyridin-3-ylamino)thieno[3,2-d]pyrimidine-7-carboxamide;
185) N-(4-bromo-2,6-dichloro-3,5-dimethoxyphenyl)-4-(4-(2-(diethylamino)ethoxy)phenylamino)thieno[3,2-d]pyrimidine-7-carboxamide;
186) N-(4-bromo-2,6-dichloro-3,5-dimethoxyphenyl)-4-(4-(2-hydroxyethyl)phenylamino)thieno[3,2-d]pyrimidine-7-carboxamide;
187) 4-(4-(1-benzylpiperidine-4-ylcarbamoyl)phenylamino)-N-(4-bromo-2,6-dichloro-3,5-dimethoxyphenyl)thieno[3,2-d]pyrimidine-7-carboxamide;
188) N-(4-bromo-2,6-dichloro-3,5-dimethoxyphenyl)-4-(4-(4-ethylpiperazine-1-carbonyl)phenylamino)thieno[3,2-d]pyrimidine-7-carboxamide;
189) N-(2,6-dichloro-3,5-dimethoxyphenyl)-4-(4-((4-ethylpiperazin-1-yl)methyl)phenylamino)thieno[3,2-d]pyrimidine-7-carboxamide;
190) N-(4-bromo-2,6-dichloro-3,5-dimethoxyphenyl)-4-(4-(2-(4-ethylpiperazin-1-yl)-2-oxoethyl)phenylamino)thieno[3,2-d]pyrimidine-7-carboxamide;
191) N-(4-bromo-2,6-dichloro-3,5-dimethoxyphenyl)-4-(4-(2-(4-ethylpiperazin-1-yl)ethyl)phenylamino)thieno[3,2-d]pyrimidine-7-carboxamide;
192) 4-(7-(4-bromo-2,6-dichloro-3,5-dimethoxyphenylcarbamoyl)thieno[3,2-d]pyrimidin-4-ylamino)benzoic acid;
193) N-(4-bromo-2,6-dichloro-3,5-dimethoxyphenyl)-4-(4-((4-ethylpiperazin-1-yl)methyl)-3-(trifluoromethyl)phenylamino)thieno[3,2-d]pyrimidine-7-carboxamide;
194) N-(4-bromo-2,6-dichloro-3,5-dimethoxyphenyl)-4-(3-(4-ethylpiperazin-1-yl)phenylamino)thieno[3,2-d]pyrimidine-7-carboxamide;
195) N-(4-bromo-2,6-dichloro-3,5-dimethoxyphenyl)-4-(4-(4-(pyrrolidin-1-yl)piperidin-1-yl)phenylamino)thieno[3,2-d]pyrimidine-7-carboxamide;
196) N-(2,6-dichloro-3,5-dimethoxyphenyl)-4-(4-(2-(diethylamino)ethoxy)phenylamino)thieno[3,2-d]pyrimidine-7-carboxamide;
197) 4-(4-(1-benzylpiperidine-4-ylcarbamoyl)phenylamino)-N-(2,6-dichloro-3,5-dimethoxyphenyl)thieno[3,2-d]pyrimidine-7-carboxamide;
198) N-(2,6-dichloro-3,5-dimethoxyphenyl)-4-(4-(4-ethylpiperazine-1-carbonyl)phenylamino)thieno[3,2-d]pyrimidine-7-carboxamide;
199) N-(2,6-dichloro-3,5-dimethoxyphenyl)-4-(4-(2-(4-ethylpiperazin-1-yl)-2-oxoethyl)phenylamino)thieno[3,2-d]pyrimidine-7-carboxamide;
200) N-(2,6-dichloro-3,5-dimethoxyphenyl)-4-(4-((4-ethylpiperazin-1-yl)methyl)-3-(trifluoromethyl)phenylamino)thieno[3,2-d]pyrimidine-7-carboxamide;
201) N-(2,6-dichloro-3,5-dimethoxyphenyl)-4-(3-(4-ethylpiperazin-1-yl)phenylamino)thieno[3,2-d]pyrimidine-7-carboxamide;
202) N-(2,6-dichloro-3,5-dimethoxyphenyl)-4-(4-(4-(pyrrolidin-1-yl)piperidin-1-yl)phenylamino)thieno[3,2-d]pyrimidine-7-carboxamide;
203) N-(4-bromo-2,6-dichloro-3,5-dimethoxyphenyl)-4-(4-(4-ethylpiperazin-1-yl)benzamido)thieno[3,2-d]pyrimidine-7-carboxamide;
204) N-(2,6-dichloro-3,5-dimethoxyphenyl)-4-(4-(4-ethylpiperazin-1-yl)benzamido)thieno[3,2-d]pyrimidine-7-carboxamide;
205) N-(4-bromo-2,6-dichloro-3,5-dimethoxyphenyl)-4-(methylsulfonamido)thieno[3,2-d]pyrimidine-7-carboxamide;
206) N-(2,6-dichloro-3,5-dimethoxyphenyl)-4-(methylsulfonamido)thieno[3,2-d]pyrimidine-7-carboxamide;
207) N-(4-bromo-2,6-dichloro-3,5-dimethoxyphenyl)-4-(4-(4-hydroxypiperidin-1-yl)phenylamino)thieno[3,2-d]pyrimidine-7-carboxamide;
208) N-(2,6-dichloro-3,5-dimethoxyphenyl)-4-(6-(2-morpholinoethylamino)pyrimidin-4-ylamino)thieno[3,2-d]pyrimidine-7-carboxamide;
209) N-(2,6-dichloro-3,5-dimethoxyphenyl)-4-(6-(2-(dimethylamino)ethoxy)pyrimidin-4-ylamino)thieno[3,2-d]pyrimidine-7-carboxamide;
210) N-(2,6-dichloro-3,5-dimethoxyphenyl)-4-(6-(3-(diethylamino)propylamino)pyrimidin-4-ylamino)thieno[3,2-d]pyrimidine-7-carboxamide;
211) N-(2,6-dichloro-3,5-dimethoxyphenyl)-4-(6-(3-(4-ethylpiperazin-1-yl)propylamino)pyrimidin-4-ylamino)thieno[3,2-d]pyrimidine-7-carboxamide;
212) N-(4-bromo-2,6-dichloro-3,5-dimethoxyphenyl)-4-(4-methyl-6-(2-morpholinoethylamino)pyrimidin-2-ylamino)thieno[3,2-d]pyrimidine-7-carboxamide;
213) N-(4-bromo-2,6-dichloro-3,5-dimethoxyphenyl)-4-(5-nitrothiazol-2-ylamino)thieno[3,2-d]pyrimidine-7-carboxamide;
214) N-(2,6-dichloro-3,5-dimethoxyphenyl)-4-(4-methyl-6-(2-morpholinoethylamino)pyrimidin-2-ylamino)thieno[3,2-d]pyrimidine-7-carboxamide;

215) N-(2,6-dichloro-3,5-dimethoxyphenyl)-4-(3-(3-(trifluoromethyl)phenyl)ureido)thieno[3,2-d]pyrimidine-7-carboxamide;
216) N-(2,6-dichloro-3,5-dimethoxyphenyl)-4-(3-(ethoxycarbonyl)thioureido)thieno[3,2-d]pyrimidine-7-carboxamide;
217) 4-amino-N-(2,6-dichloro-3-hydroxy-5-methoxyphenyl)thieno[3,2-d]pyrimidine-7-carboxamide;
218) 4-amino-N-(2,6-dichloro-3,5-dihydroxyphenyl)thieno[3,2-d]pyrimidine-7-carboxamide;
219) 4-amino-N-(2,6-dichloro-3-(2-(dimethylamino)ethoxy)-5-methoxyphenyl)thieno[3,2-d]pyrimidine-7-carboxamide;
220) 4-(2-amino-5-(4-ethylpiperazin-1-yl)-6-fluoro-1H-benzo[d]imidazol-1-yl)-N-(4-bromo-2,6-dichloro-3,5-dimethoxyphenyl)thieno[3,2-d]pyrimidine-7-carboxamide;
221) N-(4-bromo-2,6-dichloro-3,5-dimethoxyphenyl)-4-(6-methylbenzo[d]thiazol-2-ylamino)thieno[3,2-d]pyrimidine-7-carboxamide;
222) 4-(2-amino-1H-benzo[d]imidazol-1-yl)-N-(4-bromo-2,6-dichloro-3,5-dimethoxyphenyl)thieno[3,2-d]pyrimidine-7-carboxamide;
223) N-(4-bromo-2,6-dichloro-3,5-dimethoxyphenyl)-4-(1-(4-methoxybenzyl)-1H-benzo[d]imidazol-2-ylamino)thieno[3,2-d]pyrimidine-7-carboxamide;
224) 4-(2-amino-5-(4-ethylpiperazin-1-yl)-6-fluoro-1H-benzo[d]imidazol-1-yl)-N-(2,6-dichloro-3,5-dimethoxyphenyl)thieno[3,2-d]pyrimidine-7-carboxamide;
225) N-(2,6-dichloro-3,5-dimethoxyphenyl)-4-(6-methylbenzo[d]thiazol-2-ylamino)thieno[3,2-d]pyrimidine-7-carboxamide;
226) 4-(2-amino-1H-benzo[d]imidazol-1-yl)-N-(2,6-dichloro-3,5-dimethoxyphenyl)thieno[3,2-d]pyrimidine-7-carboxamide;
227) N-(2,6-dichloro-3,5-dimethoxyphenyl)-4-(1-(4-methoxybenzyl)-1H-benzo[d]imidazol-2-ylamino)thieno[3,2-d]pyrimidine-7-carboxamide;
228) 4-(1H-indazol-6-ylamino)-N-(4-bromo-2,6-dichloro-3,5-dimethoxyphenyl)thieno[3,2-d]pyrimidine-7-carboxamide;
229) 4-(1H-indazol-6-ylamino)-N-(2,6-dichloro-3,5-dimethoxyphenyl)thieno[3,2-d]pyrimidine-7-carboxamide;
230) N-(4-bromo-2,6-dichloro-3,5-dimethoxyphenyl)-4-(5-methyl-1H-pyrazol-3-ylamino)thieno[3,2-d]pyrimidine-7-carboxamide;
231) N-(2,6-dichloro-3,5-dimethoxyphenyl)-4-(5-methyl-1H-pyrazol-3-ylamino)thieno[3,2-d]pyrimidine-7-carboxamide;
232) ethyl 6-(7-(2,6-dichloro-3,5-dimethoxyphenylcarbamoyl)thieno[3,2-d]pyrimidin-4-ylamino)-1H-indazole-3-carboxylate;
233) 5-benzyl-N-(4-bromo-2,6-dichloro-3,5-dimethoxyphenyl)-4-chloro-5H-pyrrolo[3,2-d]pyrimidine-7-carboxamide;
233e) 5-benzyl-N-(4-bromo-3,5-dimethoxyphenyl)-4-chloro-5H-pyrrolo[3,2-d]pyrimidine-7-carboxamide;
234) 4-amino-5-benzyl-N-(4-bromo-2,6-dichloro-3,5-dimethoxyphenyl)-5H-pyrrolo[3,2-d]pyrimidine-7-carboxamide;
235) 4-amino-5-benzyl-N-(2,6-dichloro-3,5-dimethoxyphenyl)-5H-pyrrolo[3,2-d]pyrimidine-7-carboxamide;
236) 4-amino-N-(2,6-dichloro-3,5-dimethylphenyl)thieno[3,2-d]pyrimidine-7-carboxamide;
237) 4-amino-N-(2,6-dichloro-3,5-dimethoxybenzyl)thieno[3,2-d]pyrimidine-7-carboxamide;
238) 7-((4-bromo-2,6-dichloro-3,5-dimethoxyphenoxy)methyl)thieno[3,2-d]pyrimidine-4-amine;
239) N-(2,6-dichloro-3,5-dimethoxyphenyl)-4-(4-(dimethylamino)phenylamino)thieno[3,2-d]pyrimidine-7-carboxamide;
240) N-(2,6-dichloro-3,5-dimethoxyphenyl)-4-(4-methoxyphenylamino)thieno[3,2-d]pyrimidine-7-carboxamide;
241) N-(2,6-dichloro-3,5-dimethoxyphenyl)-4-(4-(4-(2-hydroxyethyl)piperazin-1-yl)phenylamino)thieno[3,2-d]pyrimidine-7-carboxamide;
242) N-(2,6-dichloro-3,5-dimethoxyphenyl)-4-(4-(piperazin-1-yl)phenylamino)thieno[3,2-d]pyrimidine-7-carboxamide;
243) N-(2,6-dichloro-3,5-dimethoxyphenyl)-4-(4-(4-propionylpiperazin-1-yl)phenylamino)thieno[3,2-d]pyrimidine-7-carboxamide;
244) N-(2,6-dichloro-3,5-dimethoxyphenyl)-4-(4-(4-(isopropylcarbamoyl)piperazin-1-yl)phenylamino)thieno[3,2-d]pyrimidine-7-carboxamide;
245) ethyl 4-(4-(7-(2,6-dichloro-3,5-dimethoxyphenylcarbamoyl)thieno[3,2-d]pyrimidin-4-ylamino)phenyl)piperazine-1-carboxylate;
246) N-(2,6-dichloro-3,5-dimethoxyphenyl)-4-(4-morpholinophenylamino)thieno[3,2-d]pyrimidine-7-carboxamide;
247) N-(2,6-dichloro-3,5-dimethoxyphenyl)-4-(5-(morpholinomethyl)pyridin-2-ylamino)thieno[3,2-d]pyrimidine-7-carboxamide;
248) N-(2,6-dichloro-3,5-dimethoxyphenyl)-4-(4-(4-methylpiperazin-1-ylamino)phenylamino)thieno[3,2-d]pyrimidine-7-carboxamide;
249) 4-(4-(1H-imidazol-1-yl)phenylamino)-N-(2,6-dichloro-3,5-dimethoxyphenyl)thieno[3,2-d]pyrimidine-7-carboxamide;
250) 4-(5-chloropyridin-2-ylamino)-N-(2,6-dichloro-3,5-dimethoxyphenyl)thieno[3,2-d]pyrimidine-7-carboxamide;
251) N-(2,6-dichloro-3,5-dimethoxyphenyl)-4-(4-(piperidin-4-ylamino)phenylamino)thieno[3,2-d]pyrimidine-7-carboxamide;
252) N-(2,6-dichloro-3,5-dimethoxyphenyl)-4-(4-(4-(1-methylpiperidin-4-yl)piperazin-1-yl)phenylamino)thieno[3,2-d]pyrimidine-7-carboxamide;
253) N-(2,6-dichloro-3,5-dimethoxyphenyl)-4-(4-(4-(pyridin-2-yl)piperazin-1-yl)phenylamino)thieno[3,2-d]pyrimidine-7-carboxamide;
254) N-(2,6-dichloro-3,5-dimethoxyphenyl)-4-(5-((diethylamino)methyl)pyridin-2-ylamino)thieno[3,2-d]pyrimidine-7-carboxamide;
255) N-(2,6-dichloro-3,5-dimethoxyphenyl)-4-(5-(morpholine-4-carbonyl)pyridin-2-ylamino)thieno[3,2-d]pyrimidine-7-carboxamide;
256) 4-(5-((1H-imidazol-1-yl)methyl)pyridin-2-ylamino)-N-(2,6-dichloro-3,5-dimethoxyphenyl)thieno[3,2-d]pyrimidine-7-carboxamide;
257) N-(2,6-dichloro-3,5-dimethoxyphenyl)-4-(5-(2-morpholino-2-oxoethyl)pyridin-2-ylamino)thieno[3,2-d]pyrimidine-7-carboxamide;
258) N-(2,6-dichloro-3,5-dimethoxyphenyl)-4-(5-((4-methylpiperidin-1-yl)methyl)pyridin-2-ylamino)thieno[3,2-d]pyrimidine-7-carboxamide;
259) N-(2,6-dichloro-3,5-dimethoxyphenyl)-4-(5-((3-(trifluoromethyl)piperidin-1-yl)methyl)pyridin-2-ylamino)thieno[3,2-d]pyrimidine-7-carboxamide;
260) N-(2,6-dichloro-3,5-dimethoxyphenyl)-4-(5-((3,5-dimethylmorpholino)methyl)pyridin-2-ylamino)thieno[3,2-d]pyrimidine-7-carboxamide;
261) 4-(5-((4-acetylpiperazin-1-yl)methyl)pyridin-2-ylamino)-N-(2,6-dichloro-3,5-dimethoxyphenyl)thieno[3,2-d]pyrimidine-7-carboxamide;

262) N-(2,6-dichloro-3,5-dimethoxyphenyl)-4-(5-((4-morpholinopiperidin-1-yl)methyl)pyridin-2-ylamino)thieno[3,2-d]pyrimidine-7-carboxamide;

263) N-(2,6-dichloro-3,5-dimethoxyphenyl)-4-(5-((3-oxopiperazin-1-yl)methyl)pyridin-2-ylamino)thieno[3,2-d]pyrimidine-7-carboxamide;

264) N-(2,6-dichloro-3,5-dimethoxyphenyl)-4-(5-(3-(diethylamino)propylcarbamoyl)pyridin-2-ylamino)thieno[3,2-d]pyrimidine-7-carboxamide;

265) N-(2,6-dichloro-3,5-dimethoxyphenyl)-4-(5-((3-(diethylamino)propylamino)methyl)pyridin-2-ylamino)thieno[3,2-d]pyrimidine-7-carboxamide;

266) (R)—N-(2,6-dichloro-3,5-dimethoxyphenyl)-4-(5-((3-hydroxypyrrolidin-1-yl)methyl)pyridin-2-ylamino)thieno[3,2-d]pyrimidine-7-carboxamide;

267) N-(2,6-dichloro-3,5-dimethoxyphenyl)-4-(5-(3-(4-ethylpiperazin-1-yl)propylcarbamoyl)pyridin-2-ylamino)thieno[3,2-d]pyrimidine-7-carboxamide;

268) N-(2,6-dichloro-3,5-dimethoxyphenyl)-4-(5-(4-methylpiperazin-1-ylcarbamoyl)pyridin-2-ylamino)thieno[3,2-d]pyrimidine-7-carboxamide;

269) N-(2,6-dichloro-3,5-dimethoxyphenyl)-4-(5-((3-(4-ethylpiperazin-1-yl)propylamino)methyl)pyridin-2-ylamino)thieno[3,2-d]pyrimidine-7-carboxamide;

270) N-(2,6-dichloro-3,5-dimethoxyphenyl)-4-(4-methylpyridin-2-ylamino)thieno[3,2-d]pyrimidine-7-carboxamide;

271) N-(2,6-dichloro-3,5-dimethoxyphenyl)-4-(5-((2-(diethylamino)ethoxy)methyl)pyridin-2-ylamino)thieno[3,2-d]pyrimidine-7-carboxamide;

272) N-(2,6-dichloro-3,5-dimethoxyphenyl)-4-(4-((diethylamino)methyl)pyridin-2-ylamino)thieno[3,2-d]pyrimidine-7-carboxamide;

273) N-(2,6-dichloro-3,5-dimethoxyphenyl)-4-(6-((diethylamino)methyl)pyridin-2-ylamino)thieno[3,2-d]pyrimidine-7-carboxamide;

274) 4-(5-carbamoylpyridin-2-ylamino)-N-(2,6-dichloro-3,5-dimethoxyphenyl)thieno[3,2-d]pyrimidine-7-carboxamide;

275) N-(2,6-dichloro-3,5-dimethoxyphenyl)-4-(5-((2-methoxyethoxy)methyl)pyridin-2-ylamino)thieno[3,2-d]pyrimidine-7-carboxamide;

276) N-(2,6-dichloro-3,5-dimethoxyphenyl)-4-(5-((3-(diethylamino)propoxy)methyl)pyridin-2-ylamino)thieno[3,2-d]pyrimidine-7-carboxamide;

277) N-(2,6-dichloro-3,5-dimethoxyphenyl)-4-(5-((2-(piperidin-1-yl)ethoxy)methyl)pyridin-2-ylamino)thieno[3,2-d]pyrimidine-7-carboxamide;

278) N-(2,6-dichloro-3,5-dimethoxyphenyl)-4-(pyridin-4-ylamino)thieno[3,2-d]pyrimidine-7-carboxamide;

279) N-(2,6-dichloro-3,5-dimethoxyphenyl)-4-(4-((4-ethylpiperazin-1-yl)methyl)pyridin-2-ylamino)thieno[3,2-d]pyrimidine-7-carboxamide;

280) N-(2,6-dichloro-3,5-dimethoxyphenyl)-4-(4-(morpholinomethyl)pyridin-2-ylamino)thieno[3,2-d]pyrimidine-7-carboxamide;

281) N-(2,6-dichloro-3,5-dimethoxyphenyl)-4-(5-(3-(diethylamino)propoxy)pyridin-2-ylamino)thieno[3,2-d]pyrimidine-7-carboxamide;

282) N-(2,6-dichloro-3,5-dimethoxyphenyl)-4-(4-(diethylamino)pyridin-2-ylamino)thieno[3,2-d]pyrimidine-7-carboxamide;

283) 4-amino-N-(4-bromo-2,6-dichloro-3,5-dimethoxyphenyl)-5-methyl-5H-pyrrolo[3,2-d]pyrimidine-7-carboxamide;

284) 4-amino-N-(2,6-dichloro-3,5-dimethoxyphenyl)-5-methyl-5H-pyrrolo[3,2-d]pyrimidine-7-carboxamide;

285) N-(2,6-dichloro-3,5-dimethoxyphenyl)-4-(4-(3-(diethylamino)propoxy)pyridin-2-ylamino)thieno[3,2-d]pyrimidine-7-carboxamide;

286) N-(4-bromo-2,6-dichloro-3,5-dimethoxyphenyl)-4-(2,3,4-trifluorophenylamino)thieno[3,2-d]pyrimidine-7-carboxamide;

287) N-(4-bromo-2,6-dichloro-3,5-dimethoxyphenyl)-4-(3-chloro-4-fluorophenylamino)thieno[3,2-d]pyrimidine-7-carboxamide;

288) N-(2,6-dichloro-3,5-dimethoxyphenyl)-4-(4-(piperidin-1-ylmethyl)pyridin-2-ylamino)thieno[3,2-d]pyrimidine-7-carboxamide;

289) N-(2,6-dichloro-3,5-dimethoxyphenyl)-4-(2,3,4-trifluorophenylamino)thieno[3,2-d]pyrimidine-7-carboxamide;

290) 4-(3-chloro-4-fluorophenylamino)-N-(2,6-dichloro-3,5-dimethoxyphenyl)thieno[3,2-d]pyrimidine-7-carboxamide;

291) N-(2,6-dichloro-3,5-dimethoxyphenyl)-4-(4-(thiazolidin-3-ylmethyl)pyridin-2-ylamino)thieno[3,2-d]pyrimidine-7-carboxamide;

292) N-(2,6-dichloro-3,5-dimethoxyphenyl)-4-(4-(2-(diethylamino)-2-oxoethyl)pyridin-2-ylamino)thieno[3,2-d]pyrimidine-7-carboxamide;

293) N-(2,6-dichloro-3,5-dimethoxyphenyl)-4-(4-((2-(diethylamino)ethylamino)methyl)pyridin-2-ylamino)thieno[3,2-d]pyrimidine-7-carboxamide;

294) N-(2,6-dichloro-3,5-dimethoxyphenyl)-4-(4-(((2-hydroxyethyl)(methyl)amino)methyl)pyridin-2-ylamino)thieno[3,2-d]pyrimidine-7-carboxamide;

295) N-(2,6-dichloro-3,5-dimethoxyphenyl)-4-(4-((2-(diethylamino)ethoxy)methyl)pyridin-2-ylamino)thieno[3,2-d]pyrimidine-7-carboxamide;

296) N-(2,6-dichloro-3,5-dimethoxyphenyl)-4-(diethylamino)thieno[3,2-d]pyrimidine-7-carboxamide;

297) N-(2,6-dichloro-3,5-dimethoxyphenyl)-4-(piperidin-4-ylamino)thieno[3,2-d]pyrimidine-7-carboxamide;

298) 4-(4-((diethylamino)methyl)pyridin-2-ylamino)-N-(3,5-dimethoxyphenyl)thieno[3,2-d]pyrimidine-7-carboxamide;

299) N-(2,6-dichloro-3,5-dimethoxyphenyl)-4-(5-(2-(dimethylamino)acetamido)pyridin-2-ylamino)thieno[3,2-d]pyrimidine-7-carboxamide;

300) N-(2,6-dichloro-3,5-dimethoxyphenyl)-4-(phenethylamino)thieno[3,2-d]pyrimidine-7-carboxamide;

301) N-(2,6-dichloro-3,5-dimethoxyphenyl)-4-(2-hydroxyethylamino)thieno[3,2-d]pyrimidine-7-carboxamide;

302) ethyl 2-(7-(2,6-dichloro-3,5-dimethoxyphenylcarbamoyl)thieno[3,2-d]pyrimidin-4-ylamino)acetate;

303) 2-(7-(2,6-dichloro-3,5-dimethoxyphenylcarbamoyl)thieno[3,2-d]pyrimidin-4-ylamino)acetic acid; and 304) N-(2,6-dichloro-3,5-dimethoxyphenyl)-4-(2-(phenylamino)ethylamino)thieno[3,2-d]pyrimidine-7-carboxamide.

The compound of formula (I) of the present invention may be prepared, for example, by the procedure shown in Reaction Scheme (I) or (II):

[Reaction Scheme (I)]

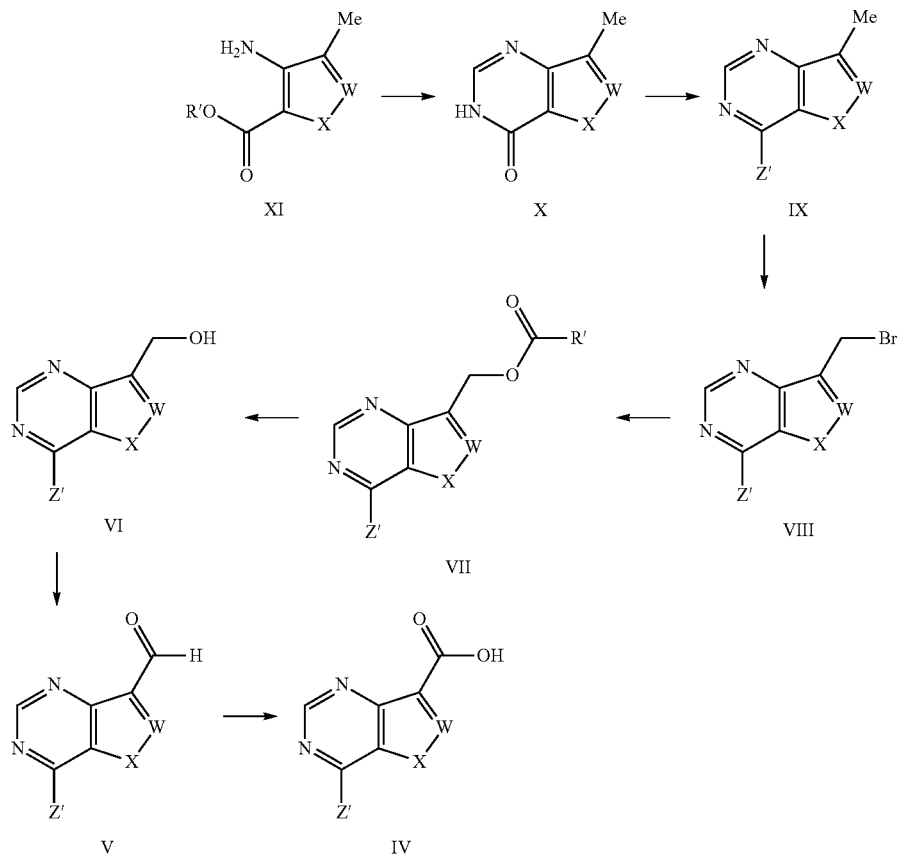

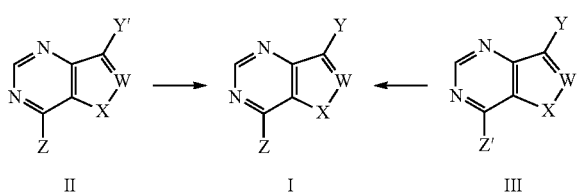

[Reaction Scheme (II)]

wherein,
R' is hydrogen or $C_{1-6}$ alkyl;
Y' is —$CHCR^2R^3$, —$CCR^3$, or —$C(O)OR^3$;
Z' is halogen, —$OR^5$, —$SR^5$, —$S(O)R^5$, —$S(O)_2R^5$, or —$NR^4R^5$; and
$R^2$, $R^3$, $R^4$, $R^5$, W, X, Y and Z have the same meanings as defined above.

In Reaction Scheme (I), a compound of formula (XI) is subjected to a condensation reaction with formamide at a high temperature (e.g., 200° C.) to form a compound of formula (X), followed by a reaction with an inorganic halogen compound such as thionylchloride and phosphorous oxychloride to form a compound of formula (IX).

Subsequently, the compound of formula (IX) is subjected to a reaction with a bromination reagent to form a compound of formula (VIII) having a bromine group. The bromination reagent may be preferably N-bromosuccinimide (NBS) or bromine ($Br_2$). A compound of formula (VII) may be prepared by subjecting the compound of formula (VIII) to a reaction with an organic acid metal compound in the presence of a catalyst. Representative examples of the organic acid metal compound may include sodium acetate, potassium acetate and a mixture thereof; and those of the catalyst, potassium iodide, tetra-n-butylammonium iodide (TBAI) and a mixture thereof.

A compound of formula (VI) may be prepared by adding the compound of formula (VII) to an aqueous base (e.g., sodium hydroxide) solution to remove an acyl group therefrom. The compound of formula (VI) thus obtained is subjected to a reaction with an oxidant to substitute an alcohol group with an aldehyde group, forming a compound of formula (V), which is continuously subjected to a reaction with another oxidant to prepare a compound of formula (IV). The oxidant used for formation of the compound of formula (V) is preferably manganese oxide, and the oxidant used for formation of the compound of formula (IV) is preferably sodium chlorite.

In Reaction Scheme (II), a compound of formula (I) of the present invention is prepared by subjecting a compound of formula (II) to a condensation reaction with a condensation agent, or to a combining reaction (e.g., Suzuki coupling reaction) using a metallic compound as a catalyst; or subjecting the compound of formula (III) to a nucleophilic aryl substitution reaction with an amine group-containing compound in a solvent with or without a metallic catalyst. The condensation agent may be preferably 1-ethyl-3-(3-dimethylaminopropyl)-carbo diimide (EDC) or 2-(1H-7-azabenzotriazol-1-yl)-1,1,3,3-tetramethyl europium hexafluorophosphate methanammonium (HATU), and it may be used in an organic solvent (e.g., tetrahydrofuran, dioxane, or N,N-dimethylformamide) with N-hydroxybenzotriazol (HOBt), N—N-dimethylaminopyridine (DMAP), and the like. The metallic compound, which is used as a catalyst in the combining reaction and the substitution reaction, may be preferably Pd/C, Pd(PPh$_3$)$_4$, Pd(OAc)$_2$, Pd$_2$(dba)$_3$, Pd(dppf)$_2$Cl$_2$, or PdCl$_2$(PPh$_3$)$_2$. The metallic compound may be used in combination with a ligand such as Xantphos (CAS No.: 161265-03-8), Davephos (CAS No.: 213697-53-1), Johnphos (CAS No.: 224311-51-7), X-phos (CAS No.: 564483-18-7), tert-butyl X-phos (CAS 564483-19-8), and a mixture thereof, or in combination with a base such as carbonate, sulfate, phosphate and alkoxide of an alkali metal or an alkaline earth metal (e.g., K$_2$CO$_3$, Cs$_2$CO$_3$, Na$_2$CO$_3$, K$_3$PO$_4$, NaOt-Bu, KOt-Bu), and a mixture thereof. Suitable for use in this reaction may be an organic solvent including tetrahydrofuran, dioxane, N,N-dimethylformamide, N,N-dimethylsulfoxide, 2-butanol, and 2-pentanol, or a mixture of the organic solvent and water. The reaction temperature may be in the range of room temperature and 200° C., preferably 80° C. and 150° C.

In one embodiment of the present invention, a compound of formula (1a) is subjected to a reaction with a compound of formula (2a) to prepare a compound of formula (1e), as shown in Reaction Scheme (III):

[Reaction Scheme (III)]

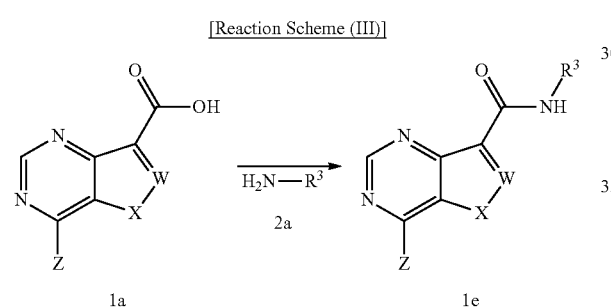

wherein, W, X, Z and R$^3$ have the same meanings as defined above.

In another embodiment of the present invention, a compound of formula (1b) is subjected to a reaction with a compound of formula (2b) to prepare a compound of formula (1f), as shown in Reaction Scheme (IV):

[Reaction Scheme (IV)]

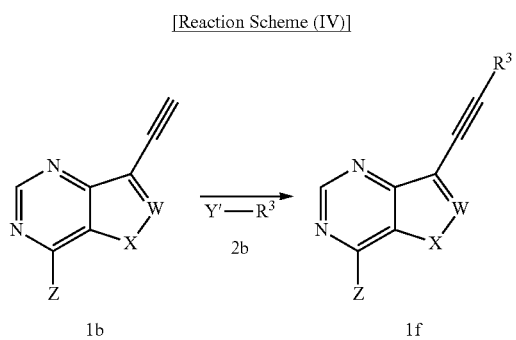

wherein, W, X, Z and R$^3$ have the same meanings as defined above; and Y' is halogen.

In a further embodiment of the present invention, a compound of formula (1c) is subjected to a reaction with a compound of formula (2c) to prepare a compound of formula (1g), as shown in Reaction Scheme (V):

[Reaction Scheme (V)]

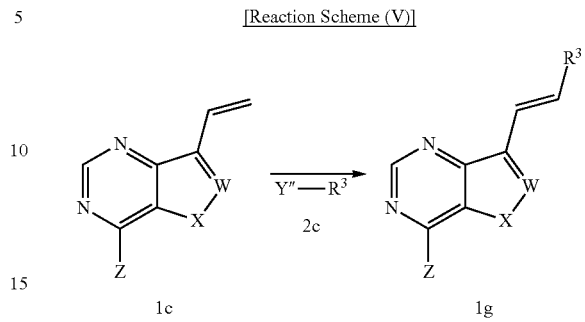

wherein, W, X, Z and R$^3$ have the same meanings as defined above; and Y" is halogen.

In a still further embodiment of the present invention, a compound of formula (1d) is subjected to a reaction with a compound of formula (2d) to prepare a compound of formula (1h), as shown in Reaction Scheme (VI):

[Reaction Scheme (VI)]

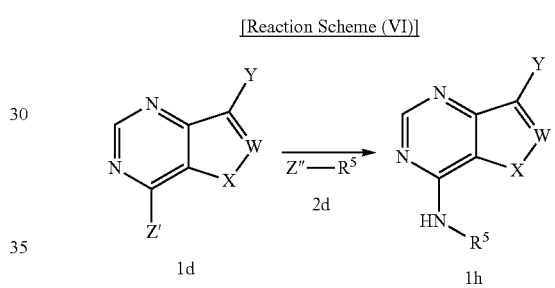

wherein, W, X, Y and R$^5$ have the same meanings as defined above; and when Z' is halogen, Z" is NH$_2$, and when Z' is NH$_2$, Z" is halogen.

The compounds of formulae (1a) to (1d) contribute as an important intermediate in the preparation of the bicyclic heteroaryl derivative of the present invention.

Accordingly, the present invention provides a use of the inventive compound for the manufacture of a medicament for preventing or treating an abnormal cell growth disorder induced by an excessive expression of a protein kinase.

In addition, the present invention provides a pharmaceutical composition for preventing or treating an abnormal cell growth disorder induced by an excessive expression of a protein kinase which comprises the inventive compound as an active ingredient.

Further, the present invention provides a method for preventing or treating an abnormal cell growth disorder induced by an excessive expression of a protein kinase, which comprises administering the inventive compound to a mammal in need thereof.

The protein kinase may be ALK, AMPK, Aurora A, Aurora B, Aurora C, Axl, Blk, Bmx, BTK, CaMK, CDK2/cyclinE, CDK5/p25, CHK1, CK2, c-RAF, DMPK, EGFR1, Her2, Her4, EphA1, EphB1, FAK, FGFR1, FGFR2, FGFR3, FGFR4, Flt-1, Flt-3, Flt-4, Fms, Fyn, GSK3beta, HIPK1, IKKbeta, IGFR-1R, IR, Itk, JAK2, JAK3, KDR, Kit, Lck, Lyn, MAPK1, MAPKAP-K2, MEK1, Met, MKK6, MLCK, NEK2, p70S6K, PAK2, PDGFR alpha, PDGFR beta, PDK1, Pim-1, PKA, PKBalpha, PKCalpha, Plk1, Ret, ROCK-I, Rsk1, SAPK2a, SGK, Src, Syk, Tie-2, Tec, Trk, or ZAP-70. The pharmaceutical composition of the present invention exhibits an improved inhibitory activity against the above-mentioned protein kinases.

The abnormal cell growth disorder may be stomach cancer, lung cancer, liver cancer, large intestine cancer, small intestine cancer, pancreas cancer, brain cancer, bone cancer, melanoma, breast cancer, sclerosing adenosis, uterine carcinoma, cervical cancer, head and neck cancer, esophageal cancer, thyroid cancer, parathyroid cancer, kidney cancer, sarcoma, prostatic carcinoma, urethral cancer, bladder cancer, leukemia, multiple myeloma, blood cancer, lymphoma, fibroadenoma, inflammation, diabetes, obesity, psoriasis, rheumatoid arthritis, angioma, acute or chronic nephrotuberculosis, coronary artery restenosis, autoimmune diseases, asthma, neurodegenerative diseases, chronic infection, or ocular diseases induced by division of blood vessel.

The inventive compound may be administered in combination with, or formulated in the complex form with another medication selected from the group consisting of: cell signal transduction inhibitors, mitosis inhibitors, alkylating agents, antimetabolites, antibiotics, growth factor inhibitors, cell cycle inhibitors, topoisomerase inhibitors, biological reaction modifiers, antihormonal agents, antiandrogen, cell differentiation/proliferation/survival inhibitors, apoptosis inhibitors, inflammation inhibitors, and P-glycoprotein inhibitors.

A proposed daily dose of the inventive pharmaceutical composition for administration to a human (of approximately 70 kg body weight) may be in the range of 0.01 mg/day and 1,000 mg/day. The inventive pharmaceutical composition may be administered in a single dose or in divided doses per day. It is understood that the daily dose should be determined in light of various relevant factors including the condition, age, body weight and sex of the subject to be treated, administration route, and disease severity; and, therefore, the dosage suggested above should not be construed to limit the scope of the present invention in anyway.

Also, the inventive pharmaceutical composition comprises the bicyclic heteroaryl derivative of formula (I), its pharmaceutically acceptable salt, its solvate, or its hydrate as an active ingredient. It may be formulated with a pharmaceutical acceptable carrier, adjuvant or excipient, in accordance with any of the conventional methods in the form of tablets, capsules, troches, aqueous solutions or suspensions for oral administration or parenteral administration.

The excipient employed in the pharmaceutical composition of the present invention comprises a sweetening agent, a binder, a dissolvent, a dissolving adjuvant, a wetting agent, an emulsifier, an isotonic agent, an adsorption agent, a disintegrating agent, an antioxidant, a preservative, a lubricant, a filler, a freshener, and the like.

Representative examples of the excipient include lactose, dextrose, sucrose, mannitol, sorbitol, cellulose, glycine, silica, talc, stearic acid, sterin, magnesium stearate, magnesium aluminium sillicate, starch, gelatin, tragacanth gum, alginic acid, sodium alginate, methylcellulose, sodium carboxylmethylcellulose, agar, water, ethanol, polyethylene glycol, polyvinylpyrrolidone, sodium chloride, potassium chloride, orange essence, strawberry essence, vanilla favor, and a mixture thereof.

Representative examples of the carrier employed in the injectable composition of the present invention include distilled water, a saline solution, a glucose solution, a glucose-like solution, alcohol, glycol ether (e.g., polyethylene glycol 400), oil, fatty acid, fatty acid ester, glyceride, a surfactant, a suspension agent, an emulsifier, and a mixture thereof.

The following Examples are intended to further illustrate the present invention without limiting its scope.

The compound of Preparation Example 1 was synthesized as shown in Reaction Scheme 1:

[Reaction Scheme 1]

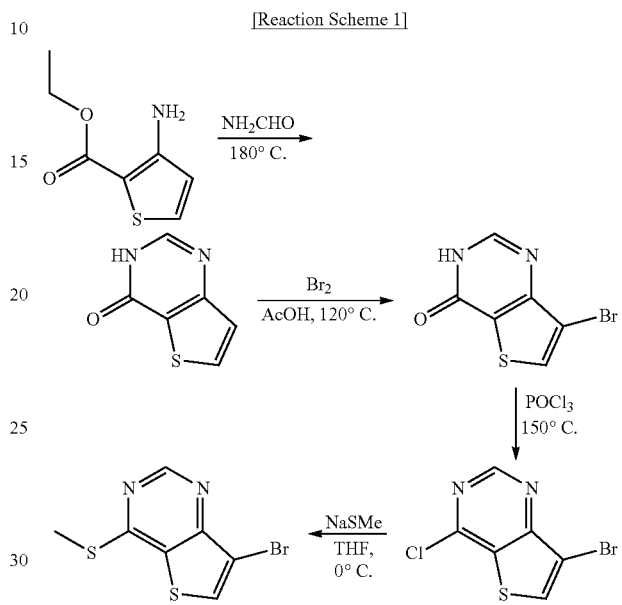

Preparation Example 1 a. Thieno[3,2-d]pyrimidin-4(3H)-one

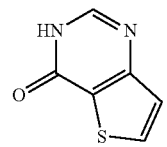

Methyl-3-aminothiophene-2-carboxylate (15 g, 98.57 mmol) was dissolved in formamide (50 mL) and stirred at 180° C. for 5 hrs. The reaction mixture was further stirred at room temperature for 2 hrs. The resulting solution was filtered to obtain the title compound as a solid.

$^1$H NMR (400 MHz, DMSO-d$_6$) δ 12.48 (br, 1H), 8.18 (d, J=5.1 Hz, 1H), 8.14 (s, 1H), 7.40 (d, J=5.1 Hz, 1H).

b. 7-Bromothieno[3,2-d]pyrimidin-4(3H)-one

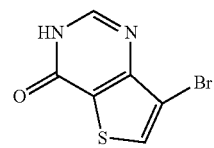 [SMILES: O=c1[nH]cnc2c(Br)csc12]

Thieno[3,2-d]pyrimidin-4(3H)-one (4.9 g) was dissolved in acetic acid (20 mL), and bromine (5 mL) was added thereto. The reaction mixture was stirred in a closed reactor at 120° C. for 10 hrs, and then cooled to room temperature. The resulting solution was allowed to evaporation under a reduced pressure to remove acetic acid. The resulting residue was poured into ice water, filtered and dried to obtain the title compound as a solid. The title compound obtained was used for a subsequent reaction without purification.

$^1$H NMR (400 MHz, DMSO-$d_6$) δ 12.75 (brs, 1H), 8.36 (s, 1H), 8.24 (s, 1H).

c. 7-Bromo-4-chlorothieno[3,2-d]pyrimidine

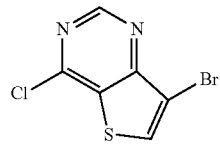 [SMILES: Clc1ncnc2c(Br)csc12]

7-Bromothieno[3,2-d]pyrimidin-4(3H)-one (5.9 g) was dissolved in POCl$_3$ (20 mL), stirred at 150° C. for 3 hrs, and then cooled to room temperature. The resulting solution was allowed to evaporation under a reduced pressure to remove POCl$_3$. The resulting residue was poured into ice water and filtered. The solid thus separated was washed with a saturated NaHCO$_3$ solution and dried over a nitrogen gas to obtain the title compound as a solid.

$^1$H NMR (400 MHz, DMSO-$d_6$) δ 9.16 (s, 1H), 8.79 (s, 1H).

d. 7-Bromo-4-(methylthio)thieno[3,2-d]pyrimidine

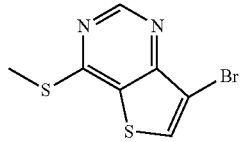

7-Bromo-4-chlorothieno[3,2-d]pyrimidine (2 g, 8.07 mmol) was dissolved in THF (27 mL), and sodium methanethiolate (650 mg, 9.28 mmol) was added thereto 0° C., which was stirred for 15 hrs. To the resulting solution, ice water was added, followed by filtration. The solid thus separated was dried over a nitrogen gas to obtain the title compound as a solid. The title compound obtained was used for a subsequent reaction without purification.

$^1$H NMR (400 MHz, DMSO-$d_6$) δ 9.09 (s, 1H), 8.57 (s, 1H), 2.76 (s, 3H).

The compound of Example 1 was synthesized as shown in Reaction Scheme 2:

[Reaction Scheme 2]

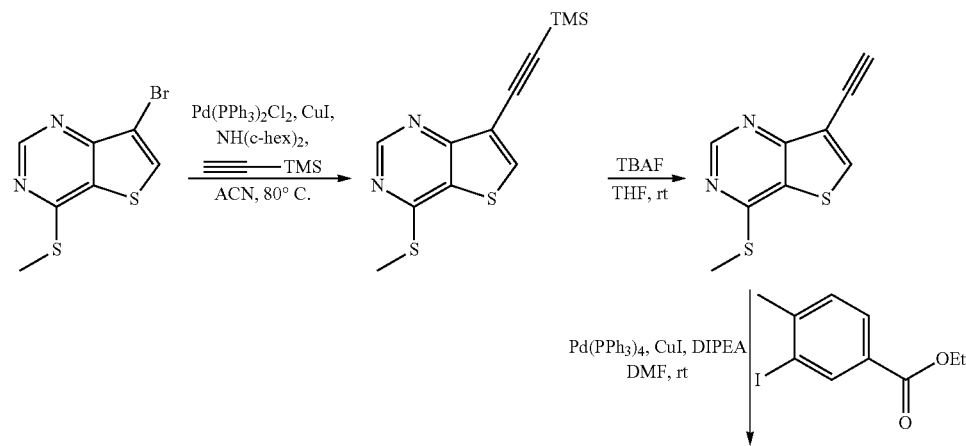

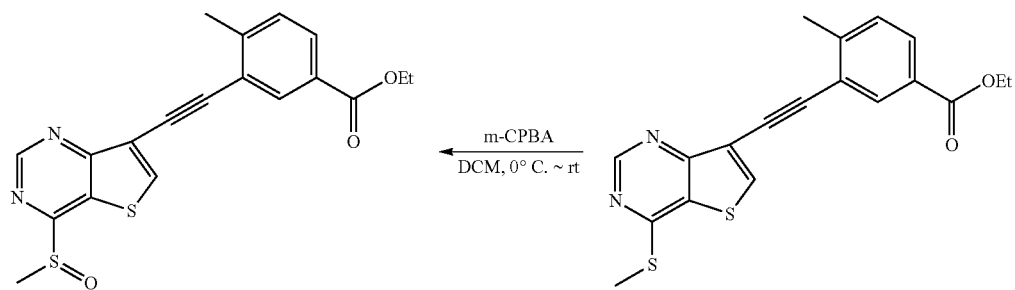

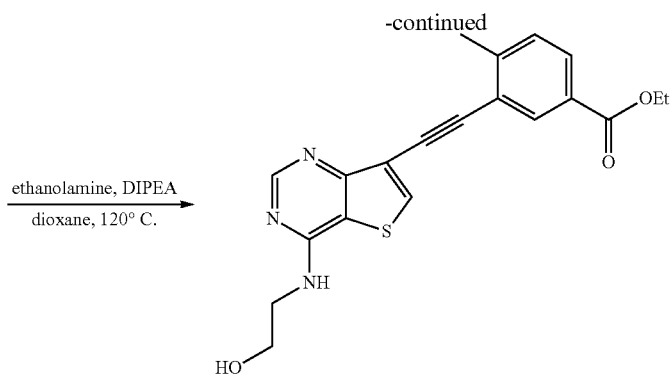

Example 1 a. 4-(Methylthio)-7-((trimethylsilyl)ethynyl)thieno[3,2-d]pyrimidine

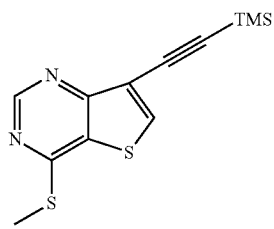 [SMILES: CSc1ncnc2c(C#C[Si](C)(C)C)csc12]

7-Bromo-4-(methylthio)thieno[3,2-d]pyrimidine (3 g, 11.49 mmol) prepared in step d of Preparation Example 1 was dissolved in acetonitrile (30 mL). Bis(triphenylphosphine) palladium(II) dichloride (204 mg, 0.29 mmol), copper(I) iodide (76 mg, 0.40 mmol), dicyclohexylamine (2.5 mL, 12.64 mmol) and ethynyltrimethylsilane (3.2 mL, 22.98 mmol) were added thereto. The reaction mixture was kept under a nitrogen gas flow for 15 min, stirred at 80° C. for 14 hrs, cooled to room temperature, and filtered with a diatomite pad, which was washed with ethyl acetate (50 mL). The filtrate was washed with a saline solution, dried over magnesium sulfate, and concentrated. The resulting concentrate was purified by silica gel chromatography (ethyl acetate/hexane=1/9~2/8) to obtain the title compound (2.1 g, 65% yield) as a yellow solid.

$^1$H NMR (400 MHz, CDCl$_3$) δ9.05 (s, 1H), 7.99 (s, 1H), 2.74 (s, 3H), 0.30 (s, 9H), MS m/z: 279.34 [M+1].

b. 7-Ethynyl-4-(methylthio)thieno[3,2-d]pyrimidine

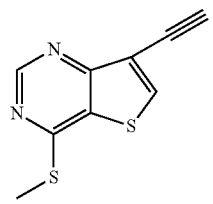

4-(Methylthio)-7-((trimethylsilyl)ethynyl)thieno[3,2-d]pyrimidine (500 mg, 1.8 mmol) was dissolved in THF (5 mL), and a tetrabutylammonium fluoride solution (3.6 mL, 3.6 mmol) was added thereto. The reaction mixture was stirred at room temperature for 30 min and concentrated. The resulting concentrate was purified by silica gel chromatography (ethyl acetate/hexane=2/8~3/7) to obtain the title compound (340 mg, 91% yield) as a yellow solid.

$^1$H NMR (400 MHz, CDCl$_3$) δ 9.07 (s, 1H), 8.03 (s, 1H), 3.44 (s, 1H), 2.88 (s, 3H), MS m/z: 207.23 [M+1].

c. Ethyl 4-methyl-3-((4-(methylthio)thieno[3,2-d]pyrimidin-7-yl)ethynyl)benzoate

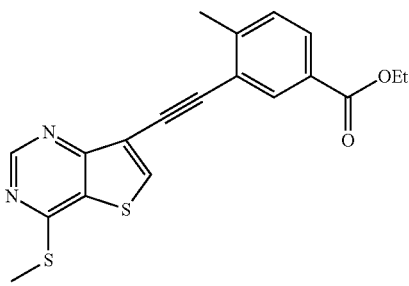 [SMILES: CCOC(=O)c1ccc(C)c(C#Cc2csc3c(SC)ncnc23)c1]

7-Ethynyl-4-(methylthio)thieno[3,2-d]pyrimidine (850 mg, 4.12 mmol) was dissolved in N,N-dimethylformamide (9 mL). Ethyl 3-iodo-4-methylbenzoate (902 mg, 4.12 mmol), Pd(PPh$_3$)$_4$ (242 mg, 0.21 mmol), copper(I) iodide (59 mg, 0.31 mmol) and diisopropylethylamine (1.0 mL, 6.18 mmol) were sequentially added thereto. The reaction mixture was stirred at room temperature for 16 hrs, filtered with a diatomite pad, and concentrated. The resulting concentrate was purified by silica gel chromatography (ethyl acetate/hexane=1/9~2/8) to obtain the title compound (1.1 g, 72% yield) as a yellow solid.

$^1$H NMR (400 MHz, CDCl$_3$) δ9.11 (s, 1H), 8.75 (s, 1H), 8.07 (s, 1H), 7.90 (d, 1H), 7.52 (d, 1H), 4.33 (q, 2H), 2.78 (s, 3H), 2.61 (s, 3H), 1.34 (t, 3H); MS m/z [M+1] 369.44.

d. Ethyl 4-methyl-3-((4-(methylsulfinyl)thieno[3,2-d]pyrimidin-7-yl)ethynyl)benzoate

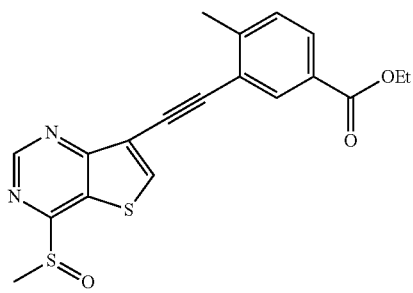 [SMILES: CCOC(=O)c1ccc(C)c(C#Cc2csc3c(S(C)=O)ncnc23)c1]

Ethyl 4-methyl-3-((4-(methylthio)thieno[3,2-d]pyrimidin-7-yl)ethynyl)benzoate (440 mg, 1.19 mmol) was dissolved in dichloromethane (6 mL), and mCPBA (616 mg, 3.57 mmol) was added thereto at 0° C. The reaction mixture was stirred at 0° C. for 30 min, and dichloromethane (20 mL) was added thereto, which was washed with a saturated sodium hydrogen carbonate solution three times. The resulting solution was dried over magnesium sulfate, and concentrated under a reduced pressure to obtain the title compound.

$^1$H NMR (400 MHz, CDCl$_3$) δ9.58 (s, 1H), 9.13 (s, 1H), 8.10 (s, 1H), 7.94 (d, 1H), 7.70 (d, 1H), 4.33 (q, 2H), 3.54 (s, 3H), 2.63 (s, 3H)), 1.34 (t, 3H); MS m/z [M+1] 385.50.

e. Ethyl 3-((4-(2-hydroxyethylamino)thieno[3,2-d]pyrimidin-7-yl)ethynyl)-4-methylbenzoate

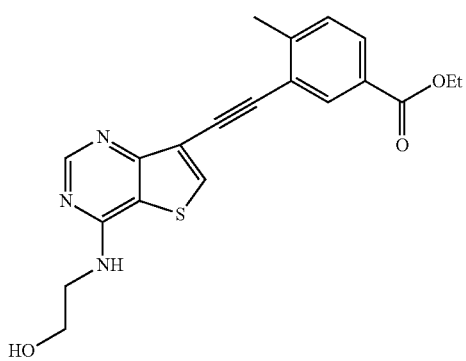 [SMILES: CCOC(=O)c1ccc(C)c(C#Cc2csc3c(NCCO)ncnc23)c1]

Ethyl 4-methyl-3-((4-(methylsulfinyl)thieno[3,2-d]pyrimidin-7-yl)ethynyl)benzoate (50 mg, 0.13 mmol) was dissolved in dioxane (1 mL), and ethanol amine (40 μL, 0.65 mmol) and diisopropylethylamine (0.1 mL, 0.65 mmol) was sequentially added thereto. The reaction mixture was stirred at 120° C. for 8 hrs, and cooled to room temperature. Water (20 mL) and ethyl acetate (5 mL) were added thereto, which was extracted with ethyl acetate. The organic layer thus obtained was washed with a saline solution, dried over magnesium sulfate, and concentrated under a reduced pressure. The resulting residue was purified by silica gel chromatography (ethyl acetate/hexane=2/8~4/6) to obtain the title compound (32 mg, 65% yield) as a yellow solid.

$^1$H NMR (400 MHz, DMSO-d$_6$) δ8.52 (s, 1H), 8.47 (s, 1H), 8.09 (m, 1H), 8.03 (s, 1H), 7.89 (dd, 1H), 7.51 (d, 1H), 4.32 (q, 2H), 3.58 (m, 4H), 2.58 (s, 3H), 1.32 (t, 3H); MS m/z [M+1] 382.59.

Examples 2 to 10

The procedures of steps c to e of Example 1 were repeated using each of corresponding starting materials to obtain respective title compounds (Table 1).

The compounds of Examples 11 to 76 were synthesized as shown in Reaction Scheme 3:

[Reaction Scheme 3]

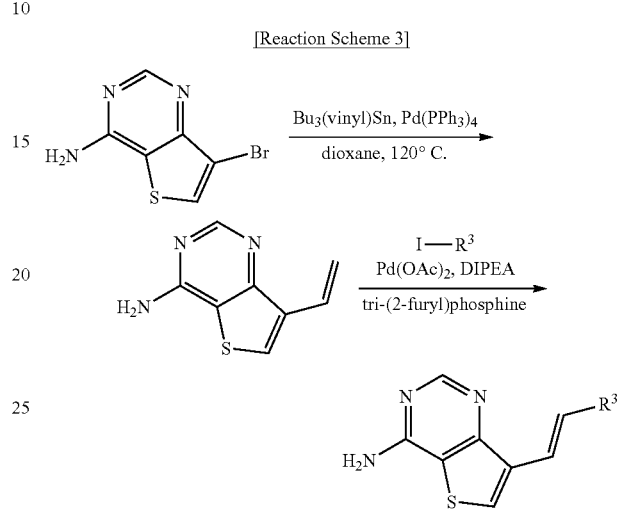

wherein, R$^3$ has the same meaning as defined in formula (I).

Example 11 a. 7-Vinylthieno[3,2-d]pyrimidin-4-amine

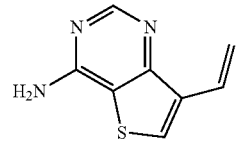

7-Bromothieno[3,2-d]pyrimidin-4-amine (2.4 g, 10.43 mmol) prepared by subjecting the compound prepared in step d of Preparation Example 1 to the procedures of steps c and d of Example 1 was dissolved in dioxane (30 mL), which was kept under a nitrogen gas flow for 20 min. Pd(PPh$_3$)$_4$ (723 mg, 0.63 mmol) and tributylvinyl tin (3.35 mL, 11.5 mmol) were added thereto, stirred at 120° C. for 7 hrs, and cooled to room temperature. An aqueous 10% potassium fluoride solution (30 mL) was added to the reaction mixture and stirred for 2 hrs. The resulting solution was filtered with a diatomite pad, which was washed with ethyl acetate. The aqueous layer was extracted with ethyl acetate. The combined organic layers were dried over magnesium sulfate and concentrated. The resulting concentrate was purified by silica gel chromatography (DCM/MeOH=95/5) to obtain the title compound as a yellow solid.

$^1$H NMR (400 MHz, DMSO-d$_6$) δ 8.41 (s, 1H), 8.14 (s, 1H), 6.95 (dd, 1H), 6.36 (d, 1H), 5.38 (d, 1H).

b. 7-(4-Bromo-3,5-dimethoxystyryl)thieno[3,2-d]pyrimidin-4-amine

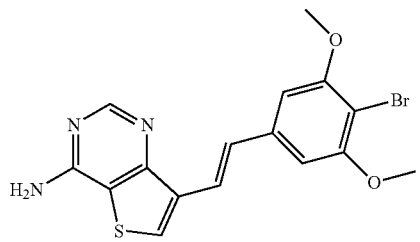 [SMILES: COc1cc(/C=C/c2csc3c(N)ncnc23)cc(OC)c1Br]

7-Vinylthieno[3,2-d]pyrimidine-4-amine (94 mg, 0.53 mmol), 2-bromo-5-iodo-1,3-dimethoxybenzene (200 mg, 0.58 mmol), Pd(OAc)$_2$ (7.1 mg, 0.032 mmol), tri-(2-furyl)phosphine (11 mg, 0.048 mmol) and diisopropylamine (0.207 mL, 1.17 mmol) was dissolved in N,N-dimethylformamide (3 mL), and stirred at 120° C. for 18 hrs. Water and ethyl acetate were added thereto, which was extracted with ethyl acetate. The organic layer thus obtained was washed with a saline solution, dried over magnesium sulfate, and concentrated under a reduced pressure. The resulting residue was purified by silica gel chromatography (DCM:MeOH=20:1) to obtain the title compound as a white solid.

$^1$H NMR (400 MHz, DMSO-d$_6$) δ8.48 (s, 1H), 8.19 (s, 1H), 7.91 (d, 1H), 7.48 (s, 2H), 7.45 (d, 1H), 6.93 (s, 2H), 3.90 (s, 6H); MS m/z [M+1] 392.01, 393.99.

Examples 12 to 76

The procedure of step b of Example 11 was repeated using each of corresponding starting materials to obtain respective title compounds (Table 1).

The compound of Example 77 was synthesized as shown in Reaction Scheme 4:

[Reaction Scheme 4]

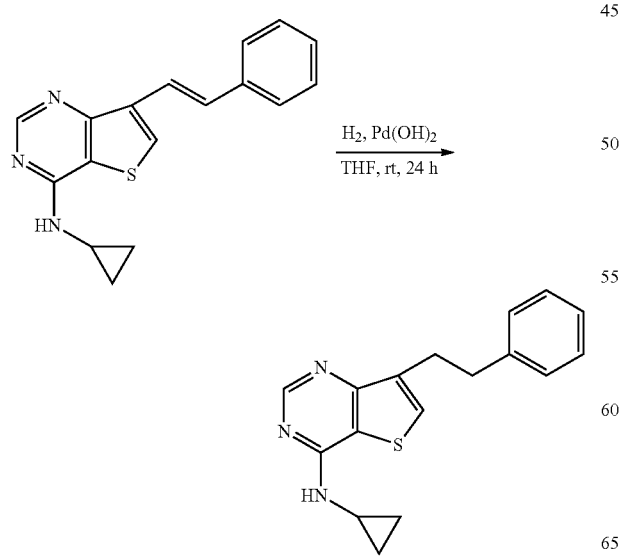

Example 77: 7-Phenethylthieno[3,2-d]pyrimidine-4-amine (E)-N-cyclopropyl-7-styrylthieno[3,2-d]pyrimidine-4-amine (20 mg, 0.068 mmol) prepared in Example 31 and Pd(OH)$_2$ (20 mg) were dissolved in THF (2 mL), and stirred at room temperature under a hydrogen gas of 1 atmospheric pressure for 24 hrs. The resulting solution was filtered with a diatomite pad, which was concentrated under a reduced pressure to obtain the title compound.

MS m/z [M+1] 256.22.

Examples 78 to 104

The procedure of Example 77 was repeated using each of the compounds prepared in Examples 11 to 76 as a starting material to obtain respective title compounds (Table 1).

The compound of Example 105 was synthesized as shown in Reaction Scheme 5:

[Reaction Scheme 5]

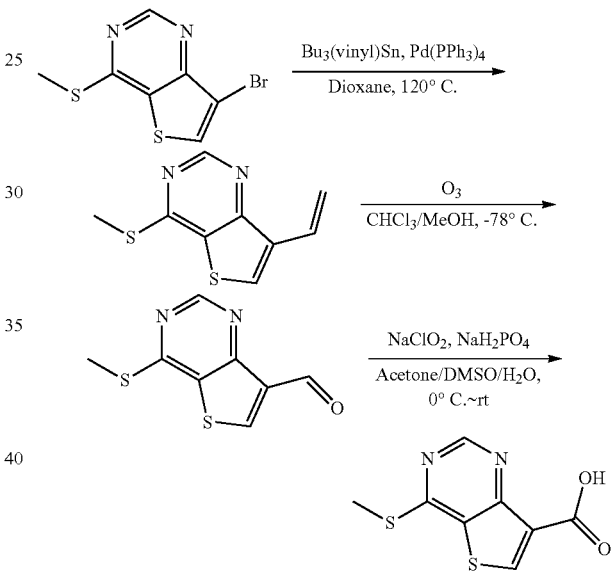

Example 105 a. 4-(Methylthio)-7-vinylthieno[3,2-d]pyrimidine

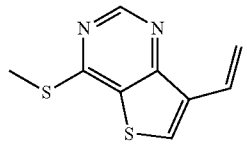

7-Bromo-4-(methylthio)thieno[3,2-d]pyrimidine (500 mg, 1.92 mmol) prepared in step d of Preparation Example 1 and Pd(PPh$_3$)$_4$ (138 mg, 0.12 mmol) were dissolved in dioxane (6.5 mL). Tributylvinyl tin (1.62 mL, 2.11 mmol) was added thereto, stirred at 120° C. for 2.5 hrs, and cooled to room temperature. An aqueous 10% potassium fluoride solution was added to the reaction mixture and stirred at room temperature for 1 hr. The resulting solution was filtered with a diatomite pad, which was washed with ethyl acetate. The aqueous layer was extracted with ethyl acetate dichloromethane. The combined organic layers were washed with a saline solution, dried over magnesium sulfate and concentrated under a reduced pressure. The resulting concentrate was purified by silica gel chromatography (ethyl acetate/hexane=5/95) to obtain the title compound as a yellow solid.

$^1$H NMR (400 MHz, DMSO-d$_6$) δ 9.05 (s, 1H), 8.40 (s, 1H), 7.02 (dd, 1H), 6.45 (d, 1H), 5.49 (d, 1H), 2.74 (s, 3H).

b. 4-(Methylthio)thieno[3,2-d]pyrimidine-7-carbaldehyde

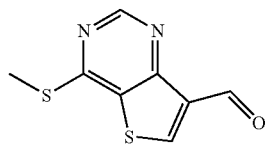

4-(Methylthio)-7-vinylthieno[3,2-d]pyrimidine (350 mg, 1.68 mmol) was dissolved in CHCl$_3$/MeOH (2 mL/2 mL), and cooled to −78° C. The reaction mixture was kept under an ozone atmosphere for 30 min and further under a nitrogen atmosphere for min, which was heated to room temperature. Dimethyl sulfide (0.37 mL, 5.04 mmol) was added thereto, which was concentrated under a reduced pressure. The resulting concentrate was solidified with diethyl ether. The resulting solid was filtered and dried over nitrogen to obtain the title compound.

$^1$H NMR (400 MHz, DMSO-d$_6$) δ10.30 (s, 1H), 9.21 (s, 1H), 9.13 (s, 1H), 2.77 (s, 3H).

c. 4-(Methylthio)thieno[3,2-d]pyrimidine-7-carboxylic acid

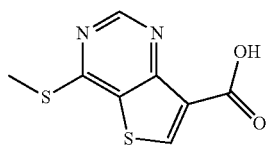

An aqueous solution (2 mL) of NaH$_2$PO$_4$-2H$_2$O (513 mg, 3.29 mmol) was added to a solution (acetone:dimethyl sulfoxide=1:1, 6 mL) of 4-(methylthio)thieno[3,2-d]pyrimidine-7-carbaldehyde (300 mg, 1.68 mmol) at 0° C. An aqueous solution (2 mL) of NaClO$_2$ (194 mg, 2.15 mmol) was added thereto at 0° C., and stirred at room temperature for 2 hrs. Water (10 mL) was added to the reaction solution and stirred at room temperature for 2 hrs. The resulting solid was filtered, washed with water, and dried to obtain the title compound as a white solid.

$^1$H NMR (400 MHz, DMSO-d$_6$) δ8.98 (s, 1H), 8.49 (s, 1H), 2.72 (s, 1H).

The compound of Example 106 was synthesized as shown in Reaction Scheme 6:

[Reaction Scheme 6]

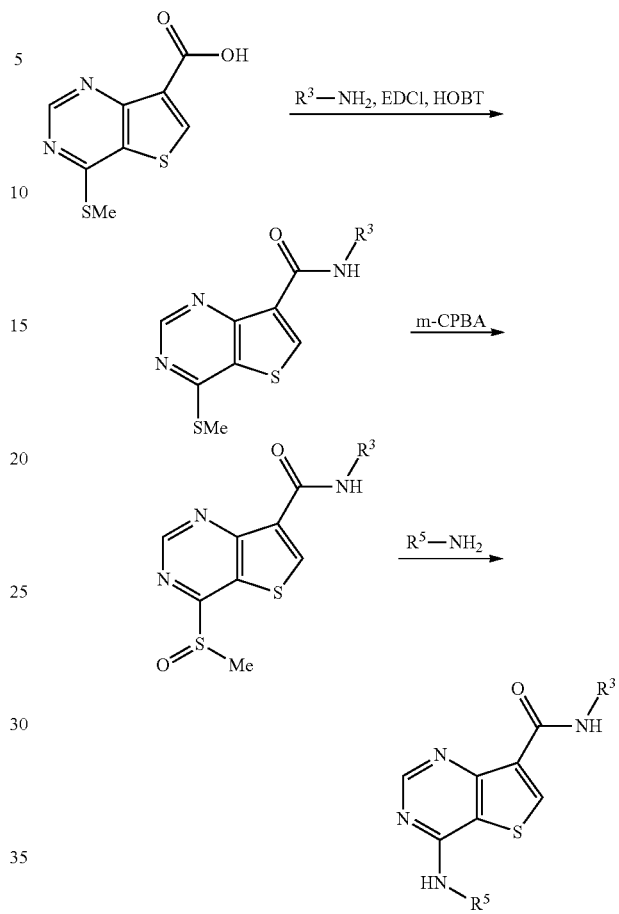

wherein, R$^3$ and R$^5$ have the same meanings as defined in formula (I).

Example 106 a. N-(3,5-dimethoxyphenyl)-4-(methylthio)thieno[3,2-d]pyrimidine-7-carboxamide

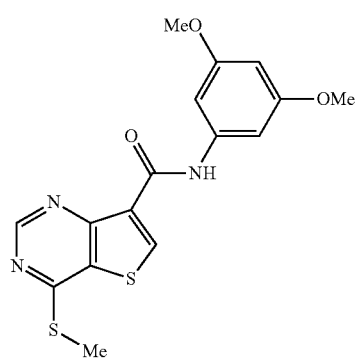 [SMILES: COc1cc(NC(=O)c2csc3c(SC)ncnc23)cc(OC)c1]

4-(Methylthio)thieno[3,2-d]pyrimidine-7-carboxylic acid (15 mg, 0.065 mmol) prepared in step c of Example 105, 3,5-dimethoxyaniline (10 mg, 0.065 mmol) and HOBt (N-hydroxybenzotriazole, 8.8 mg, 0.065 mmol) were dissolved in acetonitrile (2 mL). EDCI (37 mg, 0.20 mmol) was added thereto at room temperature. After 15 hrs, water was added to the reaction mixture to terminate the reaction, which was stirred at room temperature for 2 hrs and filtered. The filtrate was washed with water and dried to obtain the title compound.

$^{1}$H NMR (400 MHz, DMSO-$d_6$) δ11.31 (s, 1H), 9.22 (s, 1H), 9.09 (s, 1H), 7.00 (s, 2H), 6.32 (s, 1H), 3.76 (s, 6H), 2.80 (s, 3H).

b. N-(3,5-dimethoxyphenyl)-4-(methylsulfinyl)thieno[3,2-d]pyrimidine-7-carboxamide

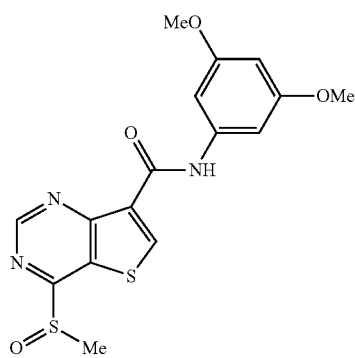 [SMILES: COc1cc(NC(=O)c2csc3c(S(C)=O)ncnc23)cc(OC)c1]

N-(3,5-dimethoxyphenyl)-4-(methylthio)thieno[3,2-d]pyrimidine-7-carboxamide (10 mg, 2.77 mmol) was dissolved in dichloromethane (1 mL), and m-CPBA (4.77 mg, 2.77 mmol) was added thereto at 0° C. After 3 hrs, the reaction mixture and an aqueous sodium bicarbonate solution were mixed, which was extracted with dichloromethane. The organic layer thus obtained was dried over magnesium sulfate, filtered, and concentrated under a reduced pressure to obtain the title compound.

$^{1}$H NMR (400 MHz, DMSO-$d_6$) δ11.22 (s, 1H), 9.46 (s, 1H), 9.34 (s, 1H), 7.03 (s, 2H), 6.33 (s, 1H), 3.77 (s, 6H), 3.08 (s, 3H).

c. 4-Amino-N-(3,5-dimethoxyphenyl)thieno[3,2-d]pyrimidine-7-carboxamide

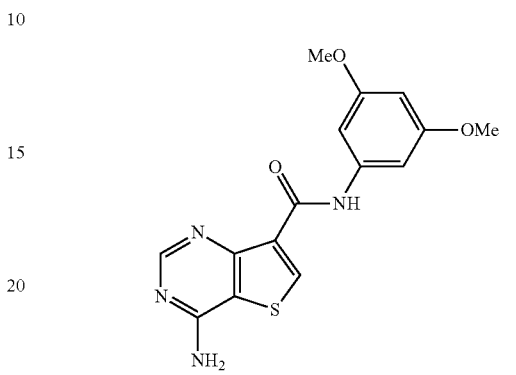

N-(3,5-dimethoxyphenyl)-4-(methylsulfinyl)thieno[3,2-d]pyrimidine-7-carboxamide (2 mg, 0.005 mmol) and 2.0M ammonia isopropanol (0.8 mL) were mixed in a closed vessel, which was stirred at 110° C. for 15 hrs. The reaction mixture was cooled to room temperature and concentrated under a reduced pressure, which was purified by silica gel chromatography (DCM:MeOH=20:1) to obtain the title compound as a white solid.

$^{1}$H NMR (400 MHz, DMSO-$d_6$) δ11.87 (s, 1H), 8.89 (s, 1H), 8.59 (s, 1H), 7.91 (s, 2H), 6.97 (s, 2H), 6.30 (s, 1H), 3.78 (s, 6H).

The compound of Example 107 was synthesized as shown in Reaction Scheme 7:

[Reaction Scheme 7]

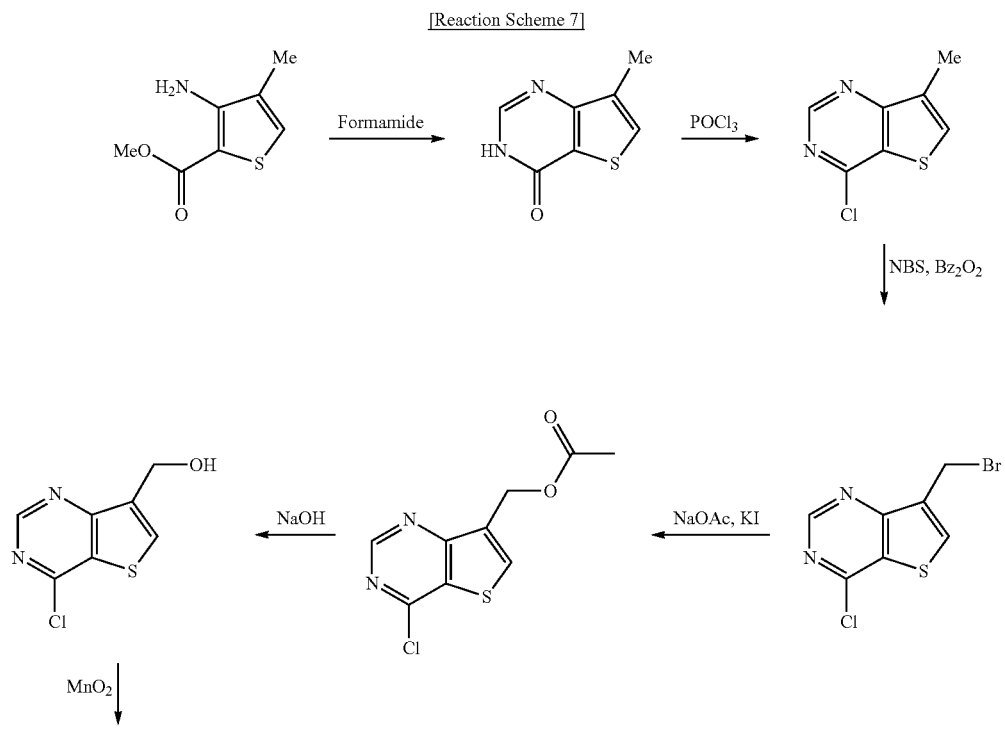

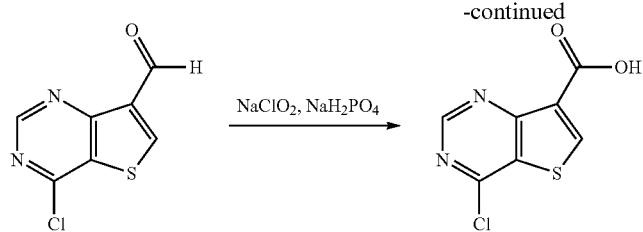

Example 107 a. 7-Methylthieno[3,2-d]pyrimidin-4(3H)-one

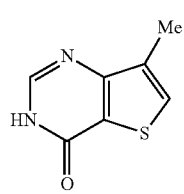

Methyl 3-amino-4-methylthiophene-2-carboxylate (3.0 g) (Aldrich, Catalog No. 546658) was dissolved in formamide (5 mL), stirred at 200° C. for 3 hrs, and cooled to room temperature. Water (50 mL) was added thereto, which was stirred at room temperature for 15 hrs. The resulting solution was filtered, and the solid thus obtained was washed with water and dried. The solid was added to acetone/diethyl ether, which was stirred and filtered to obtain the title compound as a white solid.

$^1$H NMR (400 MHz, DMSO-$d_6$) δ 12.50 (br, 1H), 8.16 (s, 1H), 7.86 (s, 1H), 2.30 (s, 3H).

b. 4-Chloro-7-methylthieno[3,2-d]pyrimidine

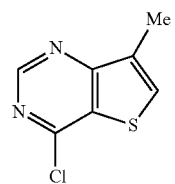 [SMILES: Cc1csc2c(Cl)ncnc12]

7-Methylthieno[3,2-d]pyrimidine-4(3H)-one (1.5 g) was dissolved in phosphorous oxychloride (10 mL) and stirred at 110° C. for 2 hrs. The reaction mixture was cooled to room temperature and concentrated under a reduced pressure. The resulting concentrate was added to a mixture of dichloromethane and a saturated sodium bicarbonate solution. The aqueous layer was extracted with dichloromethane four times. The combined organic layers were dried over magnesium sulfate and concentrated under a reduced pressure to obtain the title compound as a cream and white solid.

$^1$H NMR (400 MHz, DMSO-$d_6$) δ 9.06 (s, 1H), 8.24 (s, 1H), 2.43 (s, 3H).

c. 7-(Bromomethyl)-4-chlorothieno[3,2-d]pyrimidine

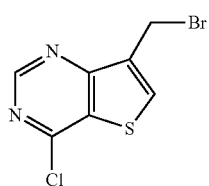 [SMILES: Clc1ncnc2c(CBr)csc12]

4-Chloro-7-methylthieno[3,2-d]pyrimidine (6.62 g, 33.0 mmol) and NBS (5.87 g, 33.0 mmol) were dissolved in carbon tetrachloride (100 mL). Benzoyl peroxide (1.0 g, 80% purity) was added thereto and stirred at 100° C. for 1 hr. The reaction mixture is cooled to room temperature, filtered with a diatomite pad, and concentrated under a reduced pressure to obtain the title compound as a yellow solid.

$^1$H NMR (400 MHz, DMSO-$d_6$) δ9.15 (s, 1H), 8.75 (s, 1H), 4.93 (s, 2H).

d. (4-Chlorothieno[3,2-d]pyrimidin-7-yl)methyl acetate

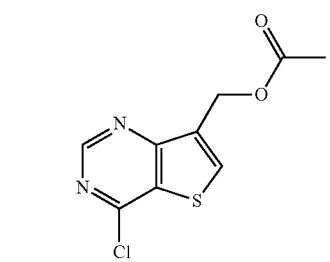

7-(Bromomethyl)-4-chlorothieno[3,2-d]pyrimidine (9.17 g, 33.0 mmol) was dissolved in N,N-dimethyl formamide (54 mL). Sodium acetate (27 g, 330 mmol) and potassium iodide (10.96 g, 66.0 mmol) were added thereto and stirred at 35° C. for 4 hrs. Ethyl acetate was added to the reaction mixture, which was washed with water five times and then with a saturated sodium thiosulfate solution. The resulting solution was dried over magnesium sulfate and concentrated under a reduced pressure. The resulting concentrate was purified by silica gel chromatography (ethyl acetate: hexane=1:4) to obtain the title compound as a cream and white solid.

$^1$H NMR (400 MHz, DMSO-$d_6$) δ 9.06 (s, 1H), 8.60 (s, 1H), 5.38 (s, 2H), 2.06 (s, 3H).

e. (4-Chlorothieno[3,2-d]pyrimidin-7-yl)methanol

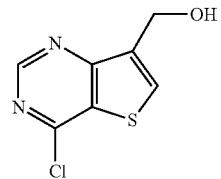

(4-Chlorothieno[3,2-d]pyrimidin-7-yl)methyl acetate (3.12 g, 12.06 mmol) was dissolved in THF (240 mL), and 1N sodium hydroxide (100 mL) was added thereto at room temperature and stirred for 30 min. Ethyl acetate was added to the reaction mixture. The aqueous layer was extracted with ethyl acetate. The combined organic layers were washed with a saline solution, dried over magnesium sulfate and concentrated under a reduced pressure to obtain the title compound as a white solid.

$^1$H NMR (400 MHz, DMSO-$d_6$) δ 9.09 (s, 1H), 8.33 (s, 1H), 5.47 (t, 1H), 4.84 (d, 2H).

f. 4-Chlorothieno[3,2-d]pyrimidine-7-carbaldehyde

(4-Chlorothieno[3,2-d]pyrimidine-7-yl)methanol (215 mg, 0.99 mmol) and manganese oxide (MnO$_2$, 863 mg, 9.9 mmol, 10 eq) were dissolved in chloroform (10 mL), stirred at 70° C. for 2 hrs, and cooled to room temperature. The resulting solution was filtered with a diatomite pad and concentrated under a reduced pressure to obtain the title compound as a white solid.

$^1$H NMR (400 MHz, DMSO-$d_6$) δ 10.30 (s, 1H), 9.40 (s, 1H), 9.20 (s, 1H).

g. 4-Chlorothieno[3,2-d]pyrimidine-7-carboxylic acid

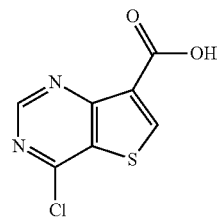 [SMILES: O=C(O)c1csc2c(Cl)ncnc12]

Chlorothieno[3,2-d]pyrimidine-7-carbaldehyde (100 mg, 0.47 mmol) was dissolved in dimethyl sulfoxide (4.8 mL), and cooled to 10° C. A solution of NaH$_2$PO$_4$·2H$_2$O (170 mg, 1.07 mmol) dissolved in water (0.6 mL) was added thereto, which was cooled to 0° C. A solution of NaClO$_2$ (170 mg, 1.88 mmol) dissolved in water (0.6 mL) was slowly added thereto at 0° C. The reaction mixture was heated to room temperature and stirred for 2 hrs. Water (10 mL) was added to the resulting solution, which caused generation of a solid. The generated solid was stirred at room temperature for 2 hrs, filtered, washed with water, and dried at room temperature to obtain the title compound as a white solid.

$^1$H NMR (400 MHz, DMSO-$d_6$) δ 9.07 (s, 1H), 8.87 (s, 1H).

The compounds of Examples 108 to 136 were synthesized as shown in Reaction Scheme 8:

[Reaction Scheme 8]

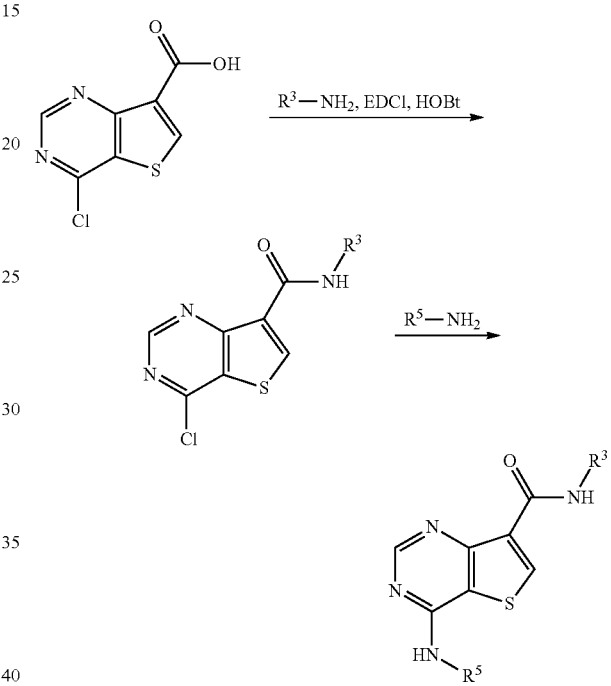

wherein, $R^3$ and $R^5$ have the same meanings as defined in formula (I).

Example 108 a. 4-Chloro-N-(2,6-difluoro-3,5-dimethoxyphenyl)thieno[3,2-d]pyrimidine-7-carboxamide

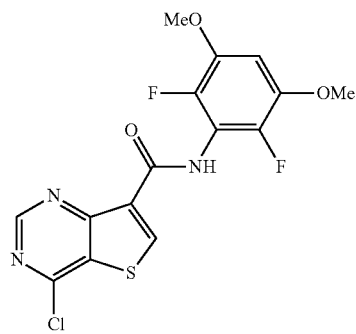 [SMILES: COc1cc(OC)c(F)c(NC(=O)c2csc3c(Cl)ncnc23)c1F]

4-Chlorothieno[3,2-d]pyrimidine-7-carboxylic acid (23 mg, 0.10 mmol) prepared in step g of Example 107, 2,6- difluoro-3,5-dimethoxybenzene amine (19 mg, 0.10 mmol), and HOBT (N-hydroxybenzotriazole, 13.5 mg, 0.10 mmol) were dissolved in acetonitrile (2 mL), and EDCI (57 mg, 0.30 mmol) was added thereto at room temperature. After 15 hrs, water and ethyl acetate were added to the reaction mixture. The aqueous layer was extracted with ethyl acetate. The combined organic layers were washed with a saline solution, dried over magnesium sulfate, and concentrated under a reduced pressure. The resulting concentrate was purified by silica gel chromatography (DCM:MeOH=20:1) to obtain the title compound.

$^1$H NMR (400 MHz, DMSO-d$_6$) δ 10.69 (s, 1H), 9.39 (s, 1H), 8.88 (s, 1H), 7.02 (s, 1H), 3.84 (s, 6H).

b. 4-Amino-N-(2,6-difluoro-3,5-dimethoxyphenyl)thieno[3,2-d]pyrimidine-7-carboxamide

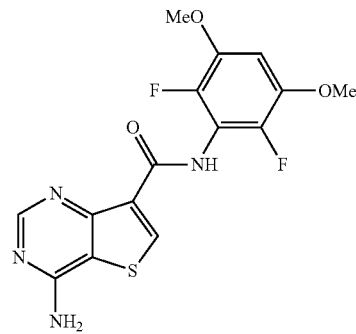 [SMILES: COc1cc(OC)c(F)c(NC(=O)c2csc3c(N)ncnc23)c1F]

4-Chloro-N-(2,6-difluoro-3,5-dimethoxyphenyl)thieno[3,2-d]pyrimidine-7-carboxamide (7 mg) and 2.0M ammonia isopropanol (2 mL) were mixed in a closed vessel, which was stirred at 70° C. for 10 hrs. The reaction mixture was cooled to room temperature and concentrated under a reduced pressure. The resulting concentrate was purified by silica gel chromatography (DCM:MeOH=20:1) to obtain the title compound as a white solid.

$^1$H NMR (400 MHz, DMSO-d$_6$) δ 11.33 (s, 1H), 8.94 (s, 1H), 8.53 (s, 1H), 7.95 (s, 2H), 6.99 (s, 1H), 3.89 (s, 6H).

c. 4-(Cyclopropylamino)-N-(2,6-difluoro-3,5-dimethoxyphenyl)thieno[3,2-d]pyrimidine-7-carboxamide

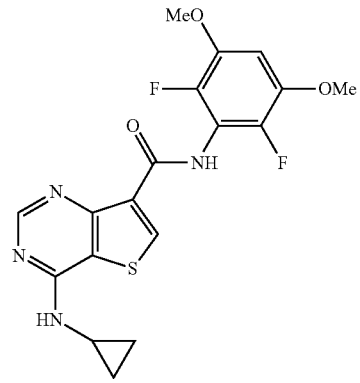 [SMILES: COc1cc(OC)c(F)c(NC(=O)c2csc3c(NC4CC4)ncnc23)c1F]

4-Chloro-N-(2,6-difluoro-3,5-dimethoxyphenyl)thieno[3,2-d]pyrimidine-7-carboxamide (5 mg, 0.013 mmol) and cyclopropylamine (10 μL) were dissolved in isopropanol (2 mL), and stirred at 110° C. for 15 hrs. The reaction mixture was cooled to room temperature and concentrated under a reduced pressure. The resulting concentrate was purified by silica gel chromatography (DCM:MeOH=20:1) to obtain the title compound as a white solid.

MS m/z [M+1] 407.14, 408.30.

Examples 109 to 136

The procedure of Example 108 was repeated using each of the corresponding starting materials to obtain respective title compounds (Table 1).

The compounds of Examples 137 to 147 were synthesized as shown in Reaction Scheme 9:

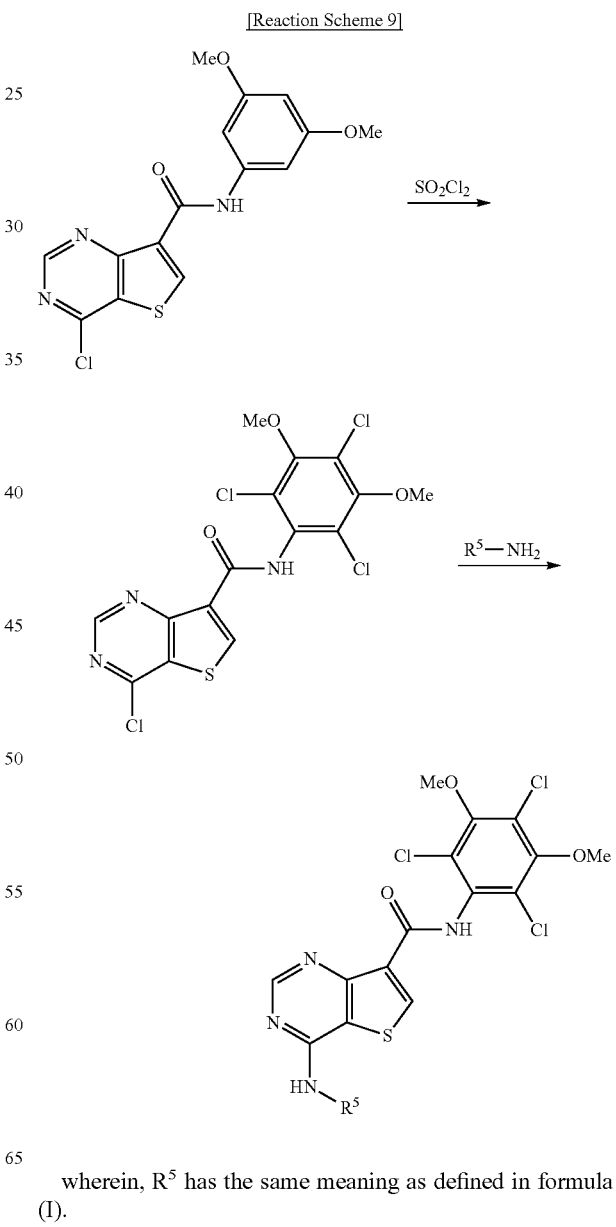

[Reaction Scheme 9]

wherein, R$^5$ has the same meaning as defined in formula (I).

Example 137: 4-Chloro-N-(2,4,6-trichloro-3,5-dimethoxyphenyl)thieno[3,2-d]pyrimidine-7-carboxamide

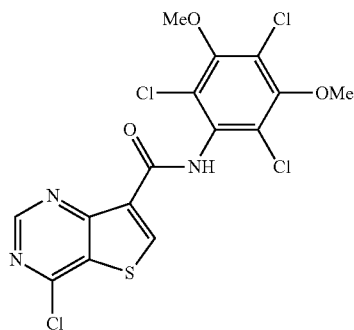 [SMILES: COc1c(Cl)c(NC(=O)c2csc3c(Cl)ncnc23)c(Cl)c(OC)c1Cl]

4-Chloro-N-(3,5-dimethoxyphenyl)thieno[3,2-d]pyrimidine-7-carboxamide (80 mg, 0.23 mmol) prepared in Example 119 was dissolved in acetonitrile (10 mL), and sulfuryl chloride (0.2M in dichloromethane, 2.3 mL, 0.46 mmol) was added thereto at 0° C. for 30 min and stirred at room temperature for 30 min. A saturated sodium bicarbonate solution was added to the reaction mixture to adjust its pH to 8. The resulting solution was extracted with dichloromethane. The combined organic layers were washed with a saline solution, dried over magnesium sulfate, and concentrated under a reduced pressure. The resulting concentrate was purified by silica gel chromatography (DCM:MeOH=40~20:1) to obtain the title compound.

$^1$H NMR (400 MHz, DMSO-$d_6$) δ 10.85 (s, 1H), 9.41 (s, 1H), 9.31 (s, 1H), 3.88 (s, 6H).

Examples 138 to 147

The procedures of Example 137, and steps b and c of Example 108 were repeated using each of the corresponding starting materials to obtain respective title compounds (Table 1).

The compounds of Examples 148 to 165 were synthesized as shown in Reaction Scheme 10:

[Reaction Scheme 10]

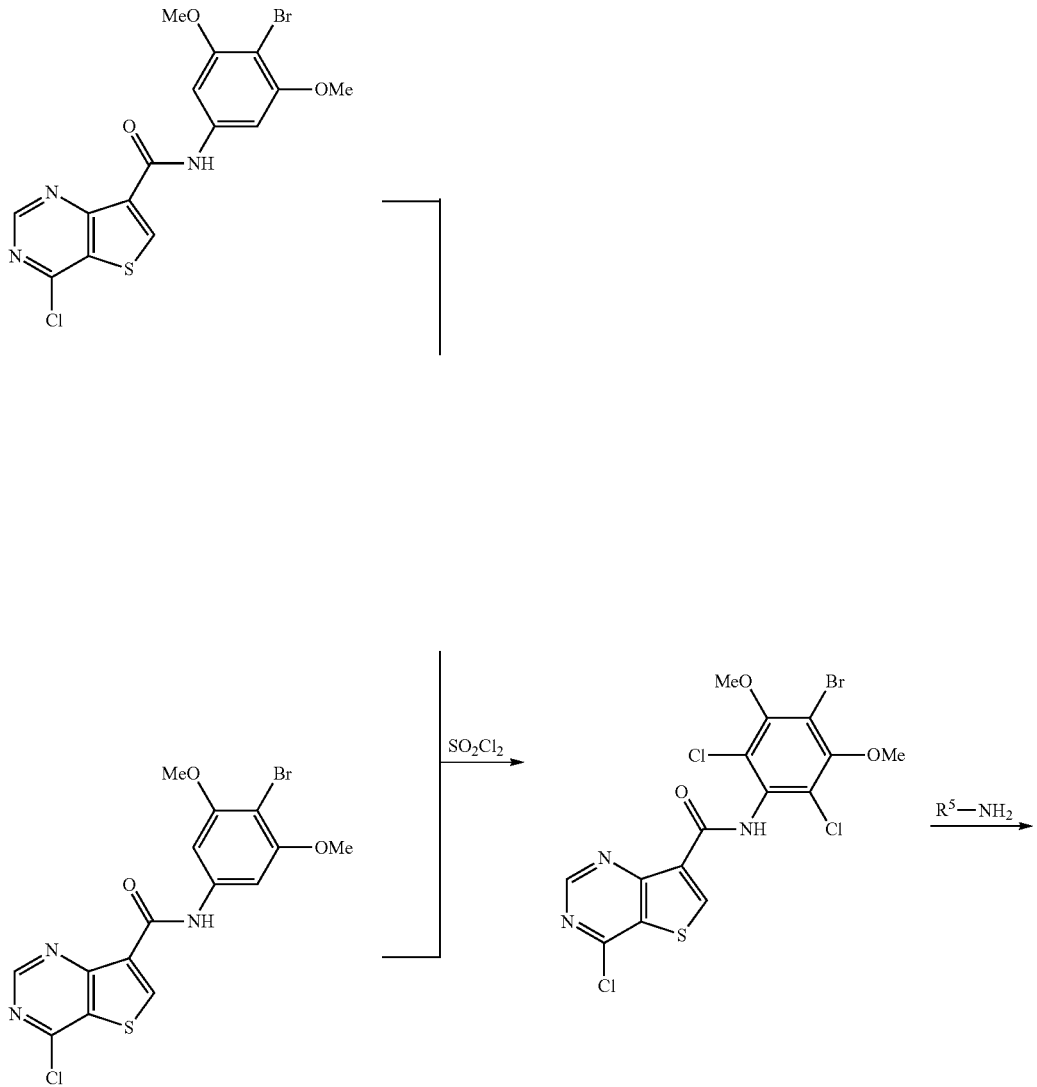

-continued

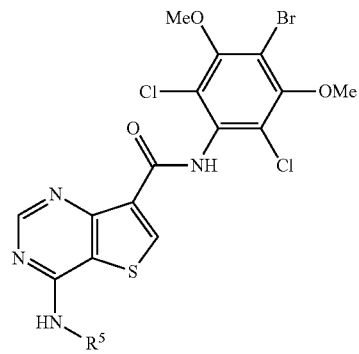

wherein, $R^5$ has the same meaning as defined in formula (I).

Example 148 a. 4-Bromo-3,5-dimethoxybenzene amine

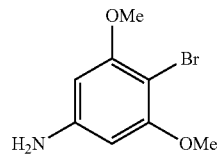

3,5-Dimethoxyaniline (5.00 g, 32.6 mmol) was dissolved in dichloromethane (50 mL) and cooled to −78° C. Tetrabutylammonium tribromide (15.7 g, 32.6 mmol) dissolved in dichloromethane (75 mL) was added thereto at −78° C. The reaction mixture was stirred for 30 min, heated to room temperature, and stirred for 5 hrs, which was added to a saturated sodium bicarbonate solution. The resulting solution was extracted with dichloromethane. The combined organic layers were washed with water and a saline solution, respectively, dried over magnesium sulfate, and concentrated under a reduced pressure. The resulting concentrate was purified by silica gel chromatography (ethyl acetate:hexane=1:1) to obtain the title compound as a cream and white solid.

$^1$H NMR (400 MHz, DMSO-$d_6$) δ 5.95 (s, 2H), 5.33 (s, 2H), 3.70 (s, 6H).

b. N-(4-Bromo-3,5-dimethoxyphenyl)-4-chlorothieno[3,2-d]pyrimidine-7-carboxamide

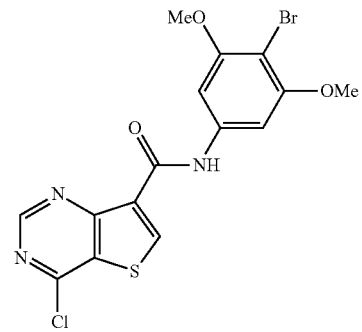 [SMILES: COc1cc(NC(=O)c2csc3c(Cl)ncnc23)cc(OC)c1Br]

4-Chlorothieno[3,2-d]pyrimidine-7-carboxylic acid (0.88 g, 3.81 mmol), 4-bromo-3,5-dimethoxybenzene amine (0.74 g, 3.18 mmol) and HOBt (0.51 g, 3.81 mmol) were dissolved in acetonitrile (15 mL). EDCI (2.18 g, 11.45 mmol) was added thereto at room temperature and stirred for 15 hrs. The resulting solution was filtered and the solid thus obtained was dried to obtain the title compound.

$^1$H NMR (400 MHz, DMSO-$d_6$) δ 11.15 (s, 1H), 9.38 (s, 1H), 8.97 (s, 1H), 7.27 (s, 2H), 3.86 (s, 6H).

c. N-(4-Bromo-3,5-dimethoxyphenyl)-4-(methylthio)thieno[3,2-d]pyrimidine-7-carboxamide

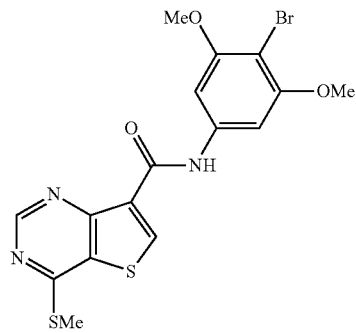 [SMILES: COc1cc(NC(=O)c2csc3c(SC)ncnc23)cc(OC)c1Br]

The procedure of step a of Example 108 was repeated except that 4-(methylthio)thieno[3,2-d]pyrimidine-7-carboxylic acid prepared in step c of Example 105 was used in spite of 4-chlorothieno[3,2-d]pyrimidine-7-carboxylic acid, and 4-bromo-3,5-dimethoxybenzene amine was used in spite of 2,6-difluoro-3,5-dimethoxybenzene amine, to obtain the title compound.

$^1$H NMR (400 MHz, DMSO-$d_6$) δ 11.36 (s, 1H), 9.22 (s, 1H), 9.08 (s, 1H), 7.25 (s, 2H), 3.87 (s, 6H), 2.80 (s, 3H).

d. N-(4-Bromo-2,6-dichloro-3,5-dimethoxyphenyl)-4-chlorothieno[3,2-d]pyrimidine-7-carboxamide

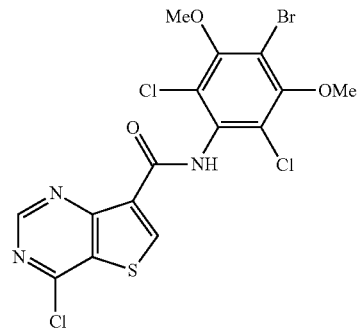 [SMILES: COc1c(Cl)c(NC(=O)c2csc3c(Cl)ncnc23)c(Cl)c(OC)c1Br]

N-(4-bromo-3,5-dimethoxyphenyl)-4-chlorothieno[3,2-d]pyrimidine-7-carboxamide (1.36 g, 3.81 mmol) was dissolved in acetonitrile (200 mL), and sulfuryl chloride (0.2M in dichloromethane, 50 mL, 10.0 mmol) was added thereto at 0° C. for 30 min and stirred at room temperature for 30 min. A saturated sodium bicarbonate solution was added to the reaction mixture to adjust its pH to 8. The resulting solution was extracted with dichloromethane. The combined organic layers were washed with a saline solution, dried over magnesium sulfate, and concentrated under a reduced pressure. The resulting concentrate was purified by silica gel chromatography (DCM:MeOH=20:1) to obtain the title compound as a white solid.

$^1$H NMR (400 MHz, DMSO-$d_6$) δ 10.84 (s, 1H), 9.36 (s, 1H), 9.18 (s, 1H), 3.86 (s, 6H); MS m/z [M+1] 496.01, 497.97, 499.96.

[Another method] N-(4-bromo-3,5-dimethoxyphenyl)-4-(methylthio)thieno[3,2-d]pyrimidine-7-carboxamide (0.58 g, 1.32 mmol) prepared in step c of Example 148 was dissolved in acetonitrile (50 mL), and a mixture of sulfuryl chloride (1.13 mL) and dichloromethane (70 mL) was added thereto at 0° C. for 30 min and stirred at room temperature for 30 min. A saturated sodium bicarbonate solution was added to the reaction mixture to adjust its pH to 8. The resulting solution was extracted with dichloromethane. The combined organic layers were washed with a saline solution, dried over magnesium sulfate, and concentrated under a reduced pressure. The resulting concentrate was purified by silica gel chromatography (DCM:MeOH=20:1) to obtain the title compound as a white solid.

Examples 149 to 165

The procedures of Example 148 and step c of Example 108 were repeated using each of the corresponding starting materials to obtain respective title compounds (Table 1).

The compound of Example 166 was synthesized as shown in Reaction Scheme 11:

[Reaction Scheme 11]

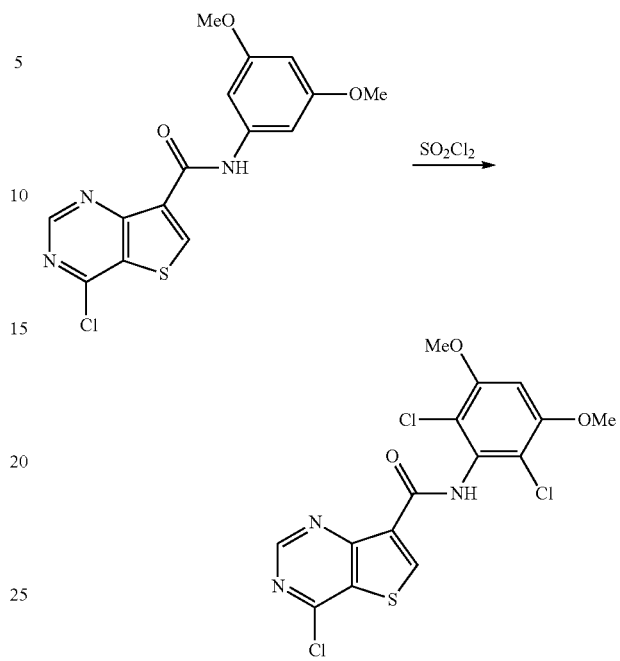

Example 166: 4-Chloro-N-(2,6-dichloro-3,5-dimethoxyphenyl)thieno[3,2-d]pyrimidine-7-carboxamide 4-Chloro-N-(3,5-dimethoxyphenyl)thieno[3,2-d]pyrimidine-7-carboxamide (80 mg, 0.23 mmol) prepared in Example 119 was dissolved in acetonitrile (10 mL), and sulfuryl chloride (0.2M in dichloromethane, 2.3 mL, 0.46 mmol) was added thereto at 0° C. for 30 min and stirred at room temperature for 30 min. A saturated sodium bicarbonate solution was added to the reaction mixture to adjust its pH to 8. The resulting solution was extracted with dichloromethane. The combined organic layers were washed with a saline solution, dried over magnesium sulfate, and concentrated under a reduced pressure. The resulting concentrate was purified by silica gel chromatography (DCM:MeOH=40~20:1) to obtain the title compound.

$^1$H NMR (400 MHz, DMSO-$d_6$) δ10.74 (s, 1H), 9.34 (s, 1H), 9.26 (s, 1H), 7.00 (s, 1H), 3.97 (s, 1H).

Examples 167 to 172

The procedures of Example 166, and steps b and c of Example 108 were repeated using each of the corresponding starting materials to obtain respective title compounds (Table 1).

The compound of Example 173 was synthesized as shown in Reaction Scheme 12:

[Reaction Scheme 12]

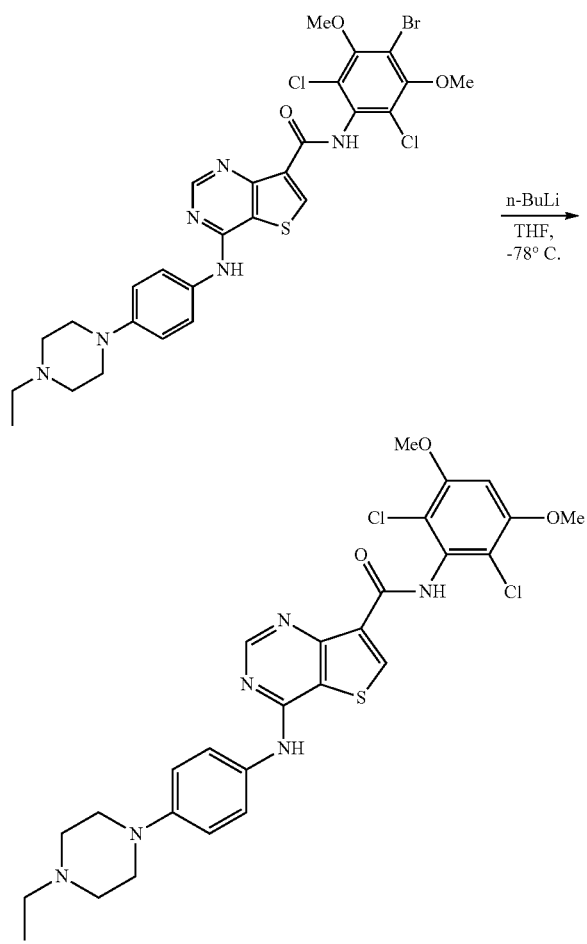

Example 173: N-(2,6-dichloro-3,5-dimethoxyphenyl)-4-(4-(4-ethylpiperazin-1-yl)phenylamino)thieno[3,2-d]pyrimidine-7-carboxamide N-(4-bromo-2,6-dichloro-3,5-dimethoxyphenyl)-4-(4-(4-ethylpiperazin-1-yl)phenylamino)thieno[3,2-d]pyrimidine-7-carboxamide (56 mg, 0.084 mmol) prepared in Example 156 was dissolved in THF (1 mL) and cooled to −78° C. N-butyl lithium (1.6M in hexane, 0.70 mL, 1.13 mmol) was added thereto at −78° C. and stirred for 30 min. A saturated ammonium chloride solution was added to the reaction mixture to terminate the reaction, which was extracted with ethyl acetate. The aqueous layer was extracted with dichloromethane. The combined organic layers were washed with a saline solution, dried over magnesium sulfate, and concentrated under a reduced pressure. The resulting concentrate was purified by silica gel chromatography (DCM:MeOH=10:1) to obtain the title compound as a white solid.

$^1$H NMR (400 MHz, DMSO-d$_6$) δ11.45 (s, 1H), 9.95 (s, 1H), 8.92 (s, 1H), 8.63 (s, 1H), 7.46 (d, 2H), 6.97 (d, 2H), 6.95 (s, 1H), 3.86 (s, 6H), 3.16 (m, 4H), 2.40 (m, 4H), 2.36 (q, 2H), 1.03 (t, 3H); MS m/z [M+1] 587.26, 589.15.

The compound of Example 174 was synthesized as shown in Reaction Scheme 13:

[Reaction Scheme 13]

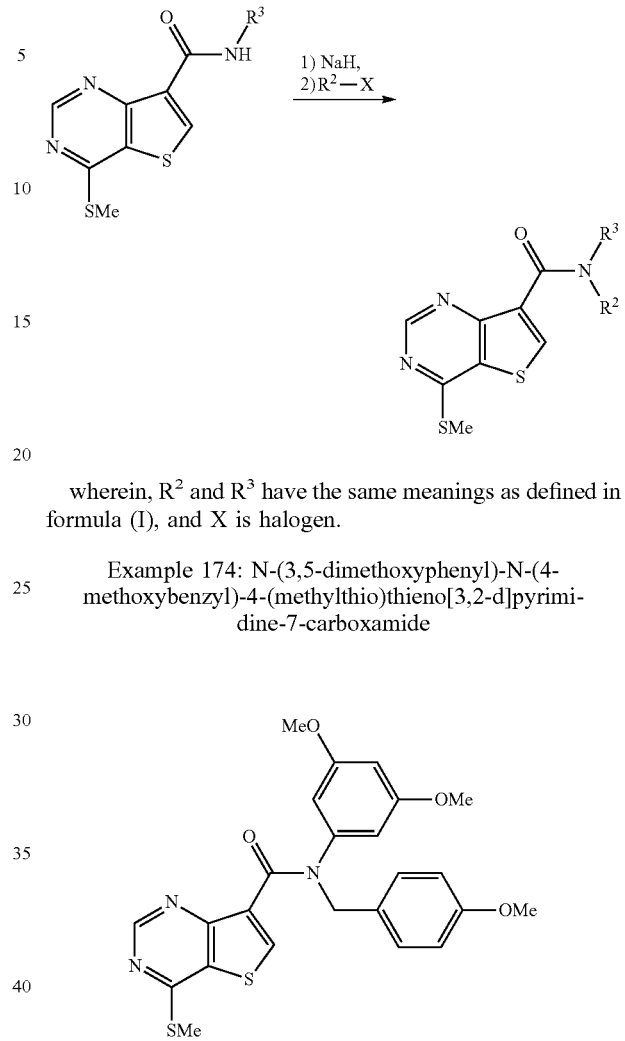

wherein, R$^2$ and R$^3$ have the same meanings as defined in formula (I), and X is halogen.

Example 174: N-(3,5-dimethoxyphenyl)-N-(4-methoxybenzyl)-4-(methylthio)thieno[3,2-d]pyrimidine-7-carboxamide N-(3,5-dimethoxyphenyl)-4-(methylthio)thieno[3,2-d]pyrimidine-7-carboxamide (30 mg, 0.083 mmol) prepared in step a of Example 106 was dissolved in N,N-dimethylformamide (0.6 mL), and sodium hydroxide (60% in mineral oil, 33 mg, 0.83 mmol) was added thereto at room temperature. After 30 min, tetrabutylammonium iodide (30 mg, 0.083 mmol) and p-methoxybenzyl chloride (17 μL, 0.125 mmol) were added to the reaction mixture. After 6 hrs, water was added to the reaction mixture to terminate the reaction. The aqueous layer was extracted with ethyl acetate. The combined organic layers were washed with a saline solution, dried over magnesium sulfate, and concentrated under a reduced pressure. The resulting concentrate was purified by silica gel chromatography (DCM:MeOH=20:1) to obtain the title compound as a cream and white solid.

MS m/z [M+1] 482.05, 483.02.

The compounds of Examples 175 to 177 were synthesized as shown in Reaction Scheme 14:

[Reaction Scheme 14]

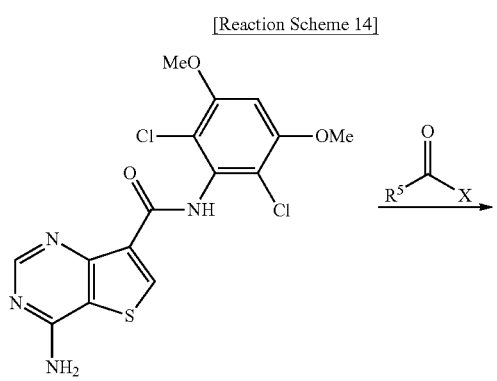

wherein, $R^5$ has the same meaning as defined in formula (I).

Example 175: 4-Acetamido-N-(2,6-dichloro-3,5-dimethoxyphenyl)thieno[3,2-d]pyrimidine-7-carboxamide

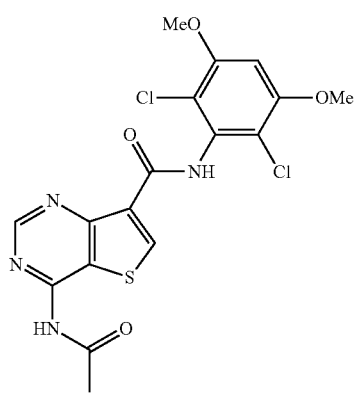 [SMILES: COc1cc(OC)c(Cl)c(NC(=O)c2csc3c(NC(C)=O)ncnc23)c1Cl]

4-Amino-N-(2,6-dichloro-3,5-dimethoxyphenyl)thieno[3,2-d]pyrimidine-7-carboxamide (10 mg, 0.025 mmol) prepared in Example 167 was dissolved in pyridine (0.1 mL), and anhydrous acetic acid (15 μL, 0.16 mmol) was added thereto at room temperature. The reaction mixture was stirred at 80° C. for 12 hrs and concentrated under a reduced pressure. The resulting concentrate was purified by silica gel chromatography (DCM:MeOH=20:1) to obtain the title compound as a white solid.

$^1$H NMR (400 MHz, DMSO-d$_6$) δ11.47 (br, 1H), 11.26 (s, 1H), 9.15 (s, 1H), 9.03 (s, 1H), 6.96 (s, 1H), 3.96 (s, 6H), 2.31 (s, 3h); MS m/z [M+1] 441.16, 443.16.

Examples 176 and 177

The procedure of Example 175 was repeated using each of the corresponding starting materials to obtain respective title compounds (Table 1).

The compounds of Examples 178 to 183 were synthesized as shown in Reaction Scheme 15:

[Reaction Scheme 15]

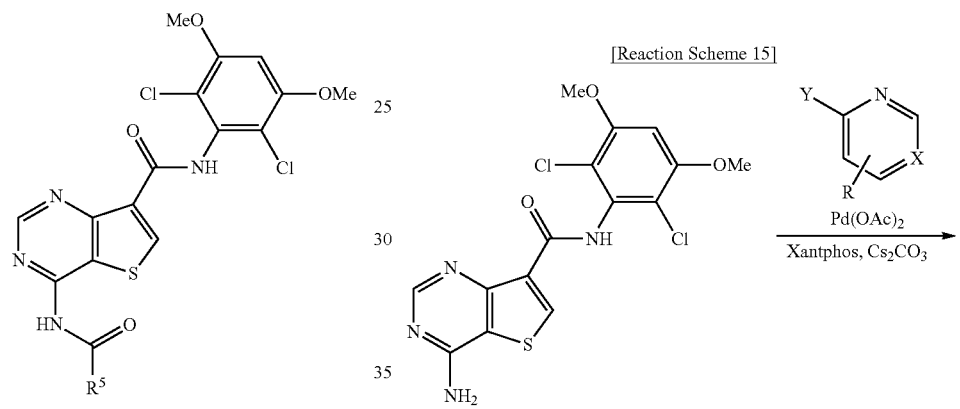

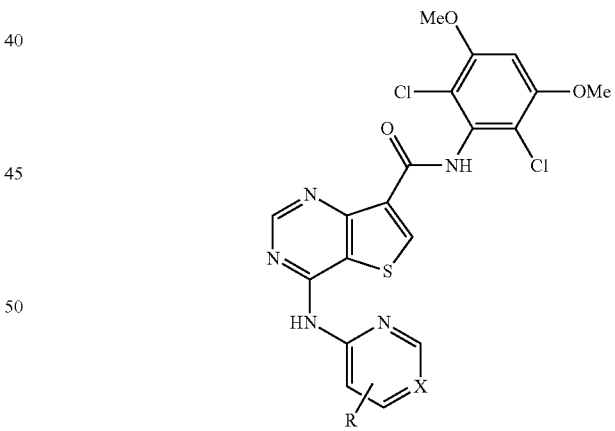

wherein, X is N or CH;

Y is halogen;

R is H, halogen, —CF$_3$, —NO$_2$, —CN, C$_{1-6}$ alkyl, C$_{3-7}$ cycloalkyl, C$_{1-6}$ alkenyl, C$_{1-6}$ alkynyl, C$_{3-14}$ aryl, C$_{2-13}$ heteroaryl, C$_{2-7}$ heterocycloalkyl, —(CH$_2$)$_m$NR$^8$R$^9$, —(CH$_2$)$_m$OR$^9$, —(CH$_2$)$_m$C(O)OR$^9$, —(CH$_2$)$_m$C(O)NR$^8$R$^9$, —(CH$_2$)$_m$NR$^8$C(O)R$^9$, —(CH$_2$)$_m$SR$^9$, —(CH$_2$)$_m$S(O)R$^9$ or —(CH$_2$)$_m$S(O)$_2$R$^9$; and R$^8$ and R$^9$ have the same meanings as defined in formula (I).

Example 178: N-(2,6-dichloro-3,5-dimethoxyphenyl)-4-(5-methylpyridin-2-ylamino)thieno[3,2-d]pyrimidine-7-carboxamide

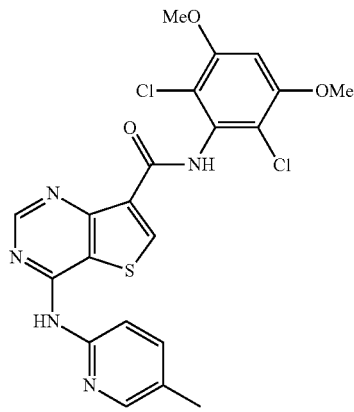 [SMILES: COc1cc(OC)c(Cl)c(NC(=O)c2csc3c(Nc4ccc(C)cn4)ncnc23)c1Cl]

4-Amino-N-(2,6-dichloro-3,5-dimethoxyphenyl)thieno[3,2-d]pyrimidine-7-carboxamide (10 mg, 0.025 mmol) prepared in Example 167, 2-bromo-5-methylpyridine (6.5 mg, 0.038 mmol), Pd(OAc)$_2$ (0.6 mg, 0.003 mmol), Xantphos (2.9 mg, 0.005 mmol), and Cs$_2$CO$_3$ (16 mg, 0.05 mmol) were dissolved in dioxane (1 mL), and stirred at 120° C. for 1.5 hrs. The aqueous layer was extracted with ethyl acetate. The combined organic layers were washed with a saline solution, dried over magnesium sulfate, and concentrated under a reduced pressure. The resulting concentrate was purified by silica gel chromatography (DCM:MeOH=20:1) to obtain the title compound as a white solid.

MS m/z [M+1] 490.23, 492.23.

Examples 179 to 183

The procedure of Example 178 was repeated using each of the corresponding starting materials to obtain respective title compounds (Table 1).

Examples 184 to 202

The procedures of steps b and c of Example 108, and Example 173 were repeated using the compound prepared in step d of Example 148 as a starting material to obtain respective title compounds (Table 1).

The compounds of Examples 203 to 206 were synthesized as shown in Reaction Scheme 16:

[Reaction Scheme 16]

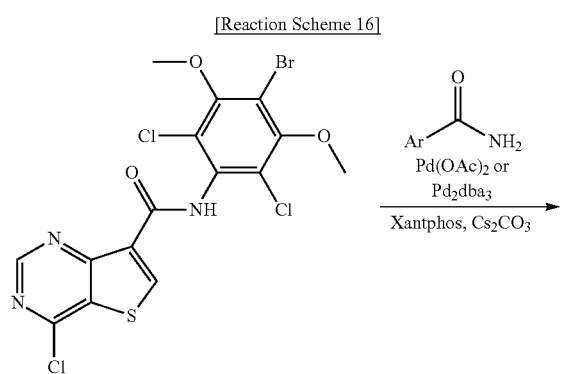

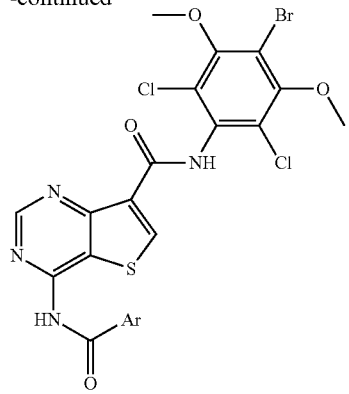

Example 203: N-(4-bromo-2,6-dichloro-3,5-dimethoxyphenyl)-4-(4-(4-ethylpiperazin-1-yl)benzamido)thieno[3,2-d]pyrimidine-7-carboxamide

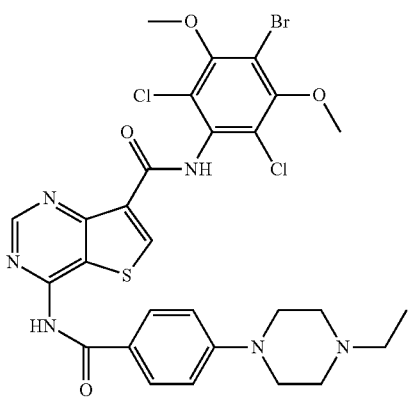 [SMILES: CCN1CCN(c2ccc(C(=O)Nc3ncnc4c(C(=O)Nc5c(Cl)c(OC)c(Br)c(OC)c5Cl)csc34)cc2)CC1]

N-(4-bromo-2,6-dichloro-3,5-dimethoxyphenyl)-4-chlorothieno[3,2-d]pyrimidine-7-carboxamide (100 mg, 0.20 mmol) prepared in step d of Example 148, 4-(4-ethylpiperazin-1-yl)benzamide (49 mg, 0.21 mmol), Pd$_2$dba$_3$ (8.2 mg, 0.008 mmol), Xantphos (14 mg, 0.024 mmol), and Cs$_2$CO$_3$ (91 mg, 0.28 mmol) were dissolved in dioxane (3 mL), and stirred at 120° C. for 2.5 hrs. The aqueous layer was extracted with ethyl acetate. The combined organic layers were washed with a saline solution, dried over magnesium sulfate, and concentrated under a reduced pressure. The resulting concentrate was purified by silica gel chromatography (DCM:MeOH=20~10:1) to obtain the title compound.

$^1$H NMR (400 MHz, DMSO-d$_6$) δ 11.57 (s, 1H), 11.40 (s, 1H), 9.20 (s, 1H), 9.08 (s, 1H), 8.03 (d, 2H), 7.03 (d, 2H), 3.86 (s, 6H), 3.35 (m, 4H), 2.50 (m, 4H), 2.36 (q, 2H), 1.04 (t, 3H); MS m/z [M+1] 693.27, 695.26.

Example 204: N-(2,6-dichloro-3,5-dimethoxyphenyl)-4-(4-(4-ethylpiperazin-1-yl)benzamido)thieno[3,2-d]pyrimidine-7-carboxamide

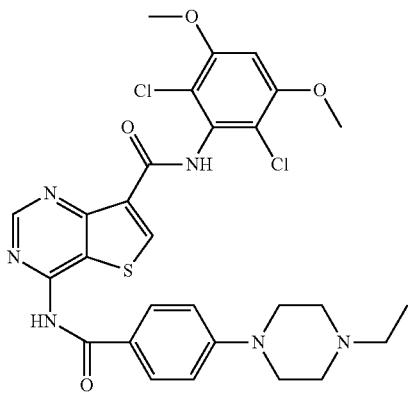 [SMILES: CCN1CCN(c2ccc(C(=O)Nc3ncnc4c(C(=O)Nc5c(Cl)c(OC)cc(OC)c5Cl)csc34)cc2)CC1]

The procedure of Example 203 was repeated except that 4-chloro-N-(2,6-dichloro-3,5-dimethoxyphenyl)thieno[3,2-d]pyrimidine-7-carboxamide prepared in Example 166 was used in spite of N-(4-bromo-2,6-dichloro-3,5-dimethoxyphenyl)-4-chlorothieno[3,2-d]pyrimidine-7-carboxamide, to obtain the title compound.

$^1$H NMR (400 MHz, DMSO-$d_6$) δ11.65 (s, 1H), 11.27 (s, 1H), 9.19 (s, 1H), 9.10 (s, 1H), 8.09 (d, 2H), 7.15 (d, 2H), 6.98 (s, 1H), 3.97 (s, 6H) 3.35 (m, 4H), 2.50 (m, 4H), 2.36 (q, 2H), 1.04 (t, 3H); MS m/z [M+1] 615.14.

Examples 205 and 206

The procedure of Example 203 was repeated using each of the corresponding starting materials to obtain respective title compounds (Table 1).

Examples 207 to 214

The procedure of Example 178 was repeated using the compound prepared in Example 148, 149, 166 or 167 as a starting material to obtain respective title compounds (Table 1).

The compound of Example 215 was synthesized as shown in Reaction Scheme 17:

[Reaction Scheme 17]

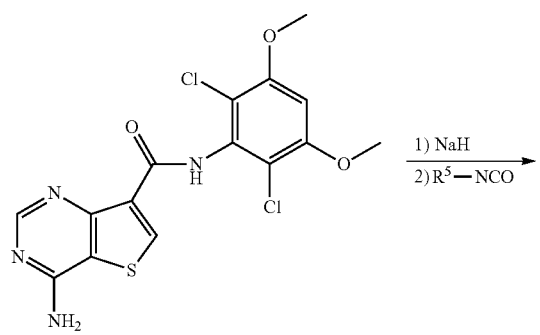

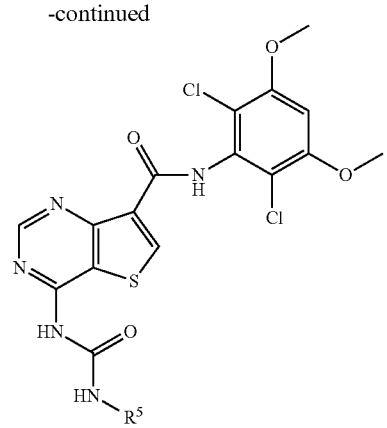

wherein, $R^5$ has the same meaning as defined in formula (I).

Example 215: N-(2,6-dichloro-3,5-dimethoxyphenyl)-4-(3-(3-(trifluoromethyl)phenyl)ureido)thieno[3,2-d]pyrimidine-7-carboxamide

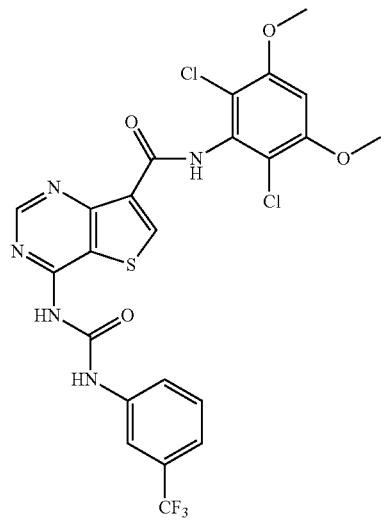

4-Amino-N-(2,6-dichloro-3,5-dimethoxyphenyl)thieno[3,2-d]pyrimidine-7-carboxamide (20 mg, 0.05 mmol) prepared in Example 167 was dissolved in N,N-dimethyl formamide, and sodium hydroxide (60% in mineral oil, 4 mg, 0.10 mmol) was added thereto at room temperature. After 30 min, trifluoro-m-tolyl isocyanate (7 μL, 0.05 mmol) was added to the reaction mixture, and after 2 hrs, a saturated ammonium chloride solution was added thereto, which was stirred at room temperature for 15 hrs. The resulting solution was filtered and the solid thus obtained was washed with water. The solid was purified by silica gel chromatography (DCM:MeOH=100~20:1) to obtain the title compound as a cream and white solid.

$^1$H NMR (400 MHz, DMSO-$d_6$) δ11.24 (s, 1H), 10.80 (s, 1H), 10.72 (s, 1H), 9.17 (s, 1H), 9.00 (s, 1H), 8.09 (s, 1H), 7.77 (d, 1H), 7.61 (t, 1H), 7.44 (d, 1H), 6.96 (s, 1H), 3.96 (s, 6H); MS m/z [M+1] 586.09, 588.11.

Example 216

The procedure of Example 215 was repeated using the corresponding starting material to obtain the title compound (Table 1).

The compounds of Examples 217 and 219 were synthesized as shown in Reaction Scheme 18:

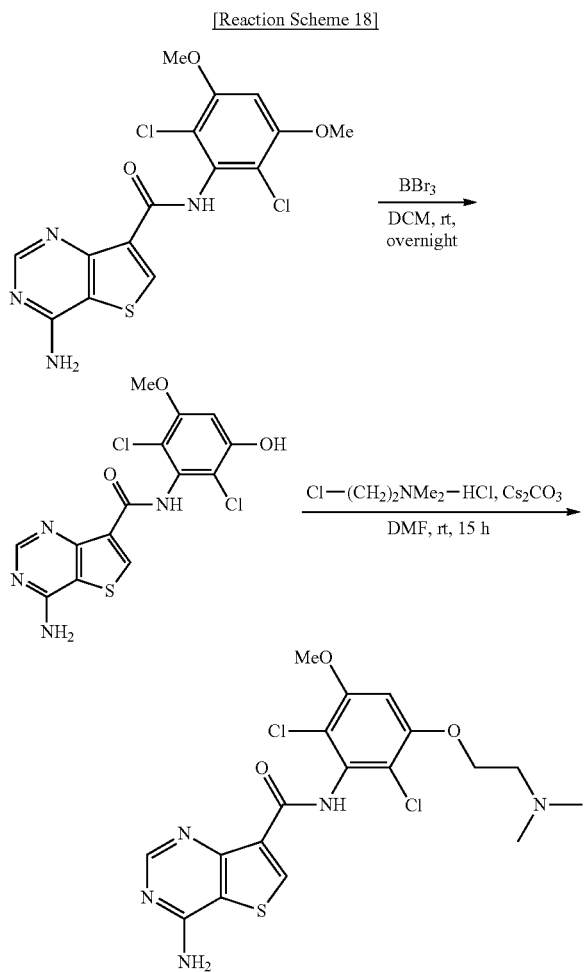

Example 217: 4-Amino-N-(2,6-dichloro-3-hydroxy-5-methoxyphenyl)thieno[3,2-d]pyrimidine-7-carboxamide

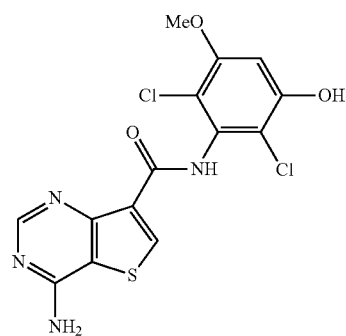 [SMILES: COc1cc(O)c(Cl)c(NC(=O)c2csc3c(N)ncnc23)c1Cl]

4-Amino-N-(2,6-dichloro-3,5-dimethoxyphenyl)thieno[3,2-d]pyrimidine-7-carboxamide (200 mg, 0.5 mmol) prepared in Example 167 was dissolved in dichloromethane (3 mL), and BBr$_3$ (95 µL, 1.0 mmol) was added thereto at 0° C. and stirred at room temperature for 15 hrs. A saturated ammonium chloride solution was added to the reaction mixture, which was added to a saturated sodium bicarbonate solution. The aqueous layer was extracted with ethyl acetate. The combined organic layers were washed with a saline solution, dried over magnesium sulfate, and concentrated under a reduced pressure. The resulting concentrate was purified by silica gel chromatography (DCM:MeOH=20~10:1) to obtain the title compound as a cream and white solid.

$^1$H NMR (400 MHz, DMSO-d$_6$) δ11.40 (s, 1H), 10.61 (s, 1H), 8.92 (s, 1H), 8.53 (s, 1H), 7.93 (s, 2H), 6.75 (s, 1H), 3.83 (s, 3H); MS m/z [M+1] 385.10, 387.10.

Example 218: 4-amino-N-(2,6-dichloro-3,5-dihydroxyphenyl)thieno[3,2-d]pyrimidine-7-carboxamide

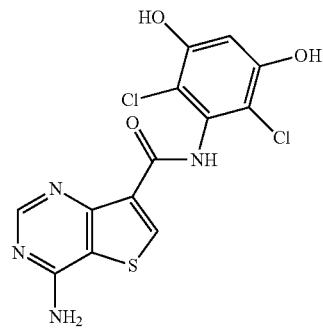 [SMILES: Nc1ncnc2c(C(=O)Nc3c(Cl)c(O)cc(O)c3Cl)csc12]

4-Amino-N-(2,6-dichloro-3,5-dimethoxyphenyl)thieno[3,2-d]pyrimidine-7-carboxamide (200 mg, 0.5 mmol) prepared in Example 167 was dissolved in dichloromethane (3 mL), and BBr$_3$ (95 µL, 1.0 mmol) was added thereto at 0° C. and stirred at room temperature for 15 hrs. A saturated ammonium chloride solution was added to the reaction mixture, which was added to a saturated sodium bicarbonate solution. The aqueous layer was extracted with ethyl acetate. The combined organic layers were washed with a saline solution, dried over magnesium sulfate, and concentrated under a reduced pressure. The resulting concentrate was purified by silica gel chromatography (DCM:MeOH=20~10:1) to obtain the title compound as a cream and white solid.

MS m/z [M+1] 371.09, 373.03.

Example 219: 4-Amino-N-(2,6-dichloro-3-(2-(dimethylamino)ethoxy)-5-methoxyphenyl)thieno[3,2-d]pyrimidine-7-carboxamide

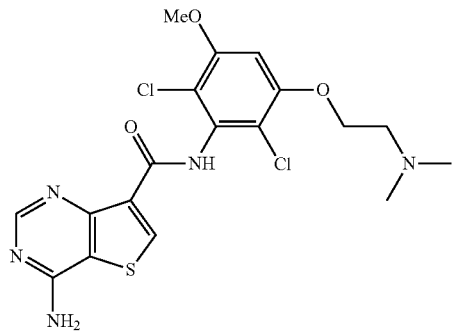 [SMILES: COc1cc(OCCN(C)C)c(Cl)c(NC(=O)c2csc3c(N)ncnc23)c1Cl]

4-Amino-N-(2,6-dichloro-3-hydroxy-5-methoxyphenyl)thieno[3,2-d]pyrimidine-7-carboxamide (15 mg, 0.039 mmol) prepared in Example 217 and $Cs_2CO_3$ (127 mg, 0.39 mmol) were dissolved in N,N-dimethyl formamide (0.1 mL), and 2-chloro-N,N-dimethylethane amine hydrochloride (28 mg, 0.195 mmol) was added thereto at room temperature. After 15 hrs, water was added to the reaction mixture. The aqueous layer was extracted with ethyl acetate. The combined organic layers were washed with a saline solution, dried over magnesium sulfate, and concentrated under a reduced pressure. The resulting concentrate was purified by chromatography (prep. TLC, DCM:MeOH=20:1, 1% 7.0M ammonia, solvent: MeOH) to obtain the title compound as a cream and white solid.

$^1$H NMR (400 MHz, DMSO-$d_6$) δ 11.45 (s, 1H), 8.92 (s, 1H), 8.53 (s, 1H), 7.93 (s, 2H), 6.98 (s, 1H), 4.21 (t, 2H), 3.94 (s, 3H), 2.68 (m, 2H), 2.66 (s, 6H); MS m/z [M+1] 456.10, 458.10.

Examples 220 to 231

The procedure of Example 178 was repeated using the compound prepared in Example 148, 149, 166 or 167 as a starting material to obtain respective title compounds (Table 1).

Example 232: Ethyl 6-(7-(2,6-dichloro-3,5-dimethoxyphenylcarbamoyl)thieno[3,2-d]pyrimidin-4-ylamino)-1H-indazole-3-carboxylate

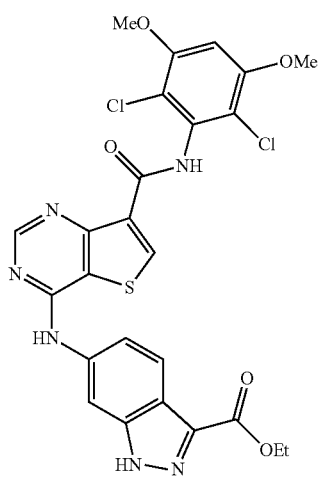 [SMILES: CCOC(=O)c1n[nH]c2cc(Nc3ncnc4c(C(=O)Nc5c(Cl)c(OC)cc(OC)c5Cl)csc34)ccc12]

4-amino-N-(2,6-dichloro-3,5-dimethoxyphenyl)thieno[3,2-d]pyrimidine-7-carboxamide (30 mg, 0.075 mmol) prepared in Example 167, 1-t-butyl 3-ethyl 6-bromo-1H-indazole-1,3-dicarboxylate (28 mg, 0.075 mmol), $Pd_2$ $dba_3$ (6.9 mg, 0.0075 mmol), Xantphos (8.7 mg, 0.015 mmol), and $Cs_2CO_3$ (49 mg, 0.15 mmol) were dissolved in dioxane (2 mL), and stirred at 120° C. for 6 hrs. Water was added to the reaction mixture, and the aqueous layer was extracted with ethyl acetate. The combined organic layers were washed with a saline solution, dried over magnesium sulfate, and concentrated under a reduced pressure. The resulting concentrate was purified by silica gel chromatography (DCM:MeOH=20:1) to obtain the title compound (9.5 mg) as a white solid.

$^1$H NMR (400 MHz, DMSO-$d_6$) δ11.37 (s, 1H), 10.36 (s, 1H), 9.04 (s, 1H), 8.82 (s, 1H), 8.39 (s, 1H), 8.04 (d, 1H), 7.63 (d, 1H), 6.96 (s, 1H), 4.39 (q, 2H), 1.38 (t, 3H); MS m/z [M+1] 586.99, 588.97.

The compounds of Examples 233 and 235 were synthesized as shown in Reaction Scheme 19:

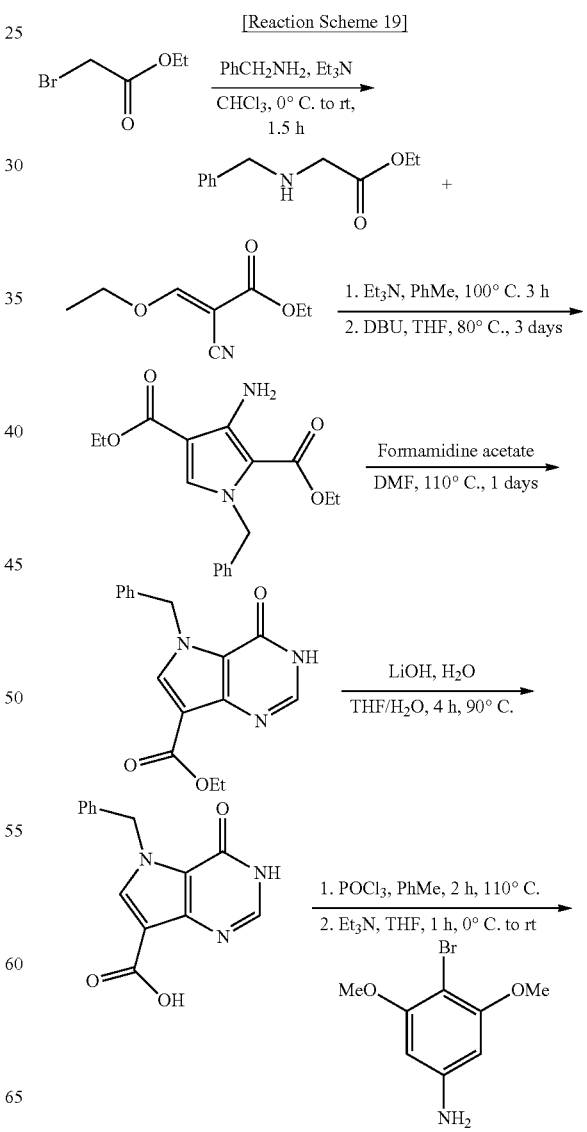

-continued

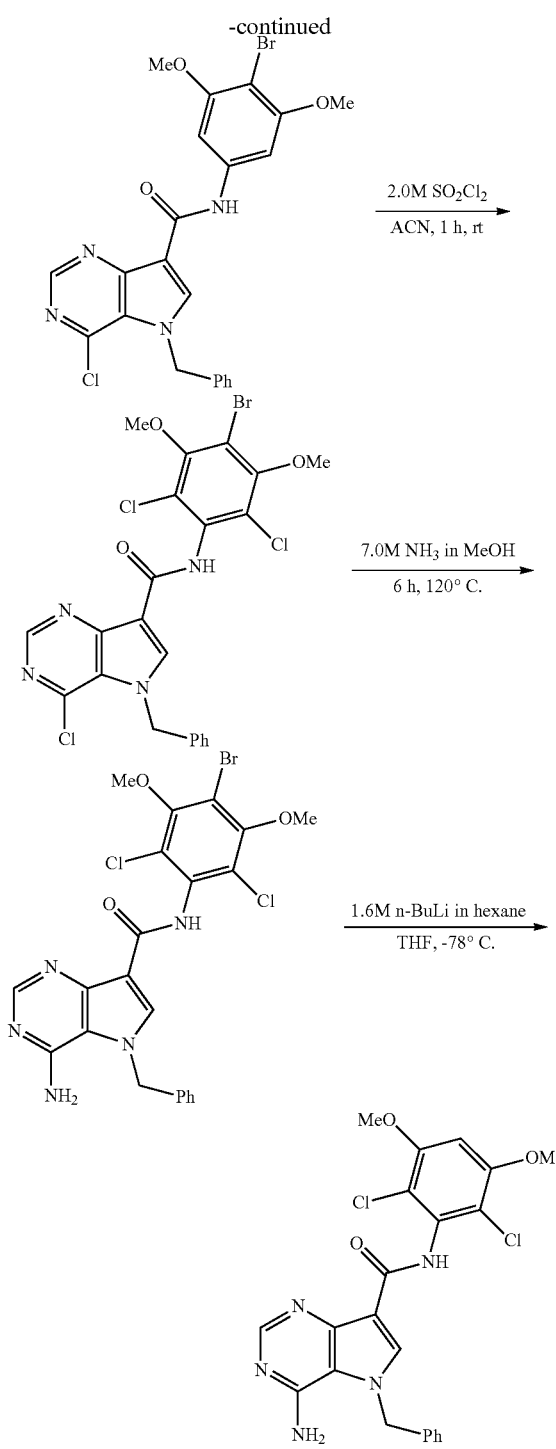

Example 233 a. Ethyl 2-(benzylamino)acetate

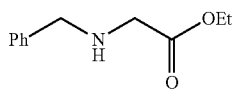 [SMILES: CCOC(=O)CNCc1ccccc1]

BnNH$_2$ (21.7 mL, 0.2 mol) and Et$_3$N (30 mL, 0.22 mol) were dissolved in CHCl$_3$ (200 mL), and ethyl bromoacetate (20 mL, 0.18 mol) was added thereto at 0° C. and stirred at room temperature for 1.5 hrs. The reaction mixture was filtered and the filtrate was concentrated. The solid and the concentrate were purified by silica gel chromatography (ethyl acetate:hexane=1:9→1:5→1:2) to obtain the title compound (24.1 g, 69%).

$^1$H NMR (CDCl$_3$) δ 7.29 (m, 5H), 3.80 (s, 2H), 3.31 (s, 2H), 1.90 (bs, 1H), 1.48 (s, 9H).

b. Diethyl 3-amino-1-benzyl-1H-pyrrole-2,4-dicarboxylate

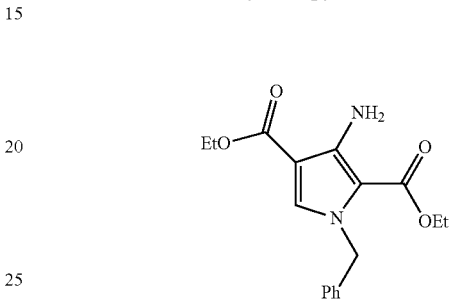

Ethyl 2-(benzylamino)acetate (24.1 g, 0.13 mol) and ethyl 2-cyano-3-ethoxyacrylate (23.2 g, 0.14 mol) were dissolved in toluene (200 mL), and Et$_3$N (19.1 mL, 0.14 mol) was added thereto at room temperature and stirred at 100° C. for 3 hrs. The reaction mixture was cooled to room temperature and concentrated under a reduced pressure. THF (200 mL) and DBU were added to the concentrate, which was stirred at 80° C. for 3 days. The resulting solution was cooled to room temperature and filtered with a silica gel pad. The filtrate was concentrated to obtain the title compound (29.5 g, 75%).

$^1$H NMR (CDCl$_3$) δ 7.33 (m, 4H), 7.12 (m, 2H), 5.76 (bs, 2H), 5.40 (s, 2H), 4.26 (m, 4H), 1.33 (m, 6H).

c. Ethyl 5-benzyl-4-oxo-4,5-dihydro-3H-pyrrolo[3,2-d]pyrimidine-7-carboxylate

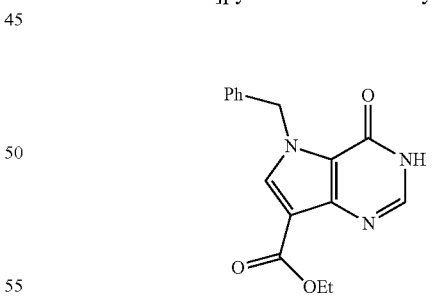

Diethyl 3-amino-1-benzyl-1H-pyrrole-2,4-dicarboxylate (29.5 g, 0.093 mol) and formamidine acetate (29.1 g, 0.28 mol) were dissolved in N,N-dimethylformamide (100 mL), stirred at 110° C. for 1 day, and cooled to room temperature. An aqueous NaHCO$_3$ solution was added to the reaction mixture to adjust its pH to 7. The resulting solution was filtered and the solid was washed with ethyl acetate to obtain the title compound (21.8 g, 79%).

$^1$H NMR (DMSO-d$_6$) δ8.19 (s, 1H), 7.93 (m, 1H), 7.29 (m, 5H), 5.64 (s, 2H), 4.24 (q, 2H), 1.25 (t, 3H).

d. 5-Benzyl-4-oxo-4,5-dihydro-3H-pyrrolo[3,2-d]pyrimidine-7-carboxylic acid

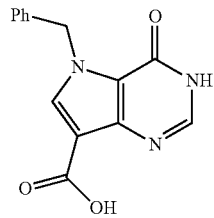 [SMILES: O=C(O)c1cn(Cc2ccccc2)c2c(=O)[nH]cnc12]

Ethyl 5-benzyl-4-oxo-4,5-dihydro-3H-pyrrolo[3,2-d]pyrimidine-7-carboxylate (1 g, 3.36 mmol) was dissolved in THF/H$_2$O (1:1, 30 mL). Lithium hydroxide monohydrate (620 mg, 14.87 mol) was added thereto at room temperature, stirred at 90° C. for 4 hrs, and cooled to room temperature. The resulting solution was filtered and the solid was washed with water to obtain the title compound (800 mg, 88%).

$^1$H NMR (CDCl$_3$+DMSO-d$_6$) δ12.1 (bs, 1H), 7.93 (s, 1H), 7.74 (s, 1H), 7.46 (s, 1H), 7.31 (m, 5H), 5.68 (m, 2H).

e. 5-Benzyl-N-(4-bromo-3,5-dimethoxyphenyl)-4-chloro-5H-pyrrolo[3,2-d]pyrimidine-7-carboxamide

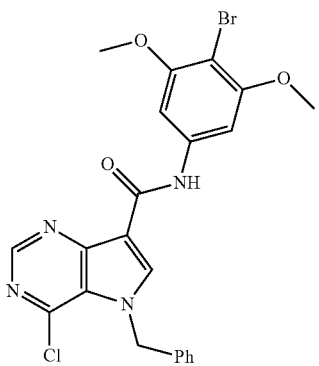 [SMILES: COc1cc(NC(=O)c2cn(Cc3ccccc3)c3c(Cl)ncnc23)cc(OC)c1Br]

5-Benzyl-4-oxo-4,5-dihydro-3H-pyrrolo[3,2-d]pyrimidine-7-carboxylic acid (793 mg, 2.94 mmol) was dissolved in POCl$_3$ (15 mL) and stirred at 110° C. for 2 hrs. The solution was cooled to room temperature and concentrated under a reduced pressure. To the resulting concentrate, THF (25 mL) was added, and then 4-bromo-3,5-dimethoxybenzene amine (682 mg, 2.94 mmol) and triethylamine (1.1 mL, 8.4 mmol) were added at 0° C., which was stirred at room temperature for 1 hr. The resulting solution was filtered and the solid was washed with THF to obtain the title compound (1.4 g, 95%).

$^1$H NMR (CDCl$_3$) δ10.20 (s, 1H), 8.89 (s, 1H), 8.27 (s, 1H), 7.38 (m, 3H), 7.18 (m, 2H), 7.12 (s, 2H), 5.78 (s, 2H), 3.95 (s, 6H).

f. 5-Benzyl-N-(4-bromo-2,6-dichloro-3,5-dimethoxyphenyl)-4-chloro-5H-pyrrolo[3,2-d]pyrimidine-7-carboxamide

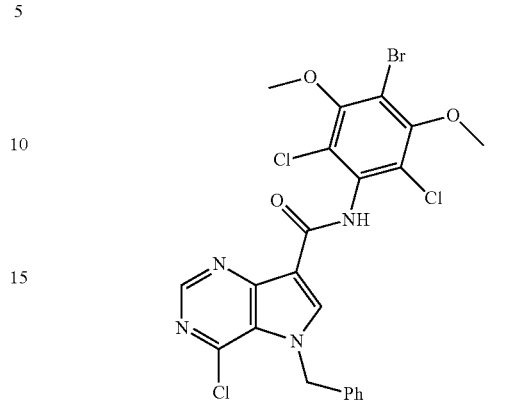

5-Benzyl-N-(4-bromo-3,5-dimethoxyphenyl)-4-chloro-5H-pyrrolo[3,2-d]pyrimidine-7-carboxamide (60 mg, 0.12 mmol) was dissolved in acetonitrile (1.5 mL), and a 2.0M SO$_2$Cl$_2$ acetonitrile solution (3.0 mL) was added thereto at 0° C. and stirred at room temperature for 1 hr. The solution was concentrated under a reduced pressure. To the resulting concentrate, dichloromethane and a saturated sodium bicarbonate solution were added. The aqueous layer was extracted with ethyl acetate dichloromethane. The combined organic layers were washed with a saline solution, dried over magnesium sulfate, and concentrated under a reduced pressure to obtain the title compound (37 mg, 54%).

$^1$H NMR (CDCl$_3$) δ0.10 (s, 1H), 8.89 (s, 1H), 8.30 (s, 1H), 7.40 (m, 3H), 7.20 (m, 2H), 5.76 (s, 2H), 3.92 (s, 6H).

Example 234: 4-Amino-5-benzyl-N-(4-bromo-2,6-dichloro-3,5-dimethoxyphenyl)-5H-pyrrolo[3,2-d]pyrimidine-7-carboxamide

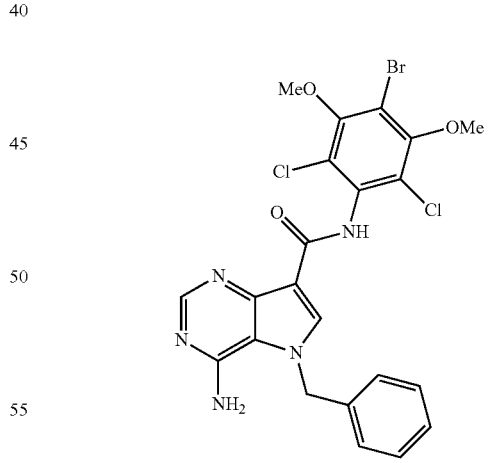

5-Benzyl-N-(4-bromo-2,6-dichloro-3,5-dimethoxyphenyl)-4-chloro-5H-pyrrolo[3,2-d]pyrimidine-7-carboxamide (200 mg, 0.30 mmol) was dissolved in a 7.0M ammonia methanol solution (6 mL), and stirred at 120° C. under a closed condition for 6 hrs. The reaction mixture was cooled to room temperature and concentrated under a reduced pressure. Ethyl acetate was added to the resulting concentrate, which was filtered to obtain the title compound (150 mg, 77%).

¹H NMR (DMSO-d₆) δ 10.32 (s. 1H), 8.29 (d, 2H), 7.48 (m, 3H), 7.26 (d, 2H), 7.02 (bs, 2H), 5.74 (d, 2H), 3.84 (s, 6H).

Example 235: 4-Amino-5-benzyl-N-(2,6-dichloro-3,5-dimethoxyphenyl)-5H-pyrrolo[3,2-d]pyrimidine-7-carboxamide

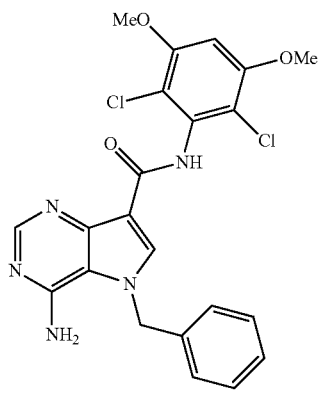 [SMILES: COc1cc(OC)c(Cl)c(NC(=O)c2cn(Cc3ccccc3)c3c(N)ncnc23)c1Cl]

4-Amino-5-benzyl-N-(4-bromo-2,6-dichloro-3,5-dimethoxyphenyl)-5H-pyrrolo[3,2-d]pyrimidine-7-carboxamide (30 mg, 0.054 mmol) was dissolved in THF (1 mL) and cooled to −78° C. A 1.6M n-BuLi hexane solution (0.34 mL, 0.54 mmol) was added thereto and stirred at −78° C. for 2 hrs. Water was added to the reaction mixture to terminate the reaction. The resulting solution was filtered and the solid was purified by silica gel chromatography (DCM:MeOH=50:1) to obtain the title compound (5 mg, 20%).

¹H NMR (DMSO-d₆) δ0.40 (s, 1H), 8.28 (s, 2H), 7.39 (m, 3H), 7.28 (m, 2H), 7.01 (s, 2H), 6.93 (s, 1H), 5.72 (s, 2H), 3.95 (s, 6H).

Examples 236 to 304

The procedure of Example 106, 108, 173 or 178 was repeated using each of the corresponding starting materials to obtain respective title compounds (Table 1).

Structures, NMR and/or Mass data of the compounds prepared in Examples 1 to 304 are shown in Table 1.

TABLE 1

| Ex. | Structure | Compound | MS m/z [M + 1] | NMR (¹H NMR 400 MHz, DMSO-d₆) |
|---|---|---|---|---|
| 1 | 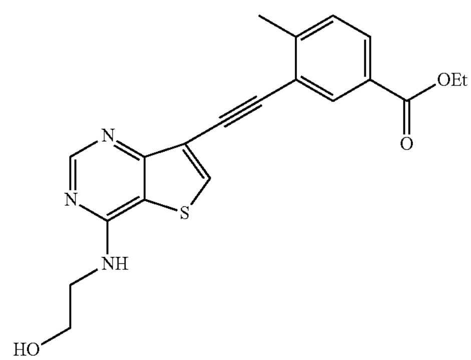 [SMILES: CCOC(=O)c1ccc(C)c(C#Cc2csc3c(NCCO)ncnc23)c1] | ethyl 3-((4-(2-hydroxyethylamino)thieno[3,2-d]pyrimidin-7-yl)ethynyl)-4-methyl benzoate | 382.59 | 8.52 (s, 1H), 8.47 (s, 1H), 8.09 (m, 1H), 8.03 (s, 1H), 7.89 (dd, 1H), 7.51 (d, 1H), 4.32 (q, 2H), 3.58 (m, 4H), 2.58 (s, 3H), 1.32 (t, 3H) |
| 2 | 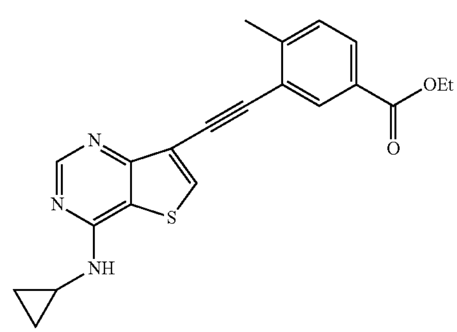 [SMILES: CCOC(=O)c1ccc(C)c(C#Cc2csc3c(NC4CC4)ncnc23)c1] | ethyl 3-((4-(cyclopropylamino)thieno[3,2-d]pyrimidin-7-yl)ethynyl)-4-methyl benzoate | 378.60 | 8.54 (s, 1H), 8.50 (s, 1H), 8.21 (m, 1H), 8.03 (d, 1H), 7.88 (dd, 1H), 7.50 (d, 1H), 4.32 (q, 2H), 2.98 (m, 1H), 2.58 (s, 3H), 1.32 (t, 3H), 0.78 (m, 2H), 0.65 (m, 2H). |

TABLE 1-continued

| Ex. | Structure | Compound | MS m/z [M + 1] | NMR (¹H NMR 400 MHz, DMSO-$d_6$) |
|---|---|---|---|---|
| 3 | 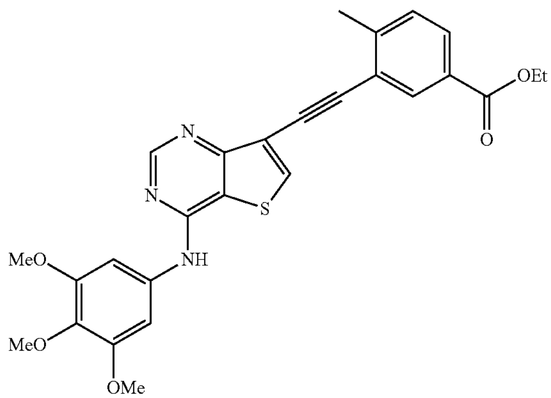 [SMILES: CCOC(=O)c1ccc(C)c(C#Cc2csc3c(Nc4cc(OC)c(OC)c(OC)c4)ncnc23)c1] | ethyl 4-methyl-3-((4-(3,4,5-trimethoxyphenyl-amino)thieno[3,2-d]pyrimidin-7-yl)ethynyl)benzoate | 504.82 | 9.80 (s, 1H), 8.67 (s, 1H), 8.56 (s, 1H), 8.05 (m, 1H), 7.89 (d, 1H), 7.49 (dd, 1H), 7.18 (s, 2H), 4.32 (q, 2H), 3.76 (s, 6H), 3.70 (s, 3H), 2.56 (s, 3H), 1.32 (t, 3H). |
| 4 | 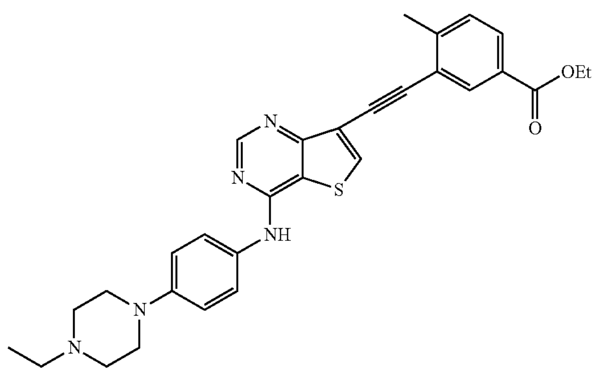 [SMILES: CCOC(=O)c1ccc(C)c(C#Cc2csc3c(Nc4ccc(N5CCN(CC)CC5)cc4)ncnc23)c1] | ethyl 3-((4-(4-(4-ethylpiperazin-1-yl)phenylamino)thieno[3,2-d]pyrimidin-7-yl)ethynyl)-4-methyl benzoate | 526.89 | 9.68 (s, 1H), 8.57 (s, 1H), 8.51 (s, 1H), 8.04 (m, 1H), 7.89 (d, 1H), 7.53 (m, 3H), 7.03 (d, 2H), 4.32 (q, 2H), 3.13 (m, 4H), 3.04 (m, 4H), 2.58 (s, 3H), 2.38 (q, 2H), 1.32 (t, 3H), 1.03 (t, 3H) |
| 5 | 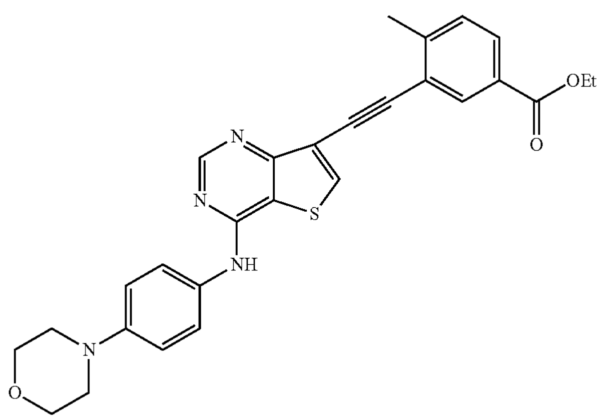 [SMILES: CCOC(=O)c1ccc(C)c(C#Cc2csc3c(Nc4ccc(N5CCOCC5)cc4)ncnc23)c1] | ethyl 4-methyl-3-((4-(4-morpholinophenyl-amino)thieno[3,2-d]pyrimidin-7-yl)ethynyl)benzoate | 499.80 | 9.70 (s, 1H), 8.58 (s, 1H), 8.51 (s, 1H), 8.04 (m, 1H), 7.87 (d, 1H), 7.52 (m, 3H), 6.98 (d, 2H), 4.32 (q, 2H), 3.73 (m, 4H), 3.10 (m, 4H), 2.59 (s, 3H), 1.33 (t, 3H) |
| 6 | 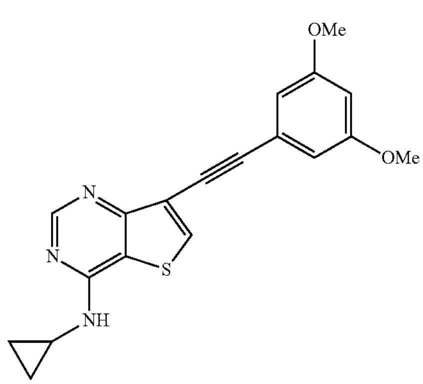 [SMILES: COc1cc(C#Cc2csc3c(NC4CC4)ncnc23)cc(OC)c1] | N-cyclopropyl-7-((3,5-dimethoxyphenyl)ethynyl)thieno[3,2-d]pyrimidine-4-amine | 352.50 | 8.67 (s, 1H), 8.63 (s, 1H), 8.55 (s, 1H), 6.75 (s, 2H), 6.60 (s, 1H), 3.79 (s, 6H), 3.07 (m, 1H), 0.87 (m, 2H), 0.70 (m, 2H) |

TABLE 1-continued

| Ex. | Structure | Compound | MS m/z [M + 1] | NMR ($^1$H NMR 400 MHz, DMSO-d$_6$) |
|---|---|---|---|---|
| 7 | 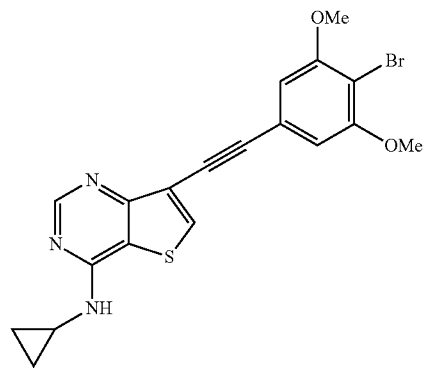 [SMILES: COc1cc(C#Cc2csc3c(NC4CC4)ncnc23)cc(OC)c1Br] | 7-((4-bromo-3,5-dimethoxyphenyl)ethynyl)-N-cyclopropylthieno[3,2-d]pyrimidine-4-amine | 430.36 | 8.62(br, 1H), 8.55(s, 1H), 8.23(s, 1H), 6.91(s, 1H), 3.90(s, 6H), 3.00(m, 1H), 0.81(m, 2H), 0.66(m, 2H) |
| 8 | 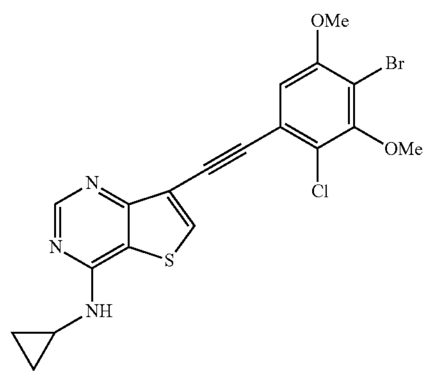 [SMILES: COc1cc(C#Cc2csc3c(NC4CC4)ncnc23)c(Cl)c(OC)c1Br] | 7-((4-bromo-2-chloro-3,5-dimethoxyphenyl)ethynyl)-N-cyclopropylthieno[3,2-d]pyrimidine-4-amine | 464.47 | 8.54(s, 2H), 8.23(s, 1H), 7.21(s, 1H), 3.93(s, 3H), 3.83(s, 3H), 3.00(m, 1H), 0.82(m, 2H), 0.66(m, 2H) |
| 9 | 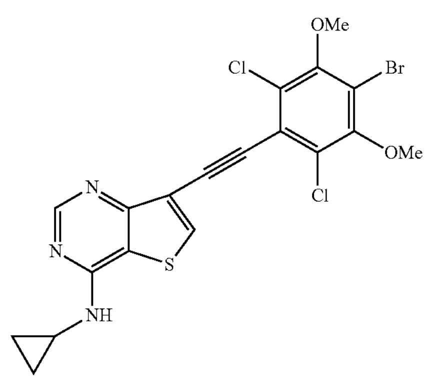 [SMILES: COc1c(Cl)c(C#Cc2csc3c(NC4CC4)ncnc23)c(Cl)c(OC)c1Br] | 7-((4-bromo-2,6-dichloro-3,5-dimethoxyphenyl)ethynyl)-N-cyclopropylthieno[3,2-d]pyrimidine-4-amine | 498.44 | 8.60(s, 1H), 8.54(s, 1H), 8.25(s, 1H), 3.86(s, 6H), 3.00(m, 1H), 0.81(m, 2H), 0.66(m, 2H) |
| 10 | 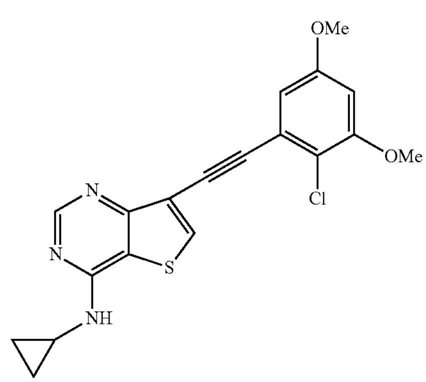 [SMILES: COc1cc(C#Cc2csc3c(NC4CC4)ncnc23)c(Cl)c(OC)c1] | 7-((2-chloro-3,5-dimethoxyphenyl)ethynyl)-N-cyclopropylthieno[3,2-d]pyrimidine-4-amine | 386.57 | 8.53(s, 1H), 8.49(s, 1H), 8.23(s, 1H), 6.81(d, 1H), 6.78(d, 1H), 2.99(m, 1H), 0.81(m, 2H), 0.65(m, 2H) |

TABLE 1-continued

| Ex. | Structure | Compound | MS m/z [M + 1] | NMR ($^1$H NMR 400 MHz, DMSO-$d_6$) |
|---|---|---|---|---|
| 11 | 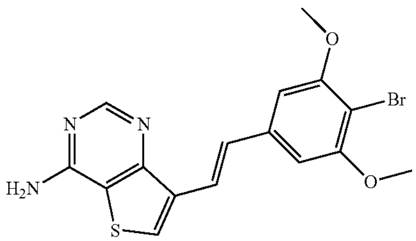 [SMILES: COc1cc(/C=C/c2csc3c(N)ncnc23)cc(OC)c1Br] | 7-(4-bromo-3,5-dimethoxystyryl)thieno[3,2-d]pyrimidine-4-amine | 392.0 393.99 | 8.48(s, 1H), 8.19(s, 1H), 7.91(d, 1H), 7.48(s, 2H), 7.45(d, 1H), 6.93(s, 2H), 3.90(s, 6H) |
| 12 | 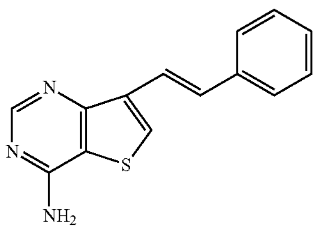 [SMILES: Nc1ncnc2c(/C=C/c3ccccc3)csc12] | (E)-7-styrylthieno[3,2-d]pyrimidine-4-amine | 254.21 | 8.48(s, 1H), 8.22(s, 1H), 7.58(d, 2H), 7.46(s, 2H), 7.41(d, 2H), 7.37(t, 2H), 7.28(t, 1H) |
| 13 | 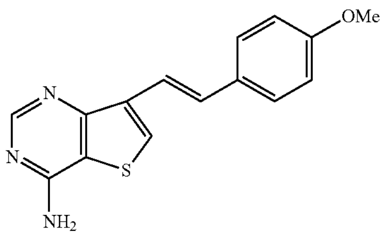 [SMILES: COc1ccc(/C=C/c2csc3c(N)ncnc23)cc1] | (E)-7-(4-methoxystyryl)thieno[3,2-d]pyrimidine-4-amine | 284.27 | 8.46(s, 1H), 8.14(s, 1H), 7.54(d, 2H), 7.47(s, 2H), 7.33(d, 2H), 6.97(d, 2H), 3.78(s, 3H) |
| 14 | 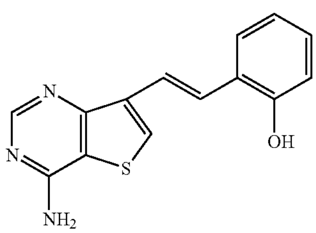 [SMILES: Nc1ncnc2c(/C=C/c3ccccc3O)csc12] | (E)-2-(2-(4-aminothieno[3,2-d]pyrimidin-7-yl)vinyl)phenol | 270.23 | 9.75(br, 1H), 8.45(s, 1H), 8.17(s, 1H), 7.93(d, 2H), 7.52(d, 1H), 7.46(s, 2H), 7.07(t, 1H), 6.88(d, 1H), 6.82(t, 1H) |
| 15 | 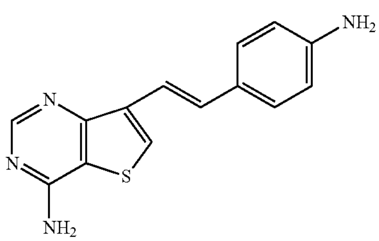 | (E)-7-(4-aminostyryl)thieno[3,2-d]pyrimidine-4-amine | 269.22 | 8.43(s, 1H), 8.01(s, 1H), 7.62(d, 1H), 7.42(s, 2H), 7.24(d, 2H), 7.12(d, 1H), 6.55(d, 2H), 5.31(s, 2H) |
| 16 | 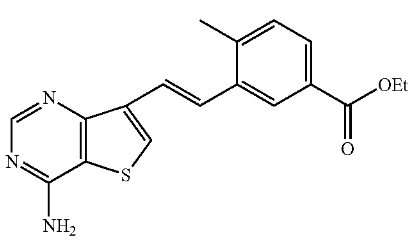 [SMILES: CCOC(=O)c1ccc(C)c(/C=C/c2csc3c(N)ncnc23)c1] | (E)-ethyl 3-(2-(4-aminothieno[3,2-d]pyrimidin-7-yl)vinyl)-4-methyl benzoate | 340.28 | 8.48(s, 1H), 8.34(s, 1H), 8.19(s, 1H), 8.14(d, 1H), 7.75(d, 1H), 7.50(s, 2H), 7.39(d, 1H), 7.36(d, 1H), 4.32(q, 2H), 2.49(s, 3H), 1.32(t, 3H), |

TABLE 1-continued

| Ex. | Structure | Compound | MS m/z [M + 1] | NMR (¹H NMR 400 MHz, DMSO-$d_6$) |
|---|---|---|---|---|
| 17 | 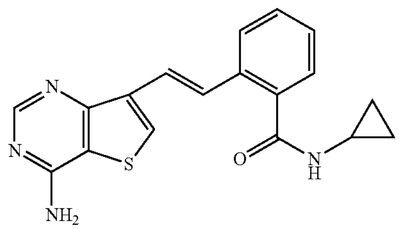 [SMILES: Nc1ncnc2c(/C=C/c3ccccc3C(=O)NC3CC3)csc12] | (E)-2-(2-(4-aminothieno[3,2-d]pyrimidin-7-yl)vinyl)-N-cyclopropylbenzamide | 337.30 | — |
| 18 | 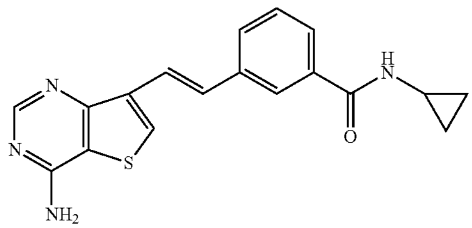 [SMILES: Nc1ncnc2c(/C=C/c3cccc(C(=O)NC4CC4)c3)csc12] | (E)-3-(2-(4-aminothieno[3,2-d]pyrimidin-7-yl)vinyl)-N-cyclopropylbenzamide | 337.30 | 8.55(d, 1H), 8.48(s, 1H), 8.25(s, 1H), 8.09(d, 1H), 8.03(s, 1H) 7.92(d, 1H), 7.71(d, 2H), 7.52(s, 2H), 7.45(t, 1H), 2.87(m, 1H), 0.70(m, 2H), 0.60(m, 2H) |
| 19 | 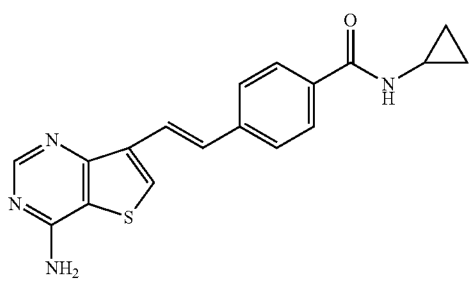 [SMILES: Nc1ncnc2c(/C=C/c3ccc(C(=O)NC4CC4)cc3)csc12] | (E)-4-(2-(4-aminothieno[3,2-d]pyrimidin-7-yl)vinyl)-N-cyclopropylbenzamide | 337.82 | 8.50(s, 1H), 8.43(d, 1H), 8.26(s, 1H), 7.95(d, 2H), 7.84(d, 2H), 7.66(d, 2H), 7.53(d, 2H), 2.84(m, 1H), 0.69(m, 2H), 0.59(m, 2H) |
| 20 | 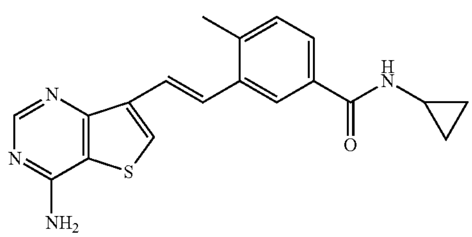 [SMILES: Cc1ccc(C(=O)NC2CC2)cc1/C=C/c1csc2c(N)ncnc12] | (E)-3-(2-(4-aminothieno[3,2-d]pyrimidin-7-yl)vinyl)-N-cyclopropyl-4-methylbenzamide | 351.33 | 8.51(d, 1H), 8.32(s, 1H), 8.48(s, 1H), 8.11(s, 1H), 8.07(d, 1H), 7.65(d, 1H), 7.52(s, 2H), 7.46(d, 1H), 7.30(d, 1H), 2.85(m, 1H), 2.44(s, 3H), 0.71(m, 2H), 0.60(m, 2H) |
| 21 | 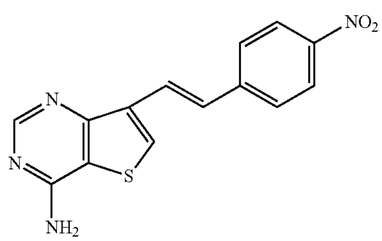 [SMILES: Nc1ncnc2c(/C=C/c3ccc([N+](=O)[O-])cc3)csc12] | (E)-7-(4-nitrostyryl)thieno[3,2-d]pyrimidine-4-amine | 299.24 | 8.48(s, 1H), 8.37(s, 1H), 8.35(d, 2H), 8.22(d, 1H), 8.06(d, 2H), 7.84(d, 1H), 7.45(s, 2H) |
| 22 | 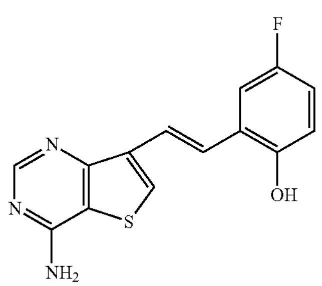 [SMILES: Nc1ncnc2c(/C=C/c3cc(F)ccc3O)csc12] | (E)-2-(2-(4-aminothieno[3,2-d]pyrimidin-7-yl)vinyl)-4-fluorophenol | 288.19 | 9.75(br, 1H), 8.46(s, 1H), 8.16(s, 1H), 8.02(d, 1H), 7.45(s, 2H), 7.44(d, 1H), 7.35(d, 1H), 6.93(t, 1H), 6.84(d, 1H) |

TABLE 1-continued

| Ex. | Structure | Compound | MS m/z [M + 1] | NMR ($^1$H NMR 400 MHz, DMSO-$d_6$) |
|---|---|---|---|---|
| 23 | 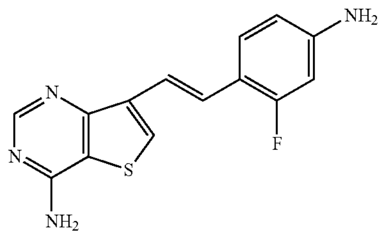 | (E)-7-(4-amino-2-fluorostyryl)thieno[3,2-d]pyrimidine-4-amine | 287.18 | — |
| 24 | 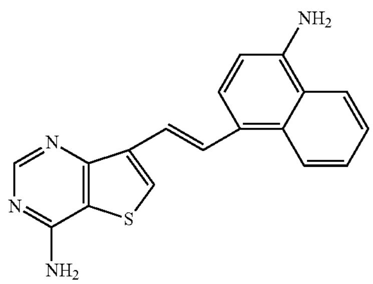 [SMILES: Nc1ccc(/C=C/c2csc3c(N)ncnc23)c2ccccc12] | (E)-7-(2-(4-aminonaphthalen-1-yl)vinyl)thieno[3,2-d]pyrimidine-4-amine | 319.29 | 8.55(d, 1H), 8.50(s, 1H), 8.23(s, 1H), 8.22(d, 1H), 8.11(d, 1H), 7.67(d, 1H), 7.53(t, 1H), 7.46(s, 2H), 7.42(t, 1H), 7.28(d, 1H), 6.75(d, 1H), 6.00(s, 2H) |
| 25 | 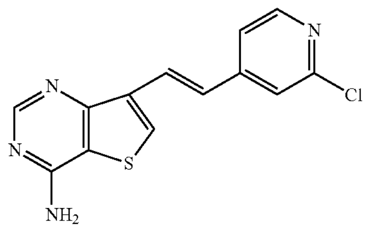 [SMILES: Nc1ncnc2c(/C=C/c3ccnc(Cl)c3)csc12] | (E)-7-(2-(2-chloropyridin-4-yl)vinyl)thieno[3,2-d]pyrimidine-4-amine | 289.21 | 8.49(s, 1H), 8.37(d, 1H), 8.33(s, 1H), 7.90(d, 1H), 7.84(d, 1H), 7.70(s, 1H), 7.59(d, 1H), 7.56(s, 2H) |
| 26 | 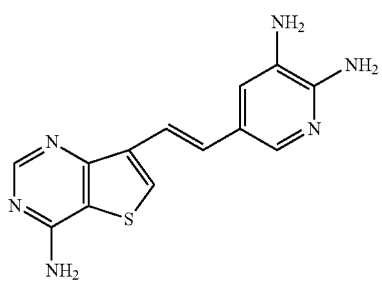 [SMILES: Nc1cc(/C=C/c2csc3c(N)ncnc23)cnc1N] | (E)-5-(2-(4-aminothieno[3,2-d]pyrimidin-7-yl)vinyl)pyridine-2,3-diamine | 285.21 | — |
| 27 | 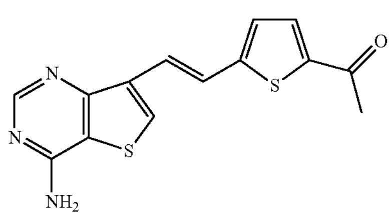 [SMILES: CC(=O)c1ccc(/C=C/c2csc3c(N)ncnc23)s1] | (E)-1-(5-(2-(4-aminothieno[3,2-d]pyrimidin-7-yl)vinyl)thiophen-2-yl)ethanone | 302.31 | 8.46(s, 1H), 8.29(s, 1H), 8.15(d, 1H), 7.86(d, 1H), 7.58(d, 1H), 7.46(s, 2H), 7.35(d, 1H), 2.51(s, 3H) |
| 28 | 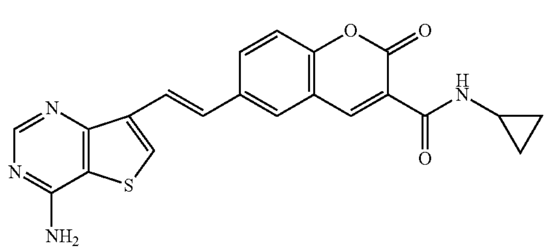 [SMILES: Nc1ncnc2c(/C=C/c3ccc4oc(=O)c(C(=O)NC5CC5)cc4c3)csc12] | (E)-6-(2-(4-aminothieno[3,2-d]pyrimidin-7-yl)vinyl)-N-cyclopropyl-2-oxo-2H-chromene-3-carboxamide | 405.34 | — |

TABLE 1-continued

| Ex. | Structure | Compound | MS m/z [M + 1] | NMR ($^1$H NMR 400 MHz, DMSO-$d_6$) |
|---|---|---|---|---|
| 29 | 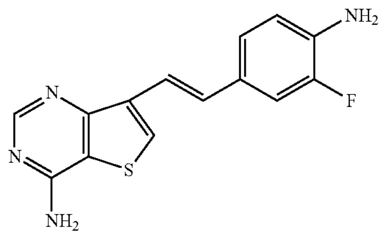 [SMILES: Nc1ccc(/C=C/c2csc3c(N)ncnc23)cc1F] | (E)-7-(4-amino-3-fluorostyryl)thieno[3,2-d]pyrimidine-4-amine | 287.25 | 8.45(s, 1H), 8.05(s, 1H), 7.66(d, 1H), 7.45(s, 2H), 7.24(d, 1H), 7.18(d, 1H), 7.10(d, 1H), 6.75(t, 1H), 5.36(br, 2H) |
| 30 | 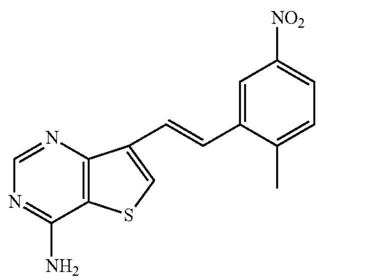 [SMILES: Cc1ccc([N+](=O)[O-])cc1/C=C/c1csc2c(N)ncnc12] | (E)-7-(2-methyl-5-nitrostyryl)thieno[3,2-d]pyrimidine-4-amine | 313.25 | 8.50(s, 1H), 8.44(d, 1H), 8.37(s, 1H), 8.25(d, 1H), 8.04(d, 1H), 7.56(d, 1H), 7.52(d, 1H), 7.45(s, 2H), 2.58(s, 3H) |
| 31 | 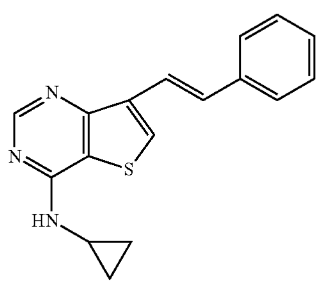 [SMILES: C(=C\c1csc2c(NC3CC3)ncnc12)/c1ccccc1] | (E)-N-cyclopropyl-7-styrylthieno[3,2-d]pyrimidine-4-amine | 294.28 | 8.62(s, 1H), 8.23(s, 1H), 8.05(s, 1H), 7.85(d, 1H), 7.59(d, 2H), 7.47(d, 1H), 7.35(d, 2H), 7.28(t, 1H), 2.98(m, 1H), 0.80(m, 2H), 0.66(m, 2H) |
| 32 | 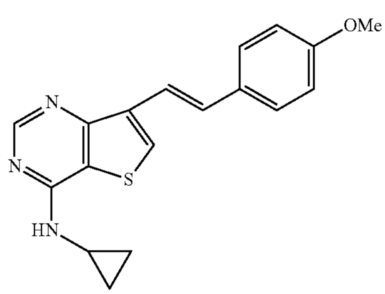 [SMILES: COc1ccc(/C=C/c2csc3c(NC4CC4)ncnc23)cc1] | (E)-N-cyclopropyl-7-(4-methoxystyryl)thieno[3,2-d]pyrimidine-4-amine | 324.33 | 8.55(s, 1H), 8.15(s, 1H), 8.03(s, 1H), 7.77(d, 1H), 7.53(d, 2H), 7.31(d, 1H), 6.95(d, 2H), 3.78(s, 3H), 2.98(m, 1H), 0.80(m, 2H), 0.65(m, 2H) |
| 33 | 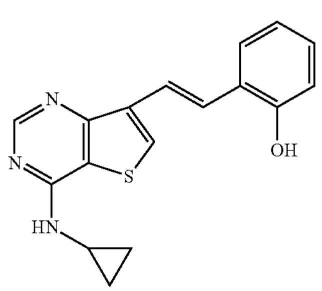 [SMILES: Oc1ccccc1/C=C/c1csc2c(NC3CC3)ncnc12] | (E)-2-(2-(4-(cyclopropylamino)thieno[3,2-d]pyrimidin-7-yl)vinyl)phenol | 310.30 | 9.74(br, 1H), 8.54(s, 1H), 8.18(s, 1H), 8.01(s, 1H), 7.95(d, 1H), 7.53(d, 1H), 7.45(d, 1H), 7.09(t, 1H), 6.87(d, 1H), 6.82(d, 1H), 2.98(m, 1H), 0.80(m, 2H), 0.65(m, 2H) |

TABLE 1-continued

| Ex. | Structure | Compound | MS m/z [M + 1] | NMR (¹H NMR 400 MHz, DMSO-d$_6$) |
|---|---|---|---|---|
| 34 | 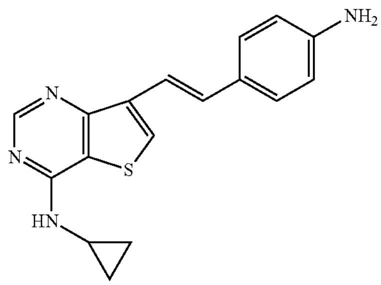 | (E)-7-(4-aminostyryl)-N-cyclopropylthieno[3,2-d]pyrimidine-4-amine | 309.32 | 8.54(s, 1H), 8.05(s, 1H), 8.02(s, 1H), 7.59(d, 1H), 7.28(d, 2H), 7.14(d, 1H), 6.57(d, 2H), 2.98(m, 1H), 0.80(m, 2H), 0.65(m, 2H) |
| 35 | 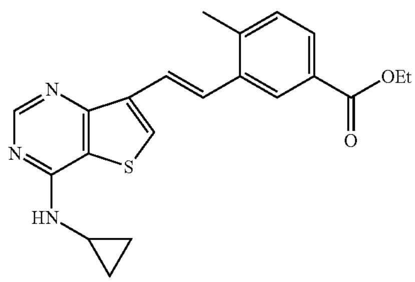 [SMILES: CCOC(=O)c1ccc(C)c(/C=C/c2csc3c(NC4CC4)ncnc23)c1] | (E)-ethyl 3-(2-(4-(cyclopropylamino)thieno[3,2-d]pyrimidin-7-yl)vinyl)-4-methyl benzoate | 380.40 | 8.57(s, 1H), 8.37(s, 1H), 8.21(s, 1H), 8.16(d, 1H), 8.08(s, 1H), 7.77(d, 1H), 7.41(d, 1H), 7.38(d, 1H), 4.34(q, 2H), 3.00(m, 1H), 1.34(t, 3H), 0.80(m, 2H), 0.66(m, 2H) |
| 36 | 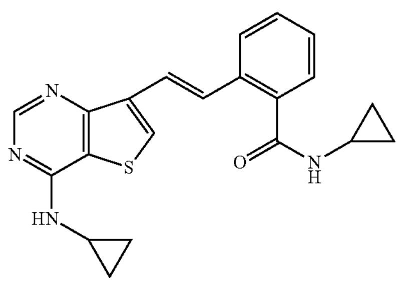 [SMILES: O=C(NC1CC1)c1ccccc1/C=C/c1csc2c(NC3CC3)ncnc12] | (E)-N-cyclopropyl-2-(2-(4-(cyclopropylamino)thieno[3,2-d]pyrimidin-7-yl)vinyl)benzamide | 377.36 | 8.53(s, 1H), 8.42(d, 1H), 8.16(s, 1H), 8.04(s, 1H), 8.02(d, 1H), 7.79(d, 1H), 7.45(d, 1H), 7.42(d, 1H), 7.40(t, 1H), 7.31(t, 1H), 2.99(m, 1H), 2.82(m, 1H), 0.80(m, 2H), 0.68(m, 2H), 0.63(m, 2H), 0.56(m, 2H) |
| 37 | 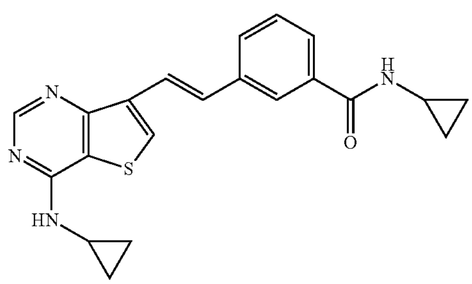 [SMILES: O=C(NC1CC1)c1cccc(/C=C/c2csc3c(NC4CC4)ncnc23)c1] | (E)-N-cyclopropyl-3-(2-(4-(cyclopropylamino)thieno[3,2-d]pyrimidin-7-yl)vinyl)benzamide | 377.36 | 8.57(s, 1H), 8.55(d, 1H), 8.26(s, 1H), 8.07(s, 1H), 8.04(s, 1H), 7.94(d, 1H), 7.72(d, 2H), 7.55(d, 1H), 7.46(t, 1H), 3.00(m, 1H), 2.88(m, 1H), 0.80(m, 2H), 0.71(m, 2H), 0.65(m, 2H), 0.60(m, 2H) |
| 38 | 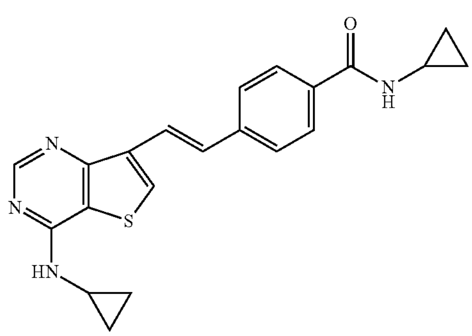 [SMILES: O=C(NC1CC1)c1ccc(/C=C/c2csc3c(NC4CC4)ncnc23)cc1] | (E)-N-cyclopropyl-4-(2-(4-(cyclopropylamino)thieno[3,2-d]pyrimidin-7-yl)vinyl)benzamide | 377.36 | — |

TABLE 1-continued

| Ex. | Structure | Compound | MS m/z [M + 1] | NMR (¹H NMR 400 MHz, DMSO-d$_6$) |
|---|---|---|---|---|
| 39 | 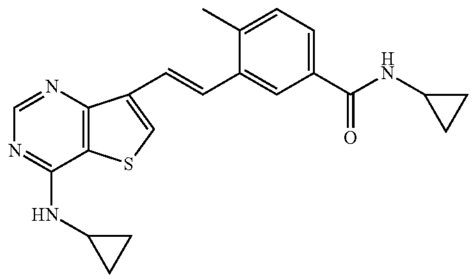 [SMILES: Cc1ccc(C(=O)NC2CC2)cc1/C=C/c1csc2c(NC3CC3)ncnc12] | (E)-N-cyclopropyl-3-(2-(4-(cyclopropylamino)thieno[3,2-d]pyrimidin-7-yl)vinyl)-4-methylbenzamide | 391.40 | 8.57(s, 1H), 8.52(d, 1H), 8.33(s, 1H), 8.12(s, 1H), 8.09(d, 1H), 8.02(s, 1H), 7.64(d, 1H), 7.45(d, 1H), 7.27(d, 1H), 3.00(m, 1H), 2.86(m, 1H), 2.44(s, 3H), 0.81(m, 2H), 0.71(m, 2H), 0.65(m, 2H), 0.60(m, 2H) |
| 40 | 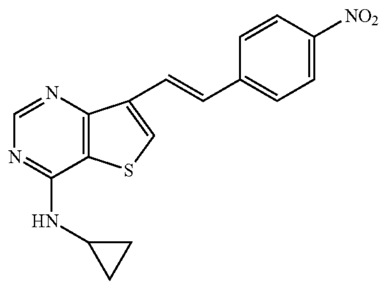 [SMILES: O=[N+]([O-])c1ccc(/C=C/c2csc3c(NC4CC4)ncnc23)cc1] | (E)-N-cyclopropyl-7-(4-nitrostyryl)thieno[3,2-d]pyrimidine-4-amine | — | 8.58(s, 1H), 8.37(s, 1H), 8.36(d, 2H), 8.22(d, 1H), 8.12(s, 1H), 8.07(d, 2H), 7.85(d, 1H), 3.00(m, 1H), 0.81(m, 2H), 0.65(m, 2H) |
| 41 | 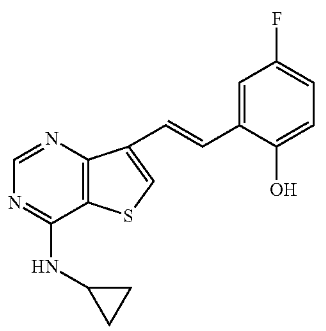 [SMILES: Oc1ccc(F)cc1/C=C/c1csc2c(NC3CC3)ncnc12] | (E)-2-(2-(4-(cyclopropylamino)thieno[3,2-d]pyrimidin-7-yl)vinyl)-4-fluorophenol | 328.26 | 9.75(br, 1H), 9.34(s, 1H), 8.56(s, 1H), 8.25(s, 1H), 8.02(s, 1H), 8.00(d, 1H), 7.47(d, 1H), 7.37(d, 1H), 6.87(d, 1H), 2.98(m, 1H), 0.80(m, 2H), 0.65(m, 2H) |
| 42 | 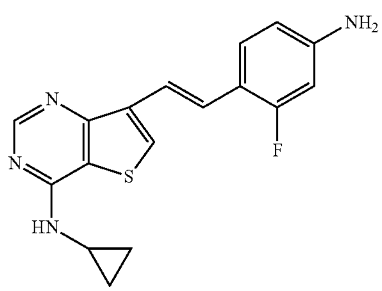 [SMILES: Nc1ccc(/C=C/c2csc3c(NC4CC4)ncnc23)c(F)c1] | (E)-7-(4-amino-2-fluorostyryl)-N-cyclopropylthieno[3,2-d]pyrimidine-4-amine | 327.25 | — |
| 43 | 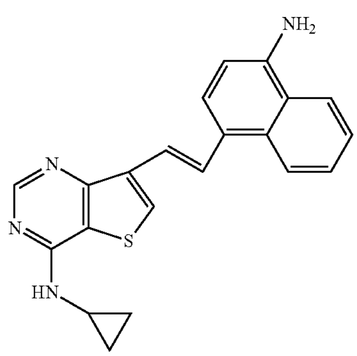 [SMILES: Nc1ccc(/C=C/c2csc3c(NC4CC4)ncnc23)c2ccccc12] | (E)-7-(2-(4-aminonaphthalen-1-yl)vinyl)-N-cyclopropylthieno[3,2-d]pyrimidine-4-amine | 359.29 | 8.59(s, 1H), 8.54(d, 1H), 8.25(s, 1H), 8.23(d, 1H), 8.11(d, 1H), 7.68(d, 1H), 7.53(t, 1H), 7.41(t, 1H), 7.29(d, 1H), 6.75(d, 1H), 6.00(s, 2H), 3.00(m, 1H), 0.81(m, 2H), 0.66(m, 2H) |

TABLE 1-continued

| Ex. | Structure | Compound | MS m/z [M + 1] | NMR (¹H NMR 400 MHz, DMSO-d$_6$) |
|---|---|---|---|---|
| 44 | 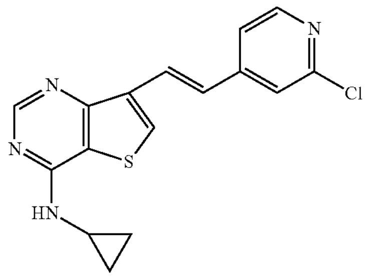 [SMILES: Clc1cc(/C=C/c2csc3c(NC4CC4)ncnc23)ccn1] | (E)-7-(2-(2-chloropyridin-4-yl)vinyl)-N-cyclopropylthieno[3,2-d]pyrimidine-4-amine | 329.27 | — |
| 45 | 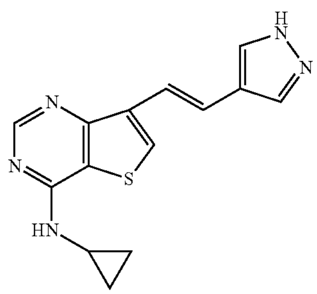 [SMILES: C(=C\c1csc2c(NC3CC3)ncnc12)/c1cn[nH]c1] | (E)-7-(2-(1H-pyrazol-4-yl)vinyl)-N-cyclopropylthieno[3,2-d]pyrimidine-4-amine | 284.27 | 8.64(s, 1H), 8.45(s, 1H), 8.25(s, 1H), 8.04(s, 1H), 7.97(s, 1H), 7.88(br, 1H), 7.73(d, 1H), 7.14(d, 1H), 2.98(m, 1H), 0.80(m, 2H), 0.63(m, 2H) |
| 46 | 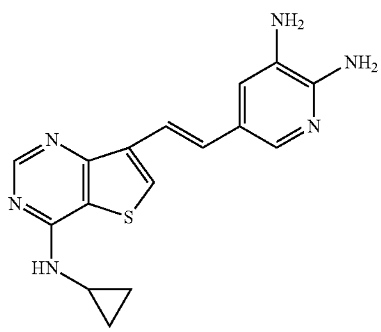 [SMILES: Nc1cc(/C=C/c2csc3c(NC4CC4)ncnc23)cnc1N] | (E)-5-(2-(4-(cyclopropylamino)thieno[3,2-d]pyrimidin-7-yl)vinyl)pyridine-2,3-diamine | 325.26 | — |
| 47 | 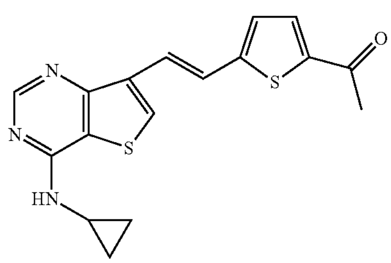 [SMILES: CC(=O)c1ccc(/C=C/c2csc3c(NC4CC4)ncnc23)s1] | (E)-1-(5-(2-(4-(cyclopropylamino)thieno[3,2-d]pyrimidin-7-yl)vinyl)thiophen-2-yl)ethanone | 342.30 | — |
| 48 | 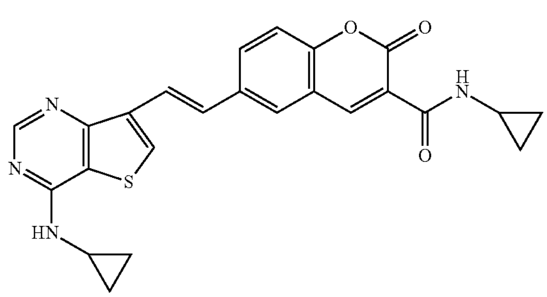 [SMILES: O=C(NC1CC1)c1cc2cc(/C=C/c3csc4c(NC5CC5)ncnc34)ccc2oc1=O] | (E)-N-cyclopropyl-6-(2-(4-(cyclopropylamino)thieno[3,2-d]pyrimidin-7-yl)vinyl)-2-oxo-2H-chromene-3-carboxamide | 445.34 | — |

TABLE 1-continued

| Ex. | Structure | Compound | MS m/z [M + 1] | NMR ($^1$H NMR 400 MHz, DMSO-$d_6$) |
|---|---|---|---|---|
| 49 | 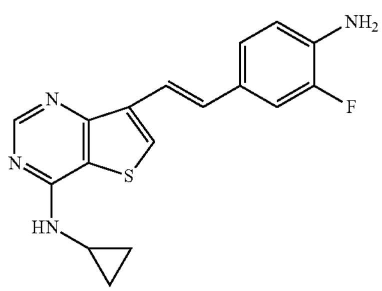 [SMILES: Nc1ccc(/C=C/c2csc3c(NC4CC4)ncnc23)cc1F] | (E)-7-(4-amino-3-fluorostyryl)-N-cyclopropylthieno[3,2-d]pyrimidine-4-amine | 327.26 | 8.54(s, 1H), 8.06(s, 1H), 8.01(d, 1H), 7.64(d, 1H), 7.24(d, 1H), 7.19(d, 1H), 7.10(d, 1H), 6.75(t, 1H), 5.36(br, 2H), 2.98(m, 1H), 0.79(m, 2H), 0.65(m, 2H) |
| 50 | 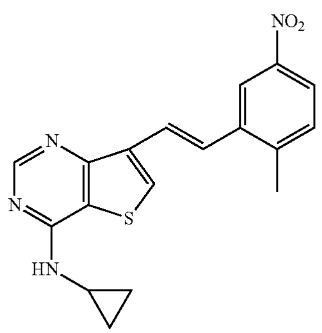 [SMILES: Cc1ccc([N+](=O)[O-])cc1/C=C/c1csc2c(NC3CC3)ncnc12] | (E)-N-cyclopropyl-7-(2-methyl-5-nitrostyryl)thieno[3,2-d]pyrimidine-4-amine | 353.28 | 8.58(s, 1H), 8.44(d, 1H), 8.37(s, 1H), 8.23(d, 1H), 8.08(d, 1H), 8.03(d, 1H), 7.54(d, 1H), 7.52(d, 1H), 3.00(m, 1H), 2.53(s, 3H), 0.80(m, 2H), 0.64(m, 2H) |
| 51 | 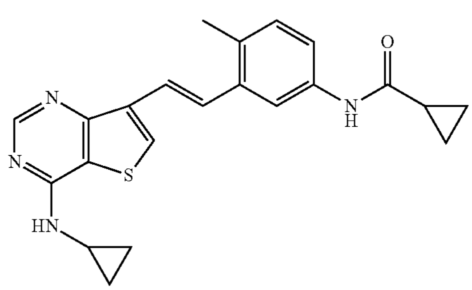 [SMILES: Cc1ccc(NC(=O)C2CC2)cc1/C=C/c1csc2c(NC3CC3)ncnc12] | (E)-N-(3-(2-(4-(cyclopropylamino)thieno[3,2-d]pyrimidin-7-yl)vinyl)-4-methylphenyl)cyclopropanecarboxamide | 391.35 | 10.17(s, 1H), 8.55(s, 1H), 8.35(s, 1H), 8.04(s, 1H), 7.97(d, 1H), 7.41(d, 1H), 7.30(d, 1H), 7.12(d, 1H), 3.00(m, 1H), 2.36(s, 3H), 1.75(m, 1H), 0.80(m, 6H), 0.64(m, 2H) |
| 52 | 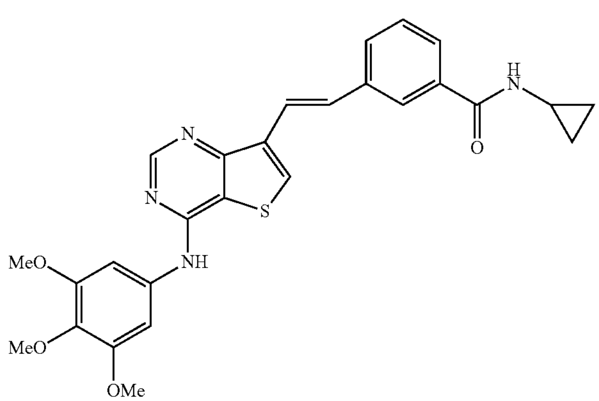 [SMILES: COc1cc(Nc2ncnc3c(/C=C/c4cccc(C(=O)NC5CC5)c4)csc23)cc(OC)c1OC] | (E)-N-cyclopropyl-3-(2-(4-(3,4,5-trimethoxyphenylamino)thieno[3,2-d]pyrimidin-7-yl)vinyl)benzamide | 503.59 | 9.71(s, 1H), 8.70(s, 1H), 8.56(d, 1H), 8.35(s, 1H), 8.05(s, 1H), 7.93(d, 1H), 7.74(d, 1H), 7.72(s, 1H), 7.58(d, 1H), 7.46(t, 1H), 7.21(s, 2H), 3.78(s, 6H), 3.66(s, 3H), 2.87(m, 1H), 0.70(m, 2H), 0.60(m, 2H) |

TABLE 1-continued

| Ex. | Structure | Compound | MS m/z [M + 1] | NMR ($^1$H NMR 400 MHz, DMSO-$d_6$) |
|---|---|---|---|---|
| 53 | 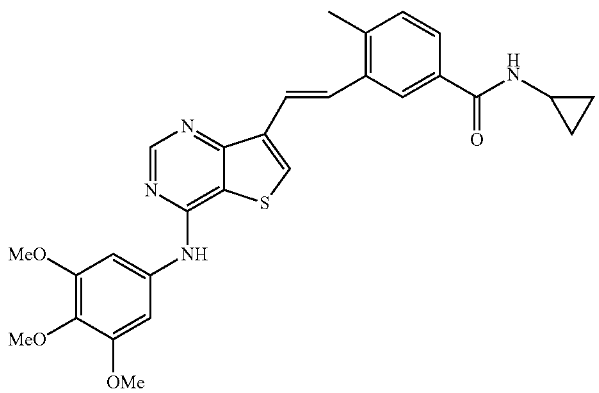 [SMILES: COc1cc(Nc2ncnc3c(/C=C/c4cc(C(=O)NC5CC5)ccc4C)csc23)cc(OC)c1OC] | (E)-N-cyclopropyl-4-methyl-3-(2-(4-(3,4,5-trimethoxyphenyl-amino)thieno[3,2-d]pyrimidin-7-yl)vinyl)benzamide | 517.62 | 9.66(s, 1H), 8.62(s, 1H), 8.52(d, 1H), 8.42(s, 1H), 8.13(s, 1H), 8.08(d, 1H), 7.64(d, 1H), 7.48(d, 1H), 7.29(d, 1H), 7.20(s, 2H), 3.78(s, 6H), 3.65(s, 3H), 2.87(m, 1H), 0.70(m, 2H), 0.59(m, 2H) |
| 54 | 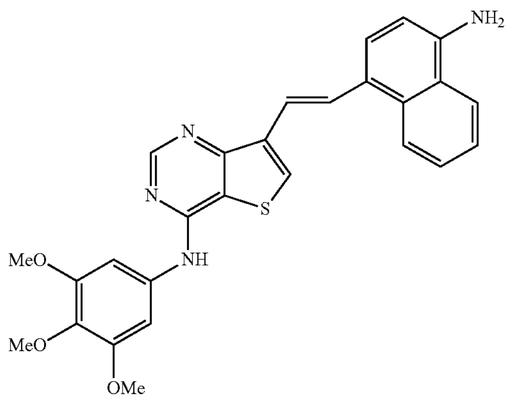 [SMILES: COc1cc(Nc2ncnc3c(/C=C/c4ccc(N)c5ccccc45)csc23)cc(OC)c1OC] | (E)-7-(2-(4-aminonaphthalen-1-yl)vinyl)-N-(3,4,5-trimethoxyphenyl)thieno[3,2-d]pyrimidine-4-amine | 485.57 | — |
| 55 | 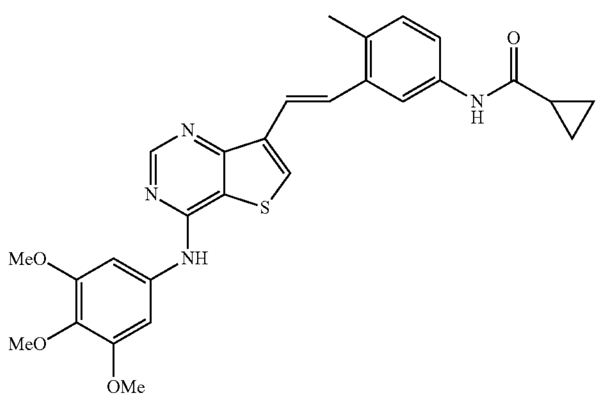 [SMILES: COc1cc(Nc2ncnc3c(/C=C/c4cc(NC(=O)C5CC5)ccc4C)csc23)cc(OC)c1OC] | (E)-N-(4-methyl-3-(2-(4-(3,4,5-trimethoxyphenyl-amino)thieno[3,2-d]pyrimidin-7-yl)vinyl)phenyl)cyclopropanecarbox-amide | 517.63 | — |
| 56 | 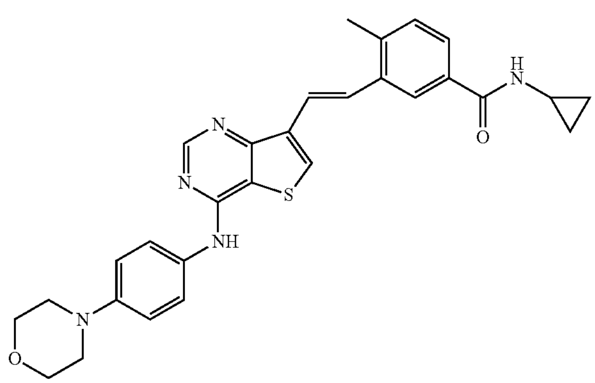 [SMILES: Cc1ccc(C(=O)NC2CC2)cc1/C=C/c1csc2c(Nc3ccc(N4CCOCC4)cc3)ncnc12] | (E)-N-cyclopropyl-4-methyl-3-(2-(4-(4-morpholinophenyl-amino)thieno[3,2-d]pyrimidin-7-yl)vinyl)benzamide | 512.65 | — |

TABLE 1-continued

| Ex. | Structure | Compound | MS m/z [M + 1] | NMR (¹H NMR 400 MHz, DMSO-d₆) |
|---|---|---|---|---|
| 57 | 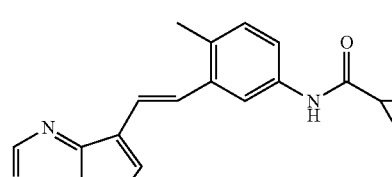 | (E)-N-(4-methyl-3-(2-(4-(4-morpholinophenyl-amino)thieno[3,2-d]pyrimidin-7-yl)vinyl)phenyl)cyclopropanecarbox-amide | 512.64 | — |
| 58 | 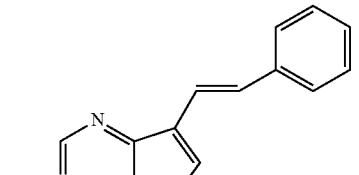 | (E)-N-(4-(4-ethylpiperazin-1-yl)phenyl)-7-styrylthieno[3,2-d]pyrimidine-4-amine | 442.47 | 9.54(s, 1H), 8.58(s, 1H), 8.25(s, 1H), 7.85(d, 1H), 7.59(d, 2H), 7.50(d, 2H), 7.47(d, 1H), 7.38(t, 2H), 7.27(t, 1H), 6.94(d, 2H), 3.12(m, 4H), 2.35(q, 2H), 2.50(m, 4H), 1.02(t, 3H) |
| 59 | 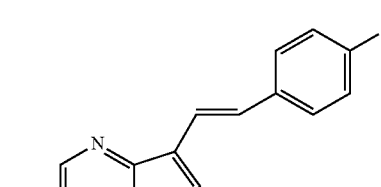 | (E)-N-(4-(4-ethylpiperazin-1-yl)phenyl)-7-(4-methoxystyryl)thieno[3,2-d]pyrimidine-4-amine | 472.49 | 9.51(s, 1H), 8.57(s, 1H), 8.17(s, 1H), 7.77(d, 1H), 7.52(d, 2H), 7.50(d, 2H), 7.32(d, 1H), 6.95(d, 2H), 6.94(d, 2H), 3.77(s, 3H), 3.12(m, 4H), 2.50(m, 4H), 2.35(q, 2H), 1.02(t, 3H) |

TABLE 1-continued

| Ex. | Structure | Compound | MS m/z [M + 1] | NMR ($^1$H NMR 400 MHz, DMSO-$d_6$) |
|---|---|---|---|---|
| 60 | 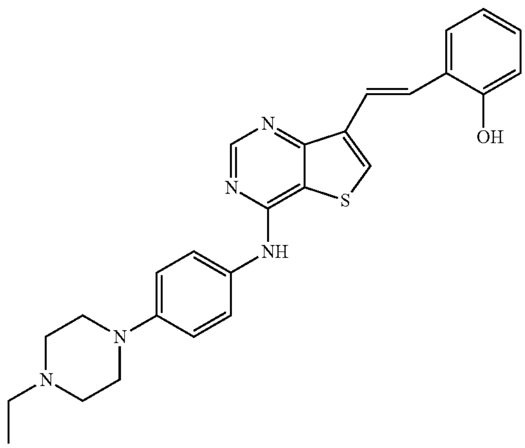 [SMILES: CCN1CCN(c2ccc(Nc3ncnc4c(/C=C/c5ccccc5O)csc34)cc2)CC1] | (E)-2-(2-(4-(4-(4-ethylpiperazin-1-yl)phenylamino)thieno[3,2-d]pyrimidin-7-yl)vinyl)phenol | 458.47 | 9.50(s, 1H), 8.57(s, 1H), 8.20(s, 1H), 7.94(d, 1H), 7.53(d, 1H), 7.49(d, 2H), 7.46(d, 1H), 7.08(t, 1H), 6.96(d, 2H), 6.87(d, 1H), 6.81(t, 1H), 3.12(m, 4H), 2.50(m, 4H), 2.35(q, 2H), 1.02(t, 3H) |
| 61 | 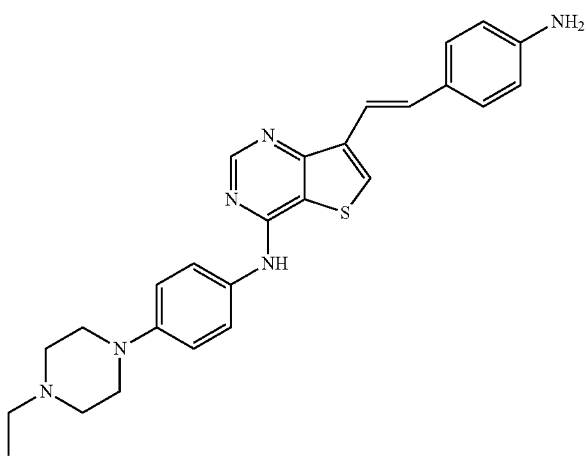 | (E)-7-(4-aminostyryl)-N-(4-(4-ethylpiperazin-1-yl)phenyl)thieno[3,2-d]pyrimidine-4-amine | 457.50 | 9.47(s, 1H), 8.55(s, 1H), 8.07(s, 1H), 7.60(d, 1H), 7.49(d, 2H), 7.25(d, 2H), 7.14(d, 1H), 6.96(d, 2H), 6.56(d, 1H), 5.32(s, 2H), 3.12(m, 4H), 2.36(q, 2H), 2.50(m, 4H), 1.02(t, 3H) |
| 62 | 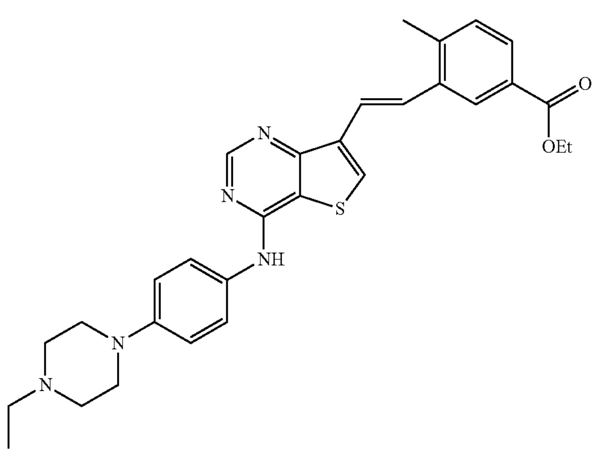 [SMILES: CCOC(=O)c1ccc(C)c(/C=C/c2csc3c(Nc4ccc(N5CCN(CC)CC5)cc4)ncnc23)c1] | (E)-ethyl 3-(2-(4-(4-(4-ethylpiperazin-1-yl)phenylamino)thieno[3,2-d]pyrimidin-7-yl)vinyl)-4-methyl benzoate | 528.57 | 9.55(s, 1H), 8.59(s, 1H), 8.38(s, 1H), 8.20(s, 1H), 8.15(d, 1H), 7.76(d, 1H), 7.49(d, 2H), 7.42(d, 1H), 7.37(d, 1H), 6.94(d, 2H), 4.33(q, 2H), 3.12(m, 4H), 2.50(m, 4H), 2.35(q, 2H), 1.33(t, 3H), 1.02(t, 3H) |

TABLE 1-continued

| Ex. | Structure | Compound | MS m/z [M + 1] | NMR (¹H NMR 400 MHz, DMSO-$d_6$) |
|---|---|---|---|---|
| 63 | 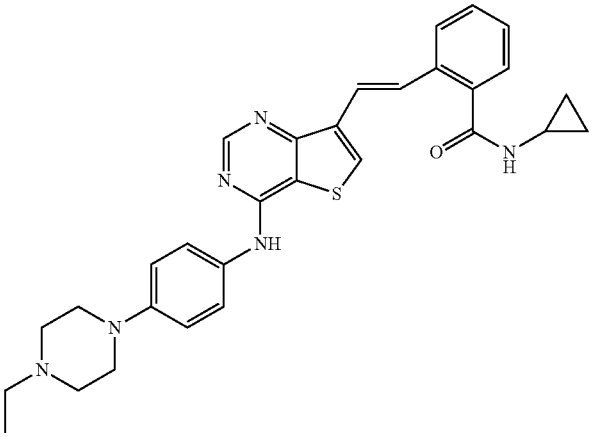 [SMILES: CCN1CCN(c2ccc(Nc3ncnc4c(/C=C/c5ccccc5C(=O)NC5CC5)csc34)cc2)CC1] | (E)-N-cyclopropyl-2-(2-(4-(4-(4-ethylpiperazin-1-yl)phenylamino)thieno[3,2-d]pyrimidin-7-yl)vinyl)benzamide | 525.58 | 9.57(s, 1H), 8.55(s, 1H), 8.42(d, 1H), 8.18(s, 1H), 8.02(d, 1H), 7.79(d, 1H), 7.47(d, 2H), 7.40(d, 1H), 7.41(d, 1H), 7.40(t, 1H), 7.31(t, 1H), 6.94(d, 2H), 3.12(m, 4H), 2.87(m, 1H), 2.50(m, 4H), 2.34(q, 2H), 1.02(t, 3H), 0.68(m, 2H), 0.61(m, 2H) |
| 64 | 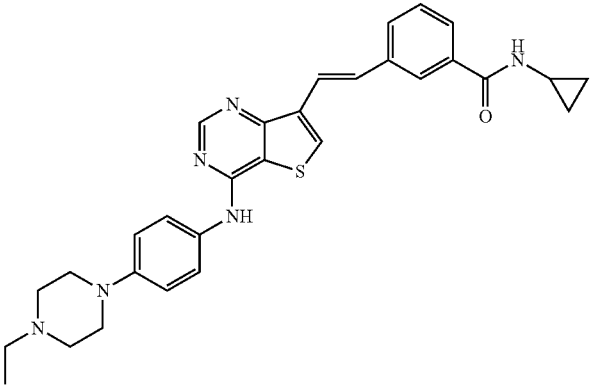 [SMILES: CCN1CCN(c2ccc(Nc3ncnc4c(/C=C/c5cccc(C(=O)NC6CC6)c5)csc34)cc2)CC1] | (E)-N-cyclopropyl-3-(2-(4-(4-(4-ethylpiperazin-1-yl)phenylamino)thieno[3,2-d]pyrimidin-7-yl)vinyl)benzamide | 525.58 | 9.55(s, 1H), 8.69(s, 1H), 8.55(d, 1H), 8.28(s, 1H), 8.03(s, 1H), 7.93(d, 1H), 7.83(t, 1H), 7.71(d, 2H), 7.55(d, 1H), 7.49(d, 1H), 7.46(d, 1H), 6.94(d, 2H), 3.12(m, 4H), 2.87(m, 1H), 2.50(m, 4H), 2.35(q, 2H), 1.02(t, 3H), 0.69(m, 2H), 0.59(m, 2H) |
| 65 | 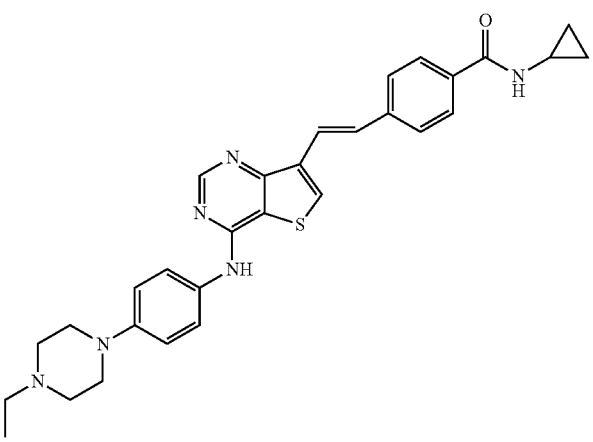 [SMILES: CCN1CCN(c2ccc(Nc3ncnc4c(/C=C/c5ccc(C(=O)NC6CC6)cc5)csc34)cc2)CC1] | (E)-N-cyclopropyl-4-(2-(4-(4-(4-ethylpiperazin-1-yl)phenylamino)thieno[3,2-d]pyrimidin-7-yl)vinyl)benzamide | 525.58 | 9.55(s, 1H), 8.58(s, 1H), 8.43(d, 1H), 8.28(s, 1H), 7.91(d, 1H), 7.83(d, 2H), 7.65(d, 2H), 7.57(d, 1H), 7.49(d, 2H), 6.94(d, 2H), 3.12(m, 4H), 2.85(m, 1H), 2.50(m, 4H), 2.35(q, 2H), 1.02(t, 3H), 0.68(m, 2H), 0.58(m, 2H) |

TABLE 1-continued

| Ex. | Structure | Compound | MS m/z [M + 1] | NMR ($^1$H NMR 400 MHz, DMSO-$d_6$) |
|---|---|---|---|---|
| 66 | 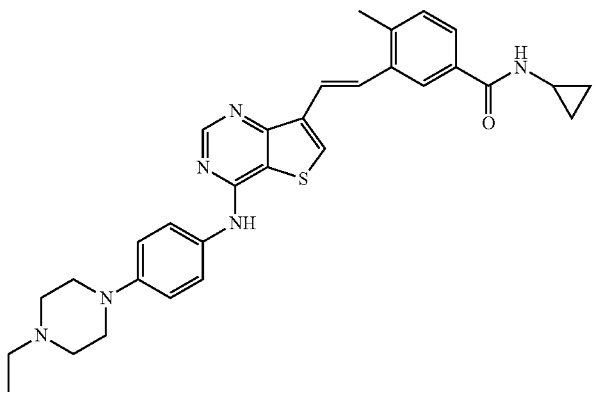 [SMILES: CCN1CCN(c2ccc(Nc3ncnc4c(/C=C/c5cc(C(=O)NC6CC6)ccc5C)csc34)cc2)CC1] | (E)-N-cyclopropyl-3-(2-(4-(4-(4-ethylpiperazin-1-yl)phenylamino)thieno[3,2-d]pyrimidin-7-yl)vinyl)-4-methylbenzamide | 539.59 | 9.55(s, 1H), 8.57(s, 1H), 8.51(d, 1H), 8.35(s, 1H), 8.12(s, 1H), 8.09(d, 1H), 7.64(d, 1H), 7.50(d, 2H), 7.46(d, 1H), 7.28(d, 1H), 6.95(d, 2H), 3.12(m, 4H), 2.85(m, 1H), 2.50(m, 4H), 2.37(q, 2H), 1.02(t, 3H), 0.68(m, 2H), 0.59(m, 2H) |
| 67 | 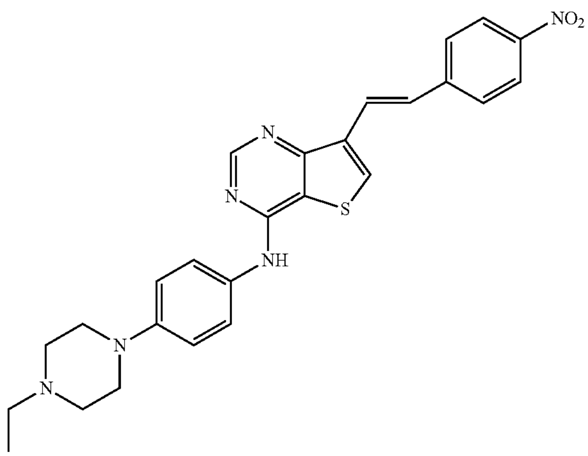 [SMILES: CCN1CCN(c2ccc(Nc3ncnc4c(/C=C/c5ccc([N+](=O)[O-])cc5)csc34)cc2)CC1] | (E)-N-(4-(4-ethylpiperazin-1-yl)phenyl)-7-(4-nitrostyryl)thieno[3,2-d]pyrimidine-4-amine | 487.46 | 9.60(s, 1H), 8.67(s, 1H), 8.37(s, 1H), 8.34(d, 2H), 8.07(d, 2H), 7.86(d, 1H), 7.54(d, 1H), 7.49(d, 2H), 6.95(d, 2H), 3.13(m, 4H), 2.50(m, 4H), 2.37(q, 2H), 1.02(t, 3H) |
| 68 | 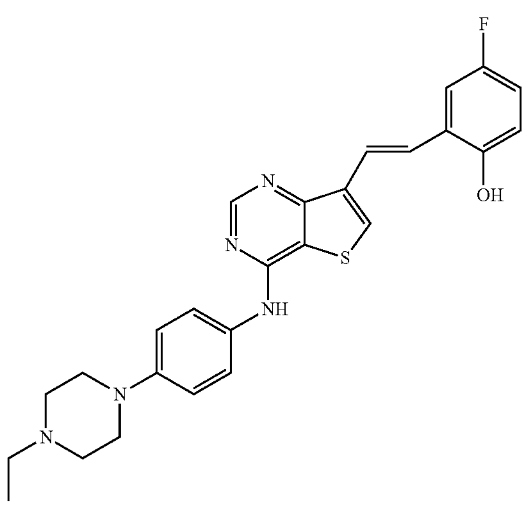 [SMILES: CCN1CCN(c2ccc(Nc3ncnc4c(/C=C/c5cc(F)ccc5O)csc34)cc2)CC1] | (E)-2-(2-(4-(4-(4-ethylpiperazin-1-yl)phenylamino)thieno[3,2-d]pyrimidin-7-yl)vinyl)-4-fluorophenol | 476.51 | 9.76(br, 1H), 9.51(s, 1H), 8.58(s, 1H), 8.20(s, 1H), 7.99(d, 1H), 7.51(s, 1H), 7.49(d, 2H), 7.47(d, 1H), 7.36(d, 1H), 6.94(d, 2H), 6.86(d, 1H), 3.12(m, 4H), 2.50(m, 4H), 2.36(q, 2H), 1.03(t, 3H) |

TABLE 1-continued

| Ex. | Structure | Compound | MS m/z [M + 1] | NMR (¹H NMR 400 MHz, DMSO-$d_6$) |
|---|---|---|---|---|
| 69 | 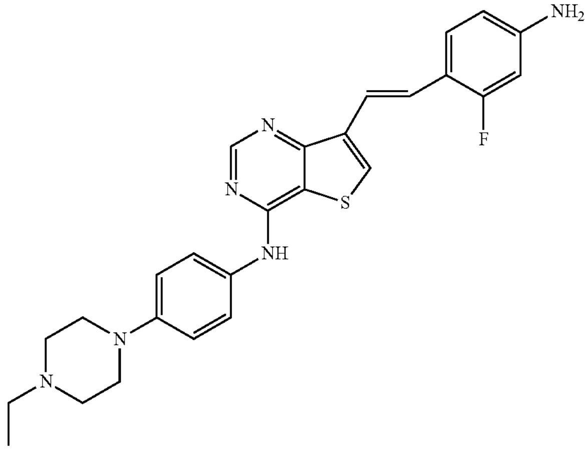 [SMILES: CCN1CCN(c2ccc(Nc3ncnc4c(/C=C/c5ccc(N)cc5F)csc34)cc2)CC1] | (E)-7-(4-amino-2-fluorostyryl)-N-(4-(4-ethylpiperazin-1-yl)phenyl)thieno[3,2-d]pyrimidine-4-amine | 475.51 | 9.45(s, 1H), 8.56(s, 1H), 8.12(s, 1H), 7.76(d, 1H), 7.49(d, 2H), 7.39(t, 1H), 7.21(d, 1H), 6.94(d, 2H), 6.41(d, 1H), 6.33(d, 1H), 5.66(s, 2H), 3.12(m, 4H), 2.50(m, 4H), 2.36(q, 2H), 1.03(t, 3H) |
| 70 | 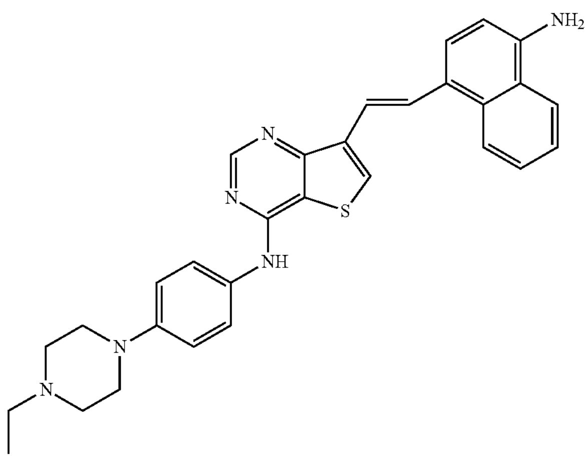 [SMILES: CCN1CCN(c2ccc(Nc3ncnc4c(/C=C/c5ccc(N)c6ccccc56)csc34)cc2)CC1] | (E)-7-(2-(4-aminonaphthalen-1-yl)vinyl)-N-(4-(4-ethylpiperazin-1-yl)phenyl)thieno[3,2-d]pyrimidine-4-amine | 507.58 | 9.50(s, 1H), 8.61(s, 1H), 8.53(d, 1H), 8.27(s, 1H), 8.22(d, 1H), 8.10(d, 1H), 7.68(d, 1H), 7.53(t, 1H), 7.50(d, 2H), 7.41(t, 1H), 7.30(d, 1H), 6.95(d, 2H), 6.74(d, 1H), 5.99(s, 2H), 3.12(m, 4H), 2.50(m, 4H), 2.36(q, 2H), 1.03(t, 3H) |
| 71 | 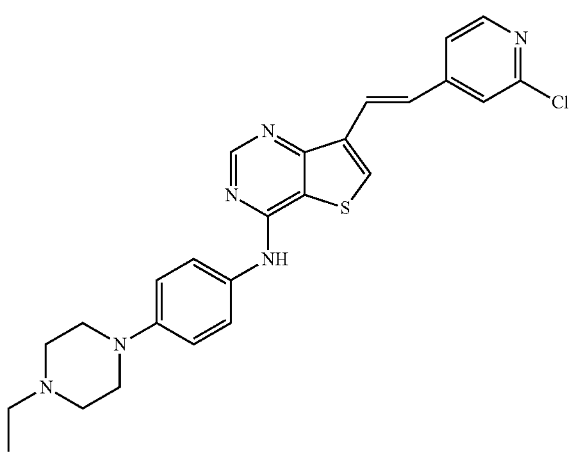 [SMILES: CCN1CCN(c2ccc(Nc3ncnc4c(/C=C/c5ccnc(Cl)c5)csc34)cc2)CC1] | (E)-7-(2-(2-chloropyridin-4-yl)vinyl)-N-(4-(4-ethylpiperazin-1-yl)phenyl)thieno[3,2-d]pyrimidine-4-amine | 477.48 | — |

TABLE 1-continued

| Ex. | Structure | Compound | MS m/z [M + 1] | NMR (¹H NMR 400 MHz, DMSO-d$_6$) |
|---|---|---|---|---|
| 72 | 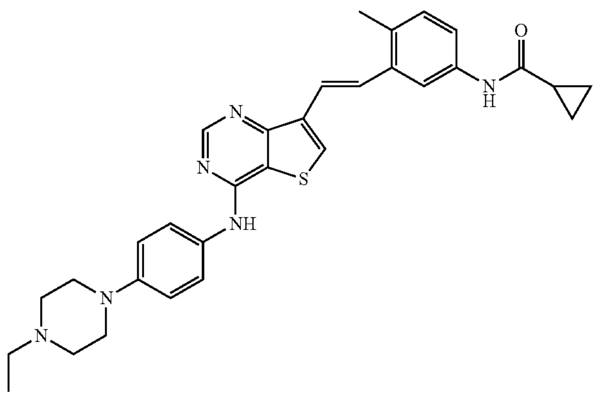 [SMILES: CCN1CCN(c2ccc(Nc3ncnc4c(/C=C/c5cc(NC(=O)C6CC6)ccc5C)csc34)cc2)CC1] | (E)-N-(3-(2-(4-(4-ethylpiperazin-1-yl)phenylamino)thieno[3,2-d]pyrimidin-7-yl)vinyl)-4-methylphenyl)cyclopropanecarboxamide | 539.66 | 10.17(s, 1H), 9.54(s, 1H), 8.58(s, 1H), 8.37(s, 1H), 7.99(s, 1H), 7.97(d, 1H), 7.50(d, 2H), 7.40(d, 1H), 7.31(d, 1H), 7.12(d, 1H), 6.95(d, 2H), 3.12(m, 4H), 2.50(m, 4H), 2.36(q, 2H), 2.35(s, 3H), 1.80(m, 1H), 1.03(t, 3H), 0.80(m, 2H), 0.77(m, 2H) |
| 73 | 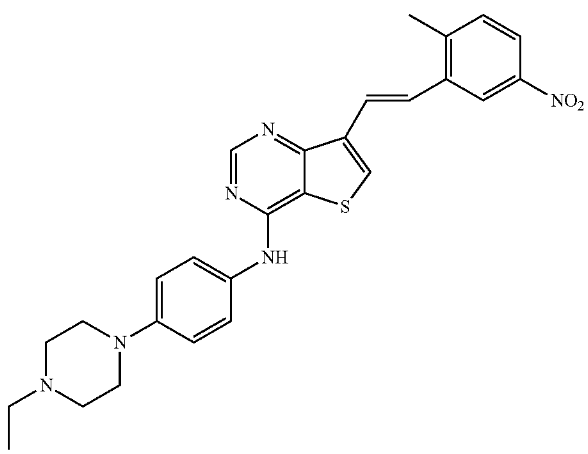 [SMILES: CCN1CCN(c2ccc(Nc3ncnc4c(/C=C/c5cc([N+](=O)[O-])ccc5C)csc34)cc2)CC1] | (E)-N-(4-(4-ethylpiperazin-1-yl)phenyl)-7-(2-methyl-5-nitrostyryl)thieno[3,2-d]pyrimidine-4-amine | 501.53 | 9.54(s, 1H), 8.60(s, 1H), 8.45(d, 1H), 8.40(s, 1H), 8.24(d, 1H), 8.01(d, 1H), 7.57(d, 1H), 7.54(d, 1H), 7.50(d, 2H), 6.95(d, 2H), 3.12(m, 4H), 2.53(s, 3H), 2.50(m, 4H), 2.36(q, 2H), 1.03(t, 3H) |
| 74 | 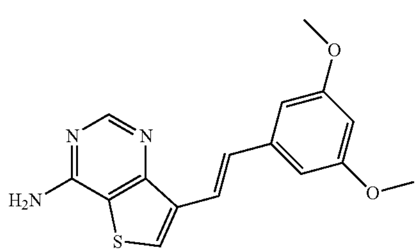 [SMILES: COc1cc(/C=C/c2csc3c(N)ncnc23)cc(OC)c1] | 7-(3,5-dimethoxystyryl)thieno[3,2-d]pyrimidine-4-amine | 314.06 315.07 | 8.47(s, 1H), 8.18(s, 1H), 7.80(d, 1H), 7.48(s, 2H), 7.44(d, 1H), 6.72(s, 2H), 6.41(s, 1H), 3.78(s, 6H) |
| 75 | 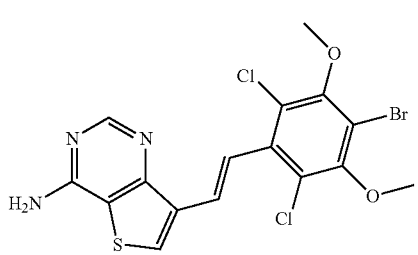 [SMILES: COc1c(Cl)c(/C=C/c2csc3c(N)ncnc23)c(Cl)c(OC)c1Br] | 7-(4-bromo-2,6-dichloro-3,5-dimethoxystyryl)thieno[3,2-d]pyrimidine-4-amine | M + Na 482.16 483.09 | 8.55(s, 1H), 8.37(s, 1H), 7.80(d, 1H), 7.48(s, 2H), 7.30(d, 1H), 3.84(s, 6H) |

TABLE 1-continued

| Ex. | Structure | Compound | MS m/z [M + 1] | NMR (¹H NMR 400 MHz, DMSO-$d_6$) |
|---|---|---|---|---|
| 76 | 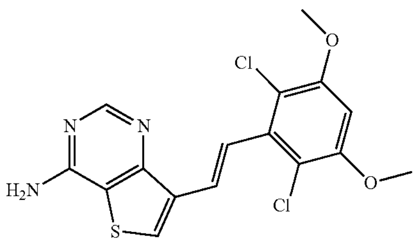 [SMILES: COc1cc(OC)c(Cl)c(/C=C/c2csc3c(N)ncnc23)c1Cl] | 7-(2,6-dichloro-3,5-dimethoxystyryl)thieno[3,2-d]pyrimidine-4-amine | 382.00 383.98 | 8.45(s, 1H), 8.30(s, 1H), 7.90(d, 1H), 7.51(s, 2H), 7.23(d, 1H), 6.89(s, 1H), 3.93(s, 6H) |
| 77 | 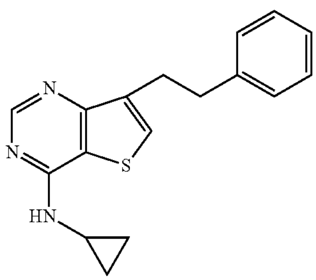 [SMILES: c1ccc(CCc2csc3c(NC4CC4)ncnc23)cc1] | 7-phenethylthieno[3,2-d]pyrimidine-4-amine | 56.22 | — |
| 78 | 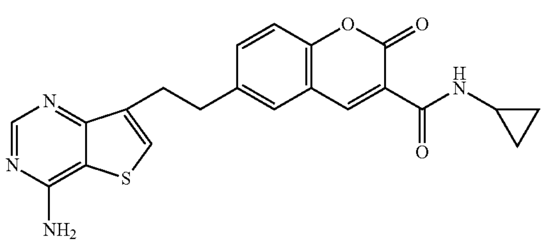 [SMILES: Nc1ncnc2c(CCc3ccc4oc(=O)c(C(=O)NC5CC5)cc4c3)csc12] | 6-(2-(4-aminothieno[3,2-d]pyrimidin-7-yl)ethyl)-N-cyclopropyl-2-oxo-2H-chromene-3-carboxamide | 407.40 | — |
| 79 | 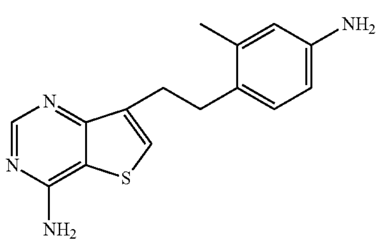 [SMILES: Cc1cc(N)ccc1CCc1csc2c(N)ncnc12] | 7-(4-amino-2-methylphenethyl)thieno[3,2-d]pyrimidine-4-amine | 285.30 | — |
| 80 | 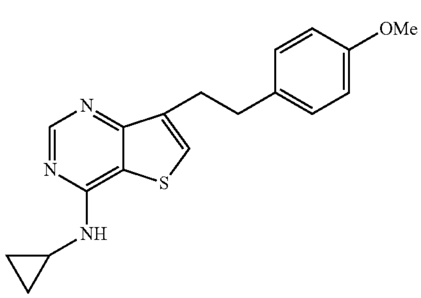 [SMILES: COc1ccc(CCc2csc3c(NC4CC4)ncnc23)cc1] | N-cyclopropyl-7-(4-methoxyphenethyl)thieno[3,2-d]pyrimidine-4-amine | 326.36 | 8.46(s, 1H), 7.91(d, 1H), 7.66(s, 1H), 7.13(d, 2H), 6.85(d, 2H), 3.03(t, 2H), 2.97(m, 1H), 2.92(t, 2H), 0.78(m, 2H), 0.62(m, 2H) |

TABLE 1-continued

| Ex. | Structure | Compound | MS m/z [M + 1] | NMR (¹H NMR 400 MHz, DMSO-$d_6$) |
|---|---|---|---|---|
| 81 | 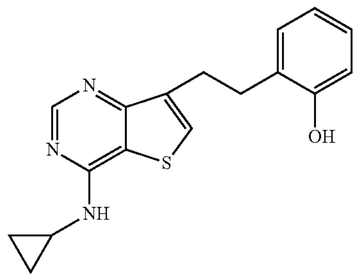 [SMILES: Oc1ccccc1CCc1csc2c(NC3CC3)ncnc12] | 2-(2-(4-(cyclopropylamino)thieno[3,2-d]pyrimidin-7-yl)ethyl)phenol | 312.29 | 9.37(br, 1H), 8.48(s, 1H), 7.92(s, 1H), 7.71(s, 1H), 7.01(d, 1H), 6.98(t, 1H), 6.76(d, 1H), 6.68(t, 1H), 3.03(t, 2H), 2.97(m, 1H), 2.92(t, 2H), 0.78(m, 2H), 0.62(m, 2H) |
| 82 | 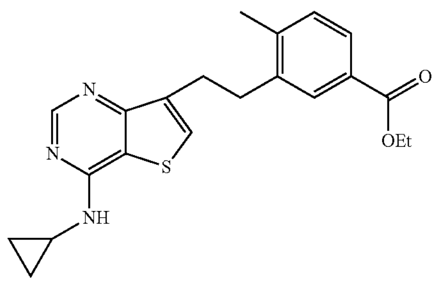 [SMILES: CCOC(=O)c1ccc(C)c(CCc2csc3c(NC4CC4)ncnc23)c1] | ethyl 3-(2-(4-(cyclopropylamino)thieno[3,2-d]pyrimidin-7-yl)ethyl)-4-methyl benzoate | 382.53 | 8.50(s, 1H), 7.94(s, 1H), 7.75(s, 1H), 7.71(s, 1H), 7.68(d, 1H), 7.30(d, 1H), 4.26(m, 2H), 3.02(m, 4H), 2.36(s, 3H), 1.34(m, 1H), 1.29(t, 3H), 0.79(d, 2H), 0.62(d, 2H) |
| 83 | 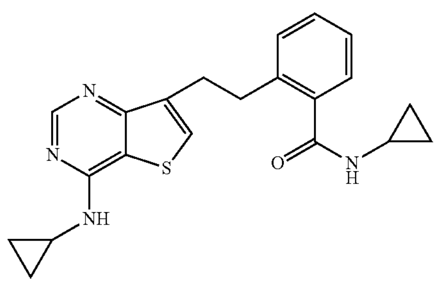 [SMILES: O=C(NC1CC1)c1ccccc1CCc1csc2c(NC3CC3)ncnc12] | N-cyclopropyl-2-(2-(4-(cyclopropylamino)thieno[3,2-d]pyrimidin-7-yl)ethyl)benzamide | 379.54 | — |
| 84 | 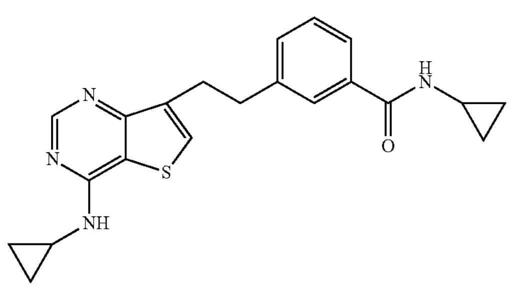 [SMILES: O=C(NC1CC1)c1cccc(CCc2csc3c(NC4CC4)ncnc23)c1] | N-cyclopropyl-3-(2-(4-(cyclopropylamino)thieno[3,2-d]pyrimidin-7-yl)ethyl)benzamide | 379.44 | 8.59(s, 1H), 8.40(d, 1H), 7.93(s, 1H), 7.71(d, 2H), 7.61(t, 1H), 7.35(s, 2H), 3.08(t, 2H), 3.03(t, 2H), 2.96(m, 1H), 2.82(m, 1H), 0.79(m, 2H), 0.69(m, 2H), 0.62(m, 2H), 0.57(m, 2H) |
| 85 | 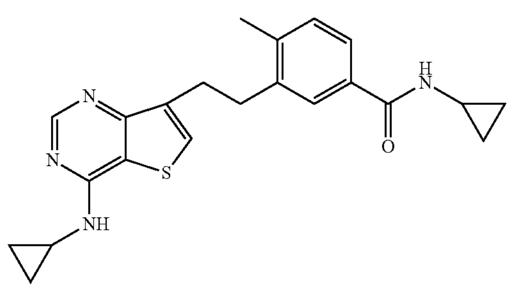 [SMILES: Cc1ccc(C(=O)NC2CC2)cc1CCc1csc2c(NC3CC3)ncnc12] | N-cyclopropyl-3-(2-(4-(cyclopropylamino)thieno[3,2-d]pyrimidin-7-yl)ethyl)-4-methylbenzamide | 393.50 | 8.50(s, 1H), 8.37(d, 1H), 8.20(d, 1H), 7.94(s, 1H), 7.76(s, 1H), 7.67(s, 1H), 7.56(d, 1H), 7.25(d, 1H), 2.98(m, 5H), 2.82(m, 1H), 0.79(m, 2H), 0.69(m, 2H), 0.55(m, 2H), 0.44(m, 2H) |

TABLE 1-continued

| Ex. | Structure | Compound | MS m/z [M + 1] | NMR ($^1$H NMR 400 MHz, DMSO-$d_6$) |
|---|---|---|---|---|
| 86 | 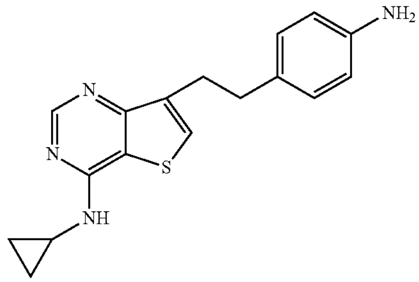 [SMILES: Nc1ccc(CCc2csc3c(NC4CC4)ncnc23)cc1] | 7-(4-aminophenethyl)-N-cyclopropylthieno[3,2-d]pyrimidine-4-amine | 311.34 | 8.52(s, 1H), 8.48(d, 1H), 7.90(s, 1H), 7.18(d, 2H), 6.56(d, 2H), 4.98(s, 2H), 2.98(m, 4H), 2.80(m, 1H), 0.77(m, 2H), 0.62(m, 2H) |
| 87 | 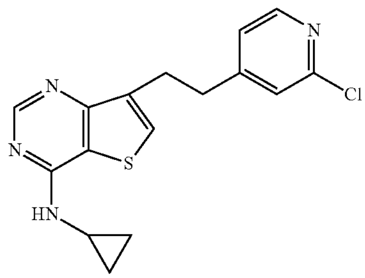 [SMILES: Clc1cc(CCc2csc3c(NC4CC4)ncnc23)ccn1] | 7-(2-(2-chloropyridin-4-yl)ethyl)-N-cyclopropylthieno[3,2-d]pyrimidine-4-amine | 331.41 | — |
| 88 | 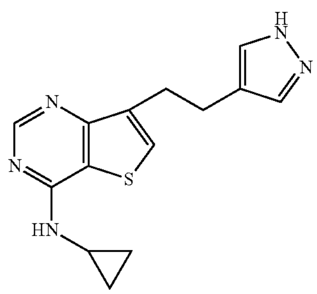 [SMILES: c1nc(NC2CC2)c2scc(CCc3cn[nH]c3)c2n1] | 7-(2-(1H-pyrazol-4-yl)ethyl)-N-cyclopropylthieno[3,2-d]pyrimidine-4-amine | 286.45 | — |
| 89 | 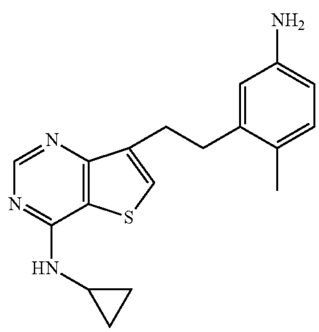 [SMILES: Cc1ccc(N)cc1CCc1csc2c(NC3CC3)ncnc12] | 7-(5-amino-2-methylphenethyl)-N-cyclopropylthieno[3,2-d]pyrimidine-4-amine | 325.49 | 8.50(s, 1H), 7.87(d, 1H), 7.76(s, 1H), 6.77(d, 1H), 6.40(s, 1H), 6.32(d, 1H), 4.74(s, 2H), 2.96(m, 4H), 2.77(m, 1H), 2.12(s, 3H), 0.80(m, 2H), 0.63(m, 2H) |
| 90 | 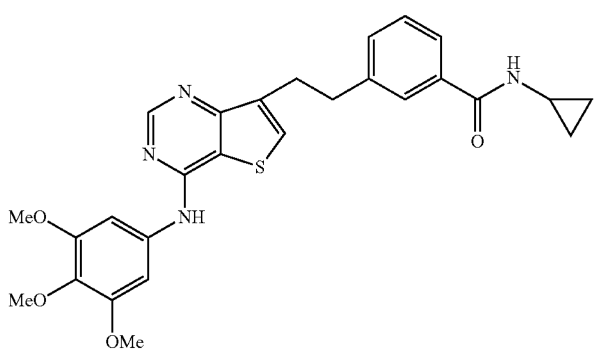 [SMILES: COc1cc(Nc2ncnc3c(CCc4cccc(C(=O)NC5CC5)c4)csc23)cc(OC)c1OC] | N-cyclopropyl-3-(2-(4-(3,4,5-trimethoxyphenyl-amino)thieno[3,2-d]pyrimidin-7-yl)ethyl)benzamide | 505.60 | 9.55(s, 1H), 8.62(s, 1H), 8.41(d, 1H), 8.19(s, 1H), 7.83(t, 1H), 7.70(s, 1H), 7.62(d, 1H), 7.33(d, 1H), 7.20(s, 2H), 3.74(s, 6H), 3.61(s, 3H), 3.11(m, 2H), 3.05(m, 2H), 2.82(m, 1H), 0.67(m, 2H), 0.55(m, 2H) |

TABLE 1-continued

| Ex. | Structure | Compound | MS m/z [M + 1] | NMR (¹H NMR 400 MHz, DMSO-d$_6$) |
|---|---|---|---|---|
| 91 | 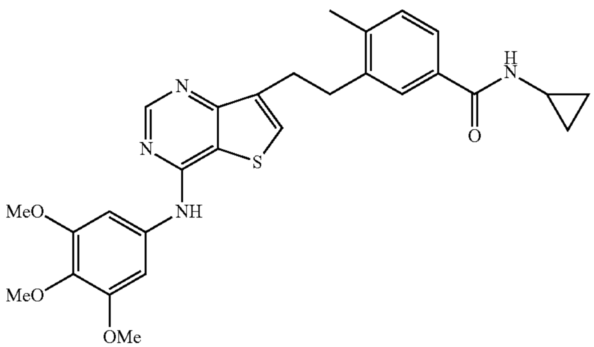 [SMILES: COc1cc(Nc2ncnc3c(CCc4cc(C(=O)NC5CC5)ccc4C)csc23)cc(OC)c1OC] | N-cyclopropyl-4-methyl-3-(2-(4-(3,4,5-trimethoxyphenyl-amino)thieno[3,2-d]pyrimidin-7-yl)ethyl)benzamide | 519.72 | 9.56(s, 1H), 8.63(s, 1H), 8.33(d, 1H), 8.19(s, 1H), 7.85(s, 1H), 7.68(d, 1H), 7.55(d, 1H), 7.20(s, 2H), 3.77(s, 6H), 3.63(s, 3H), 3.06(m, 2H), 3.02(m, 2H), 2.82(m, 1H), 2.31(s, 3H), 0.67(m, 2H), 0.55(m, 2H) |
| 92 | 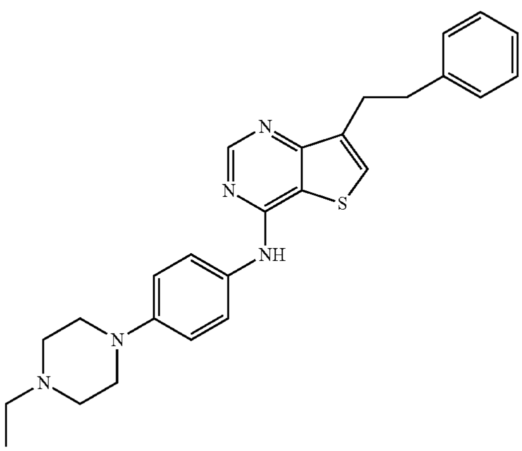 [SMILES: CCN1CCN(c2ccc(Nc3ncnc4c(CCc5ccccc5)csc34)cc2)CC1] | N-(4-(4-ethylpiperazin-1-yl)phenyl)-7-phenethylthieno[3,2-d]pyrimidine-4-amine | 444.63 | 9.43(s, 1H), 8.53(s, 1H), 7.70(s, 1H), 7.49(d, 2H), 7.25(d, 2H), 7.24(t, 2H), 7.18(t, 1H), 6.93(d, 2H), 3.12(m, 4H), 3.07(t, 2H), 3.01(t, 2H), 2.50(m, 4H), 2.36(q, 2H), 1.03(t, 3H) |
| 93 | 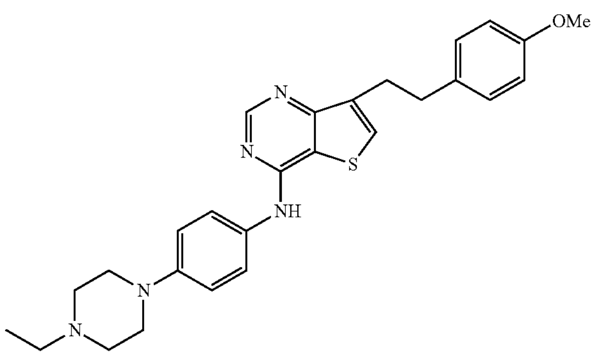 [SMILES: CCN1CCN(c2ccc(Nc3ncnc4c(CCc5ccc(OC)cc5)csc34)cc2)CC1] | N-(4-(4-ethylpiperazin-1-yl)phenyl)-7-(4-methoxyphenethyl)thieno[3,2-d]pyrimidine-4-amine | 474.66 | 9.42(s, 1H), 8.52(s, 1H), 7.73(s, 1H), 7.50(d, 2H), 7.12(d, 2H), 6.95(d, 2H), 6.84(d, 2H), 3.70(s, 3H), 3.77(s, 3H), 3.29(m, 4H), 3.12(m, 4H), 3.05(t, 2H), 2.93(t, 2H), 2.37(q, 2H), 1.02(t, 3H) |
| 94 | 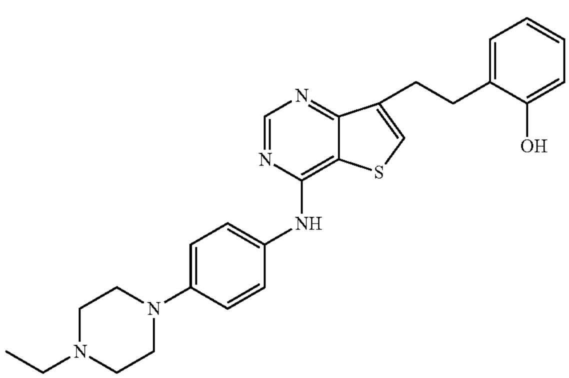 [SMILES: CCN1CCN(c2ccc(Nc3ncnc4c(CCc5ccccc5O)csc34)cc2)CC1] | 2-(2-(4-(4-(4-ethylpiperazin-1-yl)phenylamino)thieno[3,2-d]pyrimidin-7-yl)ethyl)phenol | 460.49 | — |

TABLE 1-continued

| Ex. | Structure | Compound | MS m/z [M + 1] | NMR (¹H NMR 400 MHz, DMSO-$d_6$) |
|---|---|---|---|---|
| 95 | 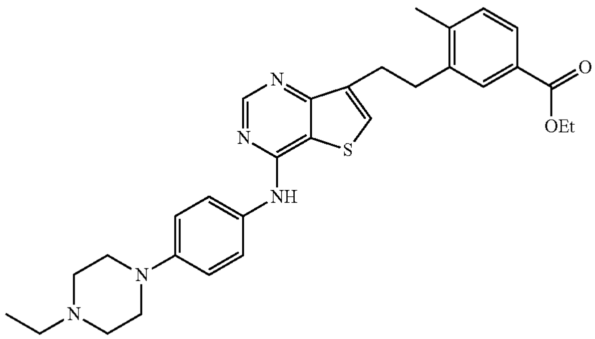 [SMILES: CCOC(=O)c1ccc(C)c(CCc2csc3c(Nc4ccc(N5CCN(CC)CC5)cc4)ncnc23)c1] | ethyl 3-(2-(4-(4-(4-ethylpiperazin-1-yl)phenylamino)thieno[3,2-d]pyrimidin-7-yl)ethyl)-4-methyl benzoate | 530.59 | 9.41(s, 1H), 8.54(s, 1H), 7.79(s, 1H), 7.72(s, 1H), 7.68(d, 1H), 7.50(d, 2H), 7.29(d, 1H), 6.94(d, 2H), 4.26(q, 2H), 3.13(m, 4H), 3.03(m, 4H), 2.50(m, 4H), 2.38(s, 3H), 2.37(q, 2H), 1.30(t, 3H), 1.03(t, 3H) |
| 96 | 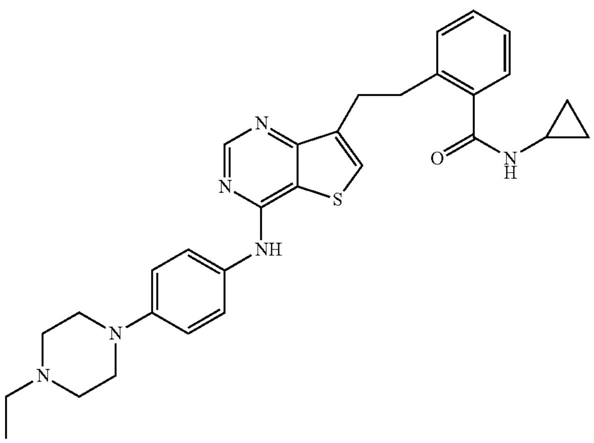 [SMILES: CCN1CCN(c2ccc(Nc3ncnc4c(CCc5ccccc5C(=O)NC5CC5)csc34)cc2)CC1] | N-cyclopropyl-2-(2-(4-(4-(4-ethylpiperazin-1-yl)phenylamino)thieno[3,2-d]pyrimidin-7-yl)ethyl)benzamide | 527.71 | — |
| 97 | 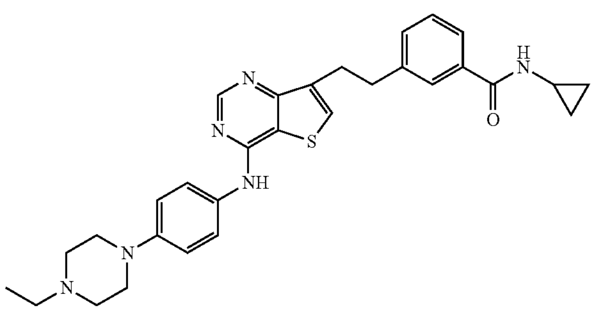 [SMILES: CCN1CCN(c2ccc(Nc3ncnc4c(CCc5cccc(C(=O)NC6CC6)c5)csc34)cc2)CC1] | N-cyclopropyl-3-(2-(4-(4-(4-ethylpiperazin-1-yl)phenylamino)thieno[3,2-d]pyrimidin-7-yl)ethyl)benzamide | 527.72 | 9.44(s, 1H), 8.53(s, 1H), 8.40(d, 1H), 8.12(s, 1H), 7.84(t, 1H), 7.77(s, 1H), 7.62(d, 1H), 7.49(d, 2H), 7.36(d, 1H), 6.94(d, 2H), 3.12(m, 4H), 3.07(m, 2H), 3.00(m, 2H), 2.82(m, 1H), 2.50(m, 4H), 2.37(q, 2H), 1.03(t, 3H), 0.68(m, 2H), 0.57(m, 2H) |
| 98 | 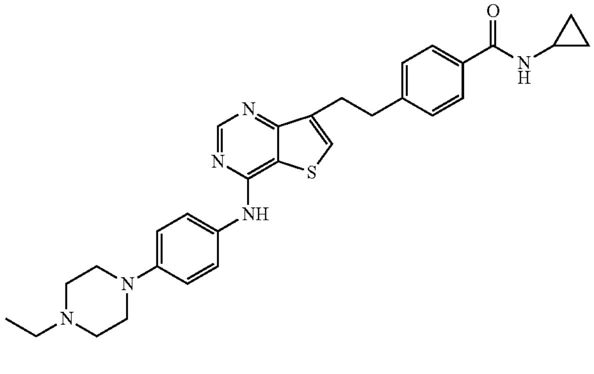 [SMILES: CCN1CCN(c2ccc(Nc3ncnc4c(CCc5ccc(C(=O)NC6CC6)cc5)csc34)cc2)CC1] | N-cyclopropyl-4-(2-(4-(4-(4-ethylpiperazin-1-yl)phenylamino)thieno[3,2-d]pyrimidin-7-yl)ethyl)benzamide | 527.61 | 9.43(s, 1H), 8.53(s, 1H), 8.47(d, 1H), 8.34(s, 1H), 7.73(d, 2H), 7.48(d, 2H), 7.30(d, 2H), 6.95(d, 2H), 3.11(m, 4H), 3.07(m, 4H), 2.81(t, 2H), 2.50(t, 2H), 1.17(m, 2H), 1.05(t, 3H), 0.86(m, 1H), 0.68(t, 2H), 0.66(m, 2H) |

TABLE 1-continued

| Ex. | Structure | Compound | MS m/z [M + 1] | NMR (¹H NMR 400 MHz, DMSO-$d_6$) |
|---|---|---|---|---|
| 99 | 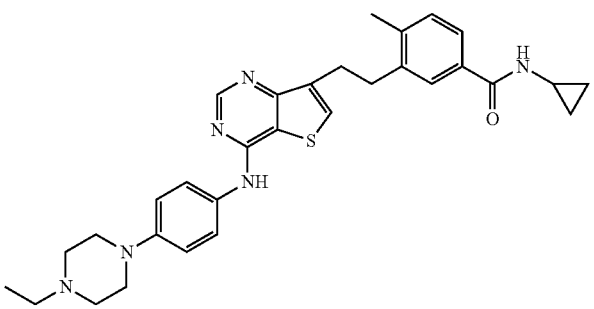 [SMILES: CCN1CCN(c2ccc(Nc3ncnc4c(CCc5cc(C(=O)NC6CC6)ccc5C)csc34)cc2)CC1] | N-cyclopropyl-3-(2-(4-(4-(4-ethylpiperazin-1-yl)phenylamino)thieno[3,2-d]pyrimidin-7-yl)ethyl)-4-methylbenzamide | 541.63 | 9.45(s, 1H), 8.54(s, 1H), 8.34(d, 1H), 7.80(s, 1H), 7.68(s, 1H), 7.56(d, 1H), 7.50(d, 2H), 7.20(d, 1H), 6.94(d, 2H), 3.12(m, 4H), 3.07(m, 2H), 3.00(m, 2H), 2.82(m, 1H), 2.50(m, 4H), 2.37(q, 2H), 2.32(s, 3H), 1.03(t, 3H), 0.68(m, 2H), 0.57(m, 2H) |
| 100 | 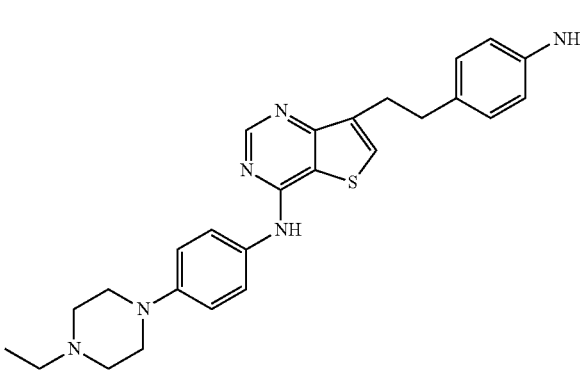 | 7-(4-aminophenethyl)-N-(4-(4-ethylpiperazin-1-yl)phenyl)thieno[3,2-d]pyrimidine-4-amine | 459.64 | — |
| 101 | 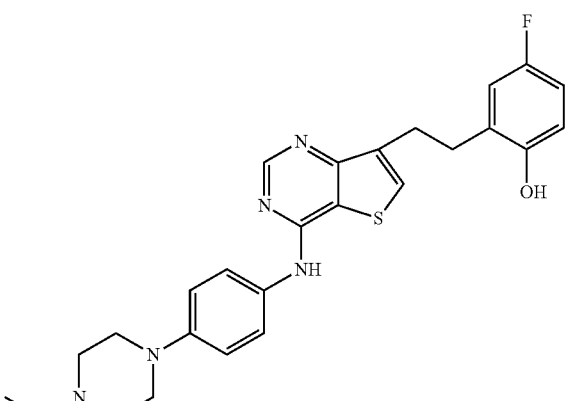 | 2-(2-(4-(4-(4-ethylpiperazin-1-yl)phenylamino)thieno[3,2-d]pyrimidin-7-yl)ethyl)-4-fluorophenol | 478.63 | 9.43(s, 1H), 8.51(s, 1H), 7.73(s, 1H), 7.49(d, 2H), 6.93(d, 2H), 6.87(d, 1H), 6.81(d, 1H), 6.78(t, 1H), 3.12(m, 4H), 3.04(t, 2H), 2.92(t, 2H), 2.50(m, 4H), 2.35(q, 2H), 1.03(t, 3H) |
| 102 | 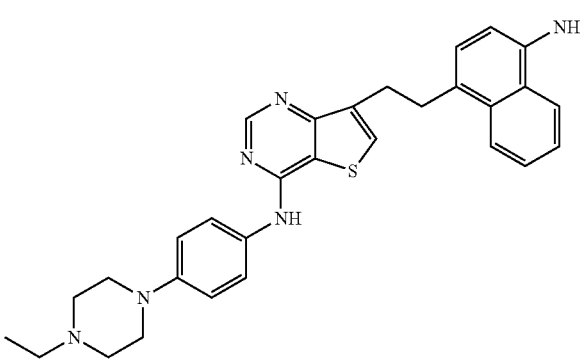 | 7-(2-(4-aminonaphthalen-1-yl)ethyl)-N-(4-(4-ethylpiperazin-1-yl)phenyl)thieno[3,2-d]pyrimidine-4-amine | 509.56 | 9.44(s, 1H), 8.58(s, 1H), 8.16(d, 1H), 8.07(d, 1H), 7.82(s, 1H), 7.50(d, 2H), 7.48(t, 1H), 7.38(t, 1H), 7.07(d, 1H), 6.94(d, 2H), 6.60(d, 1H), 3.12(m, 4H), 3.08(t, 4H), 2.50(m, 4H), 2.34(q, 2H), 1.02(t, 3H) |

TABLE 1-continued

| Ex. | Structure | Compound | MS m/z [M + 1] | NMR ($^1$H NMR 400 MHz, DMSO-d$_6$) |
|---|---|---|---|---|
| 103 | 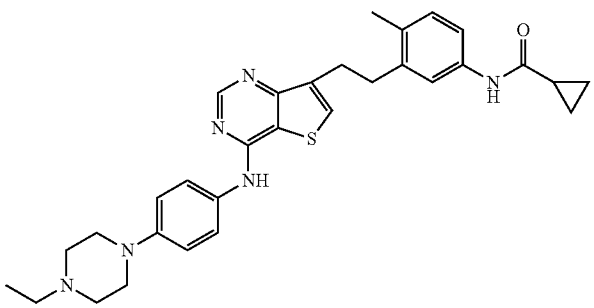 [SMILES: CCN1CCN(c2ccc(Nc3ncnc4c(CCc5cc(NC(=O)C6CC6)ccc5C)csc34)cc2)CC1] | N-(3-(2-(4-(4-(4-ethylpiperazin-1-yl)phenylamino)thieno[3,2-d]pyrimidin-7-yl)ethyl)-4-methylphenyl)cyclopropanecarboxamide | 541.72 | 10.05(s, 1H), 9.44(s, 1H), 8.54(s, 1H), 7.80(s, 1H), 7.50(d, 2H), 7.42(s, 1H), 7.37(d, 1H), 7.04(d, 1H), 6.94(d, 2H), 3.12(m, 4H), 3.00(t, 2H), 2.90(t, 2H), 2.50(m, 4H), 2.36(q, 2H), 2.23(s, 3H), 1.80(m, 1H), 1.02(t, 3H), 0.80(m, 2H), 0.77(m, 2H) |
| 104 | 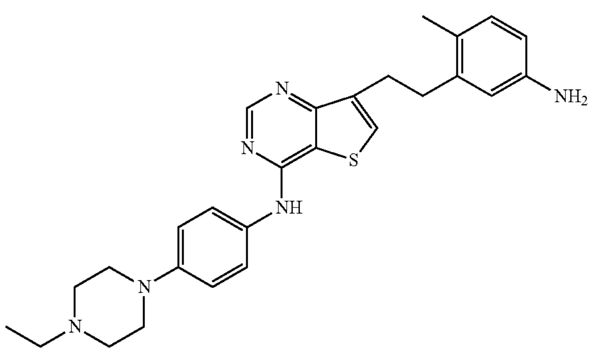 [SMILES: CCN1CCN(c2ccc(Nc3ncnc4c(CCc5cc(N)ccc5C)csc34)cc2)CC1] | 7-(5-amino-2-methylphenethyl)-N-(4-(4-ethylpiperazin-1-yl)phenyl)thieno[3,2-d]pyrimidine-4-amine | 473.57 | 9.43(s, 1H), 8.53(s, 1H), 7.79(s, 1H), 7.50(d, 2H), 6.94(d, 2H), 6.77(d, 1H), 6.41(s, 1H), 6.32(d, 1H), 4.74(s, 2H), 3.12(m, 4H), 2.98(t, 2H), 2.79(t, 2H), 2.49(m, 4H), 2.36(q, 2H), 2.12(s, 3H), 1.02(t, 3H) |
| 105 | 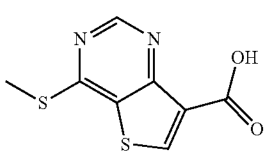 | 4-(methylthio)thieno[3,2-d]pyrimidine-7-carboxylic acid | | 8.98(s, 1H), 8.49(s, 1H), 2.72(s, 1H) |
| 106 | 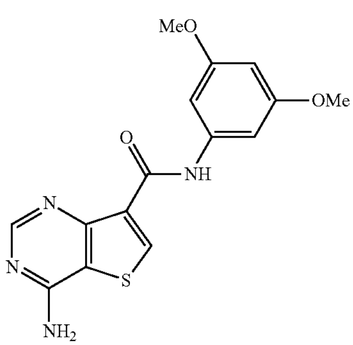 [SMILES: COc1cc(NC(=O)c2csc3c(N)ncnc23)cc(OC)c1] | 4-amino-N-(3,5-dimethoxyphenyl)thieno[3,2-d]pyrimidine-7-carboxamide | | 11.87(s, 1H), 8.89(s, 1H), 8.59(s, 1H), 7.91(s, 2H), 6.97(s, 2H), 6.30(s, 1H), 3.78(s, 6H) |
| 107 | 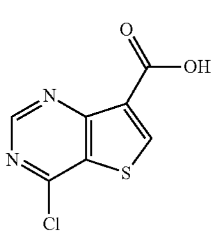 [SMILES: O=C(O)c1csc2c(Cl)ncnc12] | 4-chlorothieno[3,2-d]pyrimidine-7-carboxylic acid | | 9.07(s, 1H), 8.87(s, 1H) |

TABLE 1-continued

| Ex. | Structure | Compound | MS m/z [M + 1] | NMR (¹H NMR 400 MHz, DMSO-d$_6$) |
|---|---|---|---|---|
| 108 | 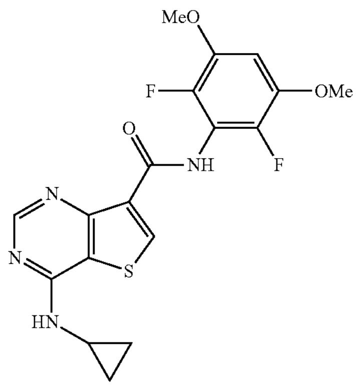 [SMILES: COc1cc(OC)c(F)c(NC(=O)c2csc3c(NC4CC4)ncnc23)c1F] | 4-(cyclopropylamino)-N-(2,6-difluoro-3,5-dimethoxyphenyl)thieno[3,2-d]pyrimidine-7-carboxamide | 407.1 408.30 | — |
| 109 | 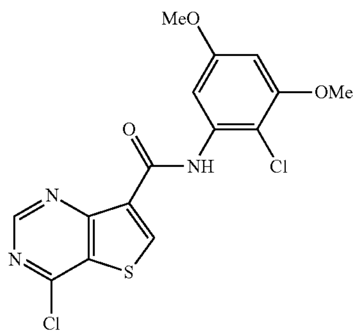 [SMILES: COc1cc(NC(=O)c2csc3c(Cl)ncnc23)c(Cl)c(OC)c1] | 4-chloro-N-(2-chloro-3,5-dimethoxyphenyl)thieno[3,2-d]pyrimidine-7-carboxamide | — | 11.62(s, 1H), 9.45(s, 1H), 8.94(s, 1H), 7.99(s, 1H), 6.59(s, 1H), 3.88(s, 3H), 3.81(s, 3H) |
| 110 | 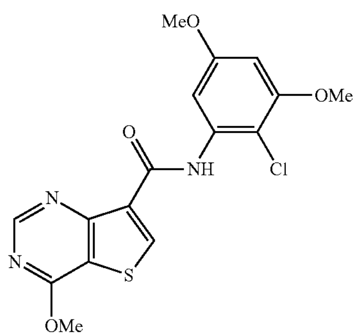 [SMILES: COc1cc(NC(=O)c2csc3c(OC)ncnc23)c(Cl)c(OC)c1] | N-(2-chloro-3,5-dimethoxyphenyl)-4-methoxythieno[3,2-d]pyrimidine-7-carboxamide | — | 11.85(s, 1H), 9.17(s, 1H), 9.02(s, 1H), 7.90(s, 1H), 6.56(s, 1H), 4.19(s, 3H), 3.88(s, 3H), 3.81(s, 3H) |
| 111 | 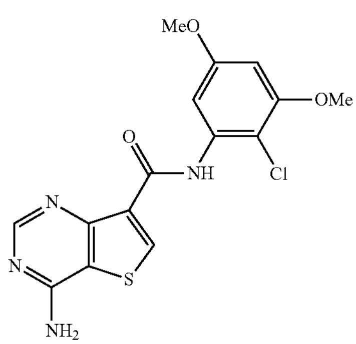 [SMILES: COc1cc(NC(=O)c2csc3c(N)ncnc23)c(Cl)c(OC)c1] | 4-amino-N-(2-chloro-3,5-dimethoxyphenyl)thieno[3,2-d]pyrimidine-7-carboxamide | — | 12.25(s, 1H), 8.96(s, 1H), 8.57(s, 1H), 7.92(m, 3H), 6.55(s, 1H), 3.87(s, 3H), 3.80(s, 3H) |

TABLE 1-continued

| Ex. | Structure | Compound | MS m/z [M+1] | NMR ($^1$H NMR 400 MHz, DMSO-$d_6$) |
|---|---|---|---|---|
| 112 | 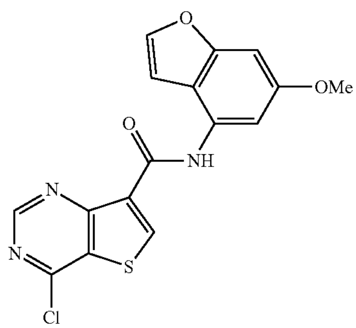 [SMILES: COc1cc(NC(=O)c2csc3c(Cl)ncnc23)c2ccoc2c1] | 4-chloro-N-(6-methoxybenzofuran-4-yl)-3-methyl-3,4-dihydrothieno[3,2-d]pyrimidine-7-carboxamide | — | 11.64(s, 1H), 9.36(s, 1H), 9.15(s, 1H), 7.93(d, 1H), 7.91(d, 1H), 7.11(s, 1H), 7.06(s, 1H), 3.81(s, 3H) |
| 113 | 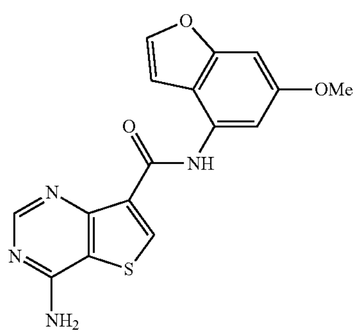 [SMILES: COc1cc(NC(=O)c2csc3c(N)ncnc23)c2ccoc2c1] | 4-amino-N-(6-methoxybenzofuran-4-yl)-3-methyl-3,4-dihydrothieno[3,2-d]pyrimidine-7-carboxamide | — | 12.39(s, 1H), 8.96(s, 1H),, 8.75(s, 1H), 7.97-7.89(m, 4H), 7.12(s, 1H), 7.01(s, 1H), 3.81(s, 3H) |
| 114 | 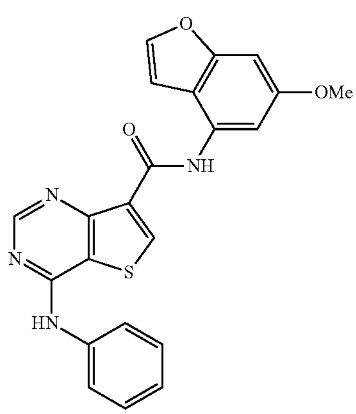 [SMILES: COc1cc(NC(=O)c2csc3c(Nc4ccccc4)ncnc23)c2ccoc2c1] | N-(6-methoxybenzofuran-4-yl)-3-methyl-4-(phenylamino)-3,4-dihydrothieno[3,2-d]pyrimidine-7-carboxamide | — | 12.33(m, 1H), 10.20(s, 1H), 9.04(s, 1H), 8.92(s, 1H), 8.31(s, 2H), 7.76(m, 2H), 7.40(m, 2H), 7.20(m, 1H), 7.15(s, 1H), 7.03(s, 1H), 3.82(s, 3H) |
| 115 | 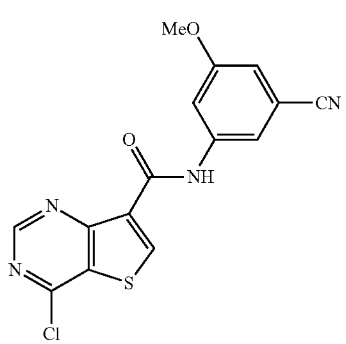 [SMILES: COc1cc(C#N)cc(NC(=O)c2csc3c(Cl)ncnc23)c1] | 4-chloro-N-(3-cyano-5-methoxyphenyl)thieno[3,2-d]pyrimidine-7-carboxamide | — | 12.84(s, 1H), 9.23(s, 1H), 8.83(s, 1H), 8.19(s, 1H), 7.75(s, 1H), 6.79(s, 1H), 3.83(s, 3H) |

TABLE 1-continued

| Ex. | Structure | Compound | MS m/z [M + 1] | NMR ($^1$H NMR 400 MHz, DMSO-$d_6$) |
|---|---|---|---|---|
| 116 | 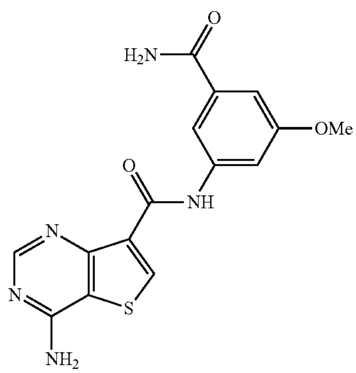 [SMILES: COc1cc(NC(=O)c2csc3c(N)ncnc23)cc(C(N)=O)c1] | 4-amino-N-(3-carbamoyl-5-methoxyphenyl)thieno[3,2-d]pyrimidine-7-carboxamide | 344.21 345.19 | 12.56(s, 1H), 8.86(s, 1H), 8.46(s, 1H), 8.08(s, 1H), 7.90(s, 1H), 7.74(s, 2H), 7.61(d, 1H), 7.37(s, 1H), 6.74(d, 1H), 3.80(s, 3H) |
| 117 | 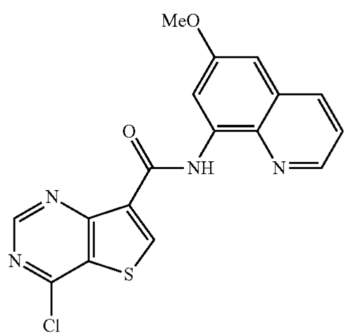 [SMILES: COc1cc(NC(=O)c2csc3c(Cl)ncnc23)c2ncccc2c1] | 4-chloro-N-(6-methoxyquinolin-8-yl)thieno[3,2-d]pyrimidine-7-carboxamide | — | 13.01(s, 1H), 9.47(s, 1H), 9.09(s, 1H), 8.80(s, 1H), 8.59(s, 1H), 8.24(d, 1H), 7.58(t, 1H), 7.15(s, 1H), 3.92(s, 3H) |
| 118 | 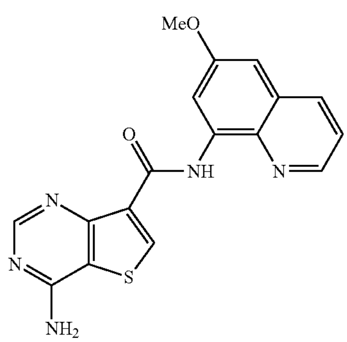 [SMILES: COc1cc(NC(=O)c2csc3c(N)ncnc23)c2ncccc2c1] | 4-amino-N-(6-methoxyquinolin-8-yl)thieno[3,2-d]pyrimidine-7-carboxamide | 352.22 353.20 | 13.36(s, 1H), 8.98(s, 1H), 8.85(d, 1H), 8.68(s, 1H), 8.60(s, 1H), 8.28(d, 1H), 7.85(s, 2H), 7.58(m, 1H), 7.11(d, 1H), 3.91(s, 3H) |
| 119 | 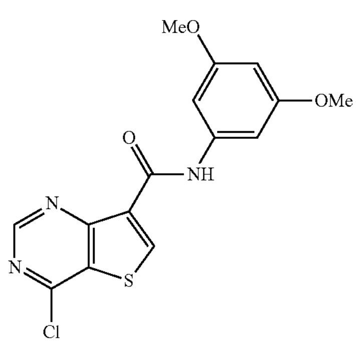 [SMILES: COc1cc(NC(=O)c2csc3c(Cl)ncnc23)cc(OC)c1] | 4-chloro-N-(3,5-dimethoxyphenyl)thieno[3,2-d]pyrimidine-7-carboxamide | — | 11.11(s, 1H), 9.33(s, 1H), 8.95(s, 1H), 6.99(s, 2H), 6.31(s, 1H), 3.74(s, 6H) |

TABLE 1-continued

| Ex. | Structure | Compound | MS m/z [M + 1] | NMR (¹H NMR 400 MHz, DMSO-$d_6$) |
|---|---|---|---|---|
| 120 | 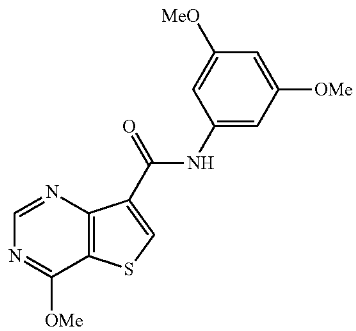 [SMILES: COc1cc(NC(=O)c2csc3c(OC)ncnc23)cc(OC)c1] | N-(3,5-dimethoxyphenyl)-4-methoxythieno[3,2-d]pyrimidine-7-carboxamide | — | 11.40(s, 1H), 9.10(s, 1H), 9.04(s, 1H), 7.00(s, 2H), 6.33(s, 1H), 4.19(s, 3H), 3.77(s, 6H) |
| 121 | 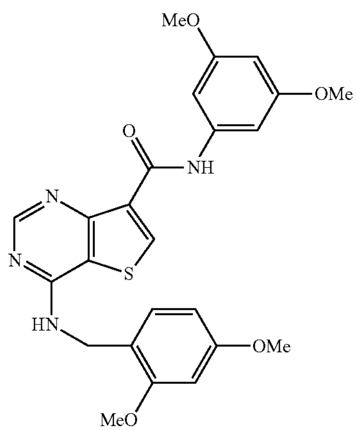 [SMILES: COc1cc(NC(=O)c2csc3c(NCc4ccc(OC)cc4OC)ncnc23)cc(OC)c1] | 4-(2,4-dimethoxybenzyl-amino)-N-(3,5-dimethoxyphenyl)thieno[3,2-d]pyrimidine-7-carboxamide | — | 11.86(s, 1H), 8.88(s, 1H), 8.68(m, 1H), 8.64(s, 1H), 7.11(d, 1H), 6.97(s, 2H), 6.58(s, 1H), 6.46(d, 1H), 6.31(s, 1H), 4.65(d, 2H), 3.82(s, 3H), 3.77(s, 6H), 3.73(s, 3H) |
| 122 | 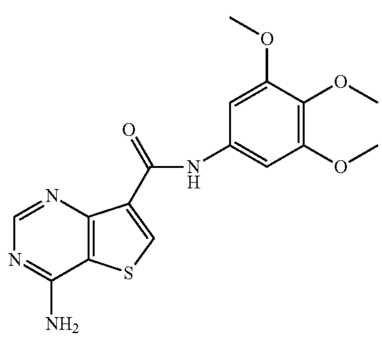 [SMILES: COc1cc(NC(=O)c2csc3c(N)ncnc23)cc(OC)c1OC] | 4-amino-N-(3,4,5-trimethoxyphenyl)thieno[3,2-d]pyrimidine-7-carboxamide | 361.30 362.29 | 11.76(s, 1H), 9.07(s, 1H), 8.60(s, 1H), 7.91(s, 2H), 7.11(s, 2H), 3.80(s, 9H) |
| 123 | 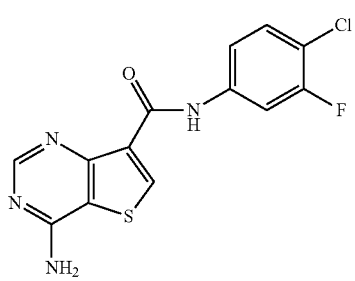 [SMILES: Nc1ncnc2c(C(=O)Nc3ccc(Cl)c(F)c3)csc12] | 4-amino-N-(4-chloro-3-fluorophenyl)thieno[3,2-d]pyrimidine-7-carboxamide | 322.99 324.97 | 12.15(s, 1H), 8.98(s, 1H), 8.58(s, 1H), 8.00(d, 1H), 7.94(s, 2H), 7.60(t, 1H), 7.48(d, 1H) |

TABLE 1-continued

| Ex. | Structure | Compound | MS m/z [M + 1] | NMR (¹H NMR 400 MHz, DMSO-$d_6$) |
|---|---|---|---|---|
| 124 | 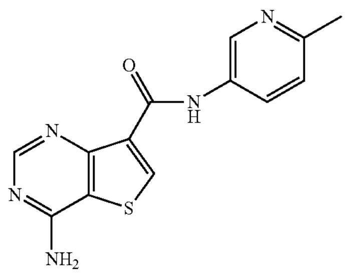 [SMILES: Cc1ccc(NC(=O)c2csc3c(N)ncnc23)cn1] | 4-amino-N-(6-methylpyridin-3-yl)thieno[3,2-d]pyrimidine-7-carboxamide | 286.06 | 11.90(s, 1 h), 8.92(S, 1H), 8.77(s, 1H), 8.58(s, 1H), 8.08(d, 1H), 7.93(s, 2H), 7.28(d, 1H), 2.44(s, 3H) |
| 125 | 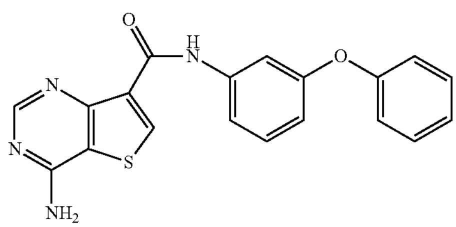 [SMILES: Nc1ncnc2c(C(=O)Nc3cccc(Oc4ccccc4)c3)csc12] | 4-amino-N-(3-phenoxyphenyl)thieno[3,2-d]pyrimidine-7-carboxamide | 363.06 | 11.97(s, 1H), 8.89(s, 1H), 8.56(s, 1H), 7.92(s, 2H), 7.63(s, 1H), 7.37(m, 4H), 7.08(m, 3H), 6.81(d, 1H) |
| 126 | 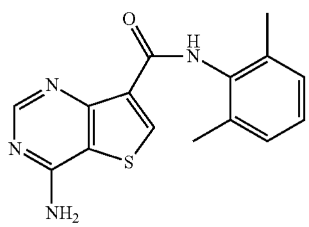 [SMILES: Cc1cccc(C)c1NC(=O)c1csc2c(N)ncnc12] | 4-amino-N-(2,6-dimethylphenyl)thieno[3,2-d]pyrimidine-7-carboxamide | 299.05 | 11.18(s, 1H), 8.87(s, 1H), 8.53(s, 1H), 7.90(s, 2H), 7.13(s, 3H), 2.20(s, 6H) |
| 127 | 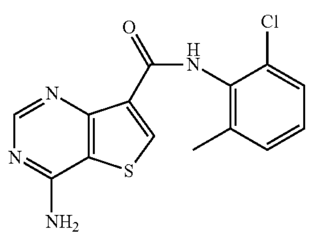 [SMILES: Cc1cccc(Cl)c1NC(=O)c1csc2c(N)ncnc12] | 4-amino-N-(2-chloro-6-methylphenyl)thieno[3,2-d]pyrimidine-7-carboxamide | 319.00 321.01 | 11.39(s, 1H), 8.91(s, 1H), 8.53(s, 1H), 7.92(s, 2H), 7.41(d, 1H), 7.28(m, 2H), 2.25(s, 3H) |
| 128 | 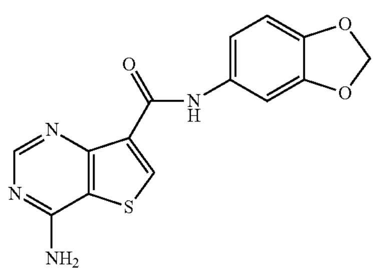 [SMILES: Nc1ncnc2c(C(=O)Nc3ccc4c(c3)OCO4)csc12] | 4-amino-N-(benzo[d][1,3]dioxol-5-yl)thieno[3,2-d]pyrimidine-7-carboxamide | 315.04 | 11.81(s, 1H), 8.87(s, 1H), 8.56(s, 1H), 7.91(s, 2H), 7.51(s, 1H), 7.07(d, 1H), 6.93(d, 1H), 6.02(s, 2H) |
| 129 | 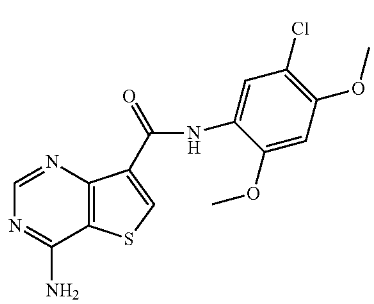 [SMILES: COc1cc(OC)c(NC(=O)c2csc3c(N)ncnc23)cc1Cl] | 4-amino-N-(5-chloro-2,4-dimethoxyphenyl)thieno[3,2-d]pyrimidine-7-carboxamide | 365.04 367.02 | 12.11(s, 1H), 8.87(s, 1H), 8.60(s, 1H), 8.52(s, 1H), 7.87(s, 2H), 6.92(s, 1H), 4.01(s, 3H), 3.89(s, 3H) |

TABLE 1-continued

| Ex. | Structure | Compound | MS m/z [M + 1] | NMR ($^1$H NMR 400 MHz, DMSO-$d_6$) |
|---|---|---|---|---|
| 130 | 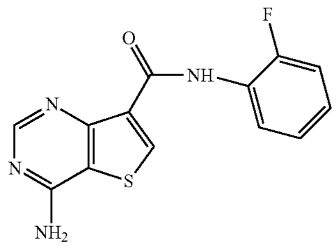 [SMILES: Nc1ncnc2c(C(=O)Nc3ccccc3F)csc12] | 4-amino-N-(2-fluorophenyl)thieno[3,2-d]pyrimidine-7-carboxamide | 289.01 290.05 | 12.11(s, 1H), 8.96(s, 1H), 8.55(s, 1H), 8.46(m, 1H), 7.36(s, 2H), 7.35(m, 1H), 7.23(m, 1H), 7.16(m, 1H) |
| 131 | 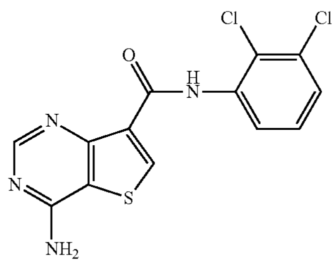 [SMILES: Nc1ncnc2c(C(=O)Nc3cccc(Cl)c3Cl)csc12] | 4-amino-N-(2,3-dichlorophenyl)thieno[3,2-d]pyrimidine-7-carboxamide | 338.98 340.96 | 12.44(s, 1H), 8.99(s, 1H), 8.60(s, 1H), 8.54(t, 1H), 7.94(s, 2H), 7.42(d, 2H) |
| 132 | 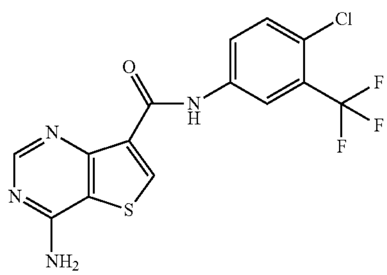 [SMILES: Nc1ncnc2c(C(=O)Nc3ccc(Cl)c(C(F)(F)F)c3)csc12] | 4-amino-N-(4-chloro-3-(trifluoromethyl)phenyl)thieno[3,2-d]pyrimidine-7-carboxamide | 373.00 374.98 | 12.19(s, 1H), 8.96(s, 1H), 8.59(s, 1H), 8.40(s, 1H), 7.95(d, 1H), 7.94(s, 2H), 7.74(d, 1H) |
| 133 | 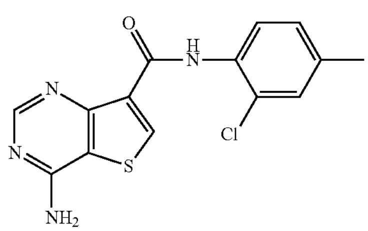 [SMILES: Cc1ccc(NC(=O)c2csc3c(N)ncnc23)c(Cl)c1] | 4-amino-N-(2-chloro-4-methylphenyl)thieno[3,2-d]pyrimidine-7-carboxamide | 319.03 321.01 | 12.15(s, 1H), 8.94(s, 1H), 8.57(s, 1H), 8.38(d, 1H), 7.91(s, 2H), 7.39(s, 1H), 7.18(d, 1H), 2.29(s, 3H) |
| 134 | 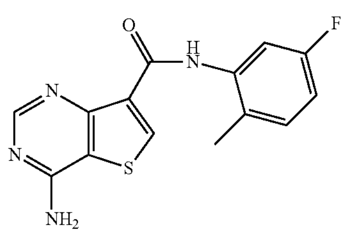 [SMILES: Cc1ccc(F)cc1NC(=O)c1csc2c(N)ncnc12] | 4-amino-N-(5-fluoro-2-methylphenyl)thieno[3,2-d]pyrimidine-7-carboxamide | 303.26 | 11.93(s, 1H), 8.95(s, 1H), 8.57(s, 1H), 8.23(d, 1H), 7.94(s, 2H), 7.30(m, 1H), 6.88(m, 1H), 2.45(s, 3H) |
| 135 | 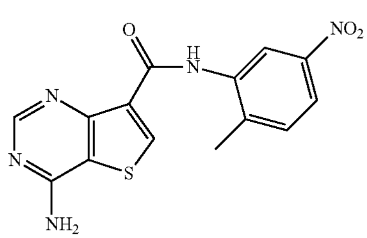 [SMILES: Cc1ccc([N+](=O)[O-])cc1NC(=O)c1csc2c(N)ncnc12] | 4-amino-N-(2-methyl-5-nitrophenyl)thieno[3,2-d]pyrimidine-7-carboxamide | 330.05 | 12.13(s, 1H), 9.32(s, 1H), 8.99(s, 1H), 8.59(s, 1H), 7.97(s, 2H), 7.91(d, 1H), 7.43(d, 1H), 2.60(s, 3H) |

TABLE 1-continued

| Ex. | Structure | Compound | MS m/z [M + 1] | NMR (¹H NMR 400 MHz, DMSO-d$_6$) |
|---|---|---|---|---|
| 136 | 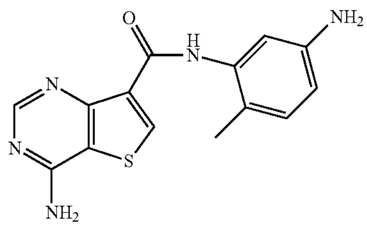 [SMILES: Cc1ccc(N)cc1NC(=O)c1csc2c(N)ncnc12] | 4-amino-N-(5-amino-2-methylphenyl)thieno[3,2-d]pyrimidine-7-carboxamide | 300.06 | 11.85(s, 1H), 8.94(s, 1H), 8.57(s, 1H), 8.26(s, 1H), 7.96(s, 2H), 7.27(d, 1H), 6.83(d, 1H), 2.44(s, 3H) |
| 137 | 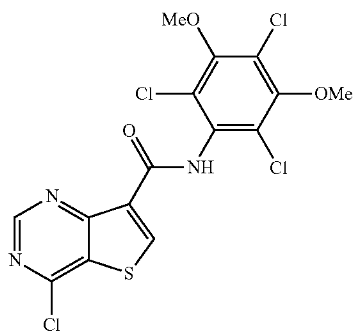 [SMILES: COc1c(Cl)c(NC(=O)c2csc3c(Cl)ncnc23)c(Cl)c(OC)c1Cl] | 4-chloro-N-(2,4,6-trichloro-3,5-dimethoxyphenyl)thieno[3,2-d]pyrimidine-7-carboxamide | | 9.41(s, 1H), 9.31(s, 1H), 3.88(s, 6H) |
| 138 | 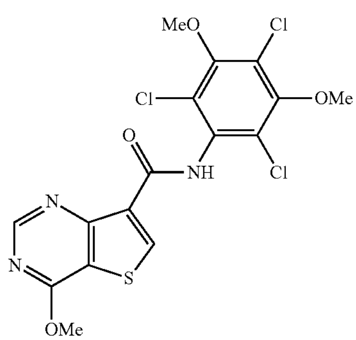 [SMILES: COc1c(Cl)c(NC(=O)c2csc3c(OC)ncnc23)c(Cl)c(OC)c1Cl] | 4-methoxy-N-(2,4,6-trichloro-3,5-dimethoxyphenyl)thieno[3,2-d]pyrimidine-7-carboxamide | — | 11.15(br, 1H), 9.17(s, 1H), 9.00(s, 1H), 4.20(s, 3H), 3.88(s, 6H) |
| 139 | 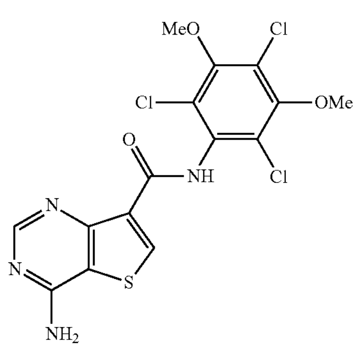 [SMILES: COc1c(Cl)c(NC(=O)c2csc3c(N)ncnc23)c(Cl)c(OC)c1Cl] | 4-amino-N-(2,4,6-trichloro-3,5-dimethoxyphenyl)thieno[3,2-d]pyrimidine-7-carboxamide | — | 11.61(s, 1H), 9.44(s, 1H), 8.54(s, 1H), 7.97(s, 2H), 3.87(s, 6H) |

TABLE 1-continued

| Ex. | Structure | Compound | MS m/z [M + 1] | NMR ($^1$H NMR 400 MHz, DMSO-$d_6$) |
|---|---|---|---|---|
| 140 | 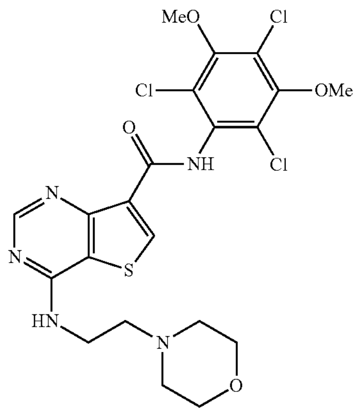 [SMILES: COc1c(Cl)c(NC(=O)c2csc3c(NCCN4CCOCC4)ncnc23)c(Cl)c(OC)c1Cl] | 4-(2-morpholinoethyl-amino)-N-(2,4,6-trichloro-3,5-dimethoxyphenyl)thieno[3,2-d]pyrimidine-7-carboxamide | — | 11.61(s, 1H), 8.93(s, 1H), 8.61(s, 1H), 8.40(m, 1H), 3.87(s, 6H), 3.67(m, 2H), 3.56(m, 4H), 2.57(m, 2H), 2.55-2.31(m, 4H) |
| 141 | 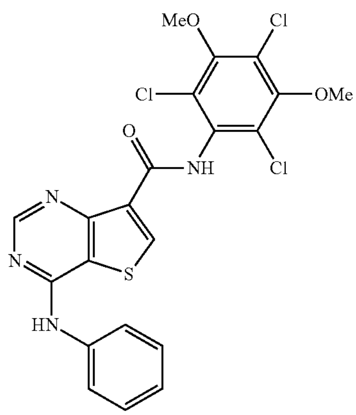 [SMILES: COc1c(Cl)c(NC(=O)c2csc3c(Nc4ccccc4)ncnc23)c(Cl)c(OC)c1Cl] | 4-(phenylamino)-N-(2,4,6-trichloro-3,5-dimethoxyphenyl)thieno[3,2-d]pyrimidine-7-carboxamide | — | 11.54(s, 1H), 10.18(s, 1H), 9.04(s, 1H), 8.74(s, 1H), 7.75(d, 2H), 7.41(t, 2H), 7.20(d, 1H) |
| 142 | 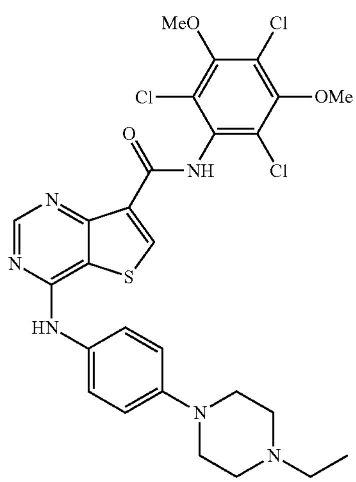 [SMILES: CCN1CCN(c2ccc(Nc3ncnc4c(C(=O)Nc5c(Cl)c(OC)c(Cl)c(OC)c5Cl)csc34)cc2)CC1] | 4-(4-(4-ethylpiperazin-1-yl)phenylamino)-N-(2,4,6-trichloro-3,5-dimethoxyphenyl)thieno[3,2-d]pyrimidine-7-carboxamide | — | 11.61(s, 1H), 9.98(s, 1H), 8.96(s, 1H), 8.64(s, 1H), 7.46(d, 2H), 6.98(d, 2H), 3.87(s, 6H), 3.16(m, 4H), 2.40(m, 4H), 2.36(q, 2H), 1.03(t, 3H) |

TABLE 1-continued

| Ex. | Structure | Compound | MS m/z [M + 1] | NMR ($^1$H NMR 400 MHz, DMSO-$d_6$) |
|---|---|---|---|---|
| 143 | 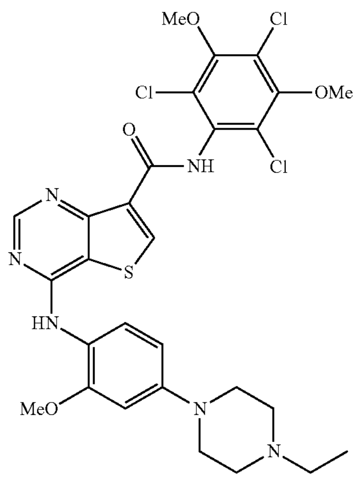 [SMILES: CCN1CCN(c2ccc(Nc3ncnc4c(C(=O)Nc5c(Cl)c(OC)c(Cl)c(OC)c5Cl)csc34)c(OC)c2)CC1] | 4-(4-(4-ethylpiperazin-1-yl)-2-methoxyphenyl-amino)-N-(2,4,6-trichloro-3,5-dimethoxyphenyl)thieno[3,2-d]pyrimidine-7-carboxamide | — | 11.66(s, 1H), 9.59(s, 1H), 8.84(s, 1H), 8.56(s, 1H), 7.16(d, 1H), 6.65(s, 1H), 6.55(d, 1H), 3.86(s, 6H), 3.68(s, 3H), 3.24(m, 4H), 2.39(m, 4H), 2.32(q, 2H), 1.04(t, 3H) |
| 144 | 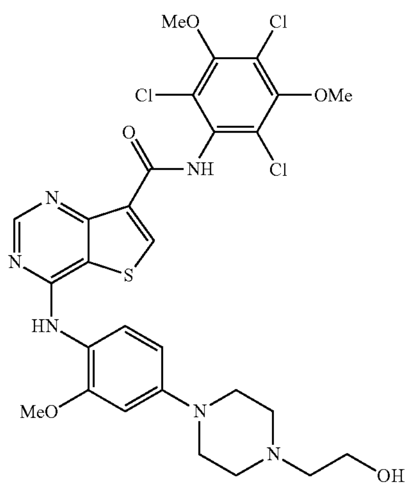 [SMILES: COc1cc(N2CCN(CCO)CC2)ccc1Nc1ncnc2c(C(=O)Nc3c(Cl)c(OC)c(Cl)c(OC)c3Cl)csc12] | 4-(4-(4-(2-hydroxyethyl)piperazin-1-yl)-2-methoxyphenyl-amino)-N-(2,4,6-trichloro-3,5-dimethoxyphenyl)thieno[3,2-d]pyrimidine-7-carboxamide | — | 11.67(s, 1H), 9.58(s, 1H), 8.83(s, 1H), 8.55(s, 1H), 7.15(d, 1H), 6.64(s, 1H), 6.54(s, 1H), 4.46(br,1H), 3.86(s, 6H), 3.68(s, 3H), 3.53(m, 2H), 3.24(m, 4H), 2.43(m, 4H), 2.40(m, 2H) |
| 145 | 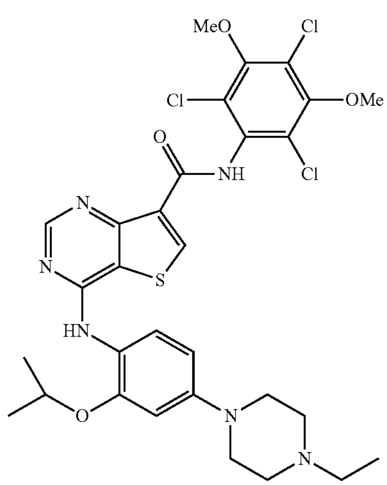 [SMILES: CCN1CCN(c2ccc(Nc3ncnc4c(C(=O)Nc5c(Cl)c(OC)c(Cl)c(OC)c5Cl)csc34)c(OC(C)C)c2)CC1] | 4-(4-(4-ethylpiperazin-1-yl)-2-isopropoxyphenyl-amino)-N-(2,4,6-trichloro-3,5-dimethoxyphenyl)thieno[3,2-d]pyrimidine-7-carboxamide | — | 11.73(s, 1H), 9.54(s, 1H), 8.84(s, 1H), 8.57(s, 1H), 7.20(d, 2H), 6.64(s, 1H), 6.54(d, 1H), 4.56(m, 1H), 3.86(s, 6H), 3.15(m, 4H), 2.31(m, 6H), 1.03(m, 9H) |

TABLE 1-continued

| Ex. | Structure | Compound | MS m/z [M + 1] | NMR (¹H NMR 400 MHz, DMSO-$d_6$) |
|---|---|---|---|---|
| 146 | 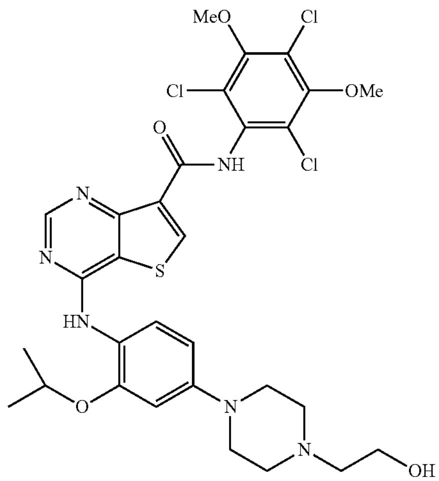 [SMILES: COc1c(Cl)c(NC(=O)c2csc3c(Nc4ccc(N5CCN(CCO)CC5)cc4OC(C)C)ncnc23)c(Cl)c(OC)c1Cl] | 4-(4-(4-(2-hydroxyethyl)piperazin-1-yl)-2-isopropoxyphenyl-amino)-N-(2,4,6-trichloro-3,5-dimethoxyphenyl)thieno[3,2-d]pyrimidine-7-carboxamide | — | 11.66(s, 1H), 9.53(s, 1H), 8.83(s, 1H), 8.57(s, 1H), 7.17(d, 1H), 6.63(s, 1H), 6.55(d, 1H), 4.55(m, 1H), 4.45(br, 1H), 3.86(s, 6H), 3.53(m, 2H), 3.20(m, 4H), 2.43(m, 4H), 2.40(m, 2H), 1.04(d, 6H) |
| 147 | 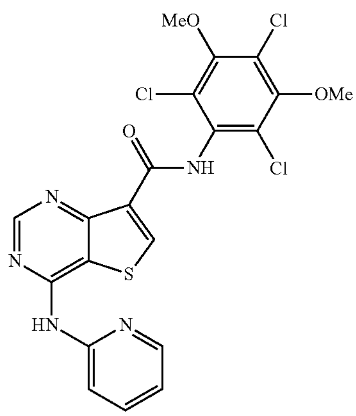 [SMILES: COc1c(Cl)c(NC(=O)c2csc3c(Nc4ccccn4)ncnc23)c(Cl)c(OC)c1Cl] | 4-(pyridin-2-ylamino)-N-(2,4,6-trichloro-3,5-dimethoxyphenyl)thieno[3,2-d]pyrimidine-7-carboxamide | — | 11.55(s, 1H), 11.00(br, 1H), 9.08(s, 1H), 8.83(s, 1H), 8.41(d, 1H), 7.95(d, 1H), 7.86(t, 1H), 7.16(m, 1H), 3.87(s, 6H) |
| 148 | 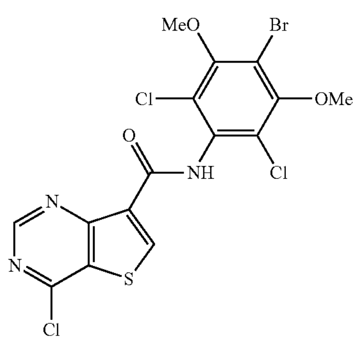 [SMILES: COc1c(Cl)c(NC(=O)c2csc3c(Cl)ncnc23)c(Cl)c(OC)c1Br] | N-(4-bromo-2,6-dichloro-3,5-dimethoxyphenyl)-4-chlorothieno[3,2-d]pyrimidine-7-carboxamide | — | 10.84(s, 1H), 9.36(s, 1H), 9.18(s, 1H), 3.86(s, 6H); MS m/z [M + 1] 496.01, 497.97, 499.96 |
| 149 | 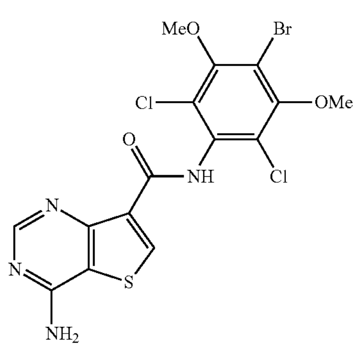 [SMILES: COc1c(Cl)c(NC(=O)c2csc3c(N)ncnc23)c(Cl)c(OC)c1Br] | 4-amino-N-(4-bromo-2,6-dichloro-3,5-dimethoxyphenyl)thieno[3,2-d]pyrimidine-7-carboxamide | 476.87 478.81 480.90 | 11.56(s, 1H), 9.04(s, 1H), 8.53(s, 1H), 7.97(s, 2H), 3.76(s, 6H) |

TABLE 1-continued

| Ex. | Structure | Compound | MS m/z [M + 1] | NMR (¹H NMR 400 MHz, DMSO-d$_6$) |
|---|---|---|---|---|
| 150 | 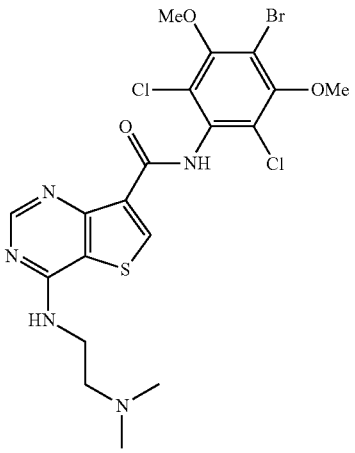 [SMILES: COc1c(Cl)c(NC(=O)c2csc3c(NCCN(C)C)ncnc23)c(Cl)c(OC)c1Br] | N-(4-bromo-2,6-dichloro-3,5-dimethoxyphenyl)-4-(2-(dimethylamino)ethylamino)thieno[3,2-d]pyrimidine-7-carboxamide | 548.16 550.16 552.15 | 11.61(s, 1H), 8.93(s, 1H), 8.16(s, 1H), 8.36(m, 1H), 3.86(s, 6H), 3.24(m, 2H), 2.50(m, 2H), 2.21(s, 6H) |
| 151 | 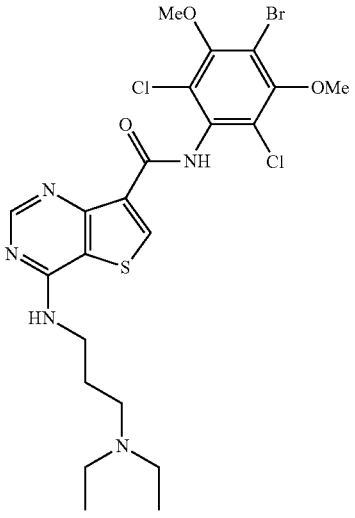 [SMILES: CCN(CC)CCCNc1ncnc2c(C(=O)Nc3c(Cl)c(OC)c(Br)c(OC)c3Cl)csc12] | N-(4-bromo-2,6-dichloro-3,5-dimethoxyphenyl)-4-(3-(diethylamino)propylamino)thieno[3,2-d]pyrimidine-7-carboxamide | 590.23 592.23 594.22 | 11.59(s, 1H), 8.95(s, 1H), 8.65(s, 1H), 8.54(m, 1H), 3.95(s, 6H), 3.60(m, 2H), 3.10(m, 6H), 1.90(m, 2H), 1.11(m, 6H) |
| 152 | 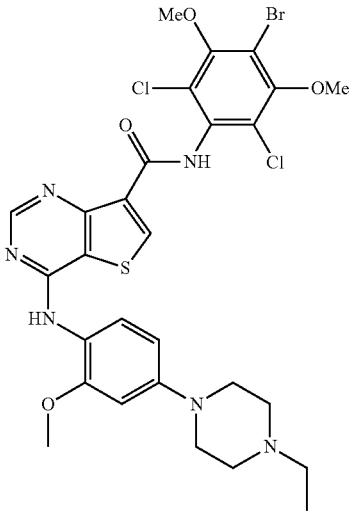 [SMILES: CCN1CCN(c2ccc(Nc3ncnc4c(C(=O)Nc5c(Cl)c(OC)c(Br)c(OC)c5Cl)csc34)c(OC)c2)CC1] | N-(4-bromo-2,6-dichloro-3,5-dimethoxyphenyl)-4-(4-(4-ethylpiperazin-1-yl)-2-methoxyphenylamino)thieno[3,2-d]pyrimidine-7-carboxamide | 695.27 697.27 699.26 | 11.66(s, 1H), 9.57(s, 1H), 8.85(s, 1H), 8.57(s, 1H), 7.19(d, 1H), 6.66(s, 1H), 6.56(d, 1H), 3.86(s, 6H), 3.68(s, 3H), 3.24(m, 4H), 2.39(m, 4H), 2.32(q, 2H), 1.04(t, 3H) |

TABLE 1-continued

| Ex. | Structure | Compound | MS m/z [M + 1] | NMR ($^1$H NMR 400 MHz, DMSO-$d_6$) |
|---|---|---|---|---|
| 153 | 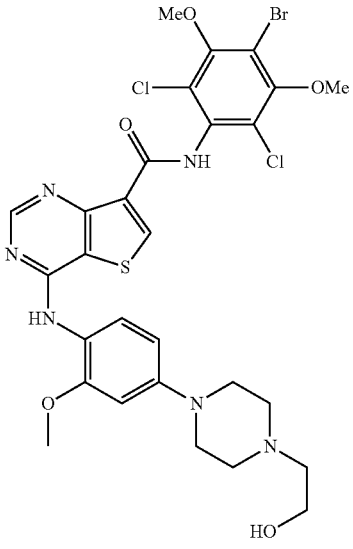 [SMILES: COc1cc(N2CCN(CCO)CC2)ccc1Nc1ncnc2c(C(=O)Nc3c(Cl)c(OC)c(Br)c(OC)c3Cl)csc12] | N-(4-bromo-2,6-dichloro-3,5-dimethoxyphenyl)-4-(4-(4-(2-hydroxyethyl)piperazin-1-yl)-2-methoxyphenylamino)thieno[3,2-d]pyrimidine-7-carboxamide | 711.24 713.27 715.26 | 11.66(s, 1H), 9.59(s, 1H), 8.85(s, 1H), 8.57(s, 1H), 7.17(d, 1H), 6.65(s, 1H), 6.55(d, 1H), 4.46(br,1H), 3.85(s, 6H), 3.70(s, 3H), 3.53(m, 2H), 3.24(m, 4H), 2.43(m, 4H), 2.40(m, 2H) |
| 154 | 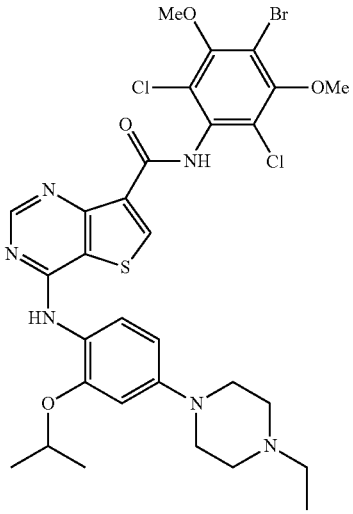 [SMILES: CCN1CCN(c2ccc(Nc3ncnc4c(C(=O)Nc5c(Cl)c(OC)c(Br)c(OC)c5Cl)csc34)c(OC(C)C)c2)CC1] | N-(4-bromo-2,6-dichloro-3,5-dimethoxyphenyl)-4-(4-(4-ethylpiperazin-1-yl)-2-isopropoxyphenylamino)thieno[3,2-d]pyrimidine-7-carboxamide | 723.28 725.31 727.30 | 11.66(s, 1H), 9.54(s, 1H), 8.84(s, 1H), 8.57(s, 1H), 7.18(d, 2H), 6.63(s, 1H), 6.57(d, 1H), 4.55(m, 1H), 3.86(s, 6H), 3.15(m, 4H), 2.31(m, 6H), 1.03(m, 9H) |

TABLE 1-continued

| Ex. | Structure | Compound | MS m/z [M + 1] | NMR ($^1$H NMR 400 MHz, DMSO-$d_6$) |
|---|---|---|---|---|
| 155 | 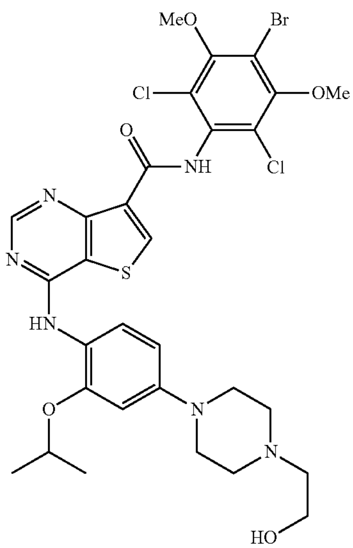 [SMILES: COc1c(Cl)c(NC(=O)c2csc3c(Nc4ccc(N5CCN(CCO)CC5)cc4OC(C)C)ncnc23)c(Cl)c(OC)c1Br] | N-(4-bromo-2,6-dichloro-3,5-dimethoxyphenyl)-4-(4-(4-(2-hydroxyethyl)piperazin-1-yl)-2-isopropoxyphenyl-amino)thieno[3,2-d]pyrimidine-7-carboxamide | 739.31 741.30 743.30 | 11.66(s, 1H), 9.53(s, 1H), 8.84(s, 1H), 8.58(s, 1H), 7.17(d, 1 h), 6.63(s, 1H), 6.55(d, 1H), 4.56(m, 1H), 4.46(br, 1H), 3.86(s, 6H), 3.53(m, 2H), 3.20(m, 4H), 2.43(m, 4H), 2.40(m, 2H), 1.04(d, 6H) |
| 156 | 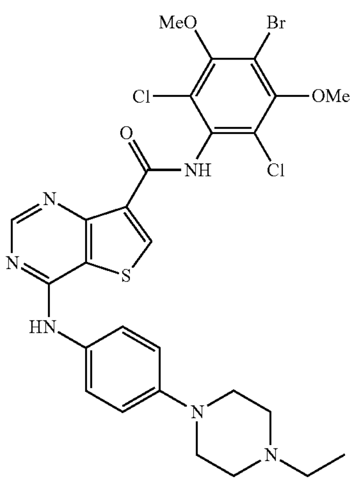 [SMILES: CCN1CCN(c2ccc(Nc3ncnc4c(C(=O)Nc5c(Cl)c(OC)c(Br)c(OC)c5Cl)csc34)cc2)CC1] | N-(4-bromo-2,6-dichloro-3,5-dimethoxyphenyl)-4-(4-(4-ethylpiperazin-1-yl)phenylamino)thieno[3,2-d]pyrimidine-7-carboxamide | 665.24 667.27 669.27 | 11.61(s, 1H), 9.98(s, 1H), 8.96(s, 1H), 8.64(s, 1H), 7.46(d, 2H), 6.97(d, 2H), 3.86(s, 6H), 3.16(m, 4H), 2.40(m, 4H), 2.36(q, 2H), 1.04(t, 3H) |
| 157 | 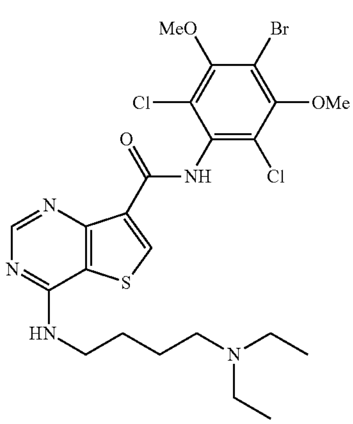 [SMILES: CCN(CC)CCCCNc1ncnc2c(C(=O)Nc3c(Cl)c(OC)c(Br)c(OC)c3Cl)csc12] | N-(4-bromo-2,6-dichloro-3,5-dimethoxyphenyl)-4-(4-(diethylamino)butyl-amino)thieno[3,2-d]pyrimidine-7-carboxamide | 604.27 606.27 608.26 | 11.60(s, 1H), 8.94(s, 1H), 8.61(s, 1H), 8.52(m, 1H), 3.85(s, 6H), 3.57(m, 2H), 3.28(m, 2H), 3.03(m, 4H), 1.68(m, 4H), 1.16(m, 6H) |

TABLE 1-continued

| Ex. | Structure | Compound | MS m/z [M + 1] | NMR ($^1$H NMR 400 MHz, DMSO-$d_6$) |
|---|---|---|---|---|
| 158 | 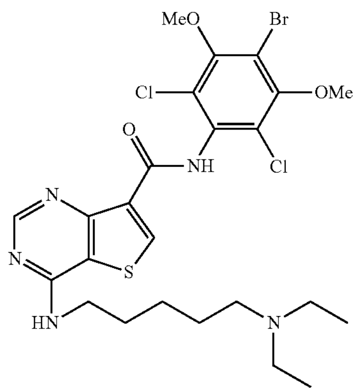 [SMILES: CCN(CC)CCCCCNc1ncnc2c(C(=O)Nc3c(Cl)c(OC)c(Br)c(OC)c3Cl)csc12] | N-(4-bromo-2,6-dichloro-3,5-dimethoxyphenyl)-4-(5-(diethylamino)pentylamino)thieno[3,2-d]pyrimidine-7-carboxamide | 618.27 620.30 622.26 | 11.60(s, 1H), 8.93(s, 1H), 8.60(s, 1H), 8.49(m, 1H), 3.86(s, 6H), 3.55(m, 2H), 3.03(m, 4H), 3.00(m, 2H), 1.67(m, 4H), 1.38(m, 2H), 1.16(t, 6H) |
| 159 | 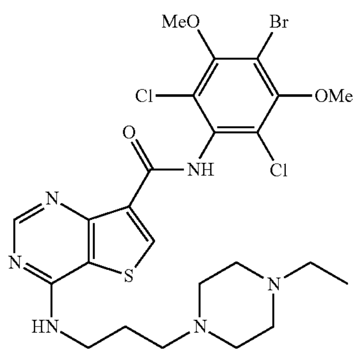 [SMILES: CCN1CCN(CCCNc2ncnc3c(C(=O)Nc4c(Cl)c(OC)c(Br)c(OC)c4Cl)csc23)CC1] | N-(4-bromo-2,6-dichloro-3,5-dimethoxyphenyl) 4-(3-(4-ethylpiperazin-1-yl)propylamino)thieno[3,2-d]pyrimidine-7-carboxamide | 631.26 633.29 635.28 | 11.61(s, 1H), 8.93(s, 1H), 8.60(s, 1H), 8.45(m, 1H), 3.85(s, 6H), 3.57(m, 2H), 2.44(m, 12H), 1.80(m, 2H), 1.08(t, 3H) |
| 160 | 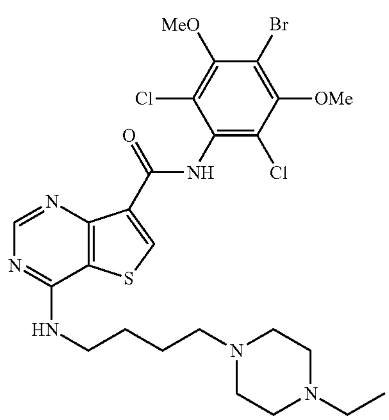 [SMILES: CCN1CCN(CCCCNc2ncnc3c(C(=O)Nc4c(Cl)c(OC)c(Br)c(OC)c4Cl)csc23)CC1] | N-(4-bromo-2,6-dichloro-3,5-dimethoxyphenyl)-4-(4-(4-ethylpiperazin-1-yl)butylamino)thieno[3,2-d]pyrimidine-7-carboxamide | 645.29 647.29 649.32 | 11.61(s, 1H), 8.92(s, 1H), 8.63(s, 1H), 8.45(m, 1H), 3.84(s, 6H), 3.54(m, 2H), 2.57(m, 12H), 1.64(m, 2H), 1.54(m, 2H), 1.05(m, 3H) |
| 161 | 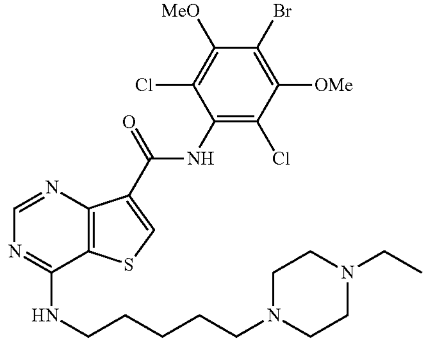 [SMILES: CCN1CCN(CCCCCNc2ncnc3c(C(=O)Nc4c(Cl)c(OC)c(Br)c(OC)c4Cl)csc23)CC1] | N-(4-bromo-2,6-dichloro-3,5-dimethoxyphenyl)-4-(5-(4-ethylpiperazin-1-yl)pentylamino)thieno[3,2-d]pyrimidine-7-carboxamide | 659.33 661.32 663.32 | 11.61(s, 1H), 8.92(s, 1H), 8.59(s, 1H), 8.43(m, 1H), 3.85(s, 6H), 3.54(m, 2H), 2.45(m, 12H), 1.64(m, 2H), 1.49(m, 2H), 1.34(m, 2H), 1.03(m, 3H) |

TABLE 1-continued

| Ex. | Structure | Compound | MS m/z [M + 1] | NMR (¹H NMR 400 MHz, DMSO-d$_6$) |
|---|---|---|---|---|
| 162 | 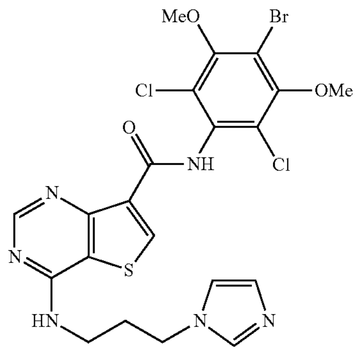 [SMILES: COc1c(Cl)c(NC(=O)c2csc3c(NCCCn4ccnc4)ncnc23)c(Cl)c(OC)c1Br] | 4-(3-(1H-imidazol-1-yl)propylamino)-N-(4-bromo-2,6-dichloro-3,5-dimethoxyphenyl)thieno[3,2-d]pyrimidine-7-carboxamide | 585.19 587.22 589.22 | 11.55(s, 1H), 8.94(s, 1H), 8.58(s, 1H), 8.46(s, 1H), 7.73(s, 1H), 7.24(s, 1H), 6.93(s, 1H), 4.08(t, 2H), 3.85(s, 6H), 3.52(m, 2H), 2.08(m, 2H) |
| 163 | 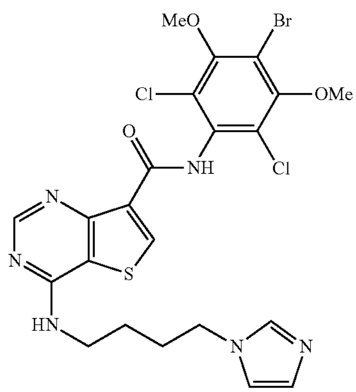 [SMILES: COc1c(Cl)c(NC(=O)c2csc3c(NCCCCn4ccnc4)ncnc23)c(Cl)c(OC)c1Br] | 4-(4-(1H-imidazol-1-yl)butylamino)-N-(4-bromo-2,6-dichloro-3,5-dimethoxyphenyl)thieno[3,2-d]pyrimidine-7-carboxamide | 599.19 601.19 603.19 | 11.60(s, 1H), 8.92(s, 1H), 8.64(s, 1H), 8.45(m, 1H), 7.65(s, 1H), 7.18(s, 1H), 6.88(s, 1H), 3.99(m, 2H), 3.84(s, 6H), 3.56(m, 2H), 1.78(m, 2H), 1.55(m, 2H) |
| 164 | 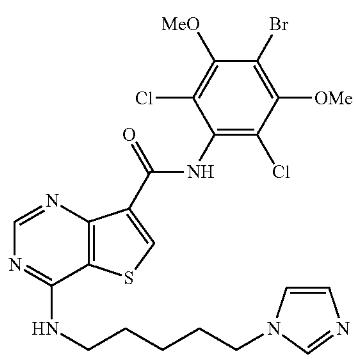 [SMILES: COc1c(Cl)c(NC(=O)c2csc3c(NCCCCCn4ccnc4)ncnc23)c(Cl)c(OC)c1Br] | 4-(5-(1H-imidazol-1-yl)pentylamino)-N-(4-bromo-2,6-dichloro-3,5-dimethoxyphenyl)thieno[3,2-d]pyrimidine-7-carboxamide | 613.23 615.23 617.26 | 11.61(s, 1H), 8.92(s, 1H), 8.59(s, 1H), 8.43(m, 1H), 7.64(s, 1H), 7.15(s, 1H), 6.87(s, 1H), 3.95(t, 2H), 3.84(s, 6H), 3.51(m, 2H), 1.74(t, 2H), 1.64(t, 2H), 1.27(m, 2H) |
| 165 | 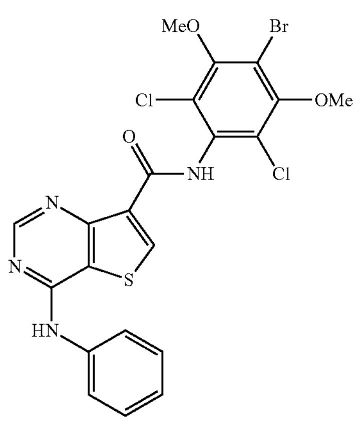 | N-(4-bromo-2,6-dichloro-3,5-dimethoxyphenyl)-4-(phenylamino)thieno[3,2-d]pyrimidine-7-carboxamide | — | 11.52(s, 1H), 10.17(s, 1H), 9.03(s, 1H), 8.73(s, 1H), 7.75(d, 2H), 7.41(t, 2H), 7.19(t, 1H), 3.82(s, 6H) |

TABLE 1-continued

| Ex. | Structure | Compound | MS m/z [M + 1] | NMR ($^1$H NMR 400 MHz, DMSO-$d_6$) |
|---|---|---|---|---|
| 166 | 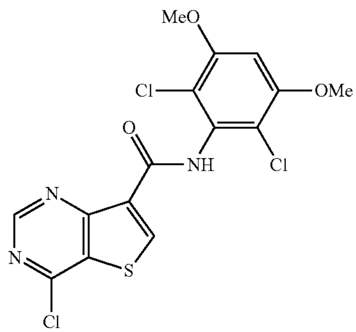 [SMILES: COc1cc(OC)c(Cl)c(NC(=O)c2csc3c(Cl)ncnc23)c1Cl] | 4-chloro-N-(2,6-dichloro-3,5-dimethoxyphenyl)thieno[3,2-d]pyrimidine-7-carboxamide | — | 10.74(s, 1H), 9.34(s, 1H), 9.26(s, 1H), 7.00(s, 1H), 3.97(s, 1H) |
| 167 | 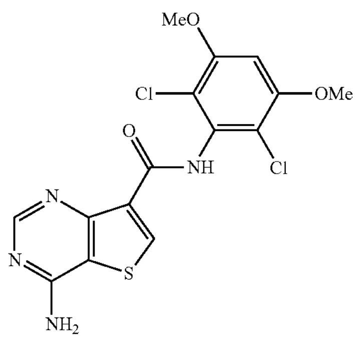 [SMILES: COc1cc(OC)c(Cl)c(NC(=O)c2csc3c(N)ncnc23)c1Cl] | 4-amino-N-(2,6-dichloro-3,5-dimethoxyphenyl)thieno[3,2-d]pyrimidine-7-carboxamide | — | 11.45(s, 1H), 8.92(s, 1H), 8.52(s, 1H), 7.94(s, 2H), 6.95(s, 1H), 3.95(s, 6H) |
| 168 | 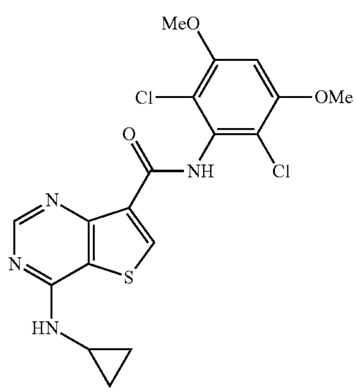 [SMILES: COc1cc(OC)c(Cl)c(NC(=O)c2csc3c(NC4CC4)ncnc23)c1Cl] | 4-(cyclopropylamino)-N-(2,6-dichloro-3,5-dimethoxyphenyl)thieno[3,2-d]pyrimidine-7-carboxamide | — | 11.45(s, 1H), 8.96(s, 1H), 8.68(s, 1H), 8.51(s, 2H), 6.95(s, 1H), 3.96(s, 6H), 1.27(m, 1H), 0.85(m, 2H), 0.68(m, 2H) |
| 169 | 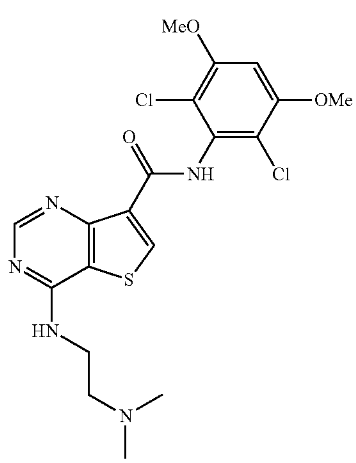 [SMILES: COc1cc(OC)c(Cl)c(NC(=O)c2csc3c(NCCN(C)C)ncnc23)c1Cl] | N-(2,6-dichloro-3,5-dimethoxyphenyl)-4-(2-(dimethylamino)ethylamino)thieno[3,2-d]pyrimidine-7-carboxamide | — | 11.46(s, 1H), 8.89(s, 1H), 8.59(s, 1H), 8.35(m, 1H), 6.95(s, 1H), 3.95(s, 6H), 3.24(m, 2H), 2.49(m, 2H), 2.18(s, 6H) |

TABLE 1-continued

| Ex. | Structure | Compound | MS m/z [M + 1] | NMR (¹H NMR 400 MHz, DMSO-$d_6$) |
|---|---|---|---|---|
| 170 | 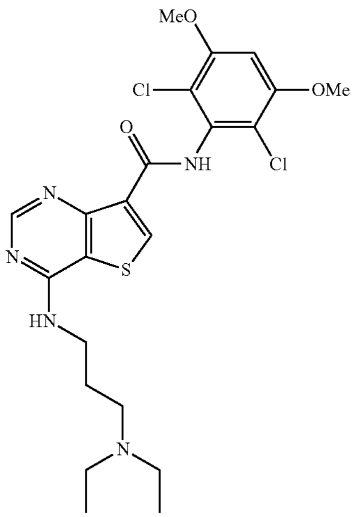 [SMILES: CCN(CC)CCCNc1ncnc2c(C(=O)Nc3c(Cl)c(OC)cc(OC)c3Cl)csc12] | N-(2,6-dichloro-3,5-dimethoxyphenyl)-4-(3-(diethylamino)propylamino)thieno[3,2-d]pyrimidine-7-carboxamide | — | 11.43(s, 1H), 8.92(s, 1H), 8.62(s, 1H), 8.47(m, 1H), 6.95(s, 1H), 3.95(s, 6H), 3.60(m, 2H), 3.10(m, 6H), 1.90(m, 2H), 1.11(m, 6H) |
| 171 | 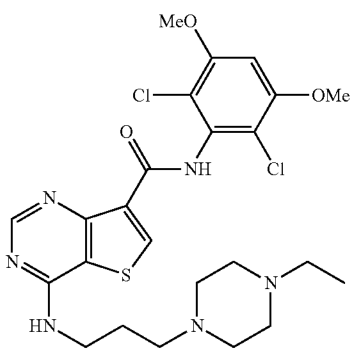 [SMILES: CCN1CCN(CCCNc2ncnc3c(C(=O)Nc4c(Cl)c(OC)cc(OC)c4Cl)csc23)CC1] | N-(2,6-dichloro-3,5-dimethoxyphenyl)-4-(3-(4-ethylpiperazin-1-yl)propylamino)thieno[3,2-d]pyrimidine-7-carboxamide | 553.31 555.30 | 11.45(s, 1H), 8.89(s, 1H), 8.59(s, 1H), 8.34(m, 1H), 6.94(S, 1 h), 3.95(s, 6H), 3.56(m, 2H), 2.33(m, 12H), 1.89(m, 2H), 0.96(t, 3H) |
| 172 | 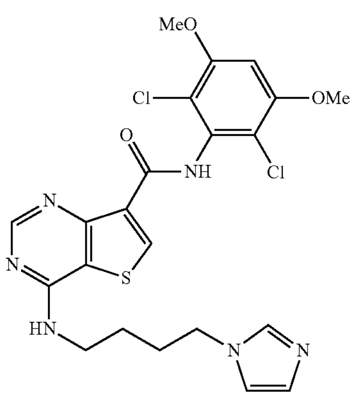 [SMILES: COc1cc(OC)c(Cl)c(NC(=O)c2csc3c(NCCCCn4ccnc4)ncnc23)c1Cl] | 4-(4-(1H-imidazol-1-yl)butylamino)-N-(2,6-dichloro-3,5-dimethoxyphenyl)thieno[3,2-d]pyrimidine-7-carboxamide | 521.25 523.28 | — |

TABLE 1-continued

| Ex. | Structure | Compound | MS m/z [M + 1] | NMR (¹H NMR 400 MHz, DMSO-$d_6$) |
|---|---|---|---|---|
| 173 | 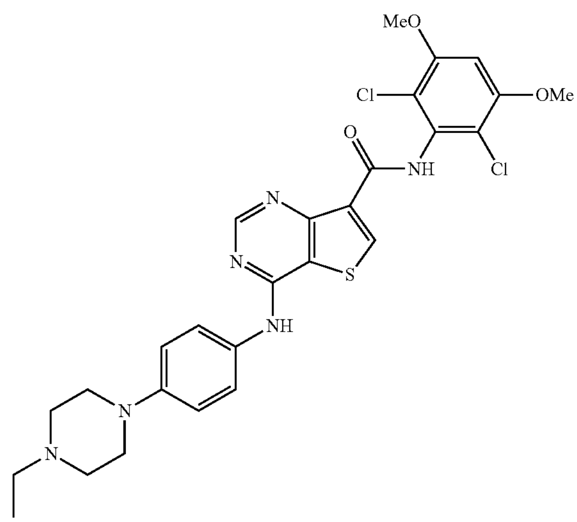 [SMILES: CCN1CCN(c2ccc(Nc3ncnc4c(C(=O)Nc5c(Cl)c(OC)cc(OC)c5Cl)csc34)cc2)CC1] | N-(2,6-dichloro-3,5-dimethoxyphenyl)-4-(4-(4-ethylpiperazin-1-yl)phenylamino)thieno[3,2-d]pyrimidine-7-carboxamide | 587.2 589.15 | 11.45(s, 1H), 9.95(s, 1H), 8.92(s, 1H), 8.63(s, 1H), 7.46(d, 2H), 6.97(d, 2H), 6.95(s, 1H), 3.86(s, 6H), 3.16(m, 4H), 2.40(m, 4H), 2.36(q, 2H), 1.03(t, 3H) |
| 174 | 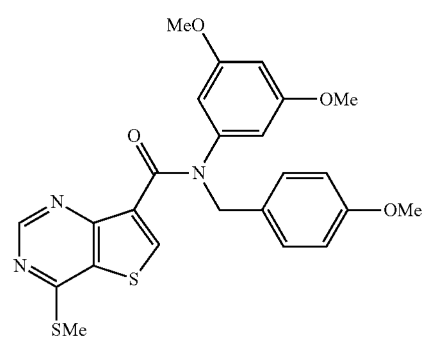 [SMILES: COc1ccc(CN(C(=O)c2csc3c(SC)ncnc23)c2cc(OC)cc(OC)c2)cc1] | N-(3,5-dimethoxyphenyl)-N-(4-methoxybenzyl)-4-(methylthio)thieno[3,2-d]pyrimidine-7-carboxamide | 482.05 483.02 | — |
| 175 | 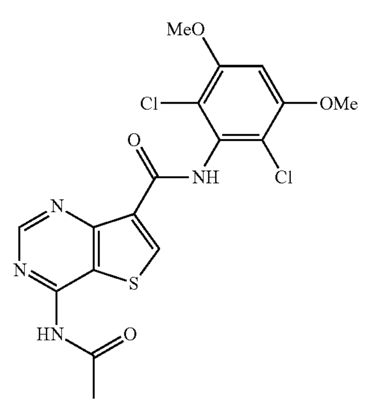 [SMILES: COc1cc(OC)c(Cl)c(NC(=O)c2csc3c(NC(C)=O)ncnc23)c1Cl] | 4-acetamido-N-(2,6-dichloro-3,5-dimethoxyphenyl)thieno[3,2-d]pyrimidine-7-carboxamide | 441.16 443.16 | 11.47(br, 1H), 11.26(s, 1H), 9.15(s, 1H), 9.03(s, 1H), 6.96(s, 1H), 3.96(s, 6H), 2.31(s, 3 h) |

TABLE 1-continued

| Ex. | Structure | Compound | MS m/z [M + 1] | NMR ($^1$H NMR 400 MHz, DMSO-$d_6$) |
|---|---|---|---|---|
| 176 | 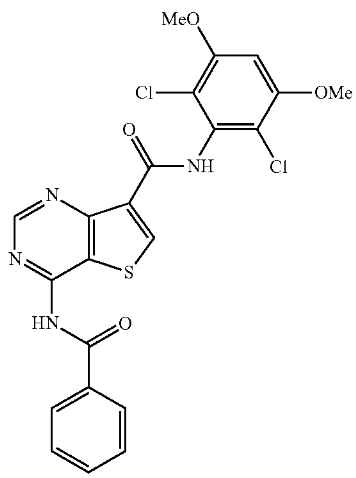 [SMILES: COc1cc(OC)c(Cl)c(NC(=O)c2csc3c(NC(=O)c4ccccc4)ncnc23)c1Cl] | 4-benzamido-N-(2,6-dichloro-3,5-dimethoxyphenyl)thieno[3,2-d]pyrimidine-7-carboxamide | 503.33 505.29 | — |
| 177 | 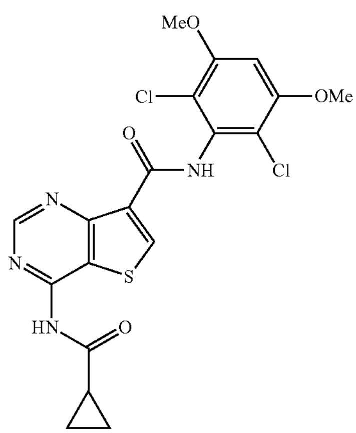 [SMILES: COc1cc(OC)c(Cl)c(NC(=O)c2csc3c(NC(=O)C4CC4)ncnc23)c1Cl] | 4-(cyclopropanecarbox-amido)-N-(2,6-dichloro-3,5-dimethoxyphenyl)thieno[3,2-d]pyrimidine-7-carboxamide | 467.31 469.30 | — |
| 178 | 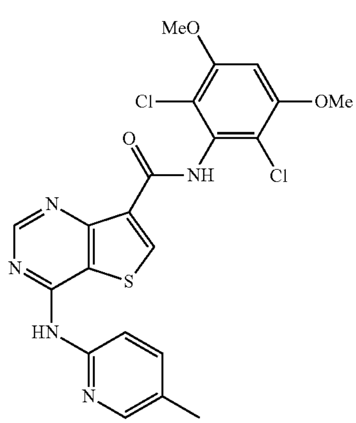 [SMILES: COc1cc(OC)c(Cl)c(NC(=O)c2csc3c(Nc4ccc(C)cn4)ncnc23)c1Cl] | N-(2,6-dichloro-3,5-dimethoxyphenyl)-4-(5-methylpyridine-2-ylamino)thieno[3,2-d]pyrimidine-7-carboxamide | 490.23 492.23 | — |

TABLE 1-continued

| Ex. | Structure | Compound | MS m/z [M + 1] | NMR ($^1$H NMR 400 MHz, DMSO-$d_6$) |
|---|---|---|---|---|
| 179 | 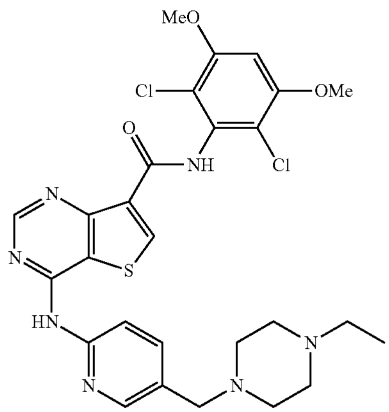 [SMILES: CCN1CCN(Cc2ccc(Nc3ncnc4c(C(=O)Nc5c(Cl)c(OC)cc(OC)c5Cl)csc34)nc2)CC1] | N-(2,6-dichloro-3,5-dimethoxyphenyl)-4-(5-((4-ethylpiperazin-1-yl)methyl)pyridin-2-ylamino)thieno[3,2-d]pyrimidine-7-carboxamide | 602.38 604.24 | — |
| 180 | 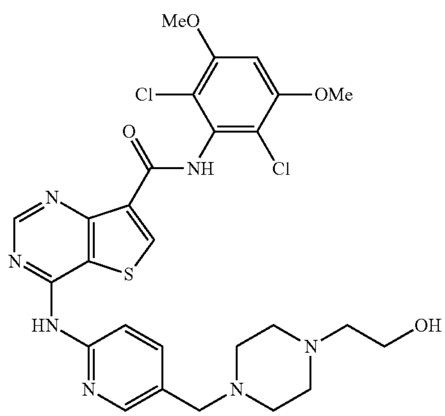 [SMILES: COc1cc(OC)c(Cl)c(NC(=O)c2csc3c(Nc4ccc(CN5CCN(CCO)CC5)cn4)ncnc23)c1Cl] | N-(2,6-dichloro-3,5-dimethoxyphenyl)-4-(5-((4-(2-hydroxyethyl)piperazin-1-yl)methyl)pyridin-2-ylamino)thieno[3,2-d]pyrimidine-7-carboxamide | 618.38 | — |
| 181 | 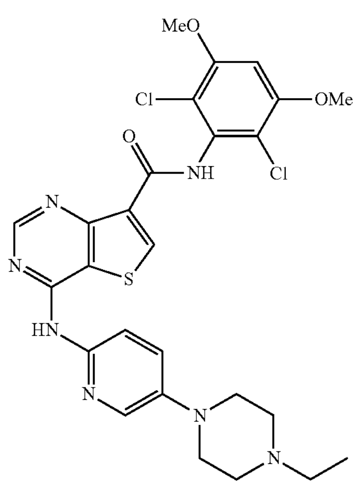 [SMILES: CCN1CCN(c2ccc(Nc3ncnc4c(C(=O)Nc5c(Cl)c(OC)cc(OC)c5Cl)csc34)nc2)CC1] | N-(2,6-dichloro-3,5-dimethoxyphenyl)-4-(5-(4-ethylpiperazin-1-yl)pyridin-2-ylamino)thieno[3,2-d]pyrimidine-7-carboxamide | 588.40 | 11.41(s, 1H), 10.76(s, 1H), 9.03(s, 1H), 8.75(s, 1H), 8.20(s, 1H), 7.83(d, 1H), 7.58(d,1H), 6.96(s, 1H), 3.96(s, 6H), 3.17(m, 4H), 2.48(m, 4H), 2.34(m, 2H), 1.01(t, 3H) |

TABLE 1-continued

| Ex. | Structure | Compound | MS m/z [M + 1] | NMR (¹H NMR 400 MHz, DMSO-d$_6$) |
|---|---|---|---|---|
| 182 | 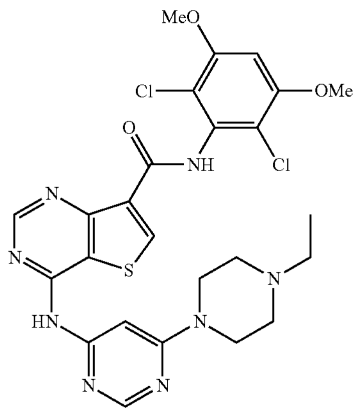 [SMILES: CCN1CCN(c2cc(Nc3ncnc4c(C(=O)Nc5c(Cl)c(OC)cc(OC)c5Cl)csc34)ncn2)CC1] | N-(2,6-dichloro-3,5-dimethoxyphenyl)-4-(6-(4-ethylpiperazin-1-yl)pyrimidin-4-ylamino)thieno[3,2-d]pyrimidine-7-carboxamide | 589.36 | 11.31(s, 1H), 11.07(br, 1H), 9.13(s, 1H), 8.92(s, 1H), 8.48(s, 1H), 7.53(s, 1H), 6.97(s, 1H), 3.96(s, 6H), 3.76(m, 4H), 2.39(m, 4H), 2.32(q, 2H), 1.00(t, 3H) |
| 183 | 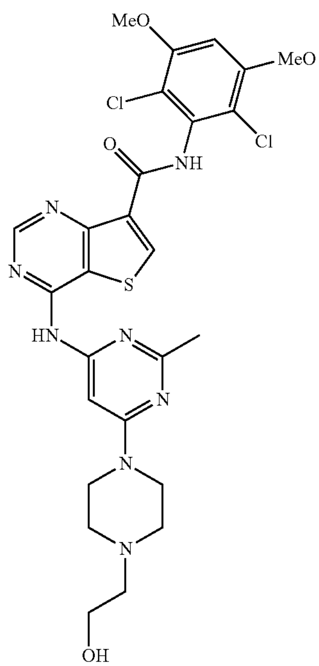 [SMILES: COc1cc(OC)c(Cl)c(NC(=O)c2csc3c(Nc4cc(N5CCN(CCO)CC5)nc(C)n4)ncnc23)c1Cl] | N-(2,6-dichloro-3,5-dimethoxyphenyl)-4-(6-(4-(2-hydroxyethyl)piperazin-1-yl)-2-methylpyrimidin-4-ylamino)thieno[3,2-d]pyrimidine-7-carboxamide | 619.36 | — |
| 184 | 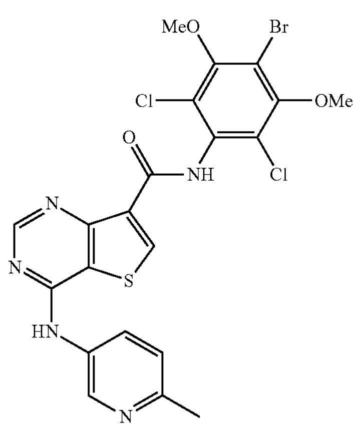 [SMILES: COc1c(Cl)c(NC(=O)c2csc3c(Nc4ccc(C)nc4)ncnc23)c(Cl)c(OC)c1Br] | N-(4-bromo-2,6-dichloro-3,5-dimethoxyphenyl)-4-(6-methylpyridin-3-ylamino)thieno[3,2-d]pyrimidine-7-carboxamide | 568.22 570.23 | — |

TABLE 1-continued

| Ex. | Structure | Compound | MS m/z [M + 1] | NMR (¹H NMR 400 MHz, DMSO-$d_6$) |
|---|---|---|---|---|
| 185 | 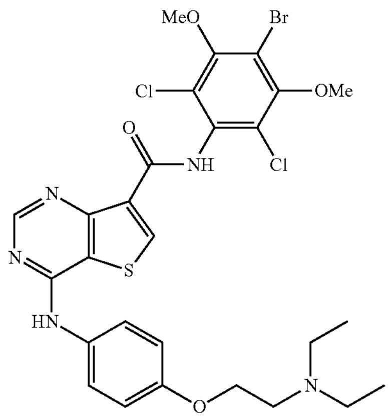 [SMILES: CCN(CC)CCOc1ccc(Nc2ncnc3c(C(=O)Nc4c(Cl)c(OC)c(Br)c(OC)c4Cl)csc23)cc1] | N-(4-bromo-2,6-dichloro-3,5-dimethoxyphenyl)-4-(4-(2-(diethylamino)ethoxy)phenylamino)thieno[3,2-d]pyrimidine-7-carboxamide | 668.33 670.33 | — |
| 186 | 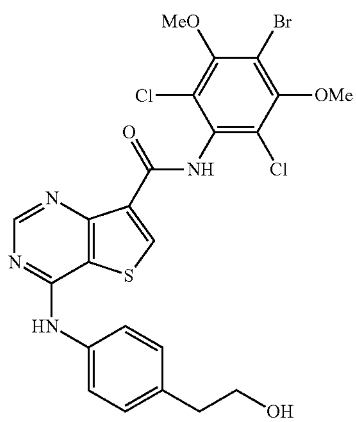 [SMILES: COc1c(Cl)c(NC(=O)c2csc3c(Nc4ccc(CCO)cc4)ncnc23)c(Cl)c(OC)c1Br] | N-(4-bromo-2,6-dichloro-3,5-dimethoxyphenyl)-4-(4-(2-hydroxyethyl)phenylamino)thieno[3,2-d]pyrimidine-7-carboxamide | 597.34 599.34 | — |
| 187 | 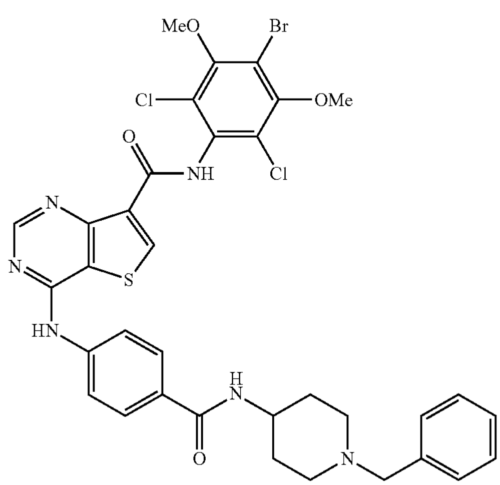 [SMILES: COc1c(Cl)c(NC(=O)c2csc3c(Nc4ccc(C(=O)NC5CCN(Cc6ccccc6)CC5)cc4)ncnc23)c(Cl)c(OC)c1Br] | 4-(4-(1-benzylpiperidine-4-ylcarbamoyl)phenylamino)-N-(4-bromo-2,6-dichloro-3,5-dimethoxyphenyl)thieno[3,2-d]pyrimidine-7-carboxamide | 769.51 771.51 773.51 | — |

TABLE 1-continued

| Ex. | Structure | Compound | MS m/z [M + 1] | NMR (¹H NMR 400 MHz, DMSO-d$_6$) |
|---|---|---|---|---|
| 188 | 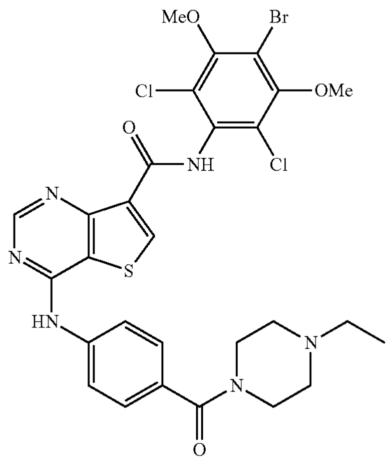 [SMILES: CCN1CCN(C(=O)c2ccc(Nc3ncnc4c(C(=O)Nc5c(Cl)c(OC)c(Br)c(OC)c5Cl)csc34)cc2)CC1] | N-(4-bromo-2,6-dichloro-3,5-dimethoxyphenyl)-4-(4-(4-ethylpiperazine-1-carbonyl)phenylamino)thieno[3,2-d]pyrimidine-7-carboxamide | 693.42<br>695.44 | — |
| 189 | 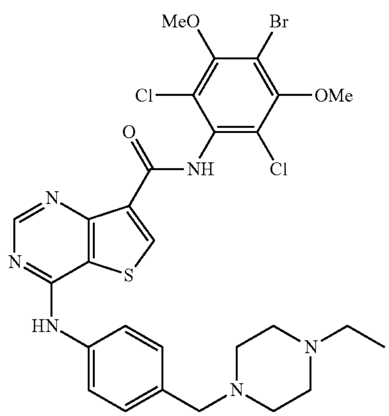 [SMILES: CCN1CCN(Cc2ccc(Nc3ncnc4c(C(=O)Nc5c(Cl)c(OC)c(Br)c(OC)c5Cl)csc34)cc2)CC1] | N-(2,6-dichloro-3,5-dimethoxyphenyl)-4-(4-((4-ethylpiperazin-1-yl)methyl)phenylamino)thieno[3,2-d]pyrimidine-7-carboxamide | 601.51<br>603.51 | — |
| 190 | 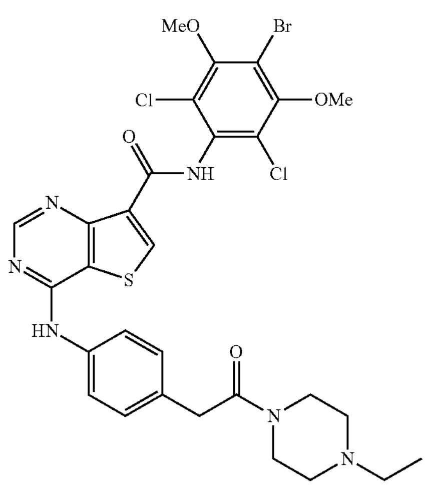 [SMILES: CCN1CCN(C(=O)Cc2ccc(Nc3ncnc4c(C(=O)Nc5c(Cl)c(OC)c(Br)c(OC)c5Cl)csc34)cc2)CC1] | N-(4-bromo-2,6-dichloro-3,5-dimethoxyphenyl)-4-(4-(2-(4-ethylpiperazin-1-yl)-2-oxoethyl)phenylamino)thieno[3,2-d]pyrimidine-7-carboxamide | 707.42<br>709.44<br>711.42 | — |

TABLE 1-continued

| Ex. | Structure | Compound | MS m/z [M + 1] | NMR (¹H NMR 400 MHz, DMSO-d$_6$) |
|---|---|---|---|---|
| 191 | 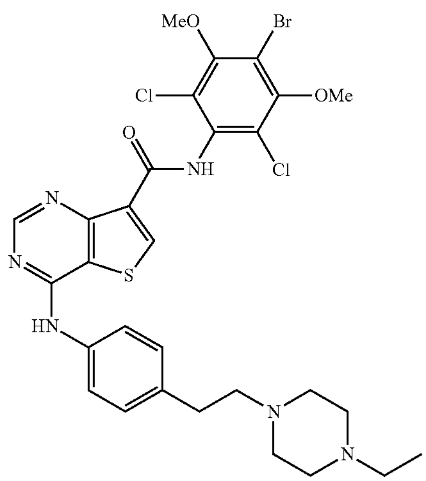 [SMILES: CCN1CCN(CCc2ccc(Nc3ncnc4c(C(=O)Nc5c(Cl)c(OC)c(Br)c(OC)c5Cl)csc34)cc2)CC1] | N-(4-bromo-2,6-dichloro-3,5-dimethoxyphenyl)-4-(4-(2-(4-ethylpiperazin-1-yl)ethyl)phenylamino)thieno[3,2-d]pyrimidine-7-carboxamide | 693.29<br>695.28<br>697.27 | — |
| 192 | 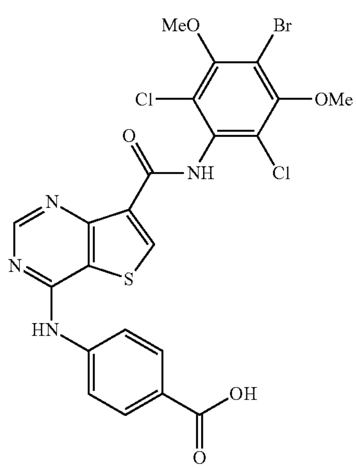 [SMILES: COc1c(Cl)c(NC(=O)c2csc3c(Nc4ccc(C(=O)O)cc4)ncnc23)c(Cl)c(OC)c1Br] | 4-(7-(4-bromo-2,6-dichloro-3,5-dimethoxyphenylcarbamoyl)thieno[3,2-d]pyrimidin-4-ylamino)benzoic acid | 597.17<br>599.16<br>601.17 | — |
| 193 | 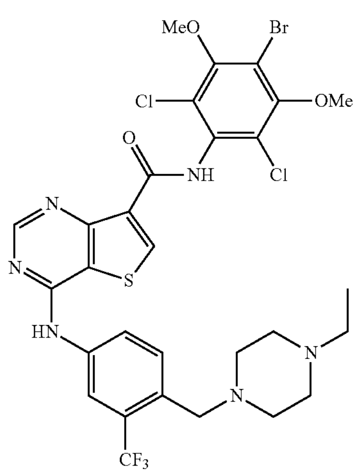 [SMILES: CCN1CCN(Cc2ccc(Nc3ncnc4c(C(=O)Nc5c(Cl)c(OC)c(Br)c(OC)c5Cl)csc34)cc2C(F)(F)F)CC1] | N-(4-bromo-2,6-dichloro-3,5-dimethoxyphenyl)-4-(4-((4-ethylpiperazin-1-yl)methyl)-3-(trifluoromethyl)phenylamino)thieno[3,2-d]pyrimidine-7-carboxamide | 747.41<br>749.42<br>751.44 | — |

TABLE 1-continued

| Ex. | Structure | Compound | MS m/z [M + 1] | NMR (¹H NMR 400 MHz, DMSO-$d_6$) |
|---|---|---|---|---|
| 194 | 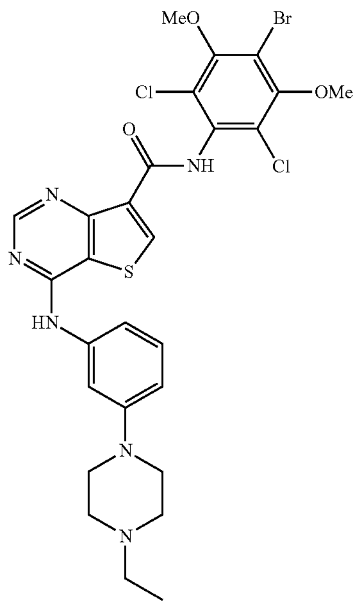 [SMILES: CCN1CCN(c2cccc(Nc3ncnc4c(C(=O)Nc5c(Cl)c(OC)c(Br)c(OC)c5Cl)csc34)c2)CC1] | N-(4-bromo-2,6-dichloro-3,5-dimethoxyphenyl)-4-(3-(4-ethylpiperazin-1-yl)phenylamino)thieno[3,2-d]pyrimidine-7-carboxamide | 665.25<br>667.24<br>669.25 | — |
| 195 | 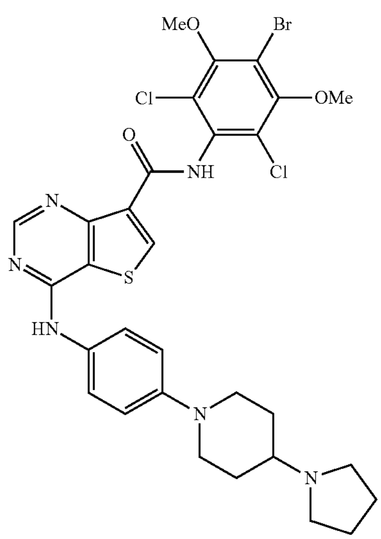 [SMILES: COc1c(Cl)c(NC(=O)c2csc3c(Nc4ccc(N5CCC(N6CCCC6)CC5)cc4)ncnc23)c(Cl)c(OC)c1Br] | N-(4-bromo-2,6-dichloro-3,5-dimethoxyphenyl)-4-(4-(4-pyrrolidin-1-yl)piperidin-1-yl)phenylamino)thieno[3,2-d]pyrimidine-7-carboxamide | 705.29<br>707.28<br>709.28 | — |
| 196 | 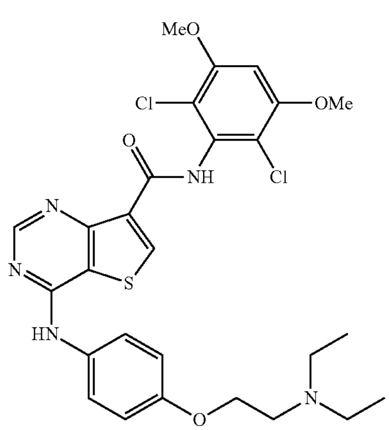 [SMILES: CCN(CC)CCOc1ccc(Nc2ncnc3c(C(=O)Nc4c(Cl)c(OC)cc(OC)c4Cl)csc23)cc1] | N-(2,6-dichloro-3,5-dimethoxyphenyl)-4-(4-(2-(diethylamino)ethoxy)phenylamino)thieno[3,2-d]pyrimidine-7-carboxamide | 590.38<br>592.39 | — |

TABLE 1-continued

| Ex. | Structure | Compound | MS m/z [M + 1] | NMR ($^1$H NMR 400 MHz, DMSO-$d_6$) |
|---|---|---|---|---|
| 197 | 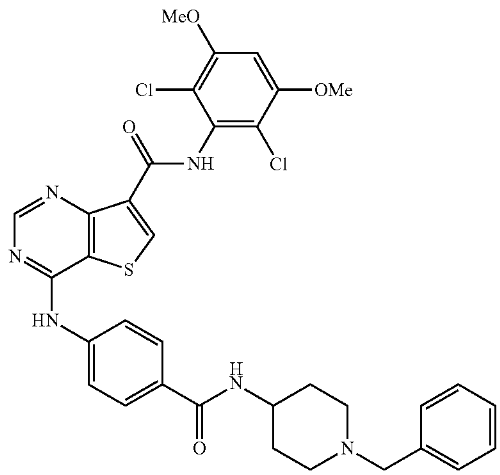 [SMILES: COc1cc(OC)c(Cl)c(NC(=O)c2csc3c(Nc4ccc(C(=O)NC5CCN(Cc6ccccc6)CC5)cc4)ncnc23)c1Cl] | 4-(4-(1-benzylpiperidine-4-ylcarbamoyl)phenyl-amino)-N-(2,6-dichloro-3,5-dimethoxyphenyl)thieno[3,2-d]pyrimidine-7-carboxamide | 691.55 693.58 | — |
| 198 | 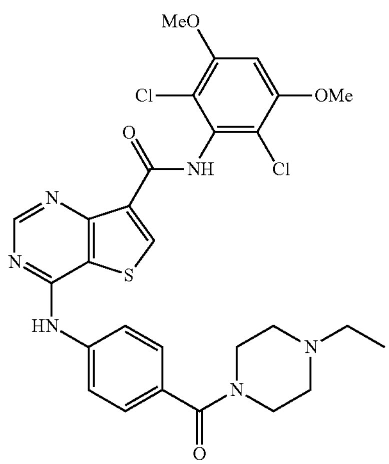 [SMILES: CCN1CCN(C(=O)c2ccc(Nc3ncnc4c(C(=O)Nc5c(Cl)c(OC)cc(OC)c5Cl)csc34)cc2)CC1] | N-(2,6-dichloro-3,5-dimethoxyphenyl)-4-(4-(4-ethylpiperazine-1-carbonyl)phenyl-amino)thieno[3,2-d]pyrimidine-7-carboxamide | 615.48 617.48 | — |
| 199 | 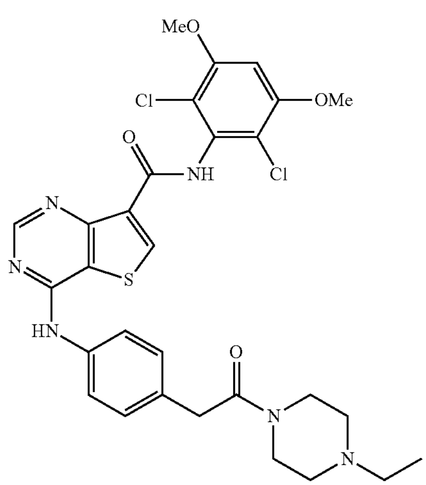 [SMILES: CCN1CCN(C(=O)Cc2ccc(Nc3ncnc4c(C(=O)Nc5c(Cl)c(OC)cc(OC)c5Cl)csc34)cc2)CC1] | N-(2,6-dichloro-3,5-dimethoxyphenyl)-4-(4-(2-(4-ethylpiperazin-1-yl)-2-oxoethyl)phenyl-amino)thieno[3,2-d]pyrimidine-7-carboxamide | 629.51 631.52 | — |

TABLE 1-continued
| Ex. | Structure | Compound | MS m/z [M + 1] | NMR ($^1$H NMR 400 MHz, DMSO-$d_6$) |
|---|---|---|---|---|
| 200 | 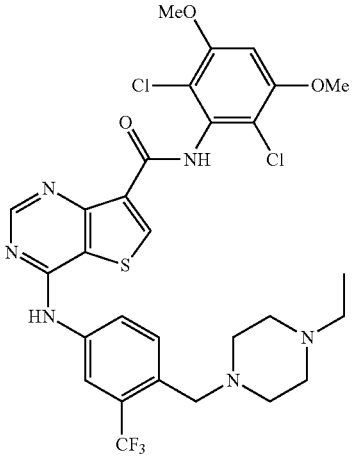 [SMILES: CCN1CCN(Cc2ccc(Nc3ncnc4c(C(=O)Nc5c(Cl)c(OC)cc(OC)c5Cl)csc34)cc2C(F)(F)F)CC1] | N-(2,6-dichloro-3,5-dimethoxyphenyl)-4-(4-((4-ethylpiperazin-1-yl)methyl)-3-(trifluoromethyl)phenylamino)thieno[3,2-d]pyrimidine-7-carboxamide | 669.49 671.49 | — |
| 201 | 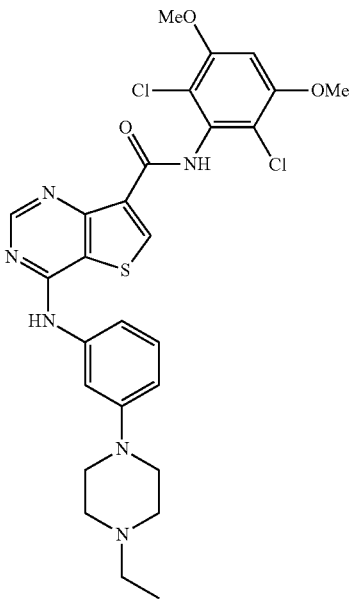 [SMILES: CCN1CCN(c2cccc(Nc3ncnc4c(C(=O)Nc5c(Cl)c(OC)cc(OC)c5Cl)csc34)c2)CC1] | N-(2,6-dichloro-3,5-dimethoxyphenyl)-4-(3-(4-ethylpiperazin-1-yl)phenylamino)thieno[3,2-d]pyrimidine-7-carboxamide | 587.47 589.47 | — |

TABLE 1-continued

| Ex. | Structure | Compound | MS m/z [M + 1] | NMR (¹H NMR 400 MHz, DMSO-$d_6$) |
|---|---|---|---|---|
| 202 | 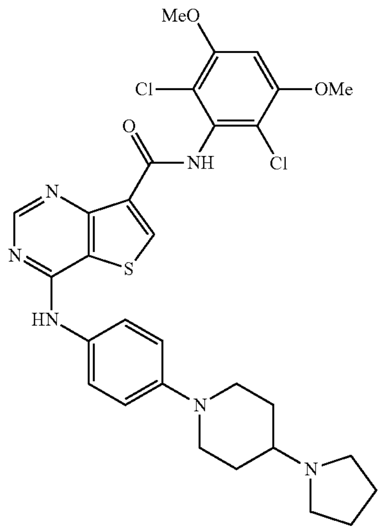 [SMILES: COc1cc(OC)c(Cl)c(NC(=O)c2csc3c(Nc4ccc(N5CCC(N6CCCC6)CC5)cc4)ncnc23)c1Cl] | N-(2,6-dichloro-3,5-dimethoxyphenyl)-4-(4-(4-(pyrrolidin-1-yl)piperidin-1-yl)phenylamino)thieno[3,2-d]pyrimidine-7-carboxamide | 627.51 629.50 | — |
| 203 | 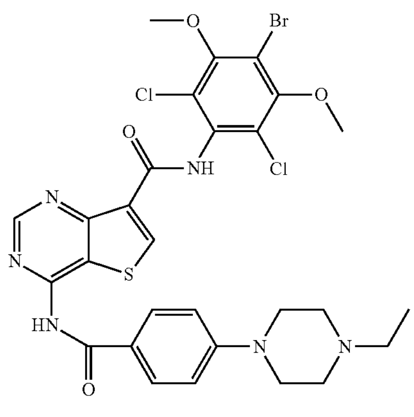 [SMILES: CCN1CCN(c2ccc(C(=O)Nc3ncnc4c(C(=O)Nc5c(Cl)c(OC)c(Br)c(OC)c5Cl)csc34)cc2)CC1] | N-(4-bromo-2,6-dichloro-3,5-dimethoxyphenyl)-4-(4-(4-ethylpiperazin-1-yl)benzamido)thieno[3,2-d]pyrimidine-7-carboxamide | 693.27 695.26 | 11.57(s, 1H), 11.40(s, 1H), 9.20(s, 1H), 9.08(s, 1H), 8.03(d, 2H), 7.03(d, 2H), 3.86(s, 6H), 3.35(m, 4H), 2.50(m, 4H), 2.36(q, 2H), 1.04(t, 3H) |
| 204 | 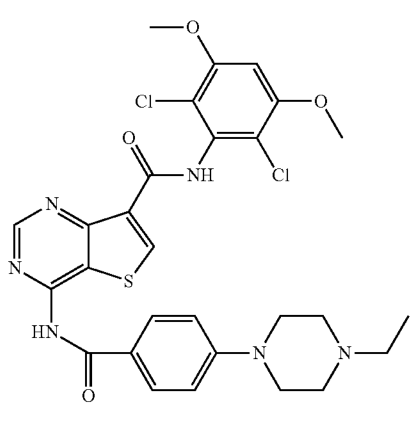 [SMILES: CCN1CCN(c2ccc(C(=O)Nc3ncnc4c(C(=O)Nc5c(Cl)c(OC)cc(OC)c5Cl)csc34)cc2)CC1] | N-(2,6-dichloro-3,5-dimethoxyphenyl)-4-(4-(4-ethylpiperazin-1-yl)benzamido)thieno[3,2-d]pyrimidine-7-carboxamide | 615.14 | 11.65(s, 1H), 11.27(s, 1H), 9.19(s, 1H), 9.10(s, 1H), 8.09(d, 2H), 7.15(d, 2H), 6.98(s, 1H), 3.97(s, 6H) 3.35(m, 4H), 2.50(m, 4H), 2.36(q, 2H), 1.04(t, 3H) |

TABLE 1-continued

| Ex. | Structure | Compound | MS m/z [M + 1] | NMR ($^1$H NMR 400 MHz, DMSO-$d_6$) |
|---|---|---|---|---|
| 205 | 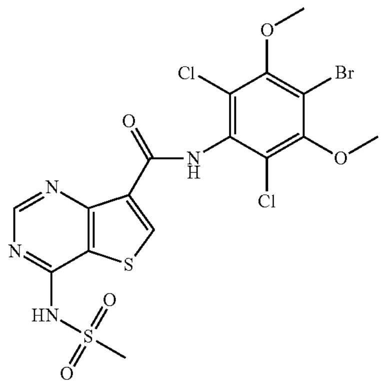 [SMILES: COc1c(Cl)c(NC(=O)c2csc3c(NS(C)(=O)=O)ncnc23)c(Cl)c(OC)c1Br] | N-(4-bromo-2,6-dichloro-3,5-dimethoxyphenyl)-4-(methylsulfonamido)thieno[3,2-d]pyrimidine-7-carboxamide | 554.90 556.89 558.90 | 11.05(s, 1H), 9.03(s, 1H), 8.62(s, 1H), 3.86(s, 6H), 2.91(s, 3H) |
| 206 | 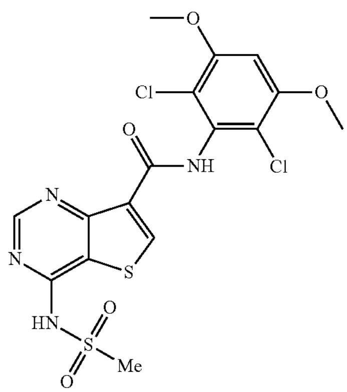 [SMILES: COc1cc(OC)c(Cl)c(NC(=O)c2csc3c(NS(C)(=O)=O)ncnc23)c1Cl] | N-(2,6-dichloro-3,5-dimethoxyphenyl)-4-(methylsulfonamido)thieno[3,2-d]pyrimidine-7-carboxamide | 477.06 479.10 | 11.05(s, 1H), 8.80(s, 1H), 8.42(s, 1H), 6.95(s, 1H), 3.96(s, 6H), 2.91(s, 3H) |
| 207 | 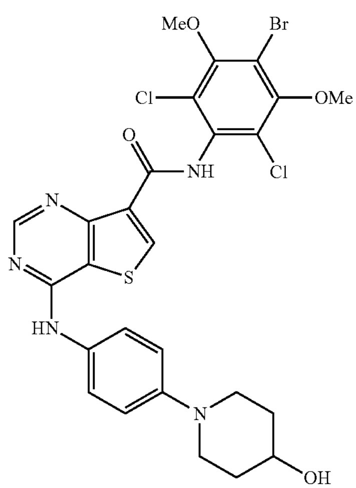 [SMILES: COc1c(Cl)c(NC(=O)c2csc3c(Nc4ccc(N5CCC(O)CC5)cc4)ncnc23)c(Cl)c(OC)c1Br] | N-(4-bromo-2,6-dichloro-3,5-dimethoxyphenyl)-4-(4-(4-hydroxypiperidin-1-yl)phenylamino)thieno[3,2-d]pyrimidine-7-carboxamide | 652.10 654.08 656.09 | 11.67(s, 1H), 9.95(s, 1H), 8.95(s, 1H), 8.63(s, 1H), 7.44(d, 2H), 6.98(d, 2H), 3.84(s, 6H), 3.27(m, 1H), 2.80(m, 4H), 1.81(m, 2H), 1.47(m, 2H) |

TABLE 1-continued

| Ex. | Structure | Compound | MS m/z [M + 1] | NMR ($^1$H NMR 400 MHz, DMSO-$d_6$) |
|---|---|---|---|---|
| 208 | 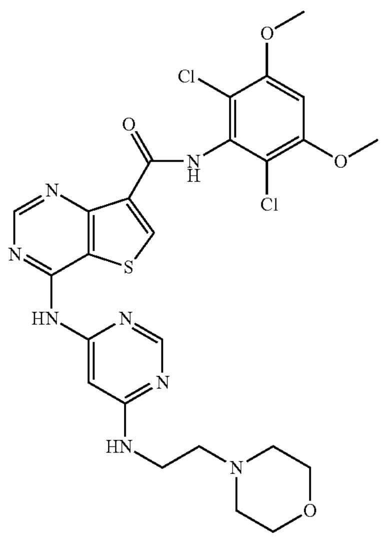 [SMILES: COc1cc(OC)c(Cl)c(NC(=O)c2csc3c(Nc4cc(NCCN5CCOCC5)ncn4)ncnc23)c1Cl] | N-(2,6-dichloro-3,5-dimethoxyphenyl)-4-(6-(2-morpholinoethylamino)pyrimidin-4-ylamino)thieno[3,2-d]pyrimidine-7-carboxamide | 605.29 607.28 | 11.33(s, 1H), 10.86(br, 1H), 9.15(s, 1H), 8.87(s, 1H), 8.28(s, 1H), 7.40(br, 1H), 7.19(s, 1H), 6.95(s, 1H), 3.96(s, 6H), 3.56(m, 4H), 3.40(m, 2H), 2.49(m, 2H), 2.41(m, 4H) |
| 209 | 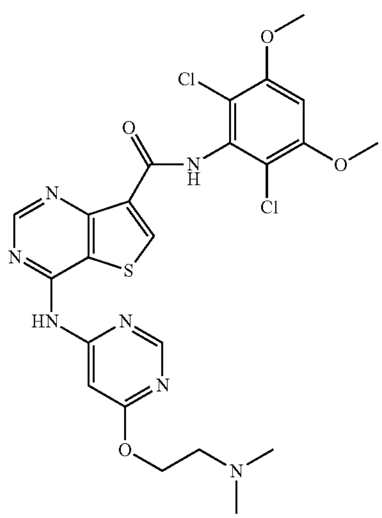 [SMILES: COc1cc(OC)c(Cl)c(NC(=O)c2csc3c(Nc4cc(OCCN(C)C)ncn4)ncnc23)c1Cl] | N-(2,6-dichloro-3,5-dimethoxyphenyl)-4-(6-(2-(dimethylamino)ethoxy)pyrimidin-4-ylamino)thieno[3,2-d]pyrimidine-7-carboxamide | 564.17 566.18 | 11.26(s, 1H), 9.17(s, 1H), 8.99(s, 1H), 8.67(s, 1H), 7.84(s, 1H), 6.97(s, 1H), 4.68(t, 2H), 3.97(s, 6H), 2.82(s, 6H), 2.78(m, 2H) |
| 210 | 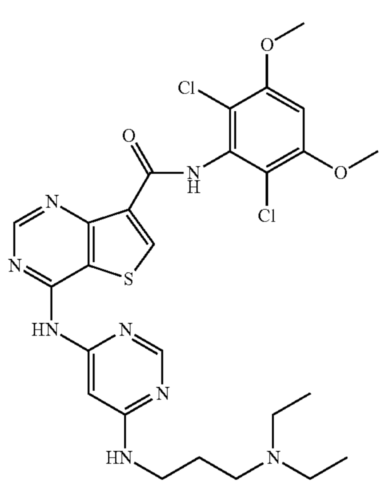 [SMILES: CCN(CC)CCCNc1cc(Nc2ncnc3c(C(=O)Nc4c(Cl)c(OC)cc(OC)c4Cl)csc23)ncn1] | N-(2,6-dichloro-3,5-dimethoxyphenyl)-4-(6-(3-(diethylamino)propylamino)pyrimidin-4-ylamino)thieno[3,2-d]pyrimidine-7-carboxamide | 605.22 607.20 | 11.33(s, 1H), 9.11(s, 1H), 8.90(s, 1H), 8.32(s, 1H), 7.29(s, 1H), 6.97(s, 1H), 3.97(s, 6H), 3.35(m, 2H), 3.01(m, 4H), 2.42(m, 2H), 1.90(m, 2H), 1.18(m, 6H) |

TABLE 1-continued

| Ex. | Structure | Compound | MS m/z [M + 1] | NMR (¹H NMR 400 MHz, DMSO-d$_6$) |
|---|---|---|---|---|
| 211 | 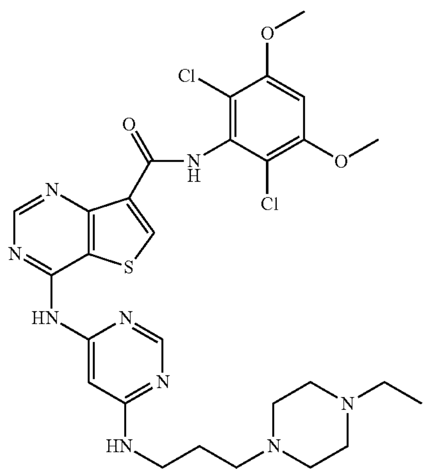 [SMILES: CCN1CCN(CCCNc2cc(Nc3ncnc4c(C(=O)Nc5c(Cl)c(OC)cc(OC)c5Cl)csc34)ncn2)CC1] | N-(2,6-dichloro-3,5-dimethoxyphenyl)-4-(6-(3-(4-ethylpiperazin-1-yl)propylamino)pyrimidin-4-ylamino)thieno[3,2-d]pyrimidine-7-carboxamide | 646.24 648.24 | 11.34(s, 1H), 9.09(s, 1H), 8.88(s, 1H), 8.28(s, 1H), 7.35(s, 1H), 6.97(s, 1H), 3.97(s, 6H), 3.35(m, 2H), 2.50-2.32(m, 12H), 1.68(m, 2H), 0.97(m, 3H) |
| 212 | 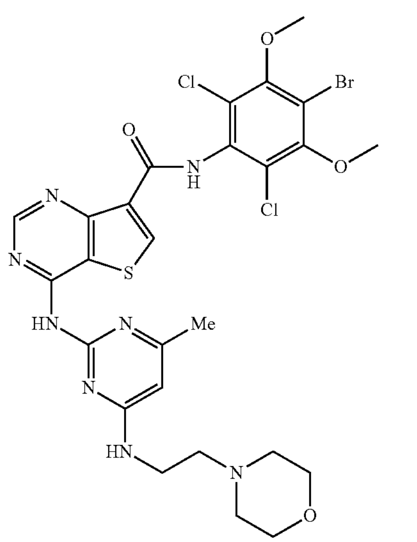 [SMILES: COc1c(Cl)c(NC(=O)c2csc3c(Nc4nc(C)cc(NCCN5CCOCC5)n4)ncnc23)c(Cl)c(OC)c1Br] | N-(4-bromo-2,6-dichloro-3,5-dimethoxyphenyl)-4-(4-methyl-6-(2-morpholinoethylamino)pyrimidin-2-ylamino)thieno[3,2-d]pyrimidine-7-carboxamide | 697.12 699.09 | 11.57(s, 1H), 10.54(br, 1H), 9.04(s, 1H), 8.84(s, 1H), 7.35(br, 1H), 6.11(s, 1H), 3.86(s, 6H), 3.53(m, 4H), 3.36(m, 2H), 2.41(m, 2H), 2.32(m, 4H), 2.25(m, 3H) |
| 213 | 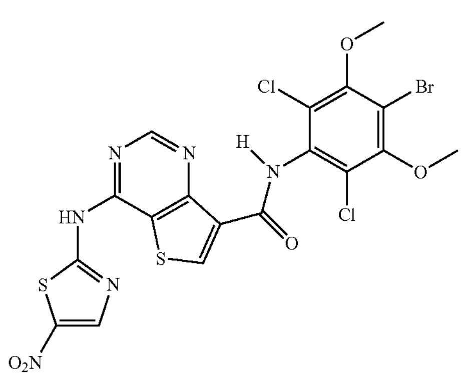 [SMILES: COc1c(Cl)c(NC(=O)c2csc3c(Nc4ncc([N+](=O)[O-])s4)ncnc23)c(Cl)c(OC)c1Br] | N-(4-bromo-2,6-dichloro-3,5-dimethoxyphenyl)-4-(5-nitrothiazol-2-ylamino)thieno[3,2-d]pyrimidine-7-carboxamide | 604.98 606.98 608.97 | 11.29(s, 1H), 9.18(s, 1H), 9.17(s, 1H), 8.77(s, 1H), 7.43(m, 1H), 3.86(s, 6H), |

TABLE 1-continued

| Ex. | Structure | Compound | MS m/z [M + 1] | NMR (¹H NMR 400 MHz, DMSO-d₆) |
|---|---|---|---|---|
| 214 | 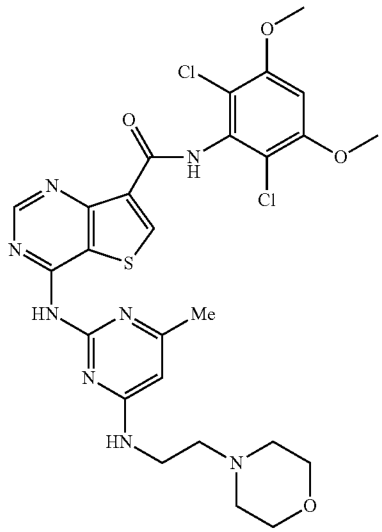 [SMILES: COc1cc(OC)c(Cl)c(NC(=O)c2csc3c(Nc4nc(C)cc(NCCN5CCOCC5)n4)ncnc23)c1Cl] | N-(2,6-dichloro-3,5-dimethoxyphenyl)-4-(4-methyl-6-(2-morpholinoethyl-amino)pyrimidin-2-ylamino)thieno[3,2-d]pyrimidine-7-carboxamide | 619.17 621.14 | 11.39(s, 1H), 10.47(br, 1H), 9.01(s, 1H), 8.83(s, 1H), 7.38(br, 1H), 6.91(s, 1H), 6.10(s, 1H), 3.96(s, 6H), 3.52(m, 4H), 3.40(m, 2H), 2.41(m, 2H), 2.32(m, 4H), 2.25(m, 3H) H) |
| 215 | 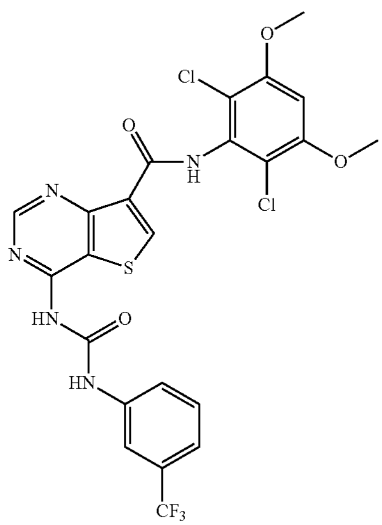 [SMILES: COc1cc(OC)c(Cl)c(NC(=O)c2csc3c(NC(=O)Nc4cccc(C(F)(F)F)c4)ncnc23)c1Cl] | N-(2,6-dichloro-3,5-dimethoxyphenyl)-4-(3-(3-(trifluoromethyl)phenyl)ureido)thieno[3,2-d]pyrimidine-7-carboxamide | 586.09 588.11 | 11.24(s, 1H), 10.80(s, 1H), 10.72(s, 1H), 9.17(s, 1H), 9.00(s, 1H), 8.09(s, 1H), 7.77(d, 1H), 7.61(t, 1H), 7.44(d, 1H), 6.96(s, 1H), 3.96(s, 6H) |
| 216 | 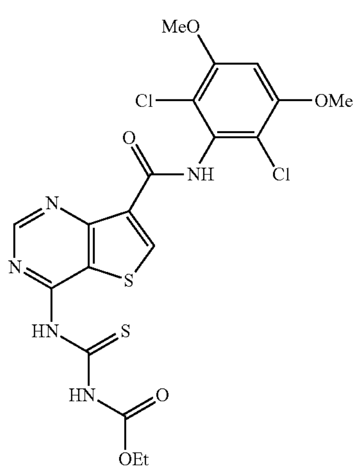 [SMILES: CCOC(=O)NC(=S)Nc1ncnc2c(C(=O)Nc3c(Cl)c(OC)cc(OC)c3Cl)csc12] | N-(2,6-dichloro-3,5-dimethoxyphenyl)-4-(3-(ethoxycarbonyl)thioureido)thieno[3,2-d]pyrimidine-7-carboxamide | 530.08 532.07 | 12.29(br, 1H), 11.05(s, 1H), 10.45(s, 1H), 9.22(s, 1H), 9.11(s, 1H), 6.96(s, 1H), 4.07(q, 2H), 1.18(t, 3H) |

TABLE 1-continued

| Ex. | Structure | Compound | MS m/z [M + 1] | NMR (¹H NMR 400 MHz, DMSO-$d_6$) |
|---|---|---|---|---|
| 217 | 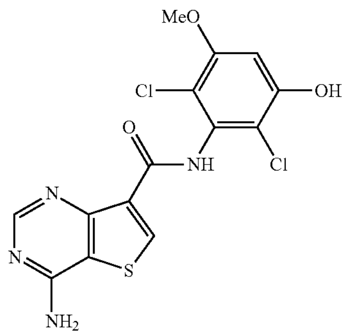 [SMILES: COc1cc(O)c(Cl)c(NC(=O)c2csc3c(N)ncnc23)c1Cl] | 4-amino-N-(2,6-dichloro-3-hydroxy-5-methoxyphenyl)thieno[3,2-d]pyrimidine-7-carboxamide | 385.10 387.10 | 1.40(s, 1H), 10.61(s, 1H), 8.92(s, 1H), 8.53(s, 1H), 7.93(s, 2H), 6.75(s, 1H), 3.83(s, 3H). |
| 218 | 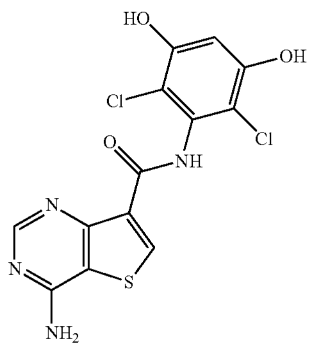 [SMILES: Nc1ncnc2c(C(=O)Nc3c(Cl)c(O)cc(O)c3Cl)csc12] | 4-amino-N-(2,6-dichloro-3,5-dihydroxyphenyl)thieno[3,2-d]pyrimidine-7-carboxamide | 371.09 373.03 | 11.40(s, 1H), 10.61(s, 1H), 8.92(s, 1H), 8.53(s, 1H), 7.93(s, 2H), 6.75(s, 1H), 3.83(s, 3H); MS m/z [M + 1] 385.10, 387.10 |
| 219 | 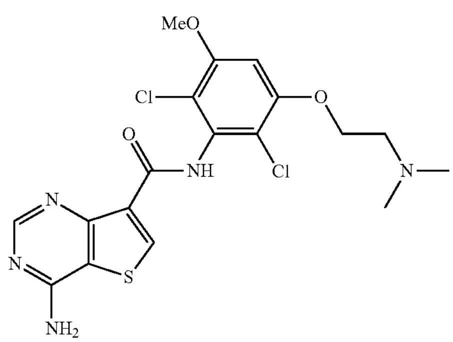 [SMILES: COc1cc(OCCN(C)C)c(Cl)c(NC(=O)c2csc3c(N)ncnc23)c1Cl] | 4-amino-N-(2,6-dichloro-3-(2-(dimethylamino)ethoxy)-5-methoxyphenyl)thieno[3,2-d]pyrimidine-7-carboxamide | 456.10 458.10 | 11.45(s, 1H), 8.92(s, 1H), 8.53(s, 1H), 7.93(s, 2H), 6.98(s, 1H), 4.21(t, 2H), 3.94(s, 3H), 2.68(m, 2H), 2.66(s, 6H) |
| 220 | 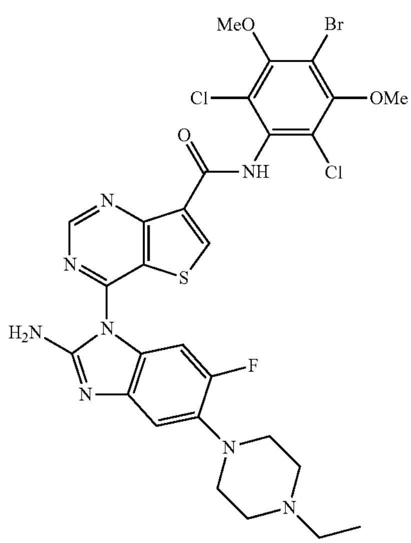 [SMILES: CCN1CCN(c2cc3nc(N)n(-c4ncnc5c(C(=O)Nc6c(Cl)c(OC)c(Br)c(OC)c6Cl)csc45)c3cc2F)CC1] | 4-(2-amino-5-(4-ethylpiperazin-1-yl)-6-fluoro-1H-benzo[d]imidazol-1-yl)-N-(4-bromo-2,6-dichloro-3,5-dimethoxyphenyl)thieno[3,2-d]pyrimidine-7-carboxamide | 723.05 725.11 727.08 | 12.62(br, 2H), 11.52(s, 1H), 8.95(s, 1H), 8.81(s, 1H), 7.24(d, 1H), 7.08(d, 1H), 3.86(s, 6H), 2.99(m, 4H), 2.54(m, 4H), 2.41(q, 2H), 1.03(t, 3H) |

TABLE 1-continued

| Ex. | Structure | Compound | MS m/z [M + 1] | NMR ($^1$H NMR 400 MHz, DMSO-d$_6$) |
|---|---|---|---|---|
| 221 | 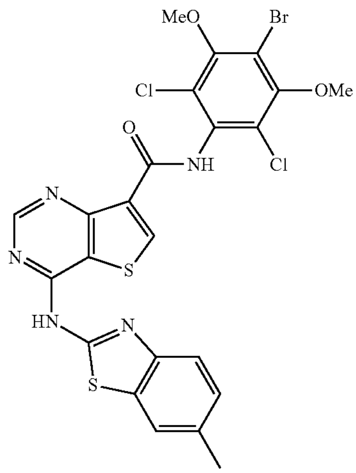 [SMILES: COc1c(Cl)c(NC(=O)c2csc3c(Nc4nc5ccc(C)cc5s4)ncnc23)c(Cl)c(OC)c1Br] | N-(4-bromo-2,6-dichloro-3,5-dimethoxyphenyl)-4-(6-methylbenzo[d]thiazol-2-ylamino)thieno[3,2-d]pyrimidine-7-carboxamide | 624.02<br>626.03<br>628.02 | 11.40(s, 1H), 9.10(s, 1H), 9.02(s, 1H), 7.72(s, 1H) 7.46(m, 1H), 7.30(d, 1H), 3.86(s, 6H), 2.43(s, 3H) |
| 222 | 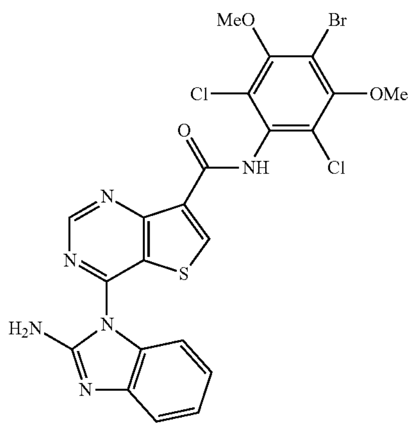 [SMILES: COc1c(Cl)c(NC(=O)c2csc3c(-n4c(N)nc5ccccc54)ncnc23)c(Cl)c(OC)c1Br] | 4-(2-amino-1H-benzo[d]imidazol-1-yl)-N-(4-bromo-2,6-dichloro-3,5-dimethoxyphenyl)thieno[3,2-d]pyrimidine-7-carboxamide | 593.06<br>595.07<br>597.06 | 12.68(br, 2H), 11.54(s, 1H), 8.96(s, 1H), 8.84(s, 1H), 7.42(m, 2H), 7.22(m, 2H), 3.86(s, 6H) |
| 223 | 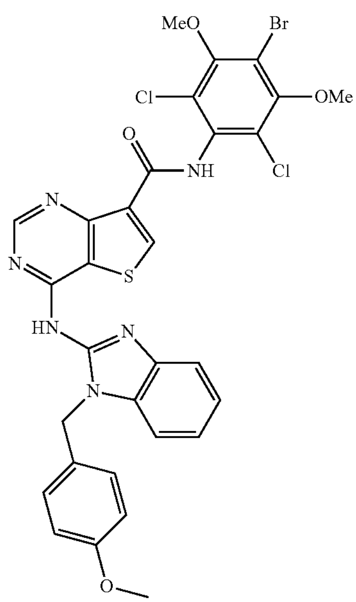 [SMILES: COc1ccc(Cn2c(Nc3ncnc4c(C(=O)Nc5c(Cl)c(OC)c(Br)c(OC)c5Cl)csc34)nc3ccccc32)cc1] | N-(4-bromo-2,6-dichloro-3,5-dimethoxyphenyl)-4-(1-(4-methoxybenzyl)-1H-benzo[d]imidazol-2-ylamino)thieno[3,2-d]pyrimidine-7-carboxamide | 712.88<br>714.89<br>716.86 | 12.80(br, 1H), 11.48(s, 1H), 9.00(s, 1H), 8.89(s, 1H), 7.60(m, 2H), 7.50(d, 1H), 7.23(m, 1H), 6.88(d, 1H), 5.44(s, 2H), 3.87(s, 6H), 3.68(s, 3H) |

TABLE 1-continued

| Ex. | Structure | Compound | MS m/z [M + 1] | NMR ($^1$H NMR 400 MHz, DMSO-$d_6$) |
|---|---|---|---|---|
| 224 | 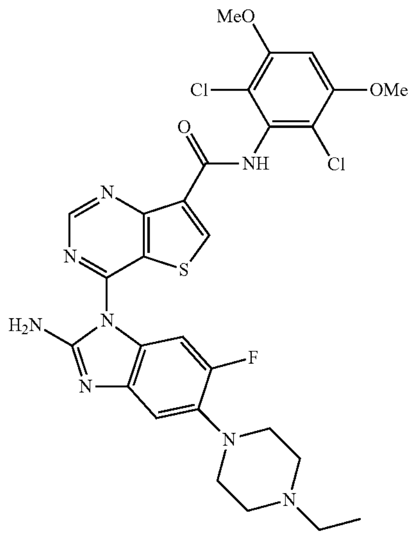 [SMILES: CCN1CCN(c2cc3nc(N)n(-c4ncnc5c(C(=O)Nc6c(Cl)c(OC)cc(OC)c6Cl)csc45)c3cc2F)CC1] | 4-(2-amino-5-(4-ethylpiperazin-1-yl)-6-fluoro-1H-benzo[d]imidazol-1-yl)-N-(2,6-dichloro-3,5-dimethoxyphenyl)thieno[3,2-d]pyrimidine-7-carboxamide | 645.05 647.05 | 12.79(br, 2H), 11.34(s, 1H), 8.96(s, 1H), 8.82(s, 1H), 7.32(d, 1H), 7.17(d, 1H), 6.97(s, 1H), 3.96(s, 6H), 2.99(m, 4H), 2.54(m, 4H), 2.41(q, 2H), 1.03(t, 3H) |
| 225 | 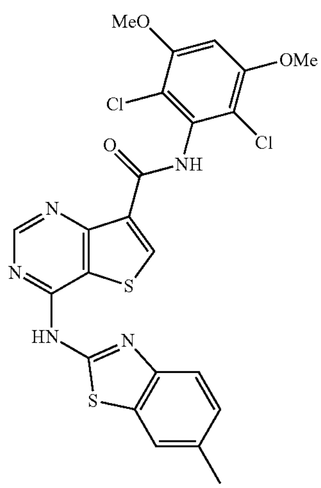 [SMILES: COc1cc(OC)c(Cl)c(NC(=O)c2csc3c(Nc4nc5ccc(C)cc5s4)ncnc23)c1Cl] | N-(2,6-dichloro-3,5-dimethoxyphenyl)-4-(6-methylbenzo[d]thiazol-2-ylamino)thieno[3,2-d]pyrimidine-7-carboxamide | 546.10 548.13 | 11.23(s, 1H), 9.07(s, 1H), 9.02(s, 1H), 7.72(s, 1H), 7.50(m, 1H), 7.26(d, 1H), 6.97(s, 1H), 3.96(s, 6H), 2.40(s, 3H) |
| 226 | 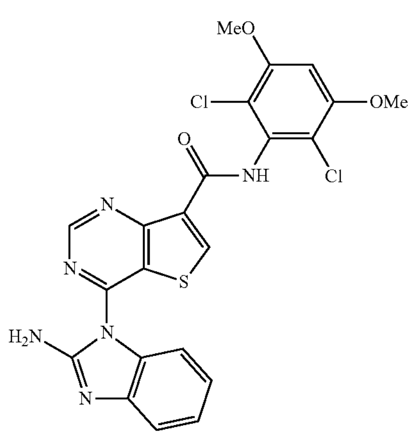 [SMILES: COc1cc(OC)c(Cl)c(NC(=O)c2csc3c(-n4c(N)nc5ccccc54)ncnc23)c1Cl] | 4-(2-amino-1H-benzo[d]imidazol-1-yl)-N-(2,6-dichloro-3,5-dimethoxyphenyl)thieno[3,2-d]pyrimidine-7-carboxamide | 515.14 517.14 | 12.67(br, 2H), 11.39(s, 1H), 8.93(s, 1H), 8.83(s, 1H), 7.43(m, 2H), 7.20(m, 2H), 6.96(s, 1H), |

TABLE 1-continued

| Ex. | Structure | Compound | MS m/z [M + 1] | NMR (¹H NMR 400 MHz, DMSO-d$_6$) |
|---|---|---|---|---|
| 227 | 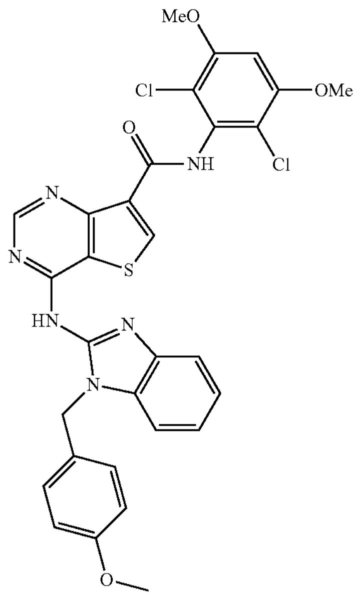 [SMILES: COc1ccc(Cn2c(Nc3ncnc4c(C(=O)Nc5c(Cl)c(OC)cc(OC)c5Cl)csc34)nc3ccccc32)cc1] | N-(2,6-dichloro-3,5-dimethoxyphenyl)-4-(1-(4-methoxybenzyl)-1H-benzo[d]imidazol-2-ylamino)thieno[3,2-d]pyrimidine-7-carboxamide | 635.01 637.00 | 12.78(br, 1H), 11.39(s, 1H), 8.92(s, 1H), 8.87(s, 1H), 7.57(m, 2H), 7.49(d, 1H), 7.23(m, 1H), 6.98(s, 1H), 6.87(d, 1H), 5.43(s, 2H), 3.97(s, 6H), 3.68(s, 3H) |
| 228 | 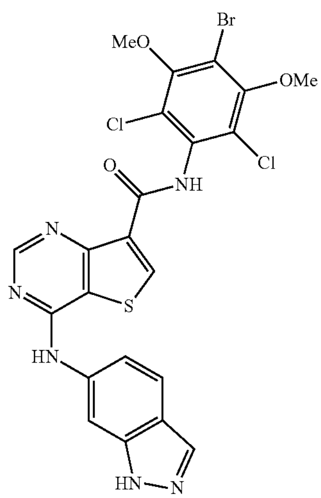 [SMILES: COc1c(Cl)c(NC(=O)c2csc3c(Nc4ccc5cn[nH]c5c4)ncnc23)c(Cl)c(OC)c1Br] | 4-(1H-indazol-6-ylamino)-N-(4-bromo-2,6-dichloro-3,5-dimethoxyphenyl)thieno[3,2-d]pyrimidine-7-carboxamide | 592.89 594.88 | 13.04(s, 1H), 11.53(s, 1H), 10.28(S, 1H), 9.04(s, 1H), 8.79(s, 1H), 8.19(s, 1H), 8.04(s, 1H), 7.76(d, 1H), 7.41(d, 1H), 3.86(s, 6H)S |
| 229 | 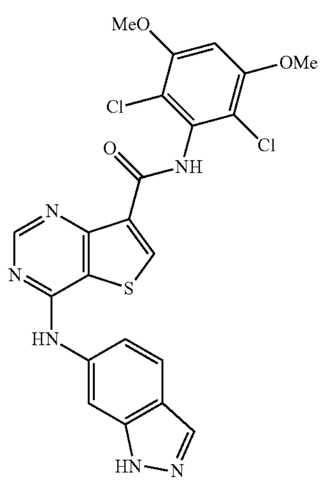 [SMILES: COc1cc(OC)c(Cl)c(NC(=O)c2csc3c(Nc4ccc5cn[nH]c5c4)ncnc23)c1Cl] | 4-(1H-indazol-6-ylamino)-N-(2,6-dichloro-3,5-dimethoxyphenyl)thieno[3,2-d]pyrimidine-7-carboxamide | 514.96 516.96 | 13.03(s, 1H), 11.39(s, 1H), 10.25(s, 1H), 9.01(s, 1H), 8.78(s, 1H), 8.19(s, 1H), 8.04(s, 1H), 7.75(d, 1H), 7.40(d, 1H), 6.96(s, 1H), 3.96(s, 6H) |

TABLE 1-continued

| Ex. | Structure | Compound | MS m/z [M + 1] | NMR ($^1$H NMR 400 MHz, DMSO-$d_6$) |
|---|---|---|---|---|
| 230 | 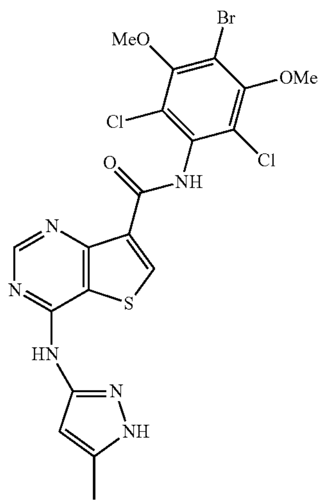 [SMILES: COc1c(Cl)c(NC(=O)c2csc3c(Nc4cc(C)[nH]n4)ncnc23)c(Cl)c(OC)c1Br] | N-(4-bromo-2,6-dichloro-3,5-dimethoxyphenyl)-4-(5-methyl-1H-pyrazol-3-ylamino)thieno[3,2-d]pyrimidine-7-carboxamide | 556.90 558.88 560.88 | 12.39(br, 1H), 11.57(s, 1H), 10.54(br, 1H), 9.01(s, 1H), 8.70(s, 1H), 6.42(s, 1H), 3.86(s, 6H), 2.27(s, 3H) |
| 231 | 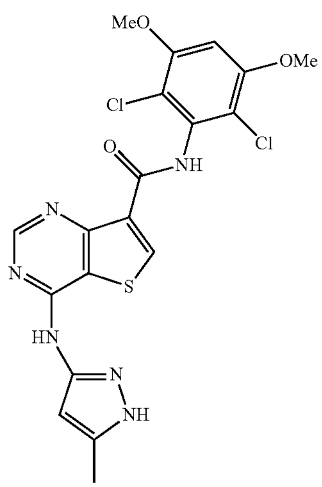 [SMILES: COc1cc(OC)c(Cl)c(NC(=O)c2csc3c(Nc4cc(C)[nH]n4)ncnc23)c1Cl] | N-(2,6-dichloro-3,5-dimethoxyphenyl)-4-(5-methyl-1H-pyrazol-3-ylamino)thieno[3,2-d]pyrimidine-7-carboxamide | 478.95 480.97 | 12.35(br, 1H), 11.43(s, 1H), 10.52(br, 1H), 8.96(s, 1H), 8.68(s, 1H), 6.96(s, 1H), 6.42(s, 1H), 3.95(s, 6H), 2.26(s, 3H) |
| 232 | 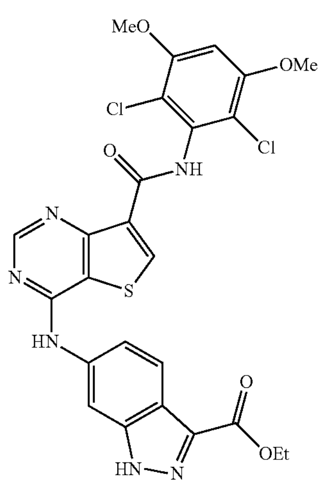 [SMILES: CCOC(=O)c1n[nH]c2cc(Nc3ncnc4c(C(=O)Nc5c(Cl)c(OC)cc(OC)c5Cl)csc34)ccc12] | ethyl 6-(7-(2,6-dichloro-3,5-dimethoxyphenylcarbamoyl)thieno[3,2-d]pyrimidin-4-ylamino)-1H-indazole-3-carboxylate | 586.99 588.97 | 11.37(s, 1H), 10.36(s, 1H), 9.04(s, 1H), 8.82(s, 1H), 8.39(s, 1H), 8.04(d, 1H), 7.63(d, 1H), 6.96(s, 1H), 4.39(q, 2H), 1.38(t, 3H) |

TABLE 1-continued

| Ex. | Structure | Compound | MS m/z [M + 1] | NMR ($^1$H NMR 400 MHz, DMSO-$d_6$) |
|---|---|---|---|---|
| 233 | 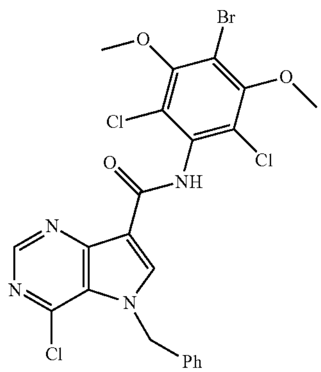 [SMILES: COc1c(Cl)c(NC(=O)c2cn(Cc3ccccc3)c3c(Cl)ncnc23)c(Cl)c(OC)c1Br] | 5-benzyl-N-(4-bromo-2,6-dichloro-3,5-dimethoxyphenyl)-4-chloro-5H-pyrrolo[3,2-d]pyrimidine-7-carboxamide | — | 10.10 (s, 1H), 8.89 (s, 1H), 8.30 (s, 1H), 7.40 (m, 3H), 7.20 (m, 2H), 5.76 (s, 2H), 3.92 (s, 6H) |
| 234 | 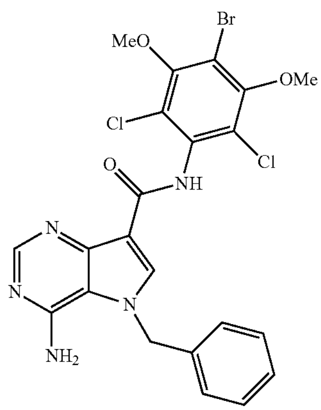 [SMILES: COc1c(Cl)c(NC(=O)c2cn(Cc3ccccc3)c3c(N)ncnc23)c(Cl)c(OC)c1Br] | 4-amino-5-benzyl-N-(4-bromo-2,6-dichloro-3,5-dimethoxyphenyl)-5H-pyrrolo[3,2-d]pyrimidine-7-carboxamide | — | 10.32 (s. 1H), 8.29 (d, 2H), 7.48 (m, 3H), 7.26 (d, 2H), 7.02 (bs, 2H), 5.74 (d, 2H), 3.84 (s, 6H) |
| 235 | 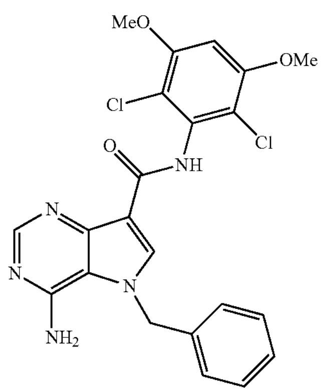 [SMILES: COc1cc(OC)c(Cl)c(NC(=O)c2cn(Cc3ccccc3)c3c(N)ncnc23)c1Cl] | 4-amino-5-benzyl-N-(2,6-dichloro-3,5-dimethoxyphenyl)-5H-pyrrolo[3,2-d]pyrimidine-7-carboxamide | — | 10.40 (s, 1H), 8.28 (s, 2H), 7.39 (m, 3H), 7.28 (m, 2H), 7.01 (s, 2H), 6.93 (s, 1H), 5.72 (s, 2H), 3.95 (s, 6H) |
| 236 | 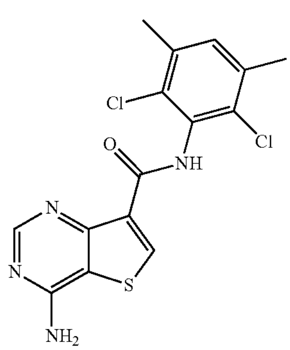 [SMILES: Cc1cc(C)c(Cl)c(NC(=O)c2csc3c(N)ncnc23)c1Cl] | 4-amino-N-(2,6-dichloro-3,5-dimethylphenyl)thieno[3,2-d]pyrimidine-7-carboxamide | — | 10.15(bt, 1H), 8.67(s, 1H), 8.50(s, 1H), 6.63(s, 1H), 5.02(t, 2H), 3.85(s, 3H) |

TABLE 1-continued
| Ex. | Structure | Compound | MS m/z [M + 1] | NMR (¹H NMR 400 MHz, DMSO-d$_6$) |
|---|---|---|---|---|
| 237 | 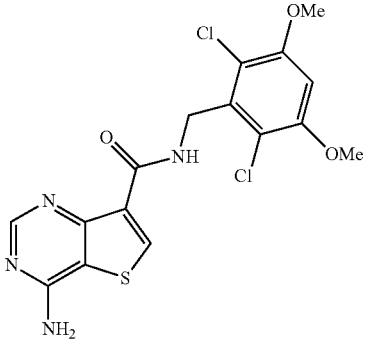 [SMILES: COc1cc(OC)c(Cl)c(CNC(=O)c2csc3c(N)ncnc23)c1Cl] | 4-amino-N-(2,6-dichloro-3,5-dimethoxybenzyl)thieno[3,2-d]pyrimidine-7-carboxamide | — | 10.15(bt, 1H), 8.67(s, 1H), 8.50(s, 1H), 6.63(s, 1H), 5.02(t, 2H), 3.85(s, 3H) |
| 238 | 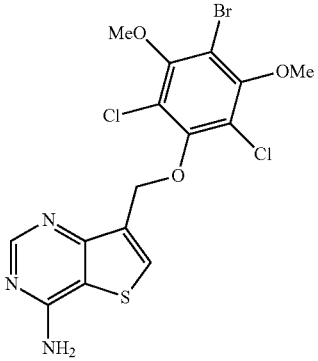 [SMILES: COc1c(Cl)c(OCc2csc3c(N)ncnc23)c(Cl)c(OC)c1Br] | 7-((4-bromo-2,6-dichloro-3,5-dimethoxyphenoxy)methyl)thieno[3,2-d]pyrimidine-4-amine | — | 8.99(s, 1H), 8.27(s, 1H), 5.44(d, 2H), 5.41(br, 2H), 3.90(d, 6H), |
| 239 | 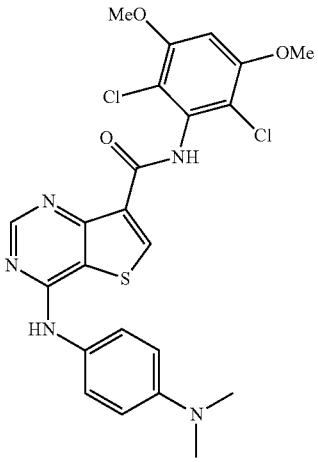 [SMILES: COc1cc(OC)c(Cl)c(NC(=O)c2csc3c(Nc4ccc(N(C)C)cc4)ncnc23)c1Cl] | N-(2,6-dichloro-3,5-dimethoxyphenyl)-4-(4-(dimethylamino)phenylamino)thieno[3,2-d]pyrimidine-7-carboxamide | — | 11.45(s, 1H), 8.61(s, 1H), 8.56(s, 1H), 7.24(d, 2H), 6.73(d, 2H), 6.56(s, 1H), 3.90(s, 6H), 2.99(s, 6H) |

TABLE 1-continued

| Ex. | Structure | Compound | MS m/z [M + 1] | NMR (¹H NMR 400 MHz, DMSO-$d_6$) |
|---|---|---|---|---|
| 240 | 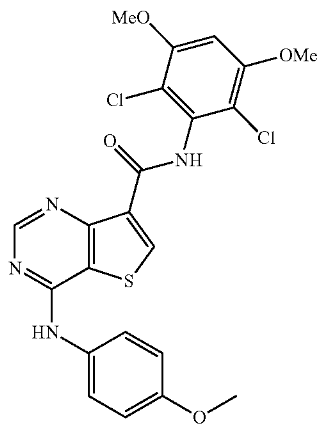 [SMILES: COc1ccc(Nc2ncnc3c(C(=O)Nc4c(Cl)c(OC)cc(OC)c4Cl)csc23)cc1] | N-(2,6-dichloro-3,5-dimethoxyphenyl)-4-(4-methoxyphenylamino)thieno[3,2-d]pyrimidine-7-carboxamide | — | 11.57(s, 1H), 8.67(s, 2H), 7.40(d, 2H), 7.09(d, 2H), 6.56(s, 1H), 3.92(s, 6H), 3.88(s, 3H) |
| 241 | 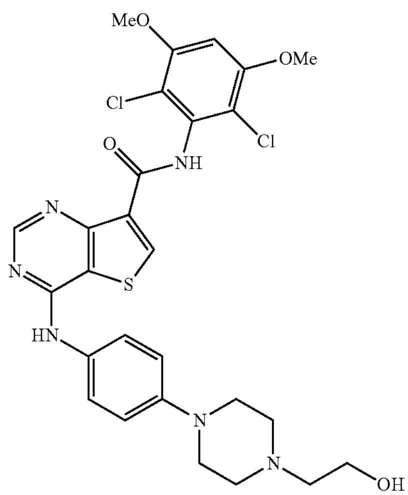 [SMILES: COc1cc(OC)c(Cl)c(NC(=O)c2csc3c(Nc4ccc(N5CCN(CCO)CC5)cc4)ncnc23)c1Cl] | N-(2,6-dichloro-3,5-dimethoxyphenyl)-4-(4-(4-(2-hydroxyethyl)piperazin-1-yl)phenylamino)thieno[3,2-d]pyrimidine-7-carboxamide | — | 11.45(s, 1H), 9.94(s, 1H), 8.92(s, 1H), 8.64(s, 1H), 7.46(d, 2H), 6.97(d, 2H), 6.95(s, 1H), 4.42(t, 1H), 3.95(s, 6H), 3.51-3.56(m, 2H), 3.15(bm, 4H), 2.56(bm, 6H) |
| 242 | 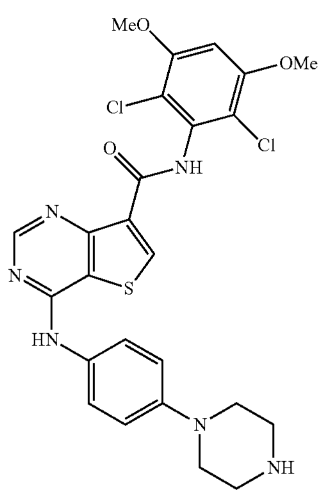 [SMILES: COc1cc(OC)c(Cl)c(NC(=O)c2csc3c(Nc4ccc(N5CCNCC5)cc4)ncnc23)c1Cl] | N-(2,6-dichloro-3,5-dimethoxyphenyl)-4-(4-(piperazin-1-yl)phenylamino)thieno[3,2-d]pyrimidine-7-carboxamide | — | 11.52(s, 1H), 10.03(br, 1H), 9.00(s, 1H), 8.71(s, 1H), 7.56(d, 2H), 7.06(d, 3H), 3.94(s, 6H), 3.19(m, 4H), 2.99(m, 4H) |

TABLE 1-continued

| Ex. | Structure | Compound | MS m/z [M + 1] | NMR ($^1$H NMR 400 MHz, DMSO-$d_6$) |
|---|---|---|---|---|
| 243 | 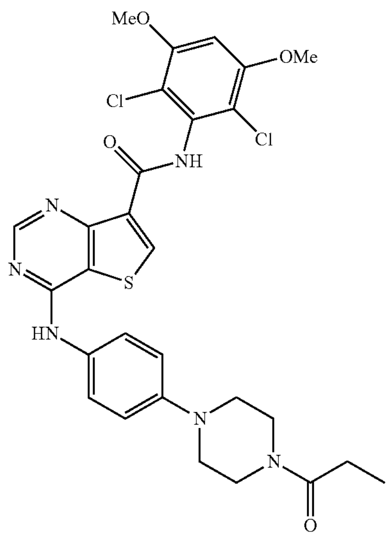 [SMILES: CCC(=O)N1CCN(c2ccc(Nc3ncnc4c(C(=O)Nc5c(Cl)c(OC)cc(OC)c5Cl)csc34)cc2)CC1] | N-(2,6-dichloro-3,5-dimethoxyphenyl)-4-(4-(4-propionylpiperazin-1-yl)phenylamino)thieno[3,2-d]pyrimidine-7-carboxamide | — | 11.37(s, 1H), 9.95(br, 1H), 8.95(s, 1H), 8.63(s, 1H), 7.50(d, 2H), 6.88(d, 2H), 6.77(s, 1H), 4.13(s, 6H), 3.84(m, 4H), 3.16(m, 4H), 2.34(q, 2H), 0.99(t, 3H) |
| 244 | 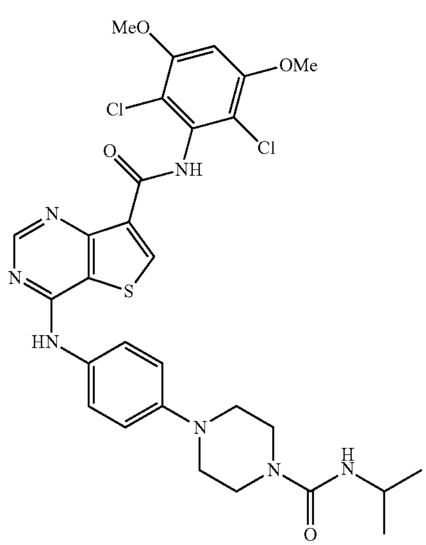 [SMILES: COc1cc(OC)c(Cl)c(NC(=O)c2csc3c(Nc4ccc(N5CCN(C(=O)NC(C)C)CC5)cc4)ncnc23)c1Cl] | N-(2,6-dichloro-3,5-dimethoxyphenyl)-4-(4-(4-(isopropylcarbamoyl)piperazin-1-yl)phenylamino)thieno[3,2-d]pyrimidine-7-carboxamide | — | 11.44(s, 1H), 9.95(br, 1H), 8.93(s, 1H), 8.61(s, 1H), 7.60(d, 2H), 7.03(d, 2H), 6.95(s, 1H), 6.28(d, 1H), 3.95(d, 6H), 3.75(s, 1H), 3.43(m, 4H), 3.24(d, 4H), 1.07(d, 6H), |

TABLE 1-continued

| Ex. | Structure | Compound | MS m/z [M + 1] | NMR (¹H NMR 400 MHz, DMSO-$d_6$) |
|---|---|---|---|---|
| 245 | 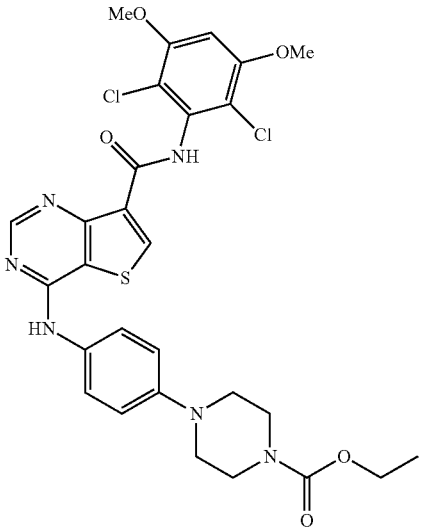 [SMILES: CCOC(=O)N1CCN(c2ccc(Nc3ncnc4c(C(=O)Nc5c(Cl)c(OC)cc(OC)c5Cl)csc34)cc2)CC1] | ethyl 4-(4-(7-(2,6-dichloro-3,5-dimethoxyphenyl-carbamoyl)thieno[3,2-d]pyrimidin-4-ylamino)phenyl)piperazine-1 carboxylate | — | 11.39(s, 1H), 9.92(br, 1H), 8.88(s, 1H), 8.60(s, 1H), 7.47(d, 2H), 6.97(d, 2H), 6.90(s, 1H), 4.03(t, 2H), 3.90(s, 6H), 3.47(m, 4H), 3.10(m, 4H), 1.15(t, 3H) |
| 246 | 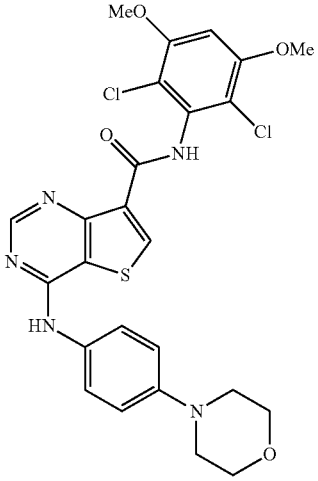 [SMILES: COc1cc(OC)c(Cl)c(NC(=O)c2csc3c(Nc4ccc(N5CCOCC5)cc4)ncnc23)c1Cl] | N-(2,6-dichloro-3,5-dimethoxyphenyl)-4-(4-morpholinophenyl-amino)thieno[3,2-d]pyrimidine-7-carboxamide | — | 11.5 (s, 1H), 9.96 (s, 1H), 8.93 (s, 1H), 8.64 (s, 1H), 7.51-7.48 (d, 2H), 7.00-6.98 (d, 2H), 6.95 (s, 1H), 3.96 (s, 6H), 3.77-3.74 (m, 4H), 3.14-3.12 (m, 4H) |
| 247 | 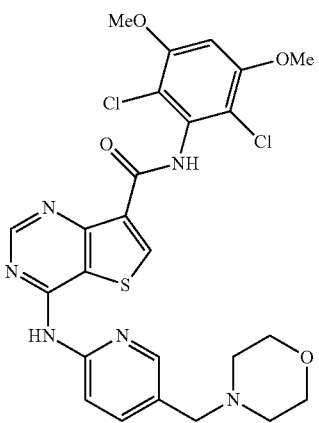 [SMILES: COc1cc(OC)c(Cl)c(NC(=O)c2csc3c(Nc4ccc(CN5CCOCC5)cn4)ncnc23)c1Cl] | N-(2,6-dichloro-3,5-dimethoxyphenyl)-4-(5-(morpholinomethyl)pyridin-2-ylamino)thieno[3,2-d]pyrimidine-7-carboxamide | — | 11.41(s, 1H), 10.95(br, 1H), 9.07(s, 1H), 8.83(s, 1H), 8.32(d, 1H), 7.96(dd, 1H), 7.85(dd, 1H), 6.97(s, 1H), 3.97(s, 6H), 3.59(m, 4H), 3.59(s, 2H), 2.77(m, 4H), |

TABLE 1-continued

| Ex. | Structure | Compound | MS m/z [M + 1] | NMR (¹H NMR 400 MHz, DMSO-$d_6$) |
|---|---|---|---|---|
| 248 | 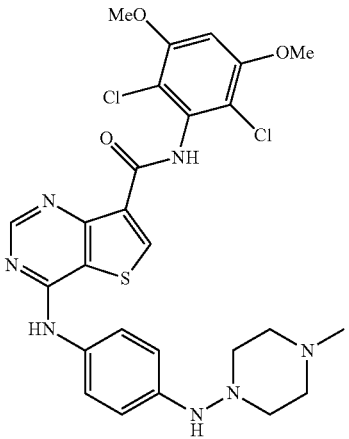 [SMILES: COc1cc(OC)c(Cl)c(NC(=O)c2csc3c(Nc4ccc(NN5CCN(C)CC5)cc4)ncnc23)c1Cl] | N-(2,6-dichloro-3,5-dimethoxyphenyl)-4-(4-(4-methylpiperazin-1-ylamino)phenyl-amino)thieno[3,2-d]pyrimidine-7-carboxamide | — | 11.58(s, 1H), 9.89(br, 1H), 8.88(s, 1H), 8.75(s, 1H), 7.34(d, 2H), 6.93(s, 1H), 6.90(d, 2H), 3.81(s, 6H), 3.09(m, 4H), 2.42(m, 4H), 2.20(s, 3H), |
| 249 | 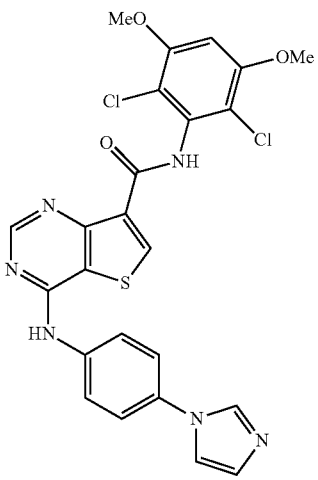 [SMILES: COc1cc(OC)c(Cl)c(NC(=O)c2csc3c(Nc4ccc(-n5ccnc5)cc4)ncnc23)c1Cl] | 4-(4-(1H-imidazol-1-yl)phenylamino)-N-(2,6-dichloro-3,5-dimethoxyphenyl)thieno[3,2-d]pyrimidine-7-carboxamide | — | 11.5 (s, 1H), 10.3 (s, 1H), 9.08 (s, 1H), 8.79 (s, 1H), 8.26 (s, 1H), 7.94-7.92 (m, 3H), 7.76 (s, 1H), 7.72-7.69 (d, 2H), 7.12 (s, 1H), 3.86 (s, 6H) |
| 250 | 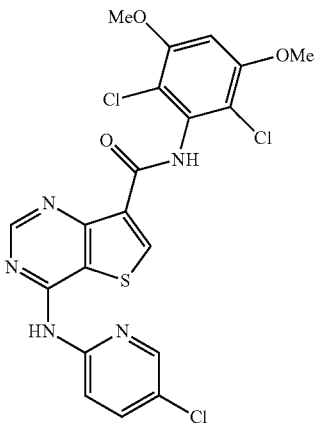 [SMILES: COc1cc(OC)c(Cl)c(NC(=O)c2csc3c(Nc4ccc(Cl)cn4)ncnc23)c1Cl] | 4-(5-chloropyridin-2-ylamino)-N-(2,6-dichloro-3,5-dimethoxyphenyl)thieno[3,2-d]pyrimidine-7-carboxamide | — | 11.35(s, 1H), 11.14(br, 1H), 9.10(s, 1H), 8.87(s, 1H), 8.48(d, 1H), 8.29(dd, 1H), 8.18(dd, 1H), 7.06(s, 1H), 3.97(s, 6H), |

TABLE 1-continued

| Ex. | Structure | Compound | MS m/z [M + 1] | NMR (¹H NMR 400 MHz, DMSO-d$_6$) |
|---|---|---|---|---|
| 251 | 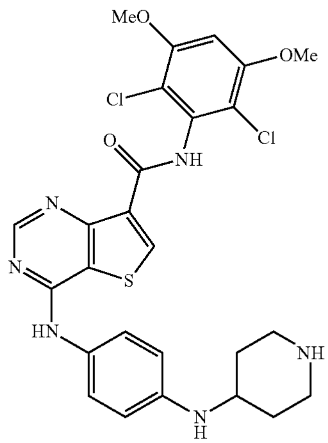 [SMILES: COc1cc(OC)c(Cl)c(NC(=O)c2csc3c(Nc4ccc(NC5CCNCC5)cc4)ncnc23)c1Cl] | N-(2,6-dichloro-3,5-dimethoxyphenyl)-4-(4-(piperidin-4-ylamino)phenyl-amino)thieno[3,2-d]pyrimidine-7-carboxamide | — | 11.47(s, 1H), 9.79(br, 1H), 8.91(s, 1H), 8.56(s, 1H), 7.18(d, 2H), 6.91(s, 1H), 6.60(d, 2H), 5.72(br, 1H), 5.61(br, 1H), 3.92(s, 6H), 3.07(m, 2H), 2.74(m, 2H), 2.39(m, 1H), 1.83(m, 2H), 1.25(m, 2H) |
| 252 | 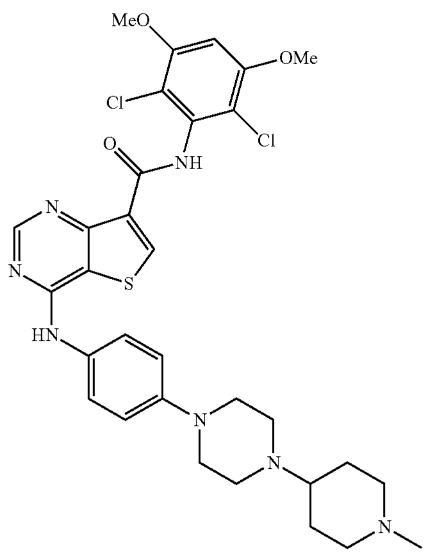 [SMILES: COc1cc(OC)c(Cl)c(NC(=O)c2csc3c(Nc4ccc(N5CCN(C6CCN(C)CC6)CC5)cc4)ncnc23)c1Cl] | N-(2,6-dichloro-3,5-dimethoxyphenyl)-4-(4-(4-(1-methylpiperidin-4-yl)piperazin-1-yl)phenylamino)thieno[3,2-d]pyrimidine-7-carboxamide | — | 11.44(s, 1H), 9.94(br, 1H), 8.92(s, 1H), 8.62(s, 1H), 7.47(d, 2H), 6.97(d, 3H), 3.95(s, 6H), 3.13(m, 4H), 2.76(d, 2H), 2.61(m, 4H), 2.12(m, 3H), 1.83(m, 5H), 1.25(m, 2H) |
| 253 | 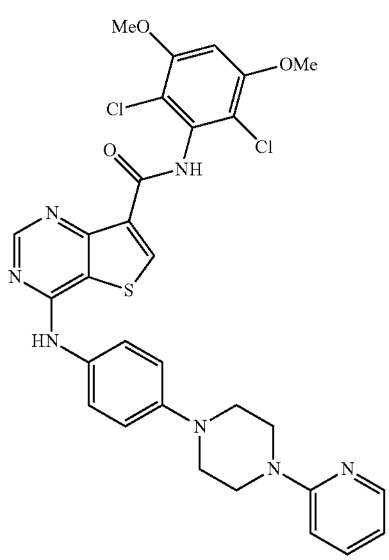 [SMILES: COc1cc(OC)c(Cl)c(NC(=O)c2csc3c(Nc4ccc(N5CCN(c6ccccn6)CC5)cc4)ncnc23)c1Cl] | N-(2,6-dichloro-3,5-dimethoxyphenyl)-4-(4-(4-(pyridin-2-yl)piperazin-1-yl)phenylamino)thieno[3,2-d]pyrimidine-7-carboxamide | — | 11.5 (s, 1H), 10.0 (s, 1H), 8.93 (s, 1H), 8.65 (s, 1H), 8.14 (s, 1H), 7.55 (m, 2H), 7.07-7.05 (d, 2H), 6.94 (s, 1H), 6.92 (d, 2H), 6.42 (m, 1H), 3.95 (s, 6H), 3.39-3.25 (m, 8H) |

TABLE 1-continued

| Ex. | Structure | Compound | MS m/z [M + 1] | NMR (¹H NMR 400 MHz, DMSO-$d_6$) |
|---|---|---|---|---|
| 254 | 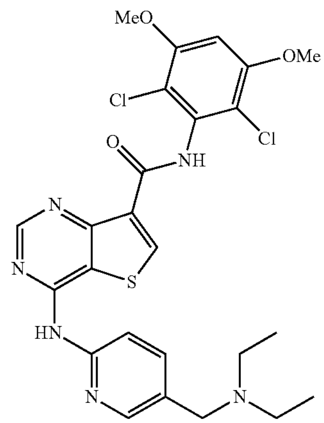 [SMILES: CCN(CC)Cc1ccc(Nc2ncnc3c(C(=O)Nc4c(Cl)c(OC)cc(OC)c4Cl)csc23)nc1] | N-(2,6-dichloro-3,5-dimethoxyphenyl)-4-(5-((diethylamino)methyl)pyridin-2-ylamino)thieno[3,2-d]pyrimidine-7-carboxamide | — | 11.40(s, 1H), 10.90(br, 1H), 9.05(s, 1H), 8.81(s, 1H), 8.30(d, 1H), 7.92(d, 1H), 7.79(dd, 1H), 6.96(s, 1H), 3.96(s, 6H), 3.55(s, 2H), 2.43(m, 4H), 0.95(t, 6H) |
| 255 | 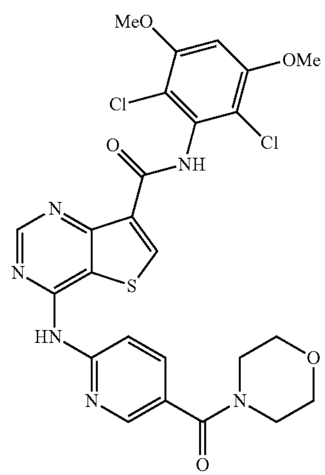 [SMILES: COc1cc(OC)c(Cl)c(NC(=O)c2csc3c(Nc4ccc(C(=O)N5CCOCC5)cn4)ncnc23)c1Cl] | N-(2,6-dichloro-3,5-dimethoxyphenyl)-4-(5-(morpholine-4-carbonyl)pyridin-2-ylamino)thieno[3,2-d]pyrimidine-7-carboxamide | — | 11.35(s, 1H), 11.18(br, 1H), 9.23(s, 1H), 8.89(s, 1H), 8.48(d, 1H), 8.18(dd, 1H), 7.93(dd, 1H), 7.04(s, 1H), 3.96(s, 6H), 3.62(m, 8H) |
| 256 | 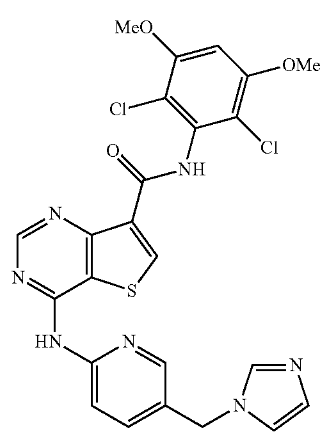 [SMILES: COc1cc(OC)c(Cl)c(NC(=O)c2csc3c(Nc4ccc(Cn5ccnc5)cn4)ncnc23)c1Cl] | 4-(5-((1H-imidazol-1-yl)methyl)pyridin-2-ylamino)-N-(2,6-dichloro-3,5-dimethoxyphenyl)thieno[3,2-d]pyrimidine-7-carboxamide | — | 11.4 (s, 1H), 9.04 (s, 1H), 8.77 (s, 1H), 8.36 (s, 1H), 7.91-7.93 (d, 1H), 7.75-7.80 (d, 1H), 7.22-7.25 (d, 1H), 6.96 (s, 1H), 6.91 (s, 1H), 5.22 (s, 2H), 3.96 (s, 6H) |

TABLE 1-continued

| Ex. | Compound | MS m/z [M + 1] | NMR (¹H NMR 400 MHz, DMSO-d$_6$) |
|---|---|---|---|
| 257 | N-(2,6-dichloro-3,5-dimethoxyphenyl)-4-(5-(2-morpholino-2-oxoethyl)pyridin-2-ylamino)thieno[3,2-d]pyrimidine-7-carboxamide | — | 11.40(s, 1H), 10.90(br, 1H), 9.04(s, 1H), 8.88(s, 1H), 8.24(d, 1H), 7.90(dd, 1H), 7.68(dd, 1H), 6.99(s, 1H), 3.96(s, 6H), 3.80(s, 2H), 3.56(m, 6H), 3.46(m, 2H) |
| 258 | N-(2,6-dichloro-3,5-dimethoxyphenyl)-4-(5-((4-methylpiperidin-1-yl)methyl)pyridin-2-ylamino)thieno[3,2-d]pyrimidine-7-carboxamide | — | 11.4 (s, 1H), 9.06 (s, 1H), 8.89 (s, 1H), 8.26 (s, 1H), 7.91 (d, 1H), 7.76-7.73 (d, 1H), 6.96 (s, 1H), 5.33 (s, 2H), 3.97 (s, 6H), 3.38-3.30 (m, 1H), 2.75 (m, 4H), 1.98-1.92 (m, 4H), 0.88 (d, 3H) |
| 259 | N-(2,6-dichloro-3,5-dimethoxyphenyl)-4-(5-((3-(trifluoromethyl)piperidin-1-yl)methyl)pyridin-2-ylamino)thieno[3,2-d]pyrimidine-7-carboxamide | — | 11.4(s, 1H), 9.06 (s, 1H), 8.89 (s, 1H), 8.27 (s, 1H), 7.93-7.92 (d, 1H), 7.78-7.76(d, 1H), 6.97 (s, 1H), 3.96 (s, 6H), 3.49 (s, 2H), 2.99-2.76 (m, 2H), 2.32 (m, 1H), 2.04-2.00 (m, 4H), 1.58-1.53 (m, 2H) |

TABLE 1-continued

| Ex. | Structure | Compound | MS m/z [M + 1] | NMR (¹H NMR 400 MHz, DMSO-d$_6$) |
|---|---|---|---|---|
| 260 | 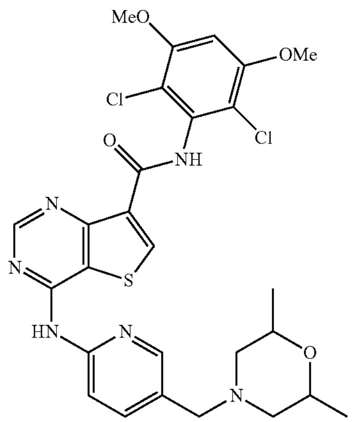 [SMILES: COc1cc(OC)c(Cl)c(NC(=O)c2csc3c(Nc4ccc(CN5CC(C)OC(C)C5)cn4)ncnc23)c1Cl] | N-(2,6-dichloro-3,5-dimethoxyphenyl)-4-(5-((3,5-dimethylmorpholino)methyl)pyridin-2-ylamino)thieno[3,2-d]pyrimidine-7-carboxamide | — | 11.4 (s, 1H), 9.06 (s, 1H), 8.82 (s, 1H), 8.30 (s, 1H), 7.94-7.92 (d, 1H), 7.76-7.74 (d, 1H), 6.96 (s, 1H), 3.97 (s, 6H), 3.87 (m, 2H), 2.70-2.67(m, 4H), 1.04 (m, 6H) |
| 261 | 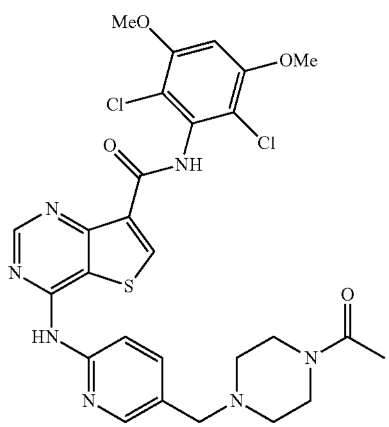 [SMILES: COc1cc(OC)c(Cl)c(NC(=O)c2csc3c(Nc4ccc(CN5CCN(C(C)=O)CC5)cn4)ncnc23)c1Cl] | 4-(5-((4-acetylpiperazin-1-yl)methyl)pyridin-2-ylamino)-N-(2,6-dichloro-3,5-dimethoxyphenyl)thieno[3,2-d]pyrimidine-7-carboxamide | — | 11.40(s, 1H), 8.85(s, 1H), 8.46(d, 1H), 8.28(s, 1H), 7.79(dd, 1H), 7.61(s, 1H), 6.60(s, 1H), 3.96(s, 6H), 3.64(m, 2H), 3.54(s, 2H), 3.48(m, 2H), 2.47(m, 4H), 2.09(s, 3H) |
| 262 | 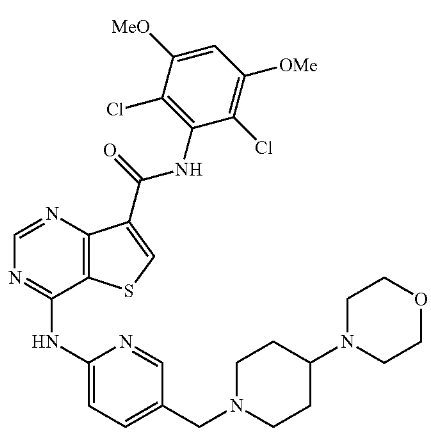 [SMILES: COc1cc(OC)c(Cl)c(NC(=O)c2csc3c(Nc4ccc(CN5CCC(N6CCOCC6)CC5)cn4)ncnc23)c1Cl] | N-(2,6-dichloro-3,5-dimethoxyphenyl)-4-(5-((4-morpholinopiperidin-1-yl)methyl)pyridin-2-ylamino)thieno[3,2-d]pyrimidine-7-carboxamide | — | 11.4 (s, 1H), 10.9 (s, 1H), 9.05 (s, 1H), 8.88 (s, 1H), 8.28 (s, 1H), 7.93-7.91 (d, 1H), 7.76-7.74 (d,1H), 4.07(s, 2H), 3.96 (s, 6H), 3.87 (m, 1H), 3.54-3.46 (m, 4H), 2.82-2.80 (m, 2H), 2.42-2.40 (m, 4H), 1.94-1.90 (m, 2H) |

TABLE 1-continued

| Ex. | Structure | Compound | MS m/z [M + 1] | NMR (¹H NMR 400 MHz, DMSO-d₆) |
|---|---|---|---|---|
| 263 | 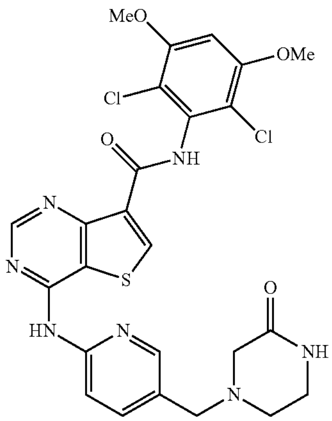 [SMILES: COc1cc(OC)c(Cl)c(NC(=O)c2csc3c(Nc4ccc(CN5CCNC(=O)C5)cn4)ncnc23)c1Cl] | N-(2,6-dichloro-3,5-dimethoxyphenyl)-4-(5-((3-oxopiperazin-1-yl)methyl)pyridin-2-ylamino)thieno[3,2-d]pyrimidine-7-carboxamide | — | 11.4 (s, 1H), 10.9 (s, 1H), 9.05 (s, 1H), 8.82 (s, 1H), 8.32 (s, 1H), 7.97-7.93 (d, 1H), 7.81-7.75 (d, 1H), 6.95 (s, 1H), 3.96 (s, 6H), 3.65 (s, 2H), 3.15-3.10 (m, 2H), 2.94-2.91 (m, 2H), 2.56-2.54 (m, 2H) |
| 264 | 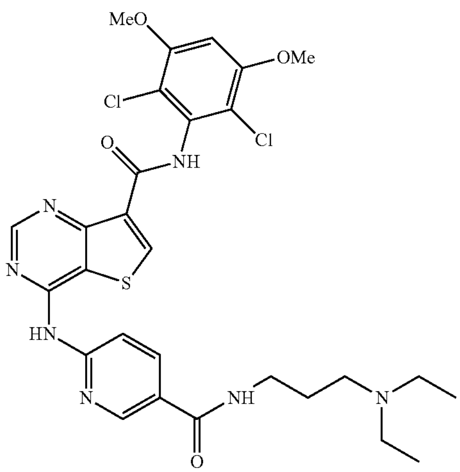 [SMILES: CCN(CC)CCCNC(=O)c1ccc(Nc2ncnc3c(C(=O)Nc4c(Cl)c(OC)cc(OC)c4Cl)csc23)nc1] | N-(2,6-dichloro-3,5-dimethoxyphenyl)-4-(5-(3-(diethylamino)propylcarbamoyl)pyridin-2-ylamino)thieno[3,2-d]pyrimidine-7-carboxamide | — | 11.35(s, 1H), 11.21(br, 1H), 9.10(s, 1H), 8.89 (s, 1H), 8.82(d, 1H), 8.70(t, 1H), 8.26(dd, 1H), 8.20(d, 1H), 6.96(s, 1H), 3.96(s, 6H), 2.55(m, 2H), 2.43(m, 2H), 1.70(m, 4H), 1.25(m, 2H), 0.94(m, 6H) |
| 265 | 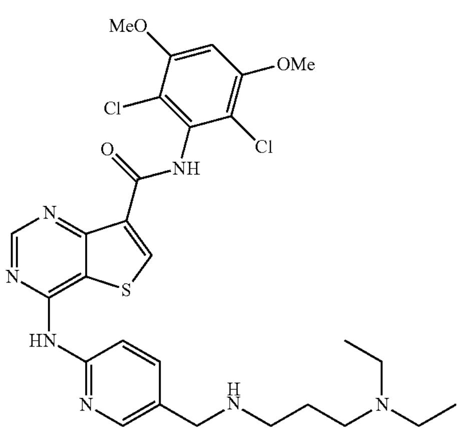 [SMILES: CCN(CC)CCCNCc1ccc(Nc2ncnc3c(C(=O)Nc4c(Cl)c(OC)cc(OC)c4Cl)csc23)nc1] | N-(2,6-dichloro-3,5-dimethoxyphenyl)-4-(5-((3-(diethylamino)propylamino)methyl)pyridin-2-ylamino)thieno[3,2-d]pyrimidine-7-carboxamide | — | 11.4 (s, 1H), 9.04 (s, 1H), 8.80 (s, 1H), 8.30 (s, 1H), 7.69-7.67 (d, 1H), 7.58-7.55 (d, 1H), 6.96 (s, 1H), 3.96 (s, 6H), 3.68 (s, 2H), 2.71-2.39 (m, 8H), 1.53 (m, 2H), 0.98-0.92 (t, 6H) |

TABLE 1-continued

| Ex. | Structure | Compound | MS m/z [M + 1] | NMR (¹H NMR 400 MHz, DMSO-d₆) |
|---|---|---|---|---|
| 266 | 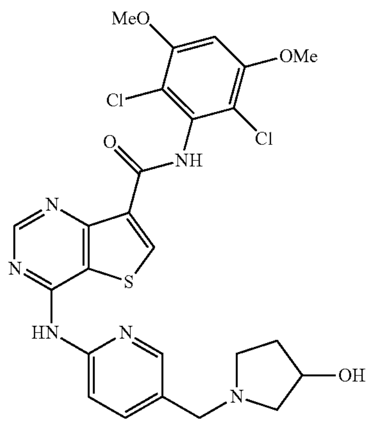 [SMILES: COc1cc(OC)c(Cl)c(NC(=O)c2csc3c(Nc4ccc(CN5CCC(O)C5)cn4)ncnc23)c1Cl] | (R)-N-(2,6-dichloro-3,5-dimethoxyphenyl)-4-(5-((3-hydroxypyrrolidin-1-yl)methyl)pyridin-2-ylamino)thieno[3,2-d]pyrimidine-7-carboxamide | — | 11.4 (s, 1H), 10.9 (s, 1H), 9.05 (s, 1H), 8.81 (s, 1H), 8.30 (s, 1H), 7.90-7.88 (d, 1H), 7.78-7.76 (d, 1H), 6.96 (s, 1H), 4.70-4.69 (d, 1H), 4.15 (s, 2H), 3.96 (s, 6H), 3.58-3.56 (d, 2H), 2.56-2.42 (m, 4H) |
| 267 | 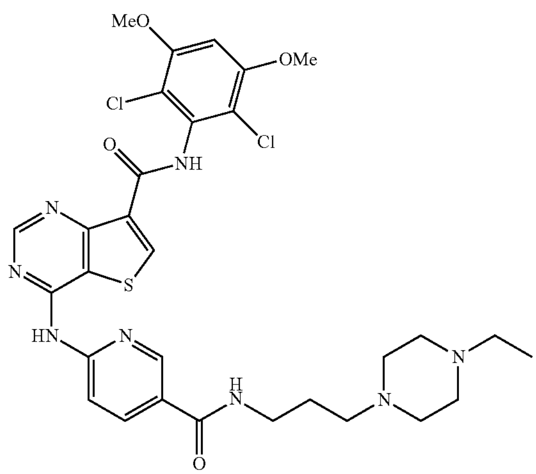 [SMILES: CCN1CCN(CCCNC(=O)c2ccc(Nc3ncnc4c(C(=O)Nc5c(Cl)c(OC)cc(OC)c5Cl)csc34)nc2)CC1] | N-(2,6-dichloro-3,5-dimethoxyphenyl)-4-(5-(3-(4-ethylpiperazin-1-yl)propylcarbamoyl)pyridin-2-ylamino)thieno[3,2-d]pyrimidine-7-carboxamide | — | 11.36(s, 1H), 11.20(br, 1H), 9.11(s, 1H), 8.90(s, 1H), 8.87(d, 1H), 8.59(m, 1H), 8.24(dd, 1H), 8.07(d, 1H), 6.97(s, 1H), 3.97(s, 6H), 3.31(m, 2H), 2.30(m, 12H), 1.67(m, 3 2H), 0.98(t, 3H) |
| 268 | 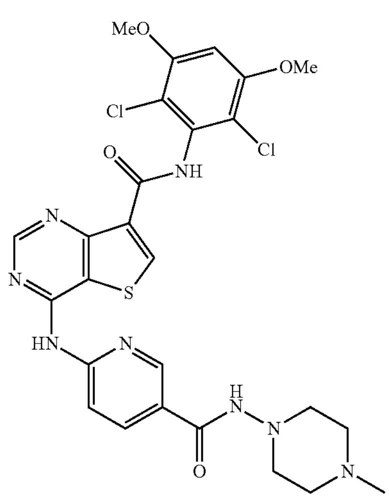 [SMILES: COc1cc(OC)c(Cl)c(NC(=O)c2csc3c(Nc4ccc(C(=O)NN5CCN(C)CC5)cn4)ncnc23)c1Cl] | N-(2,6-dichloro-3,5-dimethoxyphenyl)-4-(5-(4-methylpiperazin-1-ylcarbamoyl)pyridin-2-ylamino)thieno[3,2-d]pyrimidine-7-carboxamide | — | 11.35(s, 1H), 11.15(br, 1H), 9.54(s, 1H), 9.10(s, 1H), 8.89(s, 1H), 8.79(d, 1H), 8.18(dd, 1H), 8.05(d, 1H), 6.96(s, 1H), 3.96(s, 6H), 2.72(m, 4H), 2.43(m, 4H), 2.26(s, 3H) |

TABLE 1-continued

| Ex. | Structure | Compound | MS m/z [M + 1] | NMR (¹H NMR 400 MHz, DMSO-d$_6$) |
|---|---|---|---|---|
| 269 | 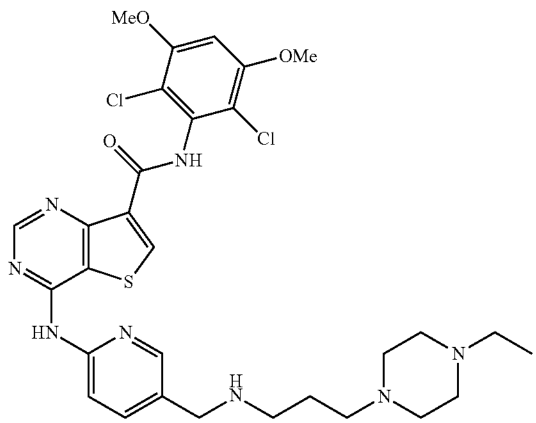 [SMILES: CCN1CCN(CCCNCc2ccc(Nc3ncnc4c(C(=O)Nc5c(Cl)c(OC)cc(OC)c5Cl)csc34)nc2)CC1] | N-(2,6-dichloro-3,5-dimethoxyphenyl)-4-(5-((3-(4-ethylpiperazin-1-yl)propylamino)methyl)pyridin-2-ylamino)thieno[3,2-d]pyrimidine-7-carboxamide | — | 11.4 (s, 1H), 10.9 (s, 1H), 9.06 (s, 1H), 8.80 (s, 1H), 8.30 (s, 1H), 7.91-7.89 (d, 1H), 7.76-7.74 (d, 1H), 6.96 (s, 1H), 3.98 (s, 6H), 3.59 (s, 2H), 2.50-2.45 (m, 12H), 1.76-1.72 (m, 0.94-0.90 (t, 3H) |
| 270 | 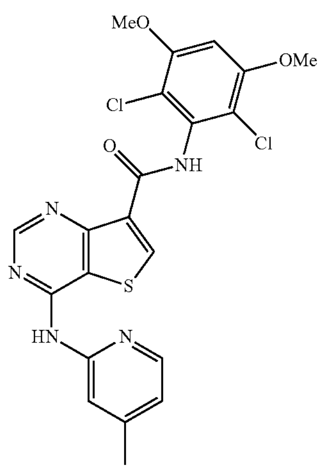 [SMILES: COc1cc(OC)c(Cl)c(NC(=O)c2csc3c(Nc4cc(C)ccn4)ncnc23)c1Cl] | N-(2,6-dichloro-3,5-dimethoxyphenyl)-4-(4-methylpyridin-2-ylamino)thieno[3,2-d]pyrimidine-7-carboxamide | — | 11.39(s, 1H), 9.03(s, 1H), 8.82(s, 1H), 8.26(d, 1H), 7.73(s, 1H), 7.01(d, 1H), 6.95(s, 1H), 3.95(s, 6H), 2.39(s, 3H) |
| 271 | 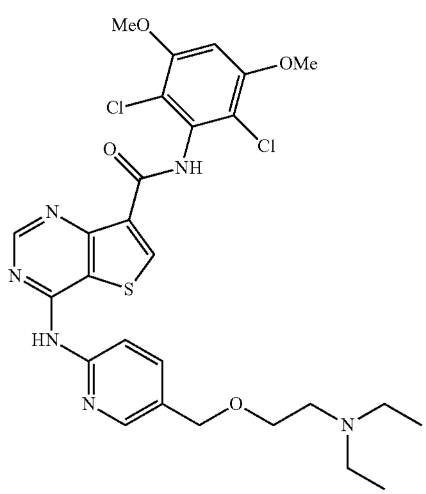 [SMILES: CCN(CC)CCOCc1ccc(Nc2ncnc3c(C(=O)Nc4c(Cl)c(OC)cc(OC)c4Cl)csc23)nc1] | N-(2,6-dichloro-3,5-dimethoxyphenyl)-4-(5-((2-(diethylamino)ethoxy)methyl)pyridin-2-ylamino)thieno[3,2-d]pyrimidine-7-carboxamide | — | 11.4 (s, 1H), 9.02 (s, 1H), 8.78 (s, 1H), 8.35 (s, 1H), 7.95-7.92 (d, 1H), 7.80-7.78 (d, 1H), 6.96 (s, 1H), 4.49 (s, 2H), 3.96 (s, 6H), 3.53-3.49 (t, 2H), 2.61-2.57 (t, 2H), 2.50-2.44 (m, 4H), 0.96-0.91 (t, 6H) |

TABLE 1-continued

| Ex. | Structure | Compound | MS m/z [M + 1] | NMR (¹H NMR 400 MHz, DMSO-$d_6$) |
|---|---|---|---|---|
| 272 | 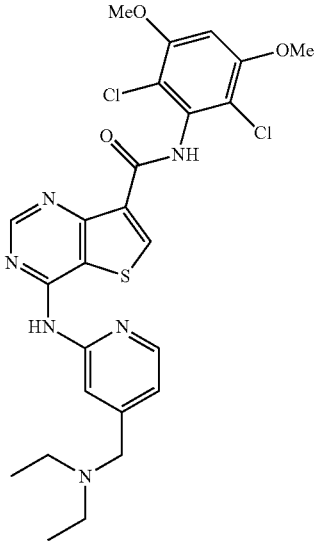 [SMILES: CCN(CC)Cc1ccnc(Nc2ncnc3c(C(=O)Nc4c(Cl)c(OC)cc(OC)c4Cl)csc23)c1] | N-(2,6-dichloro-3,5-dimethoxyphenyl)-4-(4-((diethylamino)methyl)pyridin-2-ylamino)thieno[3,2-d]pyrimidine-7-carboxamide | — | 11.40(s, 1H), 10.95(br, 1H), 9.06(s, 1H), 8.72(s, 1H), 8.24(d, 1H), 7.76(s, 1H), 7.07(d, 1H), 6.89(s, 1H), 3.94(s, 6H), 3.58(s, 2H), 2.45(q, 4H), 0.91(t, 6H) |
| 273 | 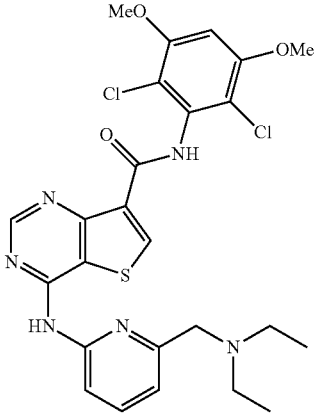 [SMILES: CCN(CC)Cc1cccc(Nc2ncnc3c(C(=O)Nc4c(Cl)c(OC)cc(OC)c4Cl)csc23)n1] | N-(2,6-dichloro-3,5-dimethoxyphenyl)-4-(6-((diethylamino)methyl)pyridin-2-ylamino)thieno[3,2-d]pyrimidine-7-carboxamide | — | 11.42(s, 1H), 10.87(br, 1H), 9.15(s, 1H), 8.88(s, 1H), 7.83(m, 2H), 7.21(m, 1H), 6.95(s, 1H), 3.95(s, 6H), 3.66(s, 2H), 2.49(q, 4H), 0.97(t, 6H) |
| 274 | 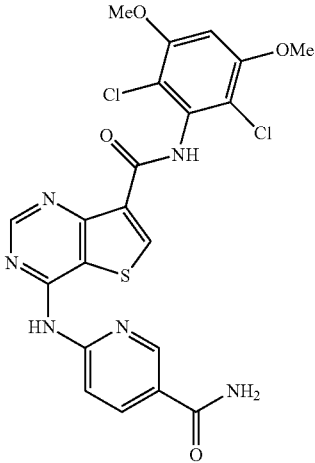 [SMILES: COc1cc(OC)c(Cl)c(NC(=O)c2csc3c(Nc4ccc(C(N)=O)cn4)ncnc23)c1Cl] | 4-(5-carbamoylpyridin-2-ylamino)-N-(2,6-dichloro-3,5-dimethoxyphenyl)thieno[3,2-d]pyrimidine-7-carboxamide | — | 11.35(s, 1H), 11.23(br, 1H), 9.13(s, 1H), 8.88(s, 1H), 8.30(m, 1H), 8.07(m, 2H), 7.46(m, 1H), 6.96(s, 1H), 3.96(s, 6H) |

TABLE 1-continued

| Ex. | Structure | Compound | MS m/z [M + 1] | NMR (¹H NMR 400 MHz, DMSO-$d_6$) |
|---|---|---|---|---|
| 275 | 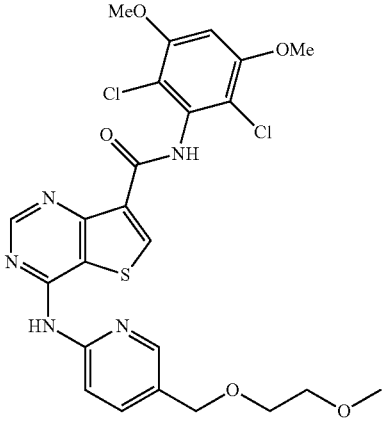 [SMILES: COCCOCc1ccc(Nc2ncnc3c(C(=O)Nc4c(Cl)c(OC)cc(OC)c4Cl)csc23)nc1] | N-(2,6-dichloro-3,5-dimethoxyphenyl)-4-(5-((2-methoxyethoxy)methyl)pyridin-2-ylamino)thieno[3,2-d]pyrimidine-7-carboxamide | — | 11.4 (s, 1H), 10.9 (s, 1H), 9.05 (s, 1H), 8.82 (s, 1H), 8.36 (s, 1H), 7.97-7.93 (d, 1H), 7.82-7.80 (d, 1H), 6.97 (s, 1H), 4.51 (s, 2H), 3.96 (s, 6H), 3.58-3.57 (t, 2H), 3.49-3.48 (t, 2H), 3.25 (s, 3H) |
| 276 | 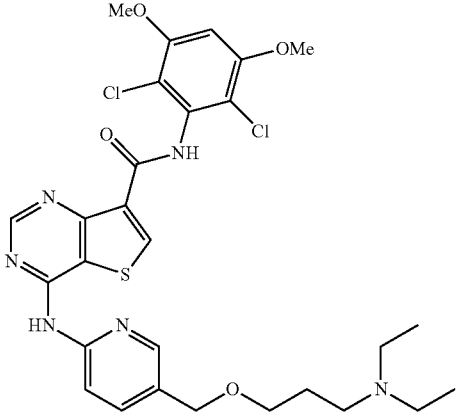 [SMILES: CCN(CC)CCCOCc1ccc(Nc2ncnc3c(C(=O)Nc4c(Cl)c(OC)cc(OC)c4Cl)csc23)nc1] | N-(2,6-dichloro-3,5-dimethoxyphenyl)-4-(5-((3-(diethylamino)propoxy)methyl)pyridin-2-ylamino)thieno[3,2-d]pyrimidine-7-carboxamide | — | 11.4 (s, 1H), 10.9 (s, 1H), 9.07 (s, 1H), 8.83 (s, 1H), 8.41 (s, 1H), 7.99-7.94 (d, 1H), 7.83-7.80 (d, 1H), 6.97 (s, 1H), 4.53 (s, 2H), 3.51-3.47 (t, 2H), 1.69-1.63 (m, 2H), 1.06-0.89 (t, 6H) |
| 277 | 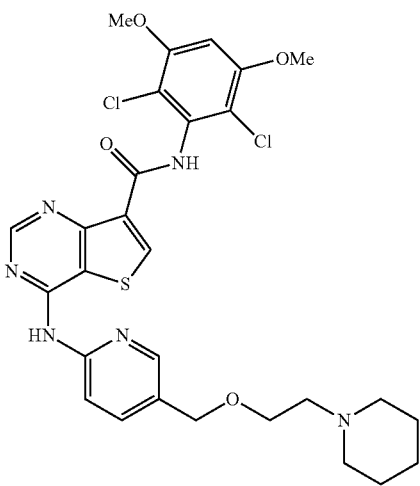 [SMILES: COc1cc(OC)c(Cl)c(NC(=O)c2csc3c(Nc4ccc(COCCN5CCCCC5)cn4)ncnc23)c1Cl] | N-(2,6-dichloro-3,5-dimethoxyphenyl)-4-(5-((2-(piperidin-1-yl)ethoxy)methyl)pyridin-2-ylamino)thieno[3,2-d]pyrimidine-7-carboxamide | — | 11.4 (s, 1H), 10.9 (s, 1H), 9.07 (s, 1H), 8.84 (s, 1H), 8.42 (s, 1H), 7.99-7.96 (d, 1H), 7.83-7.80 (d, 1H), 6.97 (s, 1H), 4.51 (s, 2H), 3.97 (s, 6H), 3.63-3.56 (t, 2H), 2.37-2.34 (m, 4H), 1.49-1.46 (m, 4H), 1.38-1.35 (m, 2H) |

TABLE 1-continued

| Ex. | Structure | Compound | MS m/z [M + 1] | NMR (¹H NMR 400 MHz, DMSO-d$_6$) |
|---|---|---|---|---|
| 278 | 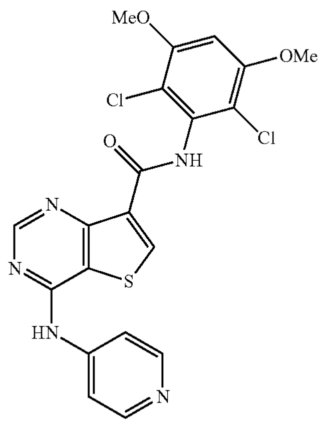 [SMILES: COc1cc(OC)c(Cl)c(NC(=O)c2csc3c(Nc4ccncc4)ncnc23)c1Cl] | N-(2,6-dichloro-3,5-dimethoxyphenyl)-4-(pyridin-4-ylamino)thieno[3,2-d]pyrimidine-7-carboxamide | — | 11.3 (s, 1H), 10.4 (s, 1H), 9.14 (s, 1H), 8.91 (s, 1H), 8.52-8.50 (s, 2H), 7.98-7.88 (s, 2H), 6.97 (s, 1H), 3.96 (s, 6H) |
| 279 | 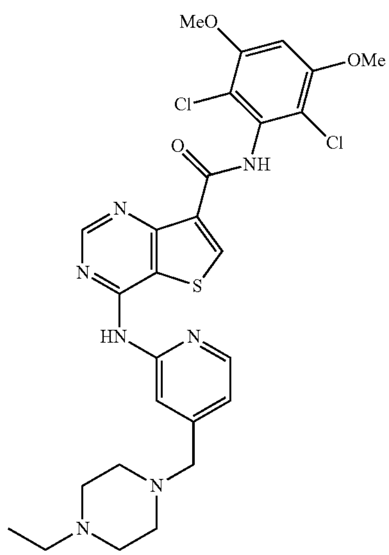 [SMILES: CCN1CCN(Cc2ccnc(Nc3ncnc4c(C(=O)Nc5c(Cl)c(OC)cc(OC)c5Cl)csc34)c2)CC1] | N-(2,6-dichloro-3,5-dimethoxyphenyl)-4-(4-((4-ethylpiperazin-1-yl)methyl)pyridin-2-ylamino)thieno[3,2-d]pyrimidine-7-carboxamide | — | 11.40(s, 1H), 9.05(s, 1H), 8.81(s, 1H), 8.32(d, 1H), 7.84(s, 1H), 7.10(d, 1H), 6.96(s, 1H), 3.96(s, 6H), 3.56(s, 2H), 2.30(m, 10H), 0.96(t, 3H) |
| 280 | 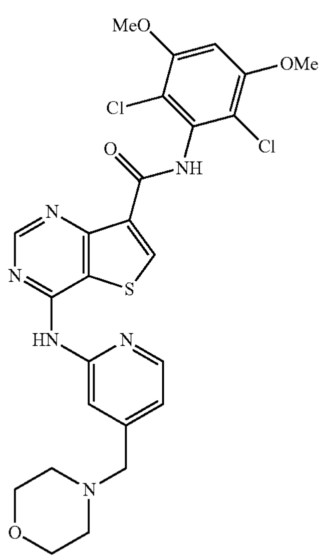 [SMILES: COc1cc(OC)c(Cl)c(NC(=O)c2csc3c(Nc4cc(CN5CCOCC5)ccn4)ncnc23)c1Cl] | N-(2,6-dichloro-3,5-dimethoxyphenyl)-4-(4-(morpholinomethyl)pyridin-2-ylamino)thieno[3,2-d]pyrimidine-7-carboxamide | — | 11.41(s, 1H), 10.90(br, 1H), 9.05(s, 1H), 8.85(s, 1H), 8.33(d, 1H), 7.86(s, 1H), 7.15(s, 1H), 6.96(s, 1H), 3.96(s, 6H), 3.61(m, 4H), 3.54(s, 2H), 2.43(m, 4H) |

TABLE 1-continued

| Ex. | Structure | Compound | MS m/z [M + 1] | NMR (¹H NMR 400 MHz, DMSO-d$_6$) |
|---|---|---|---|---|
| 281 | 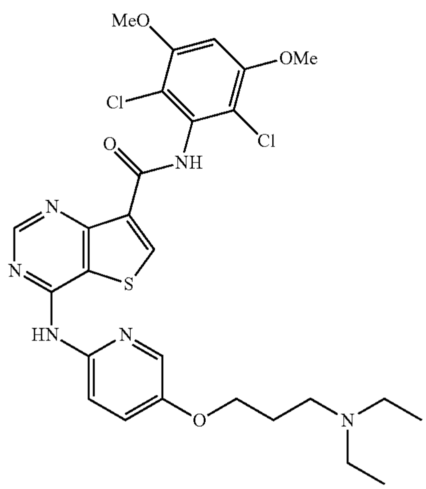 [SMILES: CCN(CC)CCCOc1ccc(Nc2ncnc3c(C(=O)Nc4c(Cl)c(OC)cc(OC)c4Cl)csc23)nc1] | N-(2,6-dichloro-3,5-dimethoxyphenyl)-4-(5-(3-(diethylamino)propoxy)pyridin-2-ylamino)thieno[3,2-d]pyrimidine-7-carboxamide | — | 11.4 (s, 1H), 10.8 (s, 1H), 9.07 (s, 1H), 8.76 (s, 1H), 8.14 (s, 1H), 7.92-7.88 (d, 1H), 7.53-7.51 (d, 1H), 6.98 (s, 1H), 4.34-4.33 (t, 2H), 3.96 (s, 6H), 2.68-2.31 (m, 6H), 1.80-1.70 (m, 2H), 1.03-1.01 (t, 6H) |
| 282 | 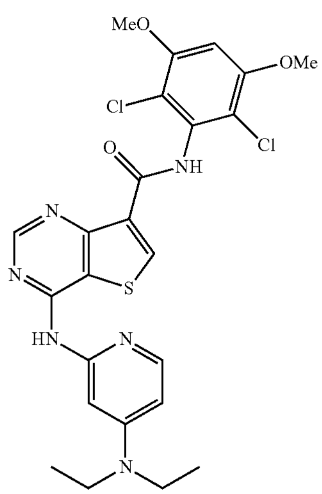 [SMILES: CCN(CC)c1ccnc(Nc2ncnc3c(C(=O)Nc4c(Cl)c(OC)cc(OC)c4Cl)csc23)c1] | N-(2,6-dichloro-3,5-dimethoxyphenyl)-4-(4-(diethylamino)pyridin-2-ylamino)thieno[3,2-d]pyrimidine-7-carboxamide | — | 11.56(s, 1H), 8.79(s, 1H), 8.71(s, 1H), 7.71(d, 1H), 7.28(s, 1H), 6.59(s, 1H), 6.27(dd, 1H), 3.96(s, 6H), 3.43(q, 4H), 1.30(t, 3H) |
| 283 | 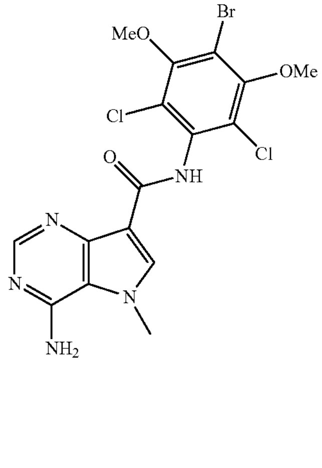 [SMILES: COc1c(Cl)c(NC(=O)c2cn(C)c3c(N)ncnc23)c(Cl)c(OC)c1Br] | 4-amino-N-(4-bromo-2,6-dichloro-3,5-dimethoxyphenyl)-5-methyl-5H-pyrrolo[3,2-d]pyrimidine-7-carboxamide | — | 10.4 (s, 1H), 8.25 (s, 1H), 8.11 (s, 1H), 7.10 (s, 2H), 4.08 (s, 3H), 3.86 (s, 6H) |

TABLE 1-continued

| Ex. | Structure | Compound | MS m/z [M + 1] | NMR ($^1$H NMR 400 MHz, DMSO-$d_6$) |
|---|---|---|---|---|
| 284 | 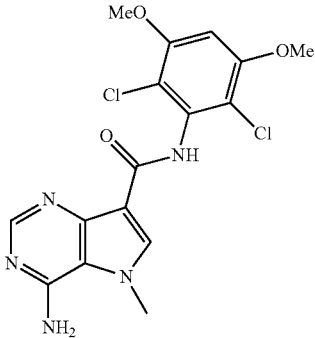 [SMILES: COc1cc(OC)c(Cl)c(NC(=O)c2cn(C)c3c(N)ncnc23)c1Cl] | 4-amino-N-(2,6-dichloro-3,5-dimethoxyphenyl)-5-methyl-5H-pyrrolo[3,2-d]pyrimidine-7-carboxamide | — | 10.3 (s, 1H), 8.24 (s, 1H), 8.08 (s, 1H), 7.05 (s, 2H), 6.92 (s, 1H), 4.08 (s, 3H), 3.94 (s, 6H) |
| 285 | 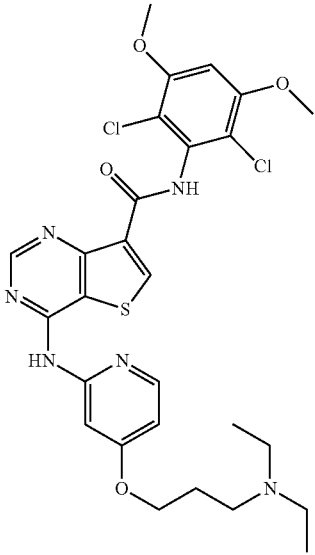 [SMILES: CCN(CC)CCCOc1ccnc(Nc2ncnc3c(C(=O)Nc4c(Cl)c(OC)cc(OC)c4Cl)csc23)c1] | N-(2,6-dichloro-3,5-dimethoxyphenyl)-4-(4-(3-(diethylamino)propoxy)pyridin-2-ylamino)thieno[3,2-d]pyrimidine-7-carboxamide | — | 11.4 (s, 1H), 10.9 (s, 1H), 9.04 (s, 1H), 8.82 (s, 1H), 8.21-8.19 (d, 1H), 7.59 (s, 1H), 6.95 (s, 1H), 6.78-6.76 (d, 1H), 4.14-4.11 (t, 2H), 3.95 (s, 6H), 2.60-2.48 (m, 6H), 1.87-1.84 (m, 2H), 0.96-0.91 (t, 6H) |
| 286 | 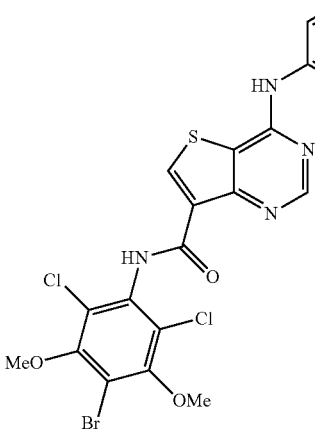 | N-(4-bromo-2,6-dichloro-3,5-dimethoxyphenyl)-4-(2,3,4-trifluorophenylamino)thieno[3,2-d]pyrimidine-7-carboxamide | — | 11.4 (s, 1H), 10.3 (s, 1H), 9.07 (s, 1H), 8.68 (s, 1H), 7.44-7.39 (m, 2H), 3.87 (s, 6H) |

TABLE 1-continued

| Ex. | Structure | Compound | MS m/z [M + 1] | NMR (¹H NMR 400 MHz, DMSO-$d_6$) |
|---|---|---|---|---|
| 287 | 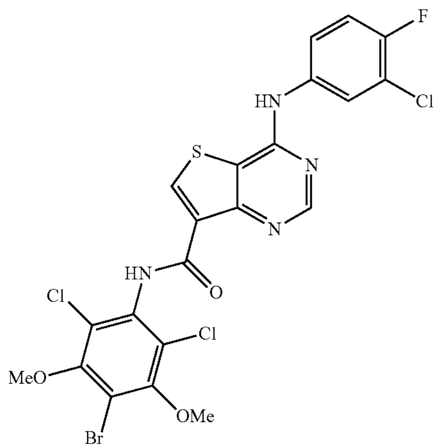 [SMILES: COc1c(Cl)c(NC(=O)c2csc3c(Nc4ccc(F)c(Cl)c4)ncnc23)c(Cl)c(OC)c1Br] | N-(4-bromo-2,6-dichloro-3,5-dimethoxyphenyl)-4-(3-chloro-4-fluorophenylamino)thieno[3,2-d]pyrimidine-7-carboxamide | — | 11.5 (s, 1H), 10.3 (s, 1H), 9.07 (s, 1H), 8.80 (s, 1H), 8.15-8.12 (m, 1H), 7.78-7.72 (m, 1H), 7.50-7.43 (t, 1H), 3.86 (s, 6H) |
| 288 | 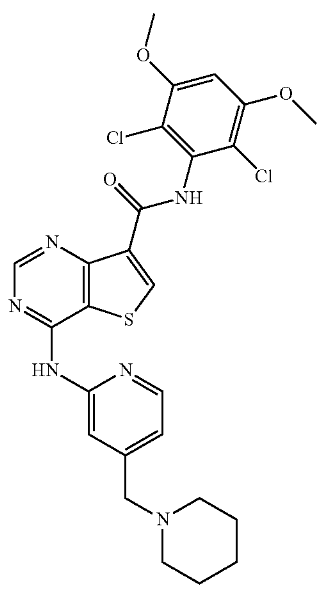 [SMILES: COc1cc(OC)c(Cl)c(NC(=O)c2csc3c(Nc4cc(CN5CCCCC5)ccn4)ncnc23)c1Cl] | N-(2,6-dichloro-3,5-dimethoxyphenyl)-4-(4-(piperidin-1-ylmethyl)pyridin-2-ylamino)thieno[3,2-d]pyrimidine-7-carboxamide | — | 11.4 (s, 1H), 9.04 (s, 1H), 8.81 (s, 1H), 8.32-8.30 (d, 1H), 7.83 (s, 1H), 7.11-7.09 (d, 1H), 6.96 (s, 1H), 3.96 (s, 6H), 3.54 (s, 2H), 2.37-2.26 (m, 4H), 1.58-1.53 (m, 4H), 1.34-1.22 (m, 2H) |
| 289 | 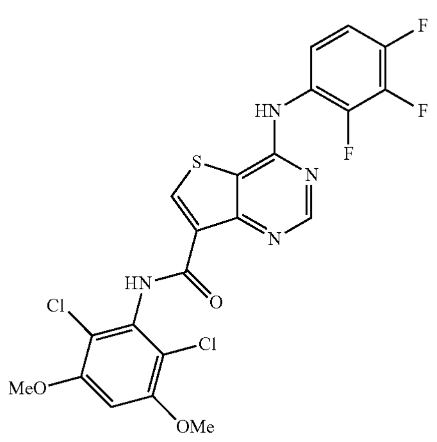 [SMILES: COc1cc(OC)c(Cl)c(NC(=O)c2csc3c(Nc4ccc(F)c(F)c4F)ncnc23)c1Cl] | N-(2,6-dichloro-3,5-dimethoxyphenyl)-4-(2,3,4-trifluorophenylamino)thieno[3,2-d]pyrimidine-7-carboxamide | — | 11.32 (s, 1H), 10.34 (bs, 1H), 9.05 (s, 1H), 8.68 (s, 1H), 7.40-7.44 (m, 2H), 6.95 (s, 1H), 3.95 (s, 6H) |

TABLE 1-continued

| Ex. | Structure | Compound | MS m/z [M + 1] | NMR (¹H NMR 400 MHz, DMSO-$d_6$) |
|---|---|---|---|---|
| 290 | 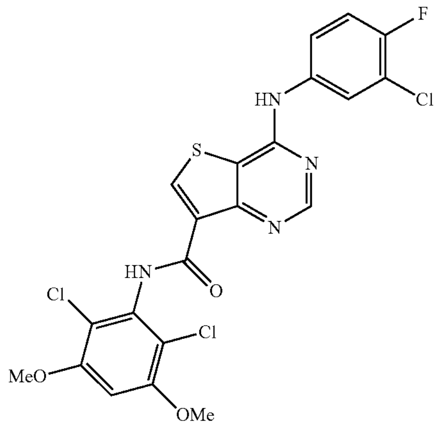 [SMILES: COc1cc(OC)c(Cl)c(NC(=O)c2csc3c(Nc4ccc(F)c(Cl)c4)ncnc23)c1Cl] | 4-(3-chloro-4-fluorophenylamino)-N-(2,6-dichloro-3,5-dimethoxyphenyl)thieno[3,2-d]pyrimidine-7-carboxamide | — | 11.33 (s, 1H), 10.26 (s, 1H), 9.05 (s, 1H), 8.79 (s, 1H), 8.12-8.15 (m, 1H), 7.72-7.77 (m, 1H), 7.47 (t, 1H), 6.96 (s, 1H), 3.96 (s, 6H) |
| 291 | 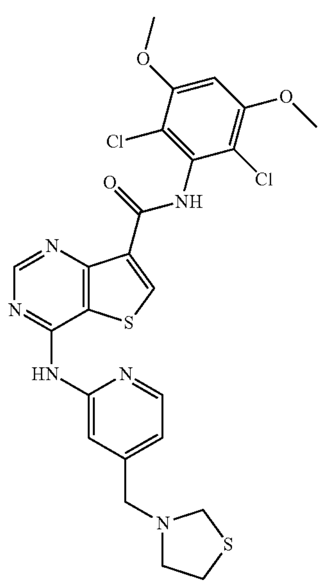 [SMILES: COc1cc(OC)c(Cl)c(NC(=O)c2csc3c(Nc4cc(CN5CCSC5)ccn4)ncnc23)c1Cl] | N-(2,6-dichloro-3,5-dimethoxyphenyl)-4-(4-(thiazolidin-3-ylmethyl)pyridin-2-ylamino)thieno[3,2-d]pyrimidine-7-carboxamide | — | 11.4 (s, 1H), 9.05 (s, 1H), 8.83 (s, 1H), 8.36-8.34(d, 1H), 7.92 (s, 1H), 7.21-7.18 (d, 1H), 6.96 (s, 1H), 4.04 (s, 2H), 3.96 (s, 6H), 3.59 (s, 2H), 3.09-3.05 (t, 2H), 2.91-2.88 (t, 2H) |

TABLE 1-continued

| Ex. | Structure | Compound | MS m/z [M + 1] | NMR ($^1$H NMR 400 MHz, DMSO-$d_6$) |
|---|---|---|---|---|
| 292 | 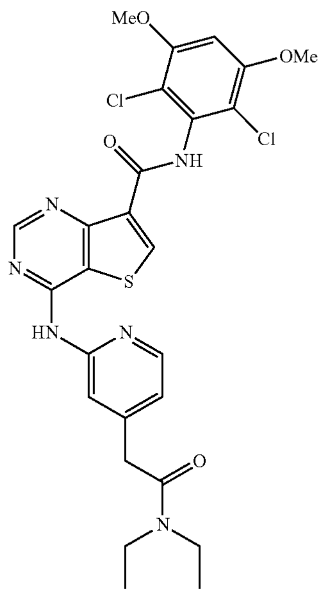 [SMILES: CCN(CC)C(=O)Cc1ccnc(Nc2ncnc3c(C(=O)Nc4c(Cl)c(OC)cc(OC)c4Cl)csc23)c1] | N-(2,6-dichloro-3,5-dimethoxyphenyl)-4-(4-(2-(diethylamino)-2-oxoethyl)pyridin-2-ylamino)thieno[3,2-d]pyrimidine-7-carboxamide | — | 11.47(s, 1H), 10.96(br, 1H), 9.08(s, 1H), 8.80(s, 1H), 8.31(d, 1H), 7.77(s, 1H), 7.04(d, 1H), 6.95(s, 1H), 3.96(s, 6H), 3.75(s, 2H), 3.33(m, 4H), 1.11(t, 3H), 1.04(t, 3H) |
| 293 | 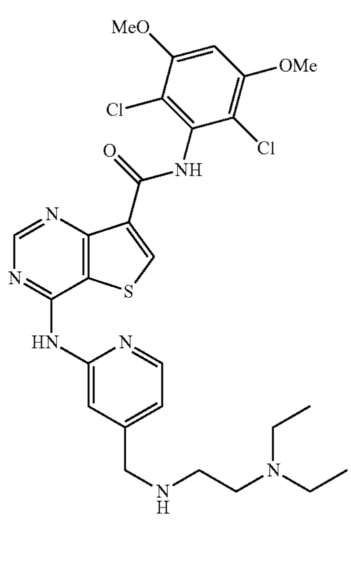 [SMILES: CCN(CC)CCNCc1ccnc(Nc2ncnc3c(C(=O)Nc4c(Cl)c(OC)cc(OC)c4Cl)csc23)c1] | N-(2,6-dichloro-3,5-dimethoxyphenyl)-4-(4-((2-(diethylamino)ethyl-amino)methyl)pyridin-2-ylamino)thieno[3,2-d]pyrimidine-7-carboxamide | — | 11.4 (s, 1H), 10.9 (s, 1H), 9.08 (s, 1H), 8.81 (s, 1H), 8.39-8.36 (d, 1H), 7.88 (s, 1H), 7.16 (d, 1H), 6.96 (s, 1H), 3.96 (s, 6H), 3.88 (s, 2H), 3.77-3.70 (m, 2H), 2.71-2.48 (m, 8H), 1.08-1.00 (t, 6H) |

TABLE 1-continued

| Ex. | Structure | Compound | MS m/z [M + 1] | NMR (¹H NMR 400 MHz, DMSO-d₆) |
|---|---|---|---|---|
| 294 | 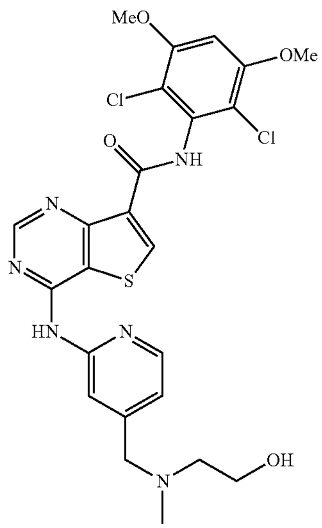 [SMILES: COc1cc(OC)c(Cl)c(NC(=O)c2csc3c(Nc4cc(CN(C)CCO)ccn4)ncnc23)c1Cl] | N-(2,6-dichloro-3,5-dimethoxyphenyl)-4-(4-(((2-hydroxyethyl)(methyl)amino)methyl)pyridin-2-ylamino)thieno[3,2-d]pyrimidine-7-carboxamide | — | 11.4 (s, 1H), 10.9 (s, 1H), 9.04 (s, 1H), 8.81 (s, 1H), 8.32-8.31 (d, 1H), 7.82 (s, 1H), 7.13-7.12 (d, 1H), 6.96 (s, 1H), 4.44-4.40 (t, 2H), 3.96 (s, 6H), 3.57-3.51 (m, 4H), 2.26-2.21 (s, 3H) |
| 295 | 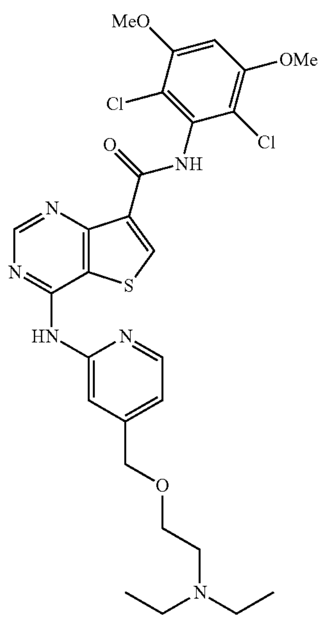 [SMILES: CCN(CC)CCOCc1ccnc(Nc2ncnc3c(C(=O)Nc4c(Cl)c(OC)cc(OC)c4Cl)csc23)c1] | N-(2,6-dichloro-3,5-dimethoxyphenyl)-4-(4-((2-(diethylamino)ethoxy)methyl)pyridin-2-ylamino)thieno[3,2-d]pyrimidine-7-carboxamide | — | 11.35(s, 1H), 11.02(br, 1H), 9.03(s, 1H), 8.79(s, 1H), 8.32(d, 1H), 7.88(s, 1H), 7.07(d, 1H), 6.92(s, 1H), 4.56(s, 2H), 3.92(s, 6H), 3.12(d, 2H), 2.90(m, 6H), 1.09(t, 6H) |
| 296 | 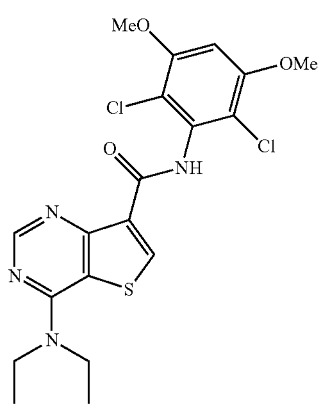 [SMILES: CCN(CC)c1ncnc2c(C(=O)Nc3c(Cl)c(OC)cc(OC)c3Cl)csc12] | N-(2,6-dichloro-3,5-dimethoxyphenyl)-4-(diethylamino)thieno[3,2-d]pyrimidine-7-carboxamide | — | 11.7 (s, 1H), 9.04 (s, 1H), 8.58 (s, 1H), 6.95 (s, 1H), 3.95 (s, 6H), 3.87-3.79 (m, 4H), 1.30-1.25 (t, 6H) |

TABLE 1-continued

| Ex. | Structure | Compound | MS m/z [M + 1] | NMR (¹H NMR 400 MHz, DMSO-$d_6$) |
|---|---|---|---|---|
| 297 | 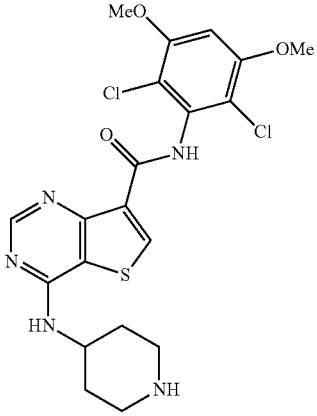 [SMILES: COc1cc(OC)c(Cl)c(NC(=O)c2csc3c(NC4CCNCC4)ncnc23)c1Cl] | N-(2,6-dichloro-3,5-dimethoxyphenyl)-4-(piperidin-4-ylamino)thieno[3,2-d]pyrimidine-7-carboxamide | — | 11.5 (s, 1H), 8.90 (s, 1H), 8.59 (s, 1H), 8.25-8.23 (d, 1H), 6.95 (s, 1H), 4.31-4.28 (m, 4H), 3.95 (s, 6H), 3.92-3.87 (m, 1H), 1.92-1.51 (m, 4H) |
| 298 | 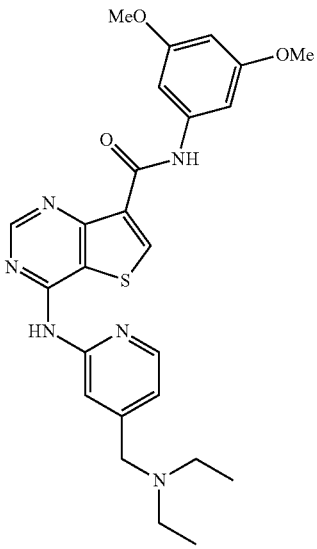 [SMILES: CCN(CC)Cc1ccnc(Nc2ncnc3c(C(=O)Nc4cc(OC)cc(OC)c4)csc23)c1] | 4-(4-((diethylamino)methyl)pyridin-2-ylamino)-N-(3,5-dimethoxyphenyl)thieno[3,2-d]pyrimidine-7-carboxamide | — | 11.8 (s, 1H), 10.9 (s, 1H), 9.00 (s, 1H), 8.86 (s, 1H), 8.30-8.29 (d, 1H), 7.85 (s, 1H), 7.12-7.11(d, 1H), 7.00 (s, 2H), 6.31 (s, 1H), 3.77 (s, 6H), 3.60 (s, 2H), 2.54-2.46 (m, 4H), 1.03-0.98 (t, 6H) |
| 299 | 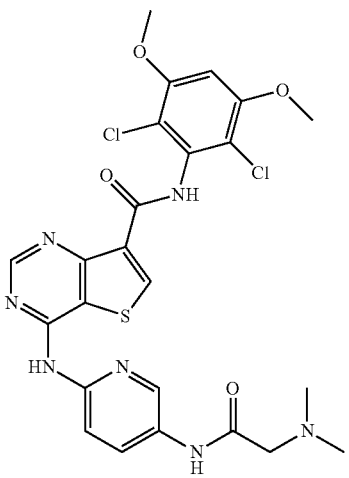 [SMILES: COc1cc(OC)c(Cl)c(NC(=O)c2csc3c(Nc4ccc(NC(=O)CN(C)C)cn4)ncnc23)c1Cl] | N-(2,6-dichloro-3,5-dimethoxyphenyl)-4-(5-(2-(dimethylamino)acetamido)pyridin-2-ylamino)thieno[3,2-d]pyrimidine-7-carboxamide | — | 11.4 (s, 1H), 10.9 (s, 1H), 9.97 (s, 1H), 9.04 (s, 1H), 8.84 (s, 1H), 8.78 (s, 1H), 8.11-8.07 (d, 1H), 7.95-7.92 (d, 1H), 6.96 (s, 1H), 3.96 (s, 6H), 3.10 (s, 2H), 2.29 (s, 6H) |

TABLE 1-continued

| Ex. | Structure | Compound | MS m/z [M + 1] | NMR ($^1$H NMR 400 MHz, DMSO-$d_6$) |
|---|---|---|---|---|
| 300 | 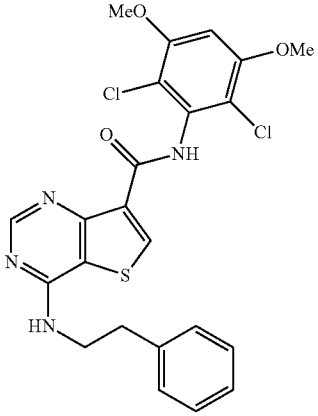 [SMILES: COc1cc(OC)c(Cl)c(NC(=O)c2csc3c(NCCc4ccccc4)ncnc23)c1Cl] | N-(2,6-dichloro-3,5-dimethoxyphenyl)-4-(phenethylamino)thieno[3,2-d]pyrimidine-7-carboxamide | — | 11.4 (s, 1H), 8.97 (s, 1H), 8.63 (s, 1H), 7.32-7.18 (m, 5H), 6.96 (s, 1H), 3.95 (s, 6H), 3.80-3.75 (m, 2H), 2.98-2.93 (t, 2H) |
| 301 | 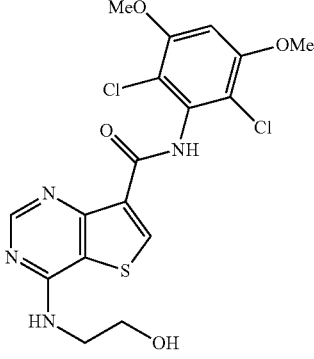 [SMILES: COc1cc(OC)c(Cl)c(NC(=O)c2csc3c(NCCO)ncnc23)c1Cl] | N-(2,6-dichloro-3,5-dimethoxyphenyl)-4-(2-hydroxyethylamino)thieno[3,2-d]pyrimidine-7-carboxamide | — | 11.44(s, 1H), 8.88(s, 1H), 8.57(s, 1H), 8.38(s, 1H), 6.93(s, 1H), 3.96(s, 8H), 3.26(m, 2H) |
| 302 | 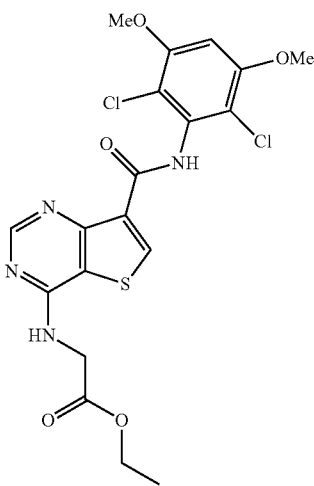 [SMILES: CCOC(=O)CNc1ncnc2c(C(=O)Nc3c(Cl)c(OC)cc(OC)c3Cl)csc12] | ethyl 2-(7-(2,6-dichloro-3,5-dimethoxyphenyl-carbamoyl)thieno[3,2-d]pyrimidin-4-ylamino)acetate | — | 11.19(s, 1H), 9.05(s, 1H), 8.98(t, 1H), 8.78(s, 1H), 7.38(s, 1H), 4.35(d, 2H), 4.15(q, 2H), 3.92(s, 6H), 1.15(t, 3H) |

TABLE 1-continued

| Ex. | Structure | Compound | MS m/z [M + 1] | NMR (¹H NMR 400 MHz, DMSO-$d_6$) |
|---|---|---|---|---|
| 303 | (structure) | 2-(7-(2,6-dichloro-3,5-dimethoxyphenyl-carbamoyl)thieno[3,2-d]pyrimidin-4-ylamino)acetic acid | — | 11.45(s, 1H), 8.97(s, 1H), 8.78(br, 1H), 8.57(s, 1H), 7.38(s, 1H), 4.21(d, 2H), 3.92(s, 6H) |
| 304 | (structure) | N-(2,6-dichloro-3,5-dimethoxyphenyl)-4-(2-(phenylamino)ethyl-amino)thieno[3,2-d]pyrimidine-7-carboxamide | — | 11.5 (s, 1H), 8.91 (s, 1H), 8.63 (s, 1H), 8.48 (m, 1H), 7.10-7.05 (t, 2H), 6.95 (s, 1H), 6.64-6.62 (d, 2H), 6.55-6.52 (m, 1H), 5.75 (m, 1H), 3.95 (s, 6H), 3.71-3.70 (m, 2H), 3.40-3.20 (m, 2H) |

The inventive compounds prepared in the Examples, active ingredients, were formulated as follows:

Preparation Example 1: Tablet (Direct Pressing)

Tablets for oral administration comprising each of active ingredients were prepared by mixing 5.0 mg of an active ingredient passed through a sieve, 14.1 mg of lactose, 0.8 mg of crospovidone USNF, and 0.1 mg of magnesium stearate; and pressing the resulting mixture.

Preparation Example 2: Tablet (Wet Pressing)

Tablets for oral administration comprising each of active ingredients were prepared by mixing 5.0 mg of an active ingredient passed through a sieve, 16.0 mg of lactose, and 4.0 mg of starch; adding thereto a solution of 0.3 mg of polysolvate 80 dissolved in purified water, which was dried and converted to particles; sieving the particles; mixing the sieved particles, 2.7 mg of colloidal silicon dioxide, and 2.0 mg of magnesium stearate; and then pressing the resulting mixture.

Preparation Example 3: Powder and Capsule

Gelatin capsules for oral administration comprising each of active ingredients were prepared by mixing 5.0 mg of an active ingredient passed through a sieve, 14.8 mg of lactose, 10.0 mg of polyvinyl pyrrolidone, and 0.2 mg of magnesium stearate; and filling the resulting mixture into a hard capsule shell (No. 5) using an apparatus.

Preparation Example 4: Injection Formulation

Injection formulations comprising each of active ingredients were prepared by mixing 100 mg of an active ingredient, 180 mg of mannitol, 26 mg of $Na_2HPO_4 12H_2O$, and 2974 mg of distilled water.

Test Examples: Inhibition of Kinase ($IC_{50}$)

Inhibition activities of kinases of the inventive compounds (test compounds) prepared in the Examples were assessed and represented as $IC_{50}$ values.

Kinases used in Test Examples 1 to 3 were purchased from Upstate Company.

Test Example 1: Inhibition of Her1, Her2, Her4, Flt1, Flt3, Flt4, KDR, PDGFRα, PDGFRβ, FGFR, Kit and Fms Kinases 100 mM HEPES (pH 7.4), 25 mM $MgCl_2$, 10 mM $MnCl_2$ and 250 μM $Na_3VO_4$ were mixed to prepare a kinase buffer. Each of kinases to be measured was diluted to a concentration of 25~300 ng per one reaction according to its activity with the kinase buffer. Also, each of the test compounds was serially diluted to a concentration starting from 100 nM up to 0.1 nM with the kinase buffer. 10 µl of the serially diluted solution of each of the test compounds and 10 µl of the diluted kinase were added to each well of a 96-well microplate, and the plate was incubated at room temperature for 10 mins. 10 µl of a substrate and 10 µl of ATP were successively added thereto to initiate a kinase reaction, and the resulting mixture was incubated at room temperature for 1 hour. The ATP was used in a form of a solution diluted to a concentration determined according to a kinase's Km value with distilled water. 10~100 ng/mL poly(Glu, Tyr) 4:1 (Sigma) was used as the substrate. 10 µl of 6 mM EDTA was added to each well and stirred for 5 mins to terminate the kinase reaction. For a measurement of phosphorylation degree, 50 µl of a solution containing anti-phosphotyrosine antibody and fluorescein-labeled phosphopeptide was added to the reaction mixture, followed by incubating for 30 mins. The FP (fluorescence polarization) value of each well was determined with a Victor™ D fluorescence meter (Perkin Elmer Lifesciences).

Test Example 2: Inhibition of IGF1R, Ret, Tie2 and Met Kinases

The procedure of Test Example 1 was repeated except changing the composition of each of a kinase buffer and a substrate to determine kinase inhibition activities. Specifically, 250 mM HEPES (pH 7.4), 0.05% BRIJ-35, 50 mM MgCl$_2$ and 5 mM EGTA were mixed to prepare a kinase buffer. 1 µM Abltide was used as the substrate of Abl; 1 µM IGF1Rtide, as the substrate of Ret, IGF1R and Met; and poly(Glu, Tyr) 4:1, as the substrate of Tie2.

Test Example 3: Inhibition of Src, Lck, Fyn and Lyn Kinases

An inhibition activity of Src kinase was determined with an Src kinase assay kit (Profluor™, Promega). Each of kinases to be measured was diluted to a concentration of 25 ng per one reaction with the kinase buffer provided in the kit. Also, each of the test compounds was serially diluted to a concentration starting from 100 µM up to 0.1 nM with 10% DMSO. 5 µl of the serially diluted solution of each of the test compounds and 20 µl of the diluted kinase were added to each well of a 96-well microplate, and the plate was incubated at room temperature for 10 mins. 25 µl of ATP was added thereto, followed by incubating for 1 hour, and a protease solution was added thereto, followed by incubating for 1 hour. 25 µl of a stabilizer solution was added to the resulting solution, followed by incubating in dark for 5 mins. The absorbance of each well was determined with a fluorescence reader (Molecular Devices) (excitation wavelength: 485 nm, emission wavelength: 530 nm).

IC$_{50}$, the concentration at which 50% inhibition occurs, was evaluated based on the difference between the final concentration of the test cells and the initial concentration of the cells incubated in a well not-treated with the test compound which was regarded as 100%. IC$_{50}$ values of the test compounds on the FGFR kinase were shown in Table 2, and those of the test compound obtained in Example 177 on various kinases, in Table 3.

TABLE 2

| Example | FGFR1 | FGFR3 |
| --- | --- | --- |
| 76 | — | **** |
| 113 | — | **** |
| 114 | — | **** |
| 157 | — | **** |
| 168 | — | * |
| 171 | — | **** |
| 178 | — | ** |
| 179 | * | * |
| 182 | — | * |
| 196 | ** | *** |
| 201 | ** | ** |
| 202 | ** | * |
| 203 | — | **** |
| 204 | — | ** |
| 206 | — | **** |
| 208 | — | * |
| 209 | — | ** |
| 216 | ** | *** |
| 217 | * | ** |
| 225 | *** | *** |
| 229 | * | *** |
| 247 | * | * |
| 255 | — | * |
| 257 | — | * |
| 259 | — | **** |
| 263 | — | * |
| 268 | — | * |
| 270 | — | * |
| 273 | — | **** |
| 274 | — | * |
| 287 | — | **** |
| 291 | — | * |
| 292 | — | * |
| 299 | * | * |
| 302 | **** | **** |
| 304 | **** | **** |

* IC$_{50}$ value of 1~100 nM
** IC$_{50}$ value of 100~500 nM
*** IC$_{50}$ value of 500~1,000 nM
**** IC$_{50}$ value of 1,000~5,000 nM

TABLE 3

| Kinase | IC$_{50}$ (nM) |
| --- | --- |
| EGFR | >1,000 |
| Her2 | >1,000 |
| FGFR1 | <100 |
| FGFR3 | <100 |
| Flt1 | >1,000 |
| KDR | <200 |
| Flt3 | >1,000 |
| PDGFRα | >1,000 |
| PDGFRβ | >1,000 |
| Fms | <200 |
| Kit | >1,000 |
| Ret | >1,000 |
| Tie2 | >1,000 |
| Met | >1,000 |
| Src | >1,000 |
| Lck | >1,000 |
| Fyn | >1,000 |
| Lyn | >1,000 |

As shown in Tables 2 and 3, each of the inventive compounds showed an excellent inhibition activity against various kinases including FGFR kinase.

While the invention has been described with respect to the above specific embodiments, it should be recognized that various modifications and changes may be made to the invention by those skilled in the art which also fall within the scope of the invention as defined by the appended claims.

What is claimed is:

1. A bicyclic heteroaryl compound of formula (I), a pharmaceutically acceptable salt thereof, a hydrate thereof, or a solvate thereof:

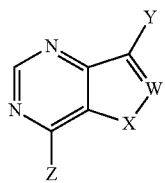

(I)

wherein,

W is CH;

X is S;

Y is —(CH$_2$)$_2$R$^3$, —CHCR$^2$R$^3$, —CCR$^3$, —C(O)OH, or —C(O)NR$^2$R$^3$;

R$^2$ is H;

R$^3$ is selected from the group consisting of phenyl, 2-fluorophenyl, 2-hydroxyphenyl, 4-aminophenyl, 4-methoxyphenyl, 4-nitrophenyl, 2-(cyclopropylcarbamoyl)phenyl, 3-(cyclopropylcarbamoyl)phenyl, 4-(cyclopropylcarbamoyl)phenyl, 2,6-dimethylphenyl, 2-chloro-6-methylphenyl, 3,5-dimethoxyphenyl, 3-cyano-5-methoxyphenyl, 3-carbamoyl-5-methoxyphenyl, 4-chloro-3-fluorophenyl, 2,3-dichlorophenyl, 4-chloro-3-(trifluoromethyl)phenyl, 2-chloro-4-methylphenyl, 5-fluoro-2-methylphenyl, 5-fluoro-2-hydroxyphenyl, 2-methyl-5-nitrophenyl, 2-methyl-5-(cyclopropylcarbamoyl)phenyl, 2-methyl-5-(cyclopropylcarbonylamino)phenyl, 4-amino-3-fluorophenyl, 4-amino-2-methylphenyl, 4-amino-2-fluorophenyl, 2-chloro-3,5-dimethoxyphenyl, 3,4,5-trimethoxyphenyl, 4-bromo-3,5-dimethoxyphenyl, 5-chloro-2,4-dimethoxyphenyl, 2,6-dichloro-3,5-dimethoxyphenyl, 2,6-dichloro-3,5-dimethylphenyl, 2,6-difluoro-3,5-dimethoxyphenyl, 2,6-dichloro-3-hydroxy-5-methoxyphenyl, 2,6-dichloro-3,5-dihydroxyphenyl, 4-bromo-3,5-dimethoxyphenyl, 2,4,6-trichloro-3,5-dimethoxyphenyl, 4-bromo-2,6-dichloro-3,5-dimethoxyphenyl, 4-aminonaphthalen-1-yl, 2-chloropyridin-4-yl, 2,3-diaminopyridin-4-yl, 3-(cyclopropylcarbamoyl) cumarin-6-yl, 1H-pyrazol-4-yl, 6-methoxybenzofuran-4-yl, 6-methoxyquinolin-8-yl, 6-methylpyridin-3-yl, and benzo[d][1,3]dioxol-5-yl;

Z is H, halogen, C$_{1-6}$ alkyl, —OR$^5$, —SR$^5$, —S(O)R$^5$, —S(O)$_2$R$^5$, —NR$^4$C(O)NR$^4$R$^5$, —NR$^4$C(S)NR$^4$R$^5$, —NR$^4$S(O)$_2$R$^5$, 5-(4-ethylpiperazin-1-yl)pentylamino, 2,4-dimethylbenzylamino, 4-(4-hydroxypiperidin-1-yl)phenylamino, 4-(4-(pyrrolidin-1-yl)piperidin-1-yl)phenylamino, 3-(4-ethylpiperazin-1-yl)phenylamino, 4-(4-ethylpiperazin-1-yl)phenylamino, 4-(4-propionylpiperazin-1-yl)phenylamino, 4-(4-(isopropylcarbamoyl)piperazin-1-yl)phenylamino, 4-(4-(ethoxycarbamoyl)piperazin-1-yl)phenylamino, 4-(4-ethylpiperazin-1-yl)-2-methoxyphenylamino, 4-(4-(2-hydroxyethyl)piperazin-1-yl)-2-methoxyphenylamino, 4-(4-ethylpiperazin-1-yl)-2-isopropoxyphenylamino, 4-(4-(2-hydroxyethyl)piperazin-1-yl)-2-isopropoxyphenylamino, 4-(4-(1-methylpiperidin-4-yl)piperazin-1-yl)phenylamino, 4-(4-(pyridin-2-yl)piperazin-1-yl)phenylamino, 4-((4-ethylpiperazin-1-yl)methyl)phenylamino, 4-(2-(4-ethylpiperazin-1-yl)-2-oxoethyl)phenylamino, 4-(2-(4-ethylpiperazin-1-yl)ethyl)phenylamino, 4-((4-ethylpiperazin-1-yl)methyl)-3-(trifluoromethyl)phenylamino, 4-(1-benzylpiperidin-4-ylcarbamoyl)phenylamino, 4-(4-ethylpiperazine-1-carbonyl)phenylamino, 5-((4-ethylpiperazin-1-yl)pyridin-2-ylamino, 5-((3-(4-ethylpiperazin-1-yl)propylamino)methyl)pyridin-2-ylamino, 5-((3-hydroxypyrrolidin-1-yl)methyl)pyridin-2-ylamino, 5-((4-methylpiperidin-1-yl)methyl)pyridin-2-ylamino, 5-((3-(trifluoromethyl)piperidin-1-yl)methyl)pyridin-2-ylamino, 5-((4-morpholinopiperidin-1-yl)methyl)pyridin-2-ylamino, 5-((4-ethylpiperazin-1-yl)methyl)pyridin-2-ylamino, 5-((4-(2-hydroxyethyl)piperazin-1-yl)methyl)pyridin-2-ylamino, 5-((4-acetylpiperazin-1-yl)methyl)pyridin-2-ylamino, 5-(morpholinomethyl)pyridin-2-ylamino, 5-((3,5-dimethylmorpholino)methyl)pyridin-2-ylamino, 5-((1H-imidazol-1-yl)methyl)pyridin-2-ylamino, 5-(2-morpholino-2-oxoethyl)pyridin-2-ylamino, 5-((3-oxopiperazin-1-yl)methyl)pyridin-2-ylamino, 5-((2-methoxyethoxy)methyl)pyridin-2-ylamino, 4-(thiazolidin-3-ylmethyl)pyridin-2-ylamino, 5-(3-(4-ethylpiperazin-1-yl)propylcarbamoyl)pyridin-2-ylamino, 5-(morpholine-4-carbonyl)pyridin-2-ylamino, 6-(4-ethylpiperazin-1-yl)pyrimidin-4-ylamino, 6-(3-(4-ethylpiperazin-1-yl)propylamino)pyrimidin-4-ylamino, 6-(2-(dimethylamino)ethoxy)pyrimidin-4-ylamino, 6-(4-(2-hydroxyethyl)piperazin-1-yl)-2-methylpyrimidin-4-ylamino, 2-amino-5-(4-ethylpiperazin-1-yl)-6-fluoro-1H-benzo[d]imidazol-1-yl, 1-(4-methoxybenzyl)-1H-benzo[d]imidazol-2-ylamino, 3-(ethoxycarbonyl)thioureido, 4-((4-ethylpiperazin-1-yl)methyl)pyridin-2-ylamino, 4-(morpholinomethyl)pyridin-2-ylamino, 4-(piperidin-1-ylmethyl)pyridin-2-ylamino, 4-(4-ethylpiperazin-1yl)benzamido, amino, diethylamino, 2-hydroxyethylamino, cyclopropylamino, 2-(dimethylamino)ethylamino, 2-morpholinoethylamino, (hydroxycarbonyl)methylamino, (ethoxycarbonyl)methylamino, 2-(phenylamino)ethylamino, 3-(diethylamino)propylamino, 3-(1H-imidazol-1-yl)propylamino, 4-(diethylamino)butylamino, 4-(1H-imidazol-1-yl)butylamino, 5-(diethylamino)phenylamino, 5-(1H-imidazol-1-yl)phenylamino, piperidin-4-ylamino, 2,3,4-trifluorophenylamino, 3-chloro-4-fluorophenylamino, 3,4,5-trimethoxyphenylamino, 4-(dimethylamino)phenylamino, 4-morpholinophenylamino, 4-(piperazin-1-yl)phenylamino, 4-(4-methylpiperazin-1-ylamino)phenylamino, 4-(1H-imidazol-1-yl)phenylamino, 4-(piperidin-4-ylamino)phenylamino, 4-methoxyphenylamino, 4-(hydroxycarbonyl)phenylamino, 4-(2-hydroxyethyl)phenylamino, 4-(2-(diethylamino)ethoxy)phenylamino, pyridin-2-ylamino, pyridin-4-ylamino, 4-methylpyridin-2-ylamino, 5-methylpyridin-2-ylamino, 6-methylpyridin-3-ylamino, 5-chloropyridin-2-ylamino, 5-(2-(dimethylamino)acetamido)pyridin-2-ylamino, 5-(3-(diethylamino)propoxy)pyridin-2-ylamino, 4-(((2-hydroxyethyl)(methyl)amino)methyl)pyridin-2-ylamino, 4-((diethylamino)methyl)pyridin-2-ylamino, 4-((2-(diethylamino)ethylamino)methyl)pyridin-2-ylamino, 5-((diethylamino)methyl)pyridin-2-ylamino, 6-((diethylamino)methyl)pyridin-2-ylamino, 5-((3-(diethylamino)propylamino)methyl)pyridin-2-ylamino, 5-((2-(diethylamino)ethoxy)methyl)pyridin-2-ylamino, 5-((2-(piperidin-1-yl)ethoxy)methyl)pyridin-2-ylamino, 5-((3-(diethylamino)propoxy)methyl)pyridin-2-ylamino, 4-(diethylamino)pyridin-2-ylamino, 4-((2-(diethylamino)ethoxy)methyl)pyridin-2-ylamino, 4-(3-(diethylamino)propoxy)pyridin-2-ylamino, 4-(2-(diethylamino)-2-oxoethyl)pyridin-2-ylamino, 5-carbamoylpyridin-2-ylamino, 5-(3-(diethylamino)propylcarbamoyl)pyridin-2-ylamino, 5-(4-methylpiperazin-1-ylcarbamoyl)pyridin-2- ylamino, 6-(2-morpholinoethylamino)pyrimidin-4-ylamino, 6-(3-(diethylamino)propylamino)pyrimidin-4-ylamino, 4-methyl-6-(2-morpholinoethylamino) pyrimidine-2-ylamino, 5-nitrothiazol-2-ylamino, 2-amino-1H-benzo[d]imidazol-1-yl, 6-methylbenzo[d] thiazol-2-ylamino, 1H-indazol-6-ylamino, 5-methyl-1H-pyrazol-3-ylamino, 3-ethoxycarbonyl-1H-indazolyl-6-amino, acetamido, cyclopropanecarboxamido, benzamido, methylsulfonamido, or 3-(3-(trifluoromethyl)phenyl)ureido;

$R^4$ is H or $C_{1-6}$ alkyl;

$R^5$ is H, $C_{1-6}$ alkyl, $C_{3-7}$ cycloalkyl, $C_{3-14}$ aryl, $C_{2-13}$ heteroaryl, or $C_{2-7}$ heterocycloalkyl, wherein $R^5$ is optionally substituted with one or more substituents selected from the group consisting of halogen, —$CF_3$, —$NO_2$, —CN, $C_{1-6}$ alkyl, $C_{3-7}$ cycloalkyl, $C_{2-6}$ alkenyl, $C_{2-6}$ alkynyl, $C_{3-14}$ aryl, $C_{2-13}$ heteroaryl, $C_{2-7}$ heterocycloalkyl, —$(CH_2)_mNR^8R^9$, —$(CH_2)_mOR^9$, —$(CH_2)_mC(O)OR^9$, —$(CH_2)_mC(O)NR^8R^9$, —$(CH_2)_mNR^8C(O)R^9$, —$(CH_2)_mSR^9$, —$(CH_2)_mS(O)R^9$, and —$(CH_2)_mS(O)_2R^9$;

m is an integer of 0 to 3;

$R^8$ and $R^9$ are each independently H, —$CF_3$, —$NO_2$, —CN, $C_{1-6}$ alkyl, $C_{3-7}$ cycloalkyl, $C_{2-6}$ alkenyl, $C_{2-6}$ alkynyl, $C_{3-14}$ aryl, $C_{2-13}$ heteroaryl, or $C_{2-7}$ heterocycloalkyl, wherein $R^8$ and $R^9$ are each independently optionally substituted with one or more substituents selected from the group consisting of halogen, —$CF_3$, —$NO_2$, —CN, $C_{1-6}$ alkyl, $C_{3-7}$ cycloalkyl, $C_{2-6}$ alkenyl, $C_{2-6}$ alkynyl, —$NR^{10}R^{10}$, —$OR^{10}$, $C_{3-14}$ aryl, $C_{2-13}$ heteroaryl, and $C_{2-7}$ heterocycloalkyl; and $R^{10}$ is H or $C_{1-6}$ alkyl, with proviso that when Y is C(O)OH, Z is not H, a halogen or 2,4-dimethoxybenzylamino; and when Y —$C(O)NR^2R^3$, Z is not H.

2. A compound selected from the group consisting of:
1) ethyl 3-((4-(2-hydroxyethylamino)thieno[3,2-d]pyrimidin-7-yl)ethynyl)-4-methyl benzoate;
1a) 4-(methylthio)-7-((trimethylsilyl)ethynyl)thieno[3,2-d]pyrimidine;
1b) 7-ethynyl-4-(methylthio)thieno[3,2-d]pyrimidine;
1c) ethyl 4-methyl-3-((4-(methylthio)thieno[3,2-d]pyrimidin-7-yl)ethynyl)benzoate;
1d) ethyl 4-methyl-3-((4-(methylsulfinyl)thieno[3,2-d]pyrimidin-7-yl)ethynyl)benzoate;
2) ethyl 3-((4-(cyclopropylamino)thieno[3,2-d]pyrimidin-7-yl)ethynyl)-4-methyl benzoate;
3) ethyl 4-methyl-3-((4-(3,4,5-trimethoxyphenylamino) thieno[3,2-d]pyrimidin-7-yl)ethynyl)benzoate;
4) ethyl 3-((4-(4-(4-ethylpiperazin-1-yl)phenylamino) thieno[3,2-d]pyrimidin-7-yl)ethynyl)-4-methyl benzoate;
5) ethyl 4-methyl-3-((4-(4-morpholinophenylamino) thieno[3,2-d]pyrimidin-7-yl)ethynyl)benzoate;
6) N-cyclopropyl-7-((3,5-dimethoxyphenyl)ethynyl) thieno[3,2-d]pyrimidine-4-amine;
7) 7-((4-bromo-3,5-dimethoxyphenyl)ethynyl)-N-cyclopropylthieno[3,2-d]pyrimidine-4-amine;
8) 7-((4-bromo-2-chloro-3,5-dimethoxyphenyl)ethynyl)-N-cyclopropylthieno[3,2-d]pyrimidine-4-amine;
9) 7-((4-bromo-2,6-dichloro-3,5-dimethoxyphenyl)ethynyl)-N-cyclopropylthieno[3,2-d]pyrimidine-4-amine;
10) 7-((2-chloro-3,5-dimethoxyphenyl)ethynyl)-N-cyclopropylthieno[3,2-d]pyrimidine-4-amine;
11) 7-(4-bromo-3,5-dimethoxystyryl)thieno[3,2-d]pyrimidine-4-amine;
11a) 7-vinylthieno[3,2-d]pyrimidine-4-amine;
12) (E)-7-styrylthieno[3,2-d]pyrimidine-4-amine;
13) (E)-7-(4-methoxystyryl)thieno[3,2-d]pyrimidine-4-amine;
14) (E)-2-(2-(4-aminothieno[3,2-d]pyrimidin-7-yl)vinyl) phenol;
15) (E)-7-(4-aminostyryl)thieno[3,2-d]pyrimidine-4-amine;
16) (E)-ethyl 3-(2-(4-aminothieno[3,2-d]pyrimidin-7-yl) vinyl)-4-methyl benzoate;
17) (E)-2-(2-(4-aminothieno[3,2-d]pyrimidin-7-yl)vinyl)-N-cyclopropylbenzamide;
18) (E)-3-(2-(4-aminothieno[3,2-d]pyrimidin-7-yl)vinyl)-N-cyclopropylbenzamide;
19) (E)-4-(2-(4-aminothieno[3,2-d]pyrimidin-7-yl)vinyl)-N-cyclopropylbenzamide;
20) (E)-3-(2-(4-aminothieno[3,2-d]pyrimidin-7-yl)vinyl)-N-cyclopropyl-4-methylbenzamide;
21) (E)-7-(4-nitrostyryl)thieno[3,2-d]pyrimidine-4-amine;
22) (E)-2-(2-(4-aminothieno[3,2-d]pyrimidin-7-yl)vinyl)-4-fluorophenol;
23) (E)-7-(4-amino-2-fluorostyryl)thieno[3,2-d]pyrimidine-4-amine;
24) (E)-7-(2-(4-aminonaphthalen-1-yl)vinyl)thieno[3,2-d]pyrimidine-4-amine;
25) (E)-7-(2-(2-chloropyridin-4-yl)vinyl)thieno[3,2-d]pyrimidine-4-amine;
26) (E)-5-(2-(4-aminothieno[3,2-d]pyrimidin-7-yl)vinyl) pyridine-2,3-diamine;
27) (E)-1-(5-(2-(4-aminothieno[3,2-d]pyrimidin-7-yl)vinyl)thiophen-2-yl)ethanone;
28) (E)-6-(2-(4-aminothieno[3,2-d]pyrimidin-7-yl)vinyl)-N-cyclopropyl-2-oxo-2H-chromene-3-carboxamide;
29) (E)-7-(4-amino-3-fluorostyryl)thieno[3,2-d]pyrimidine-4-amine;
30) (E)-7-(2-methyl-5-nitrostyryl)thieno[3,2-d]pyrimidine-4-amine;
31) (E)-N-cyclopropyl-7-styrylthieno[3,2-d]pyrimidine-4-amine;
32) (E)-N-cyclopropyl-7-(4-methoxystyryl)thieno[3,2-d]pyrimidine-4-amine;
33) (E)-2-(2-(4-(cyclopropylamino)thieno[3,2-d]pyrimidin-7-yl)vinyl)phenol;
34) (E)-7-(4-aminostyryl)-N-cyclopropylthieno[3,2-d]pyrimidine-4-amine;
35) (E)-ethyl 3-(2-(4-(cyclopropylamino)thieno[3,2-d]pyrimidin-7-yl)vinyl)-4-methyl benzoate;
36) (E)-N-cyclopropyl-2-(2-(4-(cyclopropylamino)thieno [3,2-d]pyrimidin-7-yl)vinyl)benzamide;
37) (E)-N-cyclopropyl-3-(2-(4-(cyclopropylamino)thieno [3,2-d]pyrimidin-7-yl)vinyl)benzamide;
38) (E)-N-cyclopropyl-4-(2-(4-(cyclopropylamino)thieno [3,2-d]pyrimidin-7-yl)vinyl)benzamide;
39) (E)-N-cyclopropyl-3-(2-(4-(cyclopropylamino)thieno [3,2-d]pyrimidin-7-yl)vinyl)-4-methylbenzamide;
40) (E)-N-cyclopropyl-7-(4-nitrostyryl)thieno[3,2-d]pyrimidine-4-amine;
41) (E)-2-(2-(4-(cyclopropylamino)thieno[3,2-d]pyrimidin-7-yl)vinyl)-4-fluorophenol;
42) (E)-7-(4-amino-2-fluorostyryl)-N-cyclopropylthieno [3,2-d]pyrimidine-4-amine;
43) (E)-7-(2-(4-aminonaphthalen-1-yl)vinyl)-N-cyclopropylthieno[3,2-d]pyrimidine-4-amine;
44) (E)-7-(2-(2-chloropyridin-4-yl)vinyl)-N-cyclopropylthieno[3,2-d]pyrimidine-4-amine;
45) (E)-7-(2-(1H-pyrazol-4-yl)vinyl)-N-cyclopropylthieno[3,2-d]pyrimidine-4-amine;

46) (E)-5-(2-(4-(cyclopropylamino)thieno[3,2-d]pyrimidin-7-yl)vinyl)pyridine-2,3-diamine;
47) (E)-1-(5-(2-(4-(cyclopropylamino)thieno[3,2-d]pyrimidin-7-yl)vinyl)thiophen-2-yl)ethanone;
48) (E)-N-cyclopropyl-6-(2-(4-(cyclopropylamino)thieno[3,2-d]pyrimidin-7-yl)vinyl)-2-oxo-2H-chromene-3-carboxamide;
49) (E)-7-(4-amino-3-fluorostyryl)-N-cyclopropylthieno[3,2-d]pyrimidine-4-amine;
50) (E)-N-cyclopropyl-7-(2-methyl-5-nitrostyryl)thieno[3,2-d]pyrimidine-4-amine;
51) (E)-N-(3-(2-(4-(cyclopropylamino)thieno[3,2-d]pyrimidin-7-yl)vinyl)-4-methylphenyl)cyclopropanecarboxamide;
52) (E)-N-cyclopropyl-3-(2-(4-(3,4,5-trimethoxyphenylamino)thieno[3,2-d]pyrimidin-7-yl)vinyl)benzamide;
53) (E)-N-cyclopropyl-4-methyl-3-(2-(4-(3,4,5-trimethoxyphenylamino)thieno[3,2-d]pyrimidin-7-yl)vinyl)benzamide;
54) (E)-7-(2-(4-aminonaphthalen-1-yl)vinyl)-N-(3,4,5-trimethoxyphenyl)thieno[3,2-d]pyrimidine-4-amine;
55) (E)-N-(4-methyl-3-(2-(4-(3,4,5-trimethoxyphenylamino)thieno[3,2-d]pyrimidin-7-yl)vinyl)phenyl)cyclopropanecarboxamide;
56) (E)-N-cyclopropyl-4-methyl-3-(2-(4-(4-morpholinophenylamino)thieno[3,2-d]pyrimidin-7-yl)vinyl)benzamide;
57) (E)-N-(4-methyl-3-(2-(4-(4-morpholinophenylamino)thieno[3,2-d]pyrimidin-7-yl)vinyl)phenyl)cyclopropanecarboxamide;
58) (E)-N-(4-(4-ethylpiperazin-1-yl)phenyl)-7-styrylthieno[3,2-d]pyrimidine-4-amine;
59) (E)-N-(4-(4-ethylpiperazin-1-yl)phenyl)-7-(4-methoxystyryl)thieno[3,2-d]pyrimidine-4-amine;
60) (E)-2-(2-(4-(4-(4-ethylpiperazin-1-yl)phenylamino)thieno[3,2-d]pyrimidin-7-yl)vinyl)phenol;
61) (E)-7-(4-aminostyryl)-N-(4-(4-ethylpiperazin-1-yl)phenyl)thieno[3,2-d]pyrimidine-4-amine;
62) (E)-ethyl 3-(2-(4-(4-(4-ethylpiperazin-1-yl)phenylamino)thieno[3,2-d]pyrimidin-7-yl)vinyl)-4-methyl benzoate;
63) (E)-N-cyclopropyl-2-(2-(4-(4-(4-ethylpiperazin-1-yl)phenylamino)thieno[3,2-d]pyrimidin-7-yl)vinyl)benzamide;
64) (E)-N-cyclopropyl-3-(2-(4-(4-(4-ethylpiperazin-1-yl)phenylamino)thieno[3,2-d]pyrimidin-7-yl)vinyl)benzamide;
65) (E)-N-cyclopropyl-4-(2-(4-(4-(4-ethylpiperazin-1-yl)phenylamino)thieno[3,2-d]pyrimidin-7-yl)vinyl)benzamide;
66) (E)-N-cyclopropyl-3-(2-(4-(4-(4-ethylpiperazin-1-yl)phenylamino)thieno[3,2-d]pyrimidin-7-yl)vinyl)-4-methylbenzamide;
67) (E)-N-(4-(4-ethylpiperazin-1-yl)phenyl)-7-(4-nitrostyryl)thieno[3,2-d]pyrimidine-4-amine;
68) (E)-2-(2-(4-(4-(4-ethylpiperazin-1-yl)phenylamino)thieno[3,2-d]pyrimidin-7-yl)vinyl)-4-fluorophenol;
69) (E)-7-(4-amino-2-fluorostyryl)-N-(4-(4-ethylpiperazin-1-yl)phenyl)thieno[3,2-d]pyrimidine-4-amine;
70) (E)-7-(2-(4-aminonaphthalen-1-yl)vinyl)-N-(4-(4-ethylpiperazin-1-yl)phenyl)thieno[3,2-d]pyrimidine-4-amine;
71) (E)-7-(2-(2-chloropyridin-4-yl)vinyl)-N-(4-(4-ethylpiperazin-1-yl)phenyl)thieno[3,2-d]pyrimidine-4-amine;
72) (E)-N-(3-(2-(4-(4-(4-ethylpiperazin-1-yl)phenylamino)thieno[3,2-d]pyrimidin-7-yl)vinyl)-4-methylphenyl)cyclopropanecarboxamide;
73) (E)-N-(4-(4-ethylpiperazin-1-yl)phenyl)-7-(2-methyl-5-nitrostyryl)thieno[3,2-d]pyrimidine-4-amine;
74) 7-(3,5-dimethoxystyryl)thieno[3,2-d]pyrimidine-4-amine;
75) 7-(4-bromo-2,6-dichloro-3,5-dimethoxystyryl)thieno[3,2-d]pyrimidine-4-amine;
76) 7-(2,6-dichloro-3,5-dimethoxystyryl)thieno[3,2-d]pyrimidine-4-amine;
77) 7-phenethylthieno[3,2-d]pyrimidine-4-amine;
78) 6-(2-(4-aminothieno[3,2-d]pyrimidin-7-yl)ethyl)-N-cyclopropyl-2-oxo-2H-chromene-3-carboxamide;
79) 7-(4-amino-2-methylphenethyl)thieno[3,2-d]pyrimidine-4-amine;
80) N-cyclopropyl-7-(4-methoxyphenethyl)thieno[3,2-d]pyrimidine-4-amine;
81) 2-(2-(4-(cyclopropylamino)thieno[3,2-d]pyrimidin-7-yl)ethyl)phenol;
82) ethyl 3-(2-(4-(cyclopropylamino)thieno[3,2-d]pyrimidin-7-yl)ethyl)-4-methyl benzoate;
83) N-cyclopropyl-2-(2-(4-(cyclopropylamino)thieno[3,2-d]pyrimidin-7-yl)ethyl)benzamide;
84) N-cyclopropyl-3-(2-(4-(cyclopropylamino)thieno[3,2-d]pyrimidin-7-yl)ethyl)benzamide;
85) N-cyclopropyl-3-(2-(4-(cyclopropylamino)thieno[3,2-d]pyrimidin-7-yl)ethyl)-4-methylbenzamide;
86) 7-(4-aminophenethyl)-N-cyclopropylthieno[3,2-d]pyrimidine-4-amine;
87) 7-(2-(2-chloropyridin-4-yl)ethyl)-N-cyclopropylthieno[3,2-d]pyrimidine-4-amine;
88) 7-(2-(1H-pyrazol-4-yl)ethyl)-N-cyclopropylthieno[3,2-d]pyrimidine-4-amine;
89) 7-(5-amino-2-methylphenethyl)-N-cyclopropylthieno[3,2-d]pyrimidine-4-amine;
90) N-cyclopropyl-3-(2-(4-(3,4,5-trimethoxyphenylamino)thieno[3,2-d]pyrimidin-7-yl)ethyl)benzamide;
91) N-cyclopropyl-4-methyl-3-(2-(4-(3,4,5-trimethoxyphenylamino)thieno[3,2-d]pyrimidin-7-yl)ethyl)benzamide;
92) N-(4-(4-ethylpiperazin-1-yl)phenyl)-7-phenethylthieno[3,2-d]pyrimidine-4-amine;
93) N-(4-(4-ethylpiperazin-1-yl)phenyl)-7-(4-methoxyphenethyl)thieno[3,2-d]pyrimidine-4-amine;
94) 2-(2-(4-(4-(4-ethylpiperazin-1-yl)phenylamino)thieno[3,2-d]pyrimidin-7-yl)ethyl)phenol;
95) ethyl 3-(2-(4-(4-(4-ethylpiperazin-1-yl)phenylamino)thieno[3,2-d]pyrimidin-7-yl)ethyl)-4-methyl benzoate;
96) N-cyclopropyl-2-(2-(4-(4-(4-ethylpiperazin-1-yl)phenylamino)thieno[3,2-d]pyrimidin-7-yl)ethyl)benzamide;
97) N-cyclopropyl-3-(2-(4-(4-(4-ethylpiperazin-1-yl)phenylamino)thieno[3,2-d]pyrimidin-7-yl)ethyl)benzamide;
98) N-cyclopropyl-4-(2-(4-(4-(4-ethylpiperazin-1-yl)phenylamino)thieno[3,2-d]pyrimidin-7-yl)ethyl)benzamide;
99) N-cyclopropyl-3-(2-(4-(4-(4-ethylpiperazin-1-yl)phenylamino)thieno[3,2-d]pyrimidin-7-yl)ethyl)-4-methylbenzamide;
100) 7-(4-aminophenethyl)-N-(4-(4-ethylpiperazin-1-yl)phenyl)thieno[3,2-d]pyrimidine-4-amine;
101) 2-(2-(4-(4-(4-ethylpiperazin-1-yl)phenylamino)thieno[3,2-d]pyrimidin-7-yl)ethyl)-4-fluorophenol;

102) 7-(2-(4-aminonaphthalen-1-yl)ethyl)-N-(4-(4-ethyl-piperazin-1-yl)phenyl)thieno[3,2-d]pyrimidine-4-amine;
103) N-(3-(2-(4-(4-(4-ethylpiperazin-1-yl)phenylamino)thieno[3,2-d]pyrimidin-7-yl)ethyl)-4-methylphenyl)cyclopropanecarboxamide;
104) 7-(5-amino-2-methylphenethyl)-N-(4-(4-ethylpiperazin-1-yl)phenyl)thieno[3,2-d]pyrimidine-4-amine;
105) 4-(methylthio)thieno[3,2-d]pyrimidine-7-carboxylic acid;
105a) 4-(methylthio)-7-vinylthieno[3,2-d]pyrimidine;
105b) 4-(methylthio)thieno[3,2-d]pyrimidine-7-carbaldehyde;
106) 4-amino-N-(3,5-dimethoxyphenyl)thieno[3,2-d]pyrimidine-7-carboxamide;
106a) N-(3,5-dimethoxyphenyl)-4-(methylthio)thieno[3,2-d]pyrimidine-7-carboxamide;
106b) N-(3,5-dimethoxyphenyl)-4-(methylsulfinyl)thieno[3,2-d]pyrimidine-7-carboxamide;
107d) (4-chlorothieno[3,2-d]pyrimidin-7-yl)methyl acetate;
107e) (4-chlorothieno[3,2-d]pyrimidin-7-yl)methanol;
107f) 4-chlorothieno[3,2-d]pyrimidine-7-carbaldehyde;
108) 4-(cyclopropylamino)-N-(2,6-difluoro-3,5-dimethoxyphenyl)thieno[3,2-d]pyrimidine-7-carboxamide;
108a) 4-chloro-N-(2,6-difluoro-3,5-dimethoxyphenyl)thieno[3,2-d]pyrimidine-7-carboxamide;
108b) 4-amino-N-(2,6-difluoro-3,5-dimethoxyphenyl)thieno[3,2-d]pyrimidine-7-carboxamide;
109) 4-chloro-N-(2-chloro-3,5-dimethoxyphenyl)thieno[3,2-d]pyrimidine-7-carboxamide;
110) N-(2-chloro-3,5-dimethoxyphenyl)-4-methoxythieno[3,2-d]pyrimidine-7-carboxamide;
111) 4-amino-N-(2-chloro-3,5-dimethoxyphenyl)thieno[3,2-d]pyrimidine-7-carboxamide;
112) 4-chloro-N-(6-methoxybenzofuran-4-yl)-3-methyl-3,4-dihydrothieno[3,2-d]pyrimidine-7-carboxamide;
113) 4-amino-N-(6-methoxybenzofuran-4-yl)-3-methyl-3,4-dihydrothieno[3,2-d]pyrimidine-7-carboxamide;
114) N-(6-methoxybenzofuran-4-yl)-3-methyl-4-(phenylamino)-3,4-dihydrothieno[3,2-d]pyrimidine-7-carboxamide;
115) 4-chloro-N-(3-cyano-5-methoxyphenyl)thieno[3,2-d]pyrimidine-7-carboxamide;
116) 4-amino-N-(3-carbamoyl-5-methoxyphenyl)thieno[3,2-d]pyrimidine-7-carboxamide;
117) 4-chloro-N-(6-methoxyquinolin-8-yl)thieno[3,2-d]pyrimidine-7-carboxamide;
118) 4-amino-N-(6-methoxyquinolin-8-yl)thieno[3,2-d]pyrimidine-7-carboxamide;
119) 4-chloro-N-(3,5-dimethoxyphenyl)thieno[3,2-d]pyrimidine-7-carboxamide;
120) N-(3,5-dimethoxyphenyl)-4-methoxythieno[3,2-d]pyrimidine-7-carboxamide;
121) 4-(2,4-dimethoxybenzylamino)-N-(3,5-dimethoxyphenyl)thieno[3,2-d]pyrimidine-7-carboxamide;
122) 4-amino-N-(3,4,5-trimethoxyphenyl)thieno[3,2-d]pyrimidine-7-carboxamide;
123) 4-amino-N-(4-chloro-3-fluorophenyl)thieno[3,2-d]pyrimidine-7-carboxamide;
124) 4-amino-N-(6-methylpyridin-3-yl)thieno[3,2-d]pyrimidine-7-carboxamide;
125) 4-amino-N-(3-phenoxyphenyl)thieno[3,2-d]pyrimidine-7-carboxamide;
126) 4-amino-N-(2,6-dimethylphenyl)thieno[3,2-d]pyrimidine-7-carboxamide;
127) 4-amino-N-(2-chloro-6-methylphenyl)thieno[3,2-d]pyrimidine-7-carboxamide;
128) 4-amino-N-(benzo[d][1,3]dioxol-5-yl)thieno[3,2-d]pyrimidine-7-carboxamide;
129) 4-amino-N-(5-chloro-2,4-dimethoxyphenyl)thieno[3,2-d]pyrimidine-7-carboxamide;
130) 4-amino-N-(2-fluorophenyl)thieno[3,2-d]pyrimidine-7-carboxamide;
131) 4-amino-N-(2,3-dichlorophenyl)thieno[3,2-d]pyrimidine-7-carboxamide;
132) 4-amino-N-(4-chloro-3-(trifluoromethyl)phenyl)thieno[3,2-d]pyrimidine-7-carboxamide;
133) 4-amino-N-(2-chloro-4-methylphenyl)thieno[3,2-d]pyrimidine-7-carboxamide;
134) 4-amino-N-(5-fluoro-2-methylphenyl)thieno[3,2-d]pyrimidine-7-carboxamide;
135) 4-amino-N-(2-methyl-5-nitrophenyl)thieno[3,2-d]pyrimidine-7-carboxamide;
137) 4-chloro-N-(2,4,6-trichloro-3,5-dimethoxyphenyl)thieno[3,2-d]pyrimidine-7-carboxamide;
138) 4-methoxy-N-(2,4,6-trichloro-3,5-dimethoxyphenyl)thieno[3,2-d]pyrimidine-7-carboxamide;
139) 4-amino-N-(2,4,6-trichloro-3,5-dimethoxyphenyl)thieno[3,2-d]pyrimidine-7-carboxamide;
140) 4-(2-morpholinoethylamino)-N-(2,4,6-trichloro-3,5-dimethoxyphenyl)thieno[3,2-d]pyrimidine-7-carboxamide;
141) 4-(phenylamino)-N-(2,4,6-trichloro-3,5-dimethoxyphenyl)thieno[3,2-d]pyrimidine-7-carboxamide;
142) 4-(4-(4-ethylpiperazin-1-yl)phenylamino)-N-(2,4,6-trichloro-3,5-dimethoxyphenyl)thieno[3,2-d]pyrimidine-7-carboxamide;
143) 4-(4-(4-ethylpiperazin-1-yl)-2-methoxyphenylamino)-N-(2,4,6-trichloro-3,5-dimethoxyphenyl)thieno[3,2-d]pyrimidine-7-carboxamide;
144) 4-(4-(4-(2-hydroxyethyl)piperazin-1-yl)-2-methoxyphenylamino)-N-(2,4,6-trichloro-3,5-dimethoxyphenyl)thieno[3,2-d]pyrimidine-7-carboxamide;
145) 4-(4-(4-ethylpiperazin-1-yl)-2-isopropoxyphenylamino)-N-(2,4,6-trichloro-3,5-dimethoxyphenyl)thieno[3,2-d]pyrimidine-7-carboxamide;
146) 4-(4-(4-(2-hydroxyethyl)piperazin-1-yl)-2-isopropoxyphenylamino)-N-(2,4,6-trichloro-3,5-dimethoxyphenyl)thieno[3,2-d]pyrimidine-7-carboxamide;
147) 4-(pyridin-2-ylamino)-N-(2,4,6-trichloro-3,5-dimethoxyphenyl)thieno[3,2-d]pyrimidine-7-carboxamide;
148) N-(4-bromo-2,6-dichloro-3,5-dimethoxyphenyl)-4-chlorothieno[3,2-d]pyrimidine-7-carboxamide;
148b) N-(4-bromo-3,5-dimethoxyphenyl)-4-chlorothieno[3,2-d]pyrimidine-7-carboxamide;
148c) N-(4-bromo-3,5-dimethoxyphenyl)-4-(methylthio)thieno[3,2-d]pyrimidine-7-carboxamide;
149) 4-amino-N-(4-bromo-2,6-dichloro-3,5-dimethoxyphenyl)thieno[3,2-d]pyrimidine-7-carboxamide;
150) N-(4-bromo-2,6-dichloro-3,5-dimethoxyphenyl)-4-(2-(dimethylamino)ethylamino)thieno[3,2-d]pyrimidine-7-carboxamide;
151) N-(4-bromo-2,6-dichloro-3,5-dimethoxyphenyl)-4-(3-(diethylamino)propylamino)thieno[3,2-d]pyrimidine-7-carboxamide;
152) N-(4-bromo-2,6-dichloro-3,5-dimethoxyphenyl)-4-(4-(4-ethylpiperazin-1-yl)-2-methoxyphenylamino)thieno[3,2-d]pyrimidine-7-carboxamide;
153) N-(4-bromo-2,6-dichloro-3,5-dimethoxyphenyl)-4-(4-(4-(2-hydroxyethyl)piperazin-1-yl)-2-methoxyphenylamino)thieno[3,2-d]pyrimidine-7-carboxamide;

154) N-(4-bromo-2,6-dichloro-3,5-dimethoxyphenyl)-4-(4-(4-ethylpiperazin-1-yl)-2-isopropoxyphenylamino)thieno[3,2-d]pyrimidine-7-carboxamide;
155) N-(4-bromo-2,6-dichloro-3,5-dimethoxyphenyl)-4-(4-(4-(2-hydroxyethyl)piperazin-1-yl)-2-isopropoxyphenylamino)thieno[3,2-d]pyrimidine-7-carboxamide;
156) N-(4-bromo-2,6-dichloro-3,5-dimethoxyphenyl)-4-(4-(4-ethylpiperazin-1-yl)phenylamino)thieno[3,2-d]pyrimidine-7-carboxamide;
157) N-(4-bromo-2,6-dichloro-3,5-dimethoxyphenyl)-4-(4-(diethylamino)butylamino)thieno[3,2-d]pyrimidine-7-carboxamide;
158) N-(4-bromo-2,6-dichloro-3,5-dimethoxyphenyl)-4-(5-(diethylamino)pentylamino)thieno[3,2-d]pyrimidine-7-carboxamide;
159) N-(4-bromo-2,6-dichloro-3,5-dimethoxyphenyl)-4-(3-(4-ethylpiperazin-1-yl)propylamino)thieno[3,2-d]pyrimidine-7-carboxamide;
160) N-(4-bromo-2,6-dichloro-3,5-dimethoxyphenyl)-4-(4-(4-ethylpiperazin-1-yl)butylamino)thieno[3,2-d]pyrimidine-7-carboxamide;
161) N-(4-bromo-2,6-dichloro-3,5-dimethoxyphenyl)-4-(5-(4-ethylpiperazin-1-yl)pentylamino)thieno[3,2-d]pyrimidine-7-carboxamide;
162) 4-(3-(1H-imidazol-1-yl)propylamino)-N-(4-bromo-2,6-dichloro-3,5-dimethoxyphenyl)thieno[3,2-d]pyrimidine-7-carboxamide;
163) 4-(4-(1H-imidazol-1-yl)butylamino)-N-(4-bromo-2,6-dichloro-3,5-dimethoxyphenyl)thieno[3,2-d]pyrimidine-7-carboxamide;
164) 4-(5-(1H-imidazol-1-yl)pentylamino)-N-(4-bromo-2,6-dichloro-3,5-dimethoxyphenyl)thieno[3,2-d]pyrimidine-7-carboxamide;
165) N-(4-bromo-2,6-dichloro-3,5-dimethoxyphenyl)-4-(phenylamino)thieno[3,2-d]pyrimidine-7-carboxamide;
166) 4-chloro-N-(2,6-dichloro-3,5-dimethoxyphenyl)thieno[3,2-d]pyrimidine-7-carboxamide;
167) 4-amino-N-(2,6-dichloro-3,5-dimethoxyphenyl)thieno[3,2-d]pyrimidine-7-carboxamide;
168) 4-(cyclopropylamino)-N-(2,6-dichloro-3,5-dimethoxyphenyl)thieno[3,2-d]pyrimidine-7-carboxamide;
169) N-(2,6-dichloro-3,5-dimethoxyphenyl)-4-(2-(dimethylamino)ethylamino)thieno[3,2-d]pyrimidine-7-carboxamide;
170) N-(2,6-dichloro-3,5-dimethoxyphenyl)-4-(3-(diethylamino)propylamino)thieno[3,2-d]pyrimidine-7-carboxamide;
171) N-(2,6-dichloro-3,5-dimethoxyphenyl)-4-(3-(4-ethylpiperazin-1-yl)propylamino)thieno[3,2-d]pyrimidine-7-carboxamide;
172) 4-(4-(1H-imidazol-1-yl)butylamino)-N-(2,6-dichloro-3,5-dimethoxyphenyl)thieno[3,2-d]pyrimidine-7-carboxamide;
173) N-(2,6-dichloro-3,5-dimethoxyphenyl)-4-(4-(4-ethylpiperazin-1-yl)phenylamino)thieno[3,2-d]pyrimidine-7-carboxamide;
175) 4-acetamido-N-(2,6-dichloro-3,5-dimethoxyphenyl)thieno[3,2-d]pyrimidine-7-carboxamide;
176) 4-benzamido-N-(2,6-dichloro-3,5-dimethoxyphenyl)thieno[3,2-d]pyrimidine-7-carboxamide;
177) 4-(cyclopropanecarboxamido)-N-(2,6-dichloro-3,5-dimethoxyphenyl)thieno[3,2-d]pyrimidine-7-carboxamide;
178) N-(2,6-dichloro-3,5-dimethoxyphenyl)-4-(5-methylpyridine-2-ylamino)thieno[3,2-d]pyrimidine-7-carboxamide;
179) N-(2,6-dichloro-3,5-dimethoxyphenyl)-4-(5-((4-ethylpiperazin-1-yl)methyl)pyridin-2-ylamino)thieno[3,2-d]pyrimidine-7-carboxamide;
180) N-(2,6-dichloro-3,5-dimethoxyphenyl)-4-(5-((4-(2-hydroxyethyl)piperazin-1-yl)methyl)pyridin-2-ylamino)thieno[3,2-d]pyrimidine-7-carboxamide;
181) N-(2,6-dichloro-3,5-dimethoxyphenyl)-4-(5-(4-ethylpiperazin-1-yl)pyridin-2-ylamino)thieno[3,2-d]pyrimidine-7-carboxamide;
182) N-(2,6-dichloro-3,5-dimethoxyphenyl)-4-(6-(4-ethylpiperazin-1-yl)pyrimidin-4-ylamino)thieno[3,2-d]pyrimidine-7-carboxamide;
183) N-(2,6-dichloro-3,5-dimethoxyphenyl)-4-(6-(4-(2-hydroxyethyl)piperazin-1-yl)-2-methylpyrimidin-4-ylamino)thieno[3,2-d]pyrimidine-7-carboxamide;
184) N-(4-bromo-2,6-dichloro-3,5-dimethoxyphenyl)-4-(6-methylpyridin-3-ylamino)thieno[3,2-d]pyrimidine-7-carboxamide;
185) N-(4-bromo-2,6-dichloro-3,5-dimethoxyphenyl)-4-(4-(2-(diethylamino)ethoxy)phenylamino)thieno[3,2-d]pyrimidine-7-carboxamide;
186) N-(4-bromo-2,6-dichloro-3,5-dimethoxyphenyl)-4-(4-(2-hydroxyethyl)phenylamino)thieno[3,2-d]pyrimidine-7-carboxamide;
187) 4-(4-(1-benzylpiperidine-4-ylcarbamoyl)phenylamino)-N-(4-bromo-2,6-dichloro-3,5-dimethoxyphenyl)thieno[3,2-d]pyrimidine-7-carboxamide;
188) N-(4-bromo-2,6-dichloro-3,5-dimethoxyphenyl)-4-(4-(4-ethylpiperazine-1-carbonyl)phenylamino)thieno[3,2-d]pyrimidine-7-carboxamide;
189) N-(2,6-dichloro-3,5-dimethoxyphenyl)-4-(4-((4-ethylpiperazin-1-yl)methyl)phenylamino)thieno[3,2-d]pyrimidine-7-carboxamide;
190) N-(4-bromo-2,6-dichloro-3,5-dimethoxyphenyl)-4-(4-(2-(4-ethylpiperazin-1-yl)-2-oxoethyl)phenylamino)thieno[3,2-d]pyrimidine-7-carboxamide;
191) N-(4-bromo-2,6-dichloro-3,5-dimethoxyphenyl)-4-(4-(2-(4-ethylpiperazin-1-yl)ethyl)phenylamino)thieno[3,2-d]pyrimidine-7-carboxamide;
192) 4-(7-(4-bromo-2,6-dichloro-3,5-dimethoxyphenylcarbamoyl)thieno[3,2-d]pyrimidin-4-ylamino)benzoic acid;
193) N-(4-bromo-2,6-dichloro-3,5-dimethoxyphenyl)-4-(4-((4-ethylpiperazin-1-yl)methyl)-3-(trifluoromethyl)phenylamino)thieno[3,2-d]pyrimidine-7-carboxamide;
194) N-(4-bromo-2,6-dichloro-3,5-dimethoxyphenyl)-4-(3-(4-ethylpiperazin-1-yl)phenylamino)thieno[3,2-d]pyrimidine-7-carboxamide;
195) N-(4-bromo-2,6-dichloro-3,5-dimethoxyphenyl)-4-(4-(4-(pyrrolidin-1-yl)piperidin-1-yl)phenylamino)thieno[3,2-d]pyrimidine-7-carboxamide;
196) N-(2,6-dichloro-3,5-dimethoxyphenyl)-4-(4-(2-(diethylamino)ethoxy)phenylamino)thieno[3,2-d]pyrimidine-7-carboxamide;
197) 4-(4-(1-benzylpiperidine-4-ylcarbamoyl)phenylamino)-N-(2,6-dichloro-3,5-dimethoxyphenyl)thieno[3,2-d]pyrimidine-7-carboxamide;
198) N-(2,6-dichloro-3,5-dimethoxyphenyl)-4-(4-(4-ethylpiperazine-1-carbonyl)phenylamino)thieno[3,2-d]pyrimidine-7-carboxamide;
199) N-(2,6-dichloro-3,5-dimethoxyphenyl)-4-(4-(2-(4-ethylpiperazin-1-yl)-2-oxoethyl)phenylamino)thieno[3,2-d]pyrimidine-7-carboxamide;
200) N-(2,6-dichloro-3,5-dimethoxyphenyl)-4-(4-((4-ethylpiperazin-1-yl)methyl)-3-(trifluoromethyl)phenylamino)thieno[3,2-d]pyrimidine-7-carboxamide;

201) N-(2,6-dichloro-3,5-dimethoxyphenyl)-4-(3-(4-ethylpiperazin-1-yl)phenylamino)thieno[3,2-d]pyrimidine-7-carboxamide;
202) N-(2,6-dichloro-3,5-dimethoxyphenyl)-4-(4-(4-(pyrrolidin-1-yl)piperidin-1-yl)phenylamino)thieno[3,2-d]pyrimidine-7-carboxamide;
203) N-(4-bromo-2,6-dichloro-3,5-dimethoxyphenyl)-4-(4-(4-ethylpiperazin-1-yl)benzamido)thieno[3,2-d]pyrimidine-7-carboxamide;
204) N-(2,6-dichloro-3,5-dimethoxyphenyl)-4-(4-(4-ethylpiperazin-1-yl)benzamido)thieno[3,2-d]pyrimidine-7-carboxamide;
205) N-(4-bromo-2,6-dichloro-3,5-dimethoxyphenyl)-4-(methylsulfonamido)thieno[3,2-d]pyrimidine-7-carboxamide;
206) N-(2,6-dichloro-3,5-dimethoxyphenyl)-4-(methylsulfonamido)thieno[3,2-d]pyrimidine-7-carboxamide;
207) N-(4-bromo-2,6-dichloro-3,5-dimethoxyphenyl)-4-(4-(4-hydroxypiperidin-1-yl)phenylamino)thieno[3,2-d]pyrimidine-7-carboxamide;
208) N-(2,6-dichloro-3,5-dimethoxyphenyl)-4-(6-(2-morpholinoethylamino)pyrimidin-4-ylamino)thieno[3,2-d]pyrimidine-7-carboxamide;
209) N-(2,6-dichloro-3,5-dimethoxyphenyl)-4-(6-(2-(dimethylamino)ethoxy)pyrimidin-4-ylamino)thieno[3,2-d]pyrimidine-7-carboxamide;
210) N-(2,6-dichloro-3,5-dimethoxyphenyl)-4-(6-(3-(diethylamino)propylamino)pyrimidin-4-ylamino)thieno[3,2-d]pyrimidine-7-carboxamide;
211) N-(2,6-dichloro-3,5-dimethoxyphenyl)-4-(6-(3-(4-ethylpiperazin-1-yl)propylamino)pyrimidin-4-ylamino)thieno[3,2-d]pyrimidine-7-carboxamide;
212) N-(4-bromo-2,6-dichloro-3,5-dimethoxyphenyl)-4-(4-methyl-6-(2-morpholinoethylamino)pyrimidin-2-ylamino)thieno[3,2-d]pyrimidine-7-carboxamide;
213) N-(4-bromo-2,6-dichloro-3,5-dimethoxyphenyl)-4-(5-nitrothiazol-2-ylamino)thieno[3,2-d]pyrimidine-7-carboxamide;
214) N-(2,6-dichloro-3,5-dimethoxyphenyl)-4-(4-methyl-6-(2-morpholinoethylamino)pyrimidin-2-ylamino)thieno[3,2-d]pyrimidine-7-carboxamide;
215) N-(2,6-dichloro-3,5-dimethoxyphenyl)-4-(3-(3-(trifluoromethyl)phenyl)ureido)thieno[3,2-d]pyrimidine-7-carboxamide;
216) N-(2,6-dichloro-3,5-dimethoxyphenyl)-4-(3-(ethoxycarbonyl)thioureido)thieno[3,2-d]pyrimidine-7-carboxamide;
217) 4-amino-N-(2,6-dichloro-3-hydroxy-5-methoxyphenyl)thieno[3,2-d]pyrimidine-7-carboxamide;
218) 4-amino-N-(2,6-dichloro-3,5-dihydroxyphenyl)thieno[3,2-d]pyrimidine-7-carboxamide;
219) 4-amino-N-(2,6-dichloro-3-(2-(dimethylamino)ethoxy)-5-methoxyphenyl)thieno[3,2-d]pyrimidine-7-carboxamide;
220) 4-(2-amino-5-(4-ethylpiperazin-1-yl)-6-fluoro-1H-benzo[d]imidazol-1-yl)-N-(4-bromo-2,6-dichloro-3,5-dimethoxyphenyl)thieno[3,2-d]pyrimidine-7-carboxamide;
221) N-(4-bromo-2,6-dichloro-3,5-dimethoxyphenyl)-4-(6-methylbenzo[d]thiazol-2-ylamino)thieno[3,2-d]pyrimidine-7-carboxamide;
222) 4-(2-amino-1H-benzo[d]imidazol-1-yl)-N-(4-bromo-2,6-dichloro-3,5-dimethoxyphenyl)thieno[3,2-d]pyrimidine-7-carboxamide;
223) N-(4-bromo-2,6-dichloro-3,5-dimethoxyphenyl)-4-(1-(4-methoxybenzyl)-1H-benzo[d]imidazol-2-ylamino)thieno[3,2-d]pyrimidine-7-carboxamide;
224) 4-(2-amino-5-(4-ethylpiperazin-1-yl)-6-fluoro-1H-benzo[d]imidazol-1-yl)-N-(2,6-dichloro-3,5-dimethoxyphenyl)thieno[3,2-d]pyrimidine-7-carboxamide;
225) N-(2,6-dichloro-3,5-dimethoxyphenyl)-4-(6-methylbenzo[d]thiazol-2-ylamino)thieno[3,2-d]pyrimidine-7-carboxamide;
226) 4-(2-amino-1H-benzo[d]imidazol-1-yl)-N-(2,6-dichloro-3,5-dimethoxyphenyl)thieno[3,2-d]pyrimidine-7-carboxamide;
227) N-(2,6-dichloro-3,5-dimethoxyphenyl)-4-(1-(4-methoxybenzyl)-1H-benzo[d]imidazol-2-ylamino)thieno[3,2-d]pyrimidine-7-carboxamide;
228) 4-(1H-indazol-6-ylamino)-N-(4-bromo-2,6-dichloro-3,5-dimethoxyphenyl)thieno[3,2-d]pyrimidine-7-carboxamide;
229) 4-(1H-indazol-6-ylamino)-N-(2,6-dichloro-3,5-dimethoxyphenyl)thieno[3,2-d]pyrimidine-7-carboxamide;
230) N-(4-bromo-2,6-dichloro-3,5-dimethoxyphenyl)-4-(5-methyl-1H-pyrazol-3-ylamino)thieno[3,2-d]pyrimidine-7-carboxamide;
231) N-(2,6-dichloro-3,5-dimethoxyphenyl)-4-(5-methyl-1H-pyrazol-3-ylamino)thieno[3,2-d]pyrimidine-7-carboxamide;
232) ethyl 6-(7-(2,6-dichloro-3,5-dimethoxyphenylcarbamoyl)thieno[3,2-d]pyrimidin-4-ylamino)-1H-indazole-3-carboxylate;
236) 4-amino-N-(2,6-dichloro-3,5-dimethylphenyl)thieno[3,2-d]pyrimidine-7-carboxamide;
237) 4-amino-N-(2,6-dichloro-3,5-dimethoxybenzyl)thieno[3,2-d]pyrimidine-7-carboxamide;
239) N-(2,6-dichloro-3,5-dimethoxyphenyl)-4-(4-(dimethylamino)phenylamino)thieno[3,2-d]pyrimidine-7-carboxamide;
240) N-(2,6-dichloro-3,5-dimethoxyphenyl)-4-(4-methoxyphenylamino)thieno[3,2-d]pyrimidine-7-carboxamide;
241) N-(2,6-dichloro-3,5-dimethoxyphenyl)-4-(4-(4-(2-hydroxyethyl)piperazin-1-yl)phenylamino)thieno[3,2-d]pyrimidine-7-carboxamide;
242) N-(2,6-dichloro-3,5-dimethoxyphenyl)-4-(4-(piperazin-1-yl)phenylamino)thieno[3,2-d]pyrimidine-7-carboxamide;
243) N-(2,6-dichloro-3,5-dimethoxyphenyl)-4-(4-(4-propionylpiperazin-1-yl)phenylamino)thieno[3,2-d]pyrimidine-7-carboxamide;
244) N-(2,6-dichloro-3,5-dimethoxyphenyl)-4-(4-(4-(isopropylcarbamoyl)piperazin-1-yl)phenylamino)thieno[3,2-d]pyrimidine-7-carboxamide;
245) ethyl 4-(4-(7-(2,6-dichloro-3,5-dimethoxyphenylcarbamoyl)thieno[3,2-d]pyrimidin-4-ylamino)phenyl)piperazine-1-carboxylate;
246) N-(2,6-dichloro-3,5-dimethoxyphenyl)-4-(4-morpholinophenylamino)thieno[3,2-d]pyrimidine-7-carboxamide;
247) N-(2,6-dichloro-3,5-dimethoxyphenyl)-4-(5-(morpholinomethyl)pyridin-2-ylamino)thieno[3,2-d]pyrimidine-7-carboxamide;
248) N-(2,6-dichloro-3,5-dimethoxyphenyl)-4-(4-(4-methylpiperazin-1-ylamino)phenylamino)thieno[3,2-d]pyrimidine-7-carboxamide;
249) 4-(4-(1H-imidazol-1-yl)phenylamino)-N-(2,6-dichloro-3,5-dimethoxyphenyl)thieno[3,2-d]pyrimidine-7-carboxamide;
250) 4-(5-chloropyridin-2-ylamino)-N-(2,6-dichloro-3,5-dimethoxyphenyl)thieno[3,2-d]pyrimidine-7-carboxamide;

251) N-(2,6-dichloro-3,5-dimethoxyphenyl)-4-(4-(piperidin-4-ylamino)phenylamino)thieno[3,2-d]pyrimidine-7-carboxamide;
252) N-(2,6-dichloro-3,5-dimethoxyphenyl)-4-(4-(4-(1-methylpiperidin-4-yl)piperazin-1-yl)phenylamino)thieno[3,2-d]pyrimidine-7-carboxamide;
253) N-(2,6-dichloro-3,5-dimethoxyphenyl)-4-(4-(4-(pyridin-2-yl)piperazin-1-yl)phenylamino)thieno[3,2-d]pyrimidine-7-carboxamide;
254) N-(2,6-dichloro-3,5-dimethoxyphenyl)-4-(5-((diethylamino)methyl)pyridin-2-ylamino)thieno[3,2-d]pyrimidine-7-carboxamide;
255) N-(2,6-dichloro-3,5-dimethoxyphenyl)-4-(5-(morpholine-4-carbonyl)pyridin-2-ylamino)thieno[3,2-d]pyrimidine-7-carboxamide;
256) 4-(5-((1H-imidazol-1-yl)methyl)pyridin-2-ylamino)-N-(2,6-dichloro-3,5-dimethoxyphenyl)thieno[3,2-d]pyrimidine-7-carboxamide;
257) N-(2,6-dichloro-3,5-dimethoxyphenyl)-4-(5-(2-morpholino-2-oxoethyl)pyridin-2-ylamino)thieno[3,2-d]pyrimidine-7-carboxamide;
258) N-(2,6-dichloro-3,5-dimethoxyphenyl)-4-(5-((4-methylpiperidin-1-yl)methyl)pyridin-2-ylamino)thieno[3,2-d]pyrimidine-7-carboxamide;
259) N-(2,6-dichloro-3,5-dimethoxyphenyl)-4-(5-((3-(trifluoromethyl)piperidin-1-yl)methyl)pyridin-2-ylamino)thieno[3,2-d]pyrimidine-7-carboxamide;
260) N-(2,6-dichloro-3,5-dimethoxyphenyl)-4-(5-((3,5-dimethylmorpholino)methyl)pyridin-2-ylamino)thieno[3,2-d]pyrimidine-7-carboxamide;
261) 4-(5-((4-acetylpiperazin-1-yl)methyl)pyridin-2-ylamino)-N-(2,6-dichloro-3,5-dimethoxyphenyl)thieno[3,2-d]pyrimidine-7-carboxamide;
262) N-(2,6-dichloro-3,5-dimethoxyphenyl)-4-(5-((4-morpholinopiperidin-1-yl)methyl)pyridin-2-ylamino)thieno[3,2-d]pyrimidine-7-carboxamide;
263) N-(2,6-dichloro-3,5-dimethoxyphenyl)-4-(5-((3-oxopiperazin-1-yl)methyl)pyridin-2-ylamino)thieno[3,2-d]pyrimidine-7-carboxamide;
264) N-(2,6-dichloro-3,5-dimethoxyphenyl)-4-(5-(3-(diethylamino)propylcarbamoyl)pyridin-2-ylamino)thieno[3,2-d]pyrimidine-7-carboxamide;
265) N-(2,6-dichloro-3,5-dimethoxyphenyl)-4-(5-((3-(diethylamino)propylamino)methyl)pyridin-2-ylamino)thieno[3,2-d]pyrimidine-7-carboxamide;
266) (R)—N-(2,6-dichloro-3,5-dimethoxyphenyl)-4-(5-((3-hydroxypyrrolidin-1-yl)methyl)pyridin-2-ylamino)thieno[3,2-d]pyrimidine-7-carboxamide;
267) N-(2,6-dichloro-3,5-dimethoxyphenyl)-4-(5-(3-(4-ethylpiperazin-1-yl)propylcarbamoyl)pyridin-2-ylamino)thieno[3,2-d]pyrimidine-7-carboxamide;
268) N-(2,6-dichloro-3,5-dimethoxyphenyl)-4-(5-(4-methylpiperazin-1-ylcarbamoyl)pyridin-2-ylamino)thieno[3,2-d]pyrimidine-7-carboxamide;
269) N-(2,6-dichloro-3,5-dimethoxyphenyl)-4-(5-((3-(4-ethylpiperazin-1-yl)propylamino)methyl)pyridin-2-ylamino)thieno[3,2-d]pyrimidine-7-carboxamide;
270) N-(2,6-dichloro-3,5-dimethoxyphenyl)-4-(4-methylpyridin-2-ylamino)thieno[3,2-d]pyrimidine-7-carboxamide;
271) N-(2,6-dichloro-3,5-dimethoxyphenyl)-4-(5-((2-(diethylamino)ethoxy)methyl)pyridin-2-ylamino)thieno[3,2-d]pyrimidine-7-carboxamide;
272) N-(2,6-dichloro-3,5-dimethoxyphenyl)-4-(4-((diethylamino)methyl)pyridin-2-ylamino)thieno[3,2-d]pyrimidine-7-carboxamide;
273) N-(2,6-dichloro-3,5-dimethoxyphenyl)-4-(6-((diethylamino)methyl)pyridin-2-ylamino)thieno[3,2-d]pyrimidine-7-carboxamide;
274) 4-(5-carbamoylpyridin-2-ylamino)-N-(2,6-dichloro-3,5-dimethoxyphenyl)thieno[3,2-d]pyrimidine-7-carboxamide;
275) N-(2,6-dichloro-3,5-dimethoxyphenyl)-4-(5-((2-methoxyethoxy)methyl)pyridin-2-ylamino)thieno[3,2-d]pyrimidine-7-carboxamide;
276) N-(2,6-dichloro-3,5-dimethoxyphenyl)-4-(5-((3-(diethylamino)propoxy)methyl)pyridin-2-ylamino)thieno[3,2-d]pyrimidine-7-carboxamide;
277) N-(2,6-dichloro-3,5-dimethoxyphenyl)-4-(5-((2-(piperidin-1-yl)ethoxy)methyl)pyridin-2-ylamino)thieno[3,2-d]pyrimidine-7-carboxamide;
278) N-(2,6-dichloro-3,5-dimethoxyphenyl)-4-(pyridin-4-ylamino)thieno[3,2-d]pyrimidine-7-carboxamide;
279) N-(2,6-dichloro-3,5-dimethoxyphenyl)-4-(4-((4-ethylpiperazin-1-yl)methyl)pyridin-2-ylamino)thieno[3,2-d]pyrimidine-7-carboxamide;
280) N-(2,6-dichloro-3,5-dimethoxyphenyl)-4-(4-(morpholinomethyl)pyridin-2-ylamino)thieno[3,2-d]pyrimidine-7-carboxamide;
281) N-(2,6-dichloro-3,5-dimethoxyphenyl)-4-(5-(3-(diethylamino)propoxy)pyridin-2-ylamino)thieno[3,2-d]pyrimidine-7-carboxamide;
282) N-(2,6-dichloro-3,5-dimethoxyphenyl)-4-(4-(diethylamino)pyridin-2-ylamino)thieno[3,2-d]pyrimidine-7-carboxamide;
285) N-(2,6-dichloro-3,5-dimethoxyphenyl)-4-(4-(3-(diethylamino)propoxy)pyridin-2-ylamino)thieno[3,2-d]pyrimidine-7-carboxamide;
286) N-(4-bromo-2,6-dichloro-3,5-dimethoxyphenyl)-4-(2,3,4-trifluorophenylamino)thieno[3,2-d]pyrimidine-7-carboxamide;
287) N-(4-bromo-2,6-dichloro-3,5-dimethoxyphenyl)-4-(3-chloro-4-fluorophenylamino)thieno[3,2-d]pyrimidine-7-carboxamide;
288) N-(2,6-dichloro-3,5-dimethoxyphenyl)-4-(4-(piperidin-1-ylmethyl)pyridin-2-ylamino)thieno[3,2-d]pyrimidine-7-carboxamide;
289) N-(2,6-dichloro-3,5-dimethoxyphenyl)-4-(2,3,4-trifluorophenylamino)thieno[3,2-d]pyrimidine-7-carboxamide;
290) 4-(3-chloro-4-fluorophenylamino)-N-(2,6-dichloro-3,5-dimethoxyphenyl)thieno[3,2-d]pyrimidine-7-carboxamide;
291) N-(2,6-dichloro-3,5-dimethoxyphenyl)-4-(4-(thiazolidin-3-ylmethyl)pyridin-2-ylamino)thieno[3,2-d]pyrimidine-7-carboxamide;
292) N-(2,6-dichloro-3,5-dimethoxyphenyl)-4-(4-(2-(diethylamino)-2-oxoethyl)pyridin-2-ylamino)thieno[3,2-d]pyrimidine-7-carboxamide;
293) N-(2,6-dichloro-3,5-dimethoxyphenyl)-4-(4-((2-(diethylamino)ethylamino)methyl)pyridin-2-ylamino)thieno[3,2-d]pyrimidine-7-carboxamide;
294) N-(2,6-dichloro-3,5-dimethoxyphenyl)-4-(4-(((2-hydroxyethyl)(methyl)amino)methyl)pyridin-2-ylamino)thieno[3,2-d]pyrimidine-7-carboxamide;
295) N-(2,6-dichloro-3,5-dimethoxyphenyl)-4-(4-((2-(diethylamino)ethoxy)methyl)pyridin-2-ylamino)thieno[3,2-d]pyrimidine-7-carboxamide;
296) N-(2,6-dichloro-3,5-dimethoxyphenyl)-4-(diethylamino)thieno[3,2-d]pyrimidine-7-carboxamide;
297) N-(2,6-dichloro-3,5-dimethoxyphenyl)-4-(piperidin-4-ylamino)thieno[3,2-d]pyrimidine-7-carboxamide;

298) 4-(4-((diethylamino)methyl)pyridin-2-ylamino)-N-(3,5-dimethoxyphenyl)thieno[3,2-d]pyrimidine-7-carboxamide;

299) N-(2,6-dichloro-3,5-dimethoxyphenyl)-4-(5-(2-(dimethylamino)acetamido)pyridin-2-ylamino)thieno[3,2-d]pyrimidine-7-carboxamide;

300) N-(2,6-dichloro-3,5-dimethoxyphenyl)-4-(phenethylamino)thieno[3,2-d]pyrimidine-7-carboxamide;

301) N-(2,6-dichloro-3,5-dimethoxyphenyl)-4-(2-hydroxyethylamino)thieno[3,2-d]pyrimidine-7-carboxamide;

302) ethyl 2-(7-(2,6-dichloro-3,5-dimethoxyphenylcarbamoyl)thieno[3,2-d]pyrimidin-4-ylamino)acetate;

303) 2-(7-(2,6-dichloro-3,5-dimethoxyphenylcarbamoyl)thieno[3,2-d]pyrimidin-4-ylamino)acetic acid; and 304) N-(2,6-dichloro-3,5-dimethoxyphenyl)-4-(2-(phenylamino)ethylamino)thieno[3,2-d]pyrimidine-7-carboxamide, or a pharmaceutically acceptable salt thereof, a hydrate thereof, or a solvate thereof.

3. A method for preparing a compound of formula (1e), which comprises subjecting a compound of formula (1a) to a reaction with a compound of formula (2a):

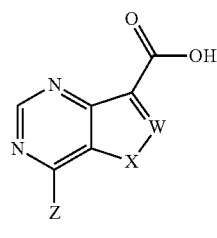

(1a)

H$_2$N—R$^3$ (2a)

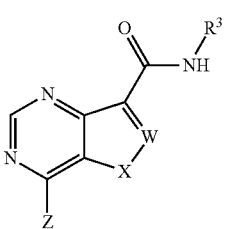

(1e)

wherein, W, X, Z and R$^3$ have the same meanings as defined in claim 1.

4. A method for preparing a compound of formula (1f), which comprises subjecting a compound of formula (1b) to a reaction with a compound of formula (2b):

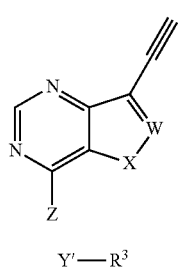

(1b)

Y'—R$^3$ (2b)

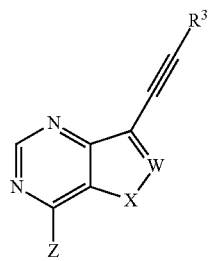

(1f)

wherein, W, X, Z and R$^3$ have the same meanings as defined in claim 1; and Y' is halogen.

5. A method for preparing a compound of formula (1g), which comprises subjecting a compound of formula (1c) to a reaction with a compound of formula (2c):

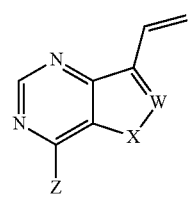

(1c)

Y"—R$^3$ (2c)

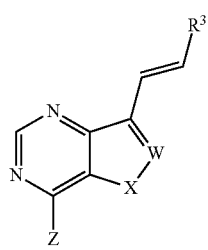

(1g)

wherein, W, X, Z and R$^3$ have the same meanings as defined in claim 1; and Y" is halogen.

6. A method for preparing a compound of formula (1h), which comprises subjecting a compound of formula (1d) to a reaction with a compound of formula (2d):

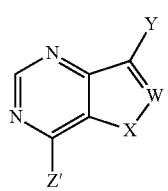

(1d)

Z"—R$^5$ (2d)

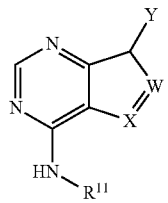

(1h)

wherein, W, X and Y have the same meanings as defined in claim 1, and $R^{11}$ has the same meaning as defined in claim 1 for the substituted amino (NH) groups at Z; and when Z' is halogen, Z" is $NH_2$, and when Z' is $NH_2$, Z" is halogen.

7. A pharmaceutical composition comprising the compound of claim 1 as an active ingredient and a pharmaceutically acceptable carrier.

\* \* \* \* \*